(12) United States Patent
Velaparthi et al.

(10) Patent No.: US 9,475,817 B2
(45) Date of Patent: Oct. 25, 2016

(54) PYRAZOLE SUBSTITUTED IMIDAZOPYRAZINES AS CASEIN KINASE 1 D/E INHIBITORS

(71) Applicant: BRISTOL-MYERS SQUIBB COMPANY, Princeton, NJ (US)

(72) Inventors: Upender Velaparthi, Cheshire, CT (US); Chetan Padmakar Darne, Orange, CT (US); Dharmpal S. Dodd, Princeton, NJ (US); Peiying Liu, Madison, CT (US); Christopher P. Mussari, Princeton, NJ (US); Mark D. Wittman, Wallingford, CT (US); Selvakumar Kumaravel, Karnataka (IN); Dibakar Mullick, West Bengal (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/653,878

(22) PCT Filed: Dec. 20, 2013

(86) PCT No.: PCT/US2013/076806
§ 371 (c)(1),
(2) Date: Jun. 19, 2015

(87) PCT Pub. No.: WO2014/100540
PCT Pub. Date: Jun. 26, 2014

(65) Prior Publication Data
US 2015/0344480 A1 Dec. 3, 2015

Related U.S. Application Data

(60) Provisional application No. 61/740,552, filed on Dec. 21, 2012.

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 7,820,665 B2 | 10/2010 | Booker et al. |
| 8,455,491 B2 | 6/2013 | Puech et al. |
| 2007/0078136 A1 | 4/2007 | Vaccaro et al. |
| 2010/0029619 A1 | 2/2010 | Uchikawa et al. |
| 2013/0190314 A1 | 7/2013 | Chiang et al. |

FOREIGN PATENT DOCUMENTS

| | | |
|---|---|---|
| EP | 2 058 309 A1 | 5/2009 |
| WO | WO 2010/070238 A1 | 6/2010 |
| WO | WO 2010/091409 A1 | 8/2010 |
| WO | WO 2014/100533 A1 | 6/2014 |

OTHER PUBLICATIONS

U.S. Appl. No. 14/653,895, filed Jun. 19, 2015.*
Pinedo et al. (2000).*
McMahon et al. (2000).*

* cited by examiner

*Primary Examiner* — Paul V Ward
(74) *Attorney, Agent, or Firm* — Elliott Korsen; Hong Liu

(57) ABSTRACT

The invention provides compounds of Formula (I) and pharmaceutically acceptable salts thereof. The compounds of Formula (I) inhibit protein kinase activity thereby making them useful as anticancer agents.

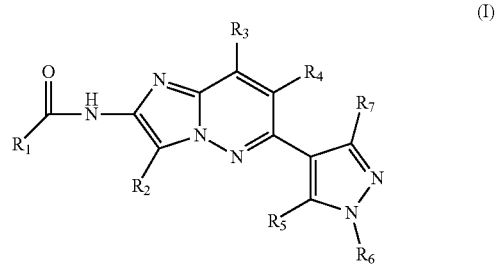

(I)

12 Claims, No Drawings

PYRAZOLE SUBSTITUTED IMIDAZOPYRAZINES AS CASEIN KINASE 1 D/E INHIBITORS

CROSS REFERENCES TO RELATED APPLICATIONS

This application is a 371 of International Application No. PCT/US2013/076806, filed on Dec. 20, 2013, which claims the benefit of U.S. Provisional Application Ser. No. 61/740,552 filed on Dec. 21, 2012 which is incorporated herein by reference.

FIELD OF THE INVENTION

The invention relates to novel substituted pyrazoles useful as protein kinase inhibitors. This invention also relates to methods of using the compounds in the treatment of proliferative and other types of diseases and to pharmaceutical compositions containing the compounds.

BACKGROUND OF THE INVENTION

The invention relates to substituted pyrazole compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases are valid drug targets for potential cancer therapies.

Casein kinase 1 (CK1) belongs to the serine/threonine kinase family. In mammals, the enzyme exists in seven isozymic forms: α, β, γ1, γ2, γ3, δ, and ε. By phosphorylating different substrate proteins, these isoforms are able to activate, inactivate, stabilize, or destabilize the functions of the proteins, regulating the functions of various types of different organisms. For example, a tumor suppressor factor p53 and an oncogene mdm2, which are both important proteins for controlling abnormal cell growth, are substrates of casein kinase 1.

Mammalian casein kinase 1δ and casein kinase 1ε are key regulators of diverse cellular growth and survival processes including Wnt signaling, DNA repair and circadian rhythms. They have a kinase domain that is similar to those of other isoforms. However, the N-terminal and C-terminal domains thereof are different from those of other isoforms. The C-terminal domain has a plurality of autophosphorylation sites, and it is considered to be involved in regulation of autoenzyme activity. Phosphorylation of p53 by casein kinase 1δ or casein kinase 1ε leads to a consequent change in the interaction between p53 and mdm2 It has also been known that casein kinase 1ε or casein kinase 1δ is involved in a regulatory protein associated with the formation of a spindle as a central body during cell division, and that the casein kinase 1δ or casein kinase 1ε is involved in apoptosis mediated by TRAIL (tumor necrosis factor-related apoptosis inducing factor) and Fas. It has been further reported that inhibition of casein kinase 1ε or casein kinase 1δ by a nonselective casein kinase 1 inhibitory compound IC261 reduces pancreatic tumor cell growth in vitro and in vivo (Brockschmidt et al., *Gut*, 57(6):799-806 (2008)). Hence, a medicament inhibiting the function of casein kinase 1δ or casein kinase 1ε would be expected to exert important phenotypic and therapeutic effects broadly in development and disease, especially cancer.

The present invention relates to a new class substituted pyrazoles found to be effective in inhibiting casein kinase 1δ or casein kinase 1ε. These novel compounds are provided to be useful as pharmaceuticals with desirable stability, bioavailability, therapeutic index and toxicity values that are important to their drugability.

SUMMARY OF THE INVENTION

The invention is directed to substituted pyrazole compounds of Formulae (I)-(III) or stereoisomers, tautomers, pharmaceutically acceptable salts, solvates or prodrugs thereof, which inhibit protein kinase enzymes, especially protein kinase CK1 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK1 comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs

DETAILED DESCRIPTION OF THE INVENTION thereof, in preparing a medicament for the treatment of cancer in a human patient, particularly a cancer receptive to treatment via inhibition of the CK1 enzyme.

These and other features of the invention will be set forth in the expanded form as the disclosure continues.

The invention provides for novel substituted pyrazole compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

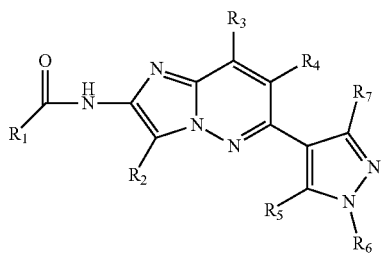

(I)

wherein:

$R_1$ is selected from $C_{1-4}$alkyl (optionally substituted with F, Cl, Br, OH, CN, and $NR_aR_a$), —$(CR_dR_d)_r$-carbocyclyl substituted with 0-5 $R_{11}$, and —$(CR_dR_d)_r$-heterocyclyl comprising carbon atoms and 1 to 4 heteroatoms selected from N, $NR_9$, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl, F, Cl, Br, and CN;

$R_5$ is selected from H, $C_{1-4}$alkyl substituted with 0-4 $R_e$, —$(CH_2)_r$—$C_{3-6}$ carbocyclyl substituted with 0-4 $R_e$, and —$(CH_2)_r$-heterocyclyl comprising carbon atoms and 1 to 3 heteroatoms selected from N, $NR_8$, O, S, and substituted with 0-4 $R_e$;

$R_6$ is selected from H, $C_{1-6}$alkyl substituted with 0-3 $R_e$, and $C_{3-6}$carbocyclyl substituted with 0-3 $R_e$; or $R_7$ is aryl substituted with 0-3 $R_e$;

$R_8$ is selected from H, $C_{1-4}$ alkyl substituted with 0-3 $R_e$, —$(CH_2)_r$CN, —$(CH_2)_r$OR$_b$, $(CH_2)_r$S(O)$_p$R$_c$, —$(CH_2)_r$C(=O)R$_b$, —$(CH_2)_r$NR$_a$R$_a$, —$(CH_2)_r$C(=O)NR$_a$R$_a$, —$(CH_2)_r$C(=O)—$C_{1-4}$ alkyl substituted with 0-3 $R_e$, —$(CH_2)_r$NR$_a$C(=O)R$_b$, —$(CH_2)_r$NR$_a$C(=O)OR$_b$, —$(CH_2)_r$OC(=O)NR$_a$R$_a$, —$(CH_2)_r$NR$_a$C(=O)NR$_a$R$_a$, —$(CH_2)_r$C(=O)OR$_b$, —$(CH_2)_r$S(O)$_2$NR$_a$R$_a$, —$(CH_2)_r$NR$_a$S(O)$_2$NR$_a$R$_a$, —$(CH_2)_r$NR$_a$S(O)$_2$R$_c$, $(CH_2)_r$-carbocyclyl substituted with 0-3 $R_e$, and —$(CH_2)_r$-heterocyclyl substituted with 0-3 $R_e$;

$R_9$ is selected from H, —C(=O)R$_b$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_{11}$, at each occurrence, is independently selected from H, F, Cl, Br, =O, CN, NO$_2$, —OR$_b$, —S(O)$_p$R$_c$, —C(=O)R$_b$, —$(CR_dR_d)_r$NR$_a$R$_a$, —$(CR_dR_d)_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —$(CR_dR_d)$C(=O)OR$_b$; —S(O)$_2$NR$_a$R$_a$, —NR$_a$S(O)$_2$NR$_a$R$_a$, —NR$_a$S(O)$_2$R$_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, NO$_2$, =O, CO$_2$H, —$(CH_2)_r$OR$_f$, S(O)$_p$R$_f$, and —$(CH_2)_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, there are disclosed compounds of Formula (II) including enantiomers, diastereomers, tautomers, pharmaceutically-acceptable salts, prodrugs, hydrates, or solvates thereof,

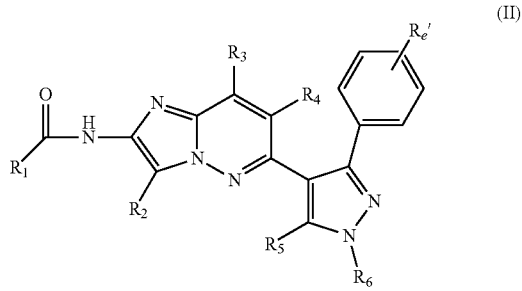

(II)

wherein:

$R_e'$ is selected from F, Cl, Br, and $C_{1-6}$ alkyl substituted with 0-5 $R_f$;

$R_5$ is selected from H, $C_{1-4}$alkyl substituted with 0-3 $R_e$, —$(CH_2)_r$—$C_{3-6}$ carbocyclyl substituted with 0-3 $R_e$, and —$(CH_2)_r$-heterocyclyl comprising carbon atoms and 1 to 3 heteroatoms selected from N, $NR_8$, O, S, and substituted with 0-3 $R_e$;

$R_6$ is selected from H, $C_{1-6}$alkyl substituted with 0-2 $R_e$, and $C_{3-6}$cycloalkyl substituted with 0-2 $R_e$; and $R_8$ is selected from H, $C_{1-4}$ alkyl substituted with 0-3 $R_e$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_d$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2R_c$, —$(CH_2)_r$—$C_{3-6}$ carbocyclyl substituted with 0-3 $R_e$, and —$(CH_2)_r$-heterocyclyl substituted with 0-3 $R_e$;

other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:

$R_5$ is selected from H, $C_{1-4}$alkyl substituted with 0-1 $R_e$, $C_{3-6}$cycloalkyl, aryl, and —$(CH_2)_r$-heterocyclyl selected from pyridyl, pyrimidinyl, pyrazinyl, pyridazinyl, triazinyl, furyl, thienyl, imidazolyl, thiazolyl, indolyl, pyrrolyl, oxazolyl, isoxazolyl, pyrazolyl, triazolyl, tetrazolyl, indazolyl, 1,2,4-thiadiazolyl, isothiazolyl, azetidinyl, pyrrolidinyl, piperidinyl, piperazinyl, and morpholinyl;

other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:

$R_5$ is selected from H,

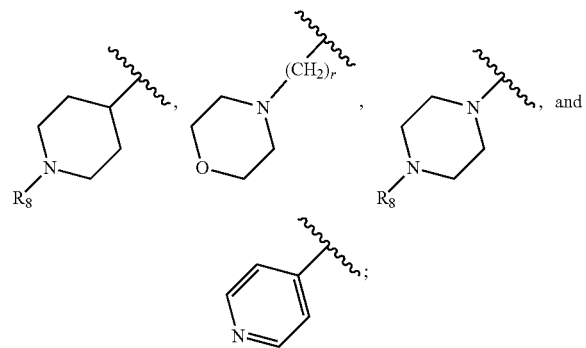

$R_8$ is selected from H, $C_{1-4}$ alkyl substituted with 0-3 $R_e$, —$(CH_2)_rOR_b$, —$(CH_2)_rC(=O)R_b$, —$(CH_2)_rNR_aR_a$, —$(CH_2)_rC(=O)NR_aR_a$, —$(CH_2)_r(C=O)CH_2NR_aR_a$, —$(CH_2)_rNR_aC(=O)R_b$, —$(CH_2)_rNR_aC(=O)OR_b$, —$(CH_2)_rC(=O)OR_b$, and —$(CH_2)_r$-heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, =O, $CO_2H$, $(CH_2)_rOC_{1-5}$alkyl, —$(CH_2)_rOH$, SH, and —$(CH_2)_rNR_fR_f$;

$R_f$, at each occurrence, is independently selected from H, $C_{1-5}$ alkyl, and phenyl, or $R_f$ and $R_f$ together with the nitrogen atom to which they are both attached form a heterocyclic ring;

other variables are as defined in Formula (I) above.

In another embodiment, there are disclosed compounds of formula (III) including enantiomers, diastereomers, tautomers, pharmaceutically-acceptable salts, prodrugs, hydrates, or solvates thereof,

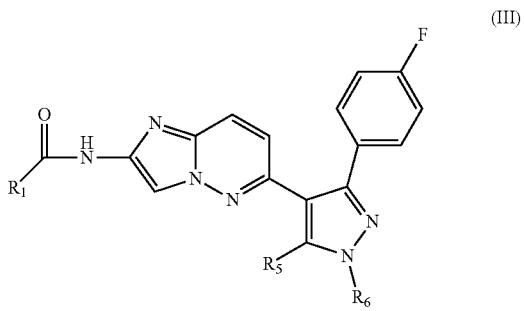

(III)

wherein:

$R_1$ is selected from $C_{1-4}$alkyl (optionally substituted with F, Cl, Br, OH, CN, and $NR_aR_a$), —$(CH_2)_r$-carbocyclyl substituted with 0-4 $R_{11}$, and —$(CH_2)_r$-heterocyclyl comprising carbon atoms and 1 to 4 heteroatoms selected from N, $NR_9$, O, S and substituted with 0-4 $R_{11}$;

$R_{11}$, at each occurrence, is independently selected from H, F, Cl, Br, =O, CN, $NO_2$, —$OR_b$, —$S(O)_pR_c$, —$C(=O)R_b$, —$(CH_2)_rNR_aR_a$, —$(CH_2)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CH_2)_rC(=O)OR_b$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, =O, $CO_2H$, —$(CH_2)_rOC_{1-5}$alkyl, —$(CH_2)_rOH$, SH, and —$(CH_2)_rNR_fR_f$; and $R_f$, at each occurrence, is independently selected from H, $C_{1-5}$ alkyl, and phenyl, or $R_f$ and $R_f$ together with the nitrogen atom to which they are both attached form a heterocyclic ring;

other variables are as defined in Formula (I) above.

In another embodiment, there are disclosed compounds of Formula (III) including enantiomers, diastereomers, tautomers, pharmaceutically-acceptable salts, prodrugs, hydrates, or solvates thereof, wherein:

$R_1$ is selected from aryl, cycloalkyl, and heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl.

In another embodiment, there are disclosed compounds of Formula (III) including enantiomers, diastereomers, tautomers, pharmaceutically-acceptable salts, prodrugs, hydrates, or solvates thereof, wherein:

$R_1$ is selected from

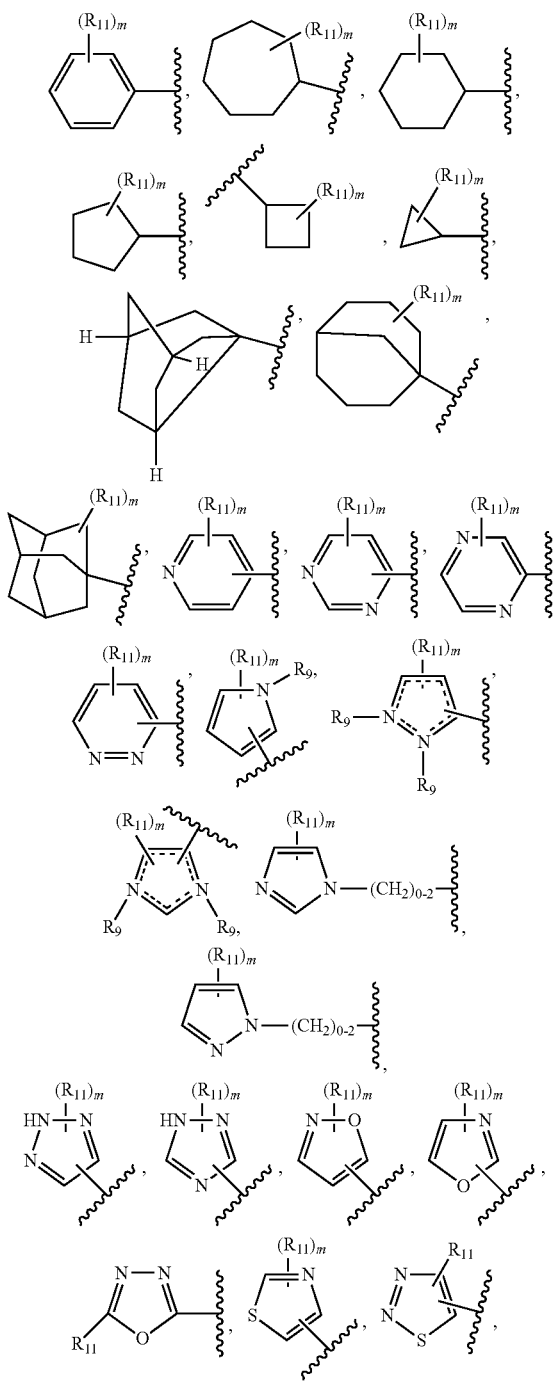

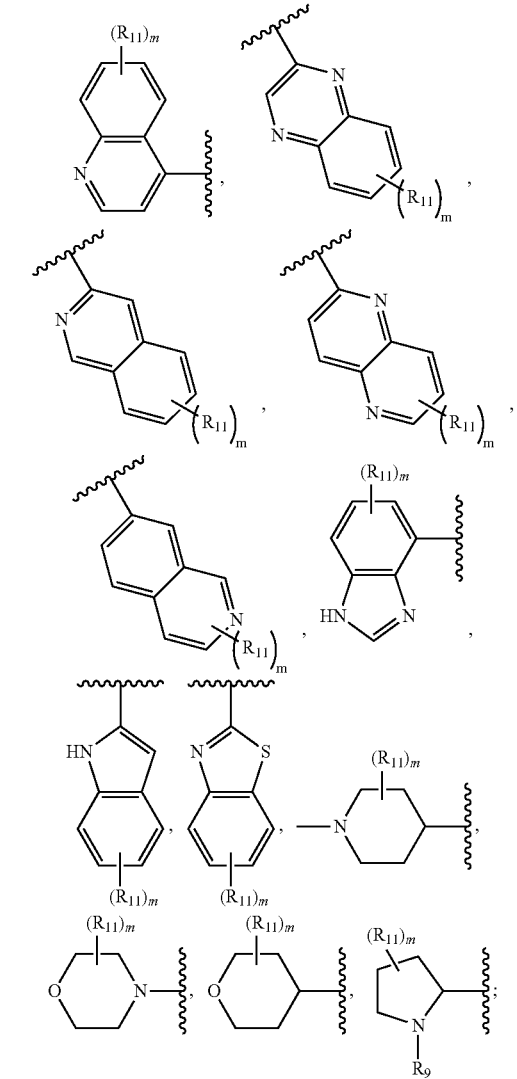

---- represents an optional bond;

$R_{11}$, at each occurrence, is independently selected from H, F, Cl, Br, =O, CN, —$OR_b$, —C(=O)$R_b$, —($CH_2$)$_r$$NR_aR_a$, —($CH_2$)$_r$C(=O)$NR_aR_a$, —$NR_aC$(=O)$R_b$, —($CH_2$)$_r$C(=O)$OR_b$, $C_{1-6}$ alkyl substituted with 0-5 $R_e$, —($CH_2$)$_r$—$C_{3-6}$carbocyclyl substituted with 0-5 $R_e$, and —($CH_2$)$_r$-heterocyclyl substituted with 0-5 $R_e$;

$R_9$, at each occurrence, is independently selected from H, —C(=O)$R_b$, $C_{1-6}$ alkyl substituted with 0-5 $R_e$; and m, at each occurrence, is independently selected from zero, 1, and 2;

other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:

$R_1$ is selected from carbocyclyl substituted with 0-4 $R_{11}$, and —($CH_2$)$_r$-5- to 10-membered heterocyclyl comprising carbon atoms and 1 to 4 heteroatoms selected from N, $NR_9$, O, S and substituted with 0-4 $R_{11}$;

$R_5$ is selected from H, $C_{1-4}$alkyl substituted with 0-3 $R_e$ and —($CH_2$)$_r$-heterocyclyl comprising carbon atoms and 1 to 3 heteroatoms selected from N, $NR_8$, O, S, and substituted with 0-3 $R_e$;

$R_6$ is selected from H, $C_{1-6}$alkyl substituted with 0-2 $R_e$, and $C_{3-6}$cycloalkyl substituted with 0-3 $R_e$;

$R_8$ is selected from H, $C_{1-4}$ alkyl substituted with 0-3 $R_e$, —$(CH_2)_rC(=O)R_b$, and —$(CH_2)_r$-heterocyclyl substituted with 0-3 $R_e$;

$R_{11}$, at each occurrence, is independently selected from H, F, Cl, CN, —$OR_b$, —$(CH_2)_rNR_aR_a$, —$NR_aC(=O)R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-5- to 10-membered heterocyclyl substituted with 0-5 $R_e$;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, =O, $CO_2H$, —$(CH_2)_rOC_{1-5}$alkyl, —$(CH_2)_rOH$, $S(O)_2C_{1-4}$alkyl, and —$(CH_2)_rNR_fR_f$;

$R_f$, at each occurrence, is independently selected from H, $C_{1-5}$ alkyl, and phenyl, or $R_f$ and $R_f$ together with the nitrogen atom to which they are both attached form a heterocyclic ring; and r, at each occurrence, is independently selected from zero, 1, 2, 3, and 4;

other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:

$R_1$ is selected from

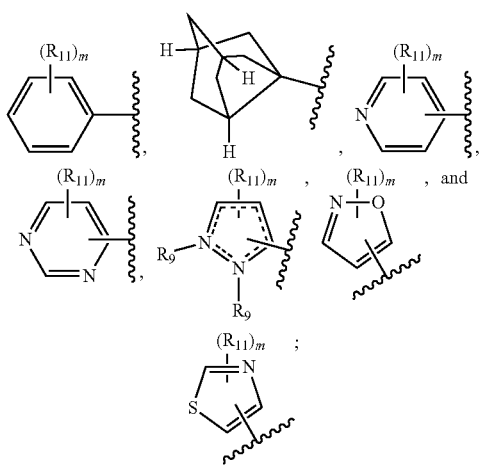

$R_5$ is selected from H, $C_{1-4}$alkyl substituted with 0-3 $R_e$,

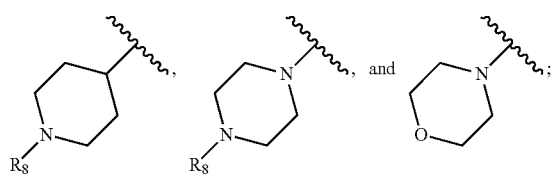

$R_6$ is selected from H, $C_{1-4}$alkyl, and $C_{3-6}$cycloalkyl;

$R_8$ is selected from H, $C_{1-4}$alkyl, —$(CH_2)_rCF_3$, —$(CH_2)_rCH_2F$, —$(CH_2)_rCN$, —$(CH_2)_rOH$, —$CH_2CH(OH)CF_3$, —$(CH_2)_rC(=O)NH_2$, —$C(=O)CH_2NH_2$, —$C(=O)CH_2CN$, —$C(=O)CH_2CF_3$, $C(=O)CH_2OH$, —$(CH_2)_r$-heterocyclyl substituted with 0-3 $R_e$, —$C(=O)$-heterocyclyl substituted with 0-3 $R_e$, wherein said heterocyclyl is selected from

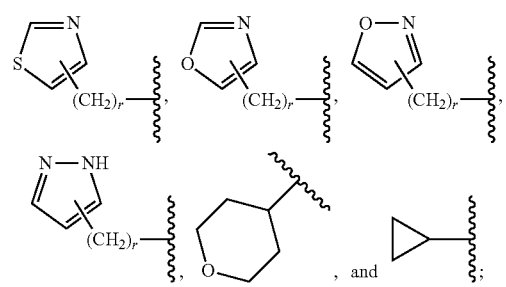

$R_{11}$, at each occurrence, is independently selected from F, Cl, CN, —$(CH_2)_rNR_aR_a$, OH, $OC_{1-4}$alkyl, $C_{1-4}$ alkyl substituted with 0-5 $R_e$,

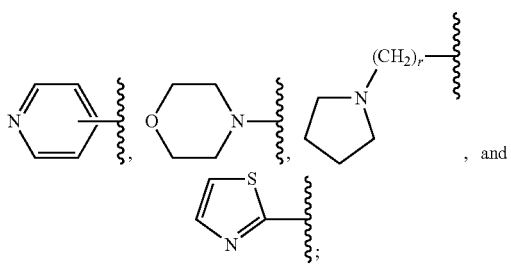

$R_9$, at each occurrence, is independently selected from H and $C_{1-4}$ alkyl;

$R_a$, at each occurrence, is independently selected from H and $C_{1-4}$ alkyl substituted with 0-5 $R_e$;

$R_e$, at each occurrence, is independently selected from $C_{1-6}$ alkyl F, Cl, Br, CN, and $NH_2$;

m, at each occurrence, is independently selected from zero, 1, and 2; and r, at each occurrence, is independently selected from zero, 1, and 2;

other variables are as defined in Formula (I) above.

In another embodiment of the compounds of Formulae (I) and (II), $R_1$ is heterocyclyl selected from pyridyl, pyrimidinyl, pyrazinyl, pyridazinyl, triazinyl, furyl, quinolinyl, dihydroquinolinyl, tetrahydroquinolinyl, isoquinolinyl, thienyl, imidazolyl, thiazolyl, indolyl, pyrrolyl, oxazolyl, benzofuryl, benzothienyl, benzthiazolyl, benzoxazinyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane, each of which is substituted with 0-4 $R_{11}$.

In still another embodiment, $R_1$ is $C_{3-6}$ cycloalkyl substituted with 0-4 $R_{11}$.

In another embodiment, $R_1$ is substituted with 0-4 $R_{11}$ and is heteroaryl selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl.

All aspects of the compounds, including individual variable definitions, may be combined with other aspects to form additional compounds. For example, in one embodiment of Formula (I), $R_1$ is heteroaryl and $R_5$ is hydrogen. In another embodiment, $R_1$ is $C_{3-6}$ cycloalkyl and $R_5$ is hydrogen. In still another embodiment, $R_1$ is heteroaryl and $R_5$ is heterocyclyl.

In certain embodiments, the present invention includes compounds of Formula (I), or stereoisomers, tautomers, pharmaceutically acceptable salts, solvates, or prodrugs thereof, wherein:

$R_1$ is selected from $—(CR_dR_d)_r$-carbocyclyl substituted with 0-5 $R_{11}$, and $—(CR_dR_d)_r$-heterocyclyl comprising carbon atoms and 1 to 4 heteroatoms selected from N, $NR_9$, O, S, and substituted with 0-5 $R_{11}$;

$R_2$ is H;

$R_3$ is H;

$R_4$ is H;

$R_5$ is selected from H, $C_{1-4}$alkyl substituted with 0-4 $R_e$, $—(CH_2)_r—C_{3-6}$ carbocyclyl substituted with 0-4 $R_e$, and $—(CH_2)_r$-heterocyclyl comprising carbon atoms and 1 to 3 heteroatoms selected from N, $NR_8$, O, S, and substituted with 0-4 $R_e$;

$R_6$ is selected from H, $C_{1-6}$alkyl substituted with 0-3 $R_e$, and $C_{3-6}$carbocyclyl substituted with 0-3 $R_e$; or $R_7$ is aryl substituted with 0-2 $R_e$;

$R_8$ is selected from H, $C_{1-4}$ alkyl substituted with 0-3 $R_e$, $—(CH_2)_r$CN, $—(CH_2)_r$OR$_b$, $(CH_2)_rS(O)_pR_c$, $—(CH_2)_rC(=O)R_b$, $—(CH_2)_rNR_aR_a$, $—(CH_2)_rC(=O)NR_aR_a$, $—(CH_2)_rC(=O)—C_{1-4}$ alkyl substituted with 0-3 $R_e$, $—(CH_2)_rNR_aC(=O)R_b$, $—(CH_2)_rNR_aC(=O)OR_b$, $—(CH_2)_rOC(=O)NR_aR_a$, $—(CH_2)_rNR_aC(=O)NR_aR_a$, $—(CH_2)_rC(=O)OR_b$, $—(CH_2)_rS(O)_2NR_aR_a$, $—(CH_2)_rNR_aS(O)_2NR_aR_a$, $—(CH_2)_rNR_aS(O)_2R_c$, $(CH_2)_r$-carbocyclyl substituted with 0-3 $R_e$, and $—(CH_2)_r$-heterocyclyl substituted with 0-3 $R_e$;

$R_9$ is selected from H, $—C(=O)R_b$, $C_{1-6}$ alkyl substituted with 0-5 $R_e$, $—(CH_2)_r—C_{3-6}$carbocyclyl substituted with 0-5 $R_e$, and $—(CH_2)_r$-heterocyclyl substituted with 0-5 $R_e$;

$R_{11}$, at each occurrence, is independently selected from H, F, Cl, Br, =O, CN, $NO_2$, $—OR_b$, $—S(O)_pR_c$, $—C(=O)R_b$, $—(CR_dR_d)_rNR_aR_a$, $—(CR_dR_d)_rC(=O)NR_aR_a$, $—NR_aC(=O)R_b$, $—NR_aC(=O)OR_b$, $—OC(=O)NR_aR_a$, $—NR_aC(=O)NR_aR_a$, $—(CR_dR_d)_rC(=O)OR_b$, $—S(O)_2NR_aR_a$, $—NR_aS(O)_2NR_aR_a$, $—NR_aS(O)_2R_c$, $C_{1-6}$ alkyl substituted with 0-5 $R_e$, $—(CR_dR_d)_r—C_{3-6}$carbocyclyl substituted with 0-5 $R_e$, and $—(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $—(CH_2)_r—C_{3-6}$ cycloalkyl, F, Cl, Br, CN, $NO_2$, =O, $CO_2H$, $—(CH_2)_rOR_f$, $S(O)_pR_f$, and $—(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (I), or stereoisomers, tautomers, pharmaceutically acceptable salts, solvates, or prodrugs thereof, wherein:

$R_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each heterocyclyl substituted with 0-5 $R_{11}$;

$R_2$ is H;

$R_3$ is H;

$R_4$ is H;

$R_5$ is H;

$R_6$ is selected from H, $C_{1-6}$alkyl substituted with 0-3 $R_e$, and $C_{3-6}$carbocyclyl substituted with 0-3 $R_e$; or $R_7$ is aryl substituted with 0-2 $R_e$;

$R_9$ is selected from H, $—C(=O)R_b$, $C_{1-6}$ alkyl substituted with 0-5 $R_e$, $—(CH_2)_r—C_{3-6}$ carbocyclyl substituted with 0-5 $R_e$, and $—(CH_2)_r$-heterocyclyl substituted with 0-5 $R_e$;

$R_{11}$, at each occurrence, is independently selected from H, F, Cl, Br, =O, CN, $NO_2$, $—OR_b$, $—S(O)_pR_c$, $—C(=O)R_b$, $—(CR_dR_d)_rNR_aR_a$, $—(CR_dR_d)_rC(=O)NR_aR_a$, $—NR_aC(=O)R_b$, $—NR_aC(=O)OR_b$, $—OC(=O)NR_aR_a$, $—NR_aC(=O)NR_aR_a$, $—(CR_dR_d)_rC(=O)OR_b$, $—S(O)_2NR_aR_a$, $—NR_aS(O)_2NR_aR_a$, $—NR_aS(O)_2R_c$, $C_{1-6}$ alkyl substituted with 0-5 $R_e$, $—(CR_dR_d)_r—C_{3-6}$carbocyclyl substituted with 0-5 $R_e$, and $—(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, S(O)$_p$R$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (I), or stereoisomers, tautomers, pharmaceutically acceptable salts, solvates, or prodrugs thereof, wherein:

R$_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each heterocyclyl substituted with 0-5 R$_{11}$;

R$_2$ is H;

R$_3$ is H;

R$_4$ is H;

R$_5$ is heterocyclyl comprising carbon atoms and 1 to 3 heteroatoms selected from N, NR$_8$, O, S, and substituted with 0-4 R$_e$;

R$_6$ is selected from H, C$_{1-6}$alkyl substituted with 0-3 R$_e$, and C$_{3-6}$carbocyclyl substituted with 0-3 R$_e$; or R$_7$ is aryl substituted with 0-2 R$_e$;

R$_8$ is selected from H, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)—C$_{1-4}$ alkyl substituted with 0-3 R$_e$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_9$ is selected from H, —C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_{11}$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, S(O)$_p$R$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (I), or stereoisomers, tautomers, pharmaceutically acceptable salts, solvates, or prodrugs thereof, wherein:

R$_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each heterocyclyl substituted with 0-5 R$_{11}$;

R$_2$ is H;

R$_3$ is H;

R$_4$ is H;

R$_5$ is heterocyclyl comprising carbon atoms and 1 to 3 heteroatoms selected from N, NR$_8$, O, S, and substituted with 0-4 R$_e$;

R$_6$ is selected from H, C$_{1-6}$alkyl substituted with 0-3 R$_e$, and C$_{3-6}$carbocyclyl substituted with 0-3 R$_e$; or R$_7$ is aryl substituted with 0-2 R$_e$;

R$_8$ is selected from H, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)—C$_{1-4}$ alkyl substituted with 0-3 R$_e$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$ NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_9$ is selected from H, —C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_{11}$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$ carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, S(O)$_p$R$_f$, and —(CH$_2$)$_r$NR$_f$R$_f$;

R$_f$, at each occurrence, is independently selected from H, C$_{1-5}$ alkyl, C$_{3-6}$cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In other embodiments, the present invention includes compounds of Formula (III), or stereoisomers, tautomers, pharmaceutically acceptable salts, solvates, or prodrugs thereof, wherein:

R$_1$ is selected from

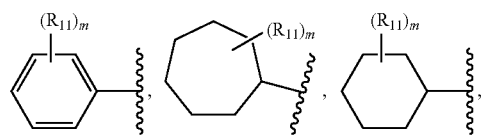

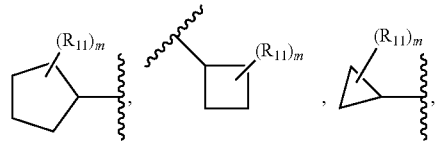

-continued

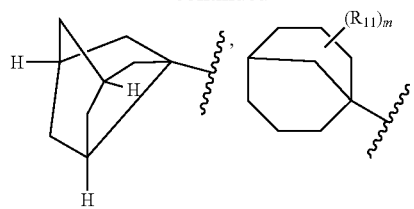

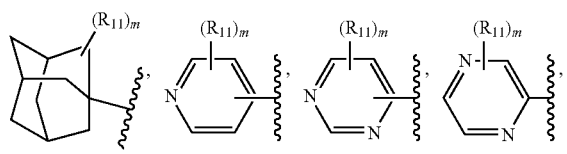

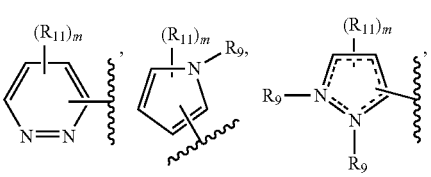

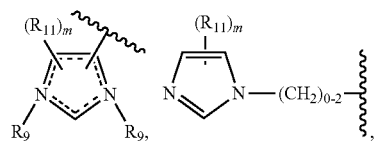

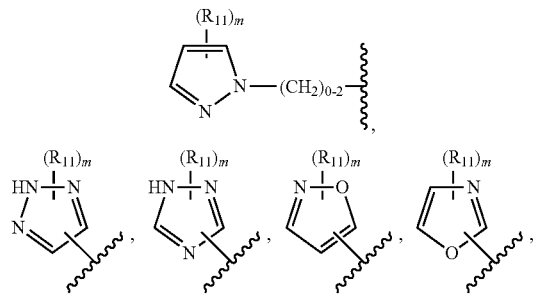

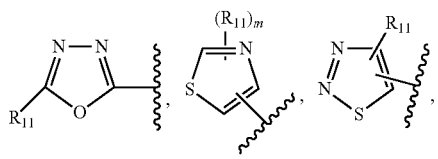

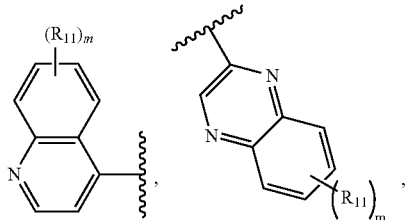

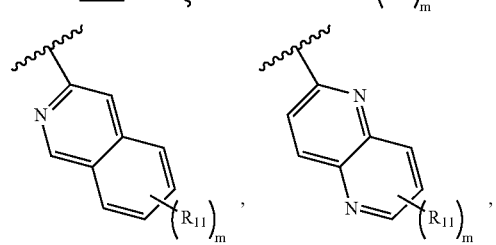

-continued

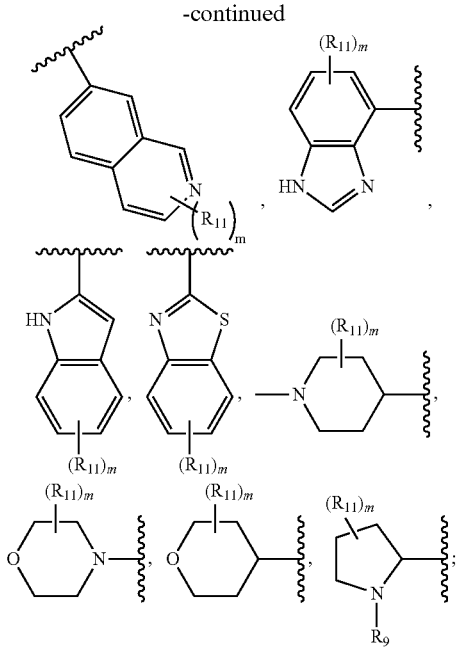

---- represents an optional bond;
R$_2$ is H;
R$_3$ is H;
R$_4$ is H;
R$_5$ is selected from H,

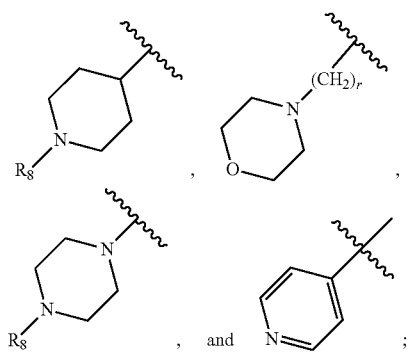

R$_6$ is selected from H, C$_{1-6}$alkyl substituted with 0-3 R$_e$, and C$_{3-6}$carbocyclyl substituted with 0-3 R$_e$; or
R$_8$ is selected from H, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)—C$_{1-4}$ alkyl substituted with 0-3 R$_e$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;
R$_9$ is selected from H, —C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;
R$_{11}$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;
R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;
R$_d$, at each occurrence, is independently selected from H and C$_{1-4}$alkyl substituted with 0-5 R$_e$;
R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, S(O)$_p$R$_f$, and —(CH$_2$)$_r$NR$_f$R$_f$;
R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;
p, at each occurrence, is independently selected from zero, 1, and 2; and
r, at each occurrence, is independently selected from zero, 1, 2, 3, and 4.

The compounds of Formulae (I)-(III) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formulae (I)-(III) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formulae (I)-(III) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992).

It should further be understood that solvates (e.g., hydrates) of the compounds of Formulae (I)-(III) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

DEFINITIONS

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_{1-10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$-C$_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle", "carbocyclic residue", or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle", "carbocyclic residue", or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle", "heterocyclyl", "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on a carbon atom or on a nitrogen atom if the resulting compound is stable. A nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle", "heterocyclyl", "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

UTILITY

The compounds of the invention may be used to modulate kinase activities.

Applicants have discovered that compounds of Formulae (I)-(III) have particular utility in treating conditions associated with the modulation of serine/threonine kinase activity, especially that of casein kinase 1δ or casein kinase 1ε. The diseases, with the pathological conditions of which the activation mechanism of casein kinase 1δ or casein kinase 1ε associated, are not limited. Examples of such diseases include circadian rhythm disorder (including sleep disorder), neurodegenerative disease, and proliferative disorder (cancer).

In the present specification, the type of circadian rhythm disorder is not limited. The circadian rhythm disorder includes mood disorder and sleep disorder. Such sleep disorder is circadian rhythm sleep disorder, and the circadian rhythm sleep disorder includes a disease selected from the group consisting of shift work sleep disorder, jet lag syndrome, advanced sleep phase syndrome, and delayed sleep phase syndrome.

Moreover, the sleep disorder includes a disease selected from the group consisting of insomnia, sleep-related breathing disorder, central hypersomnia, parasomnia, and sleep-related movement disorder. Furthermore, the above-described mood disorder is selected from either depressive disorder or bipolar disorder, and the depressive disorder is major depressive disorder. Further, the mood disorder is selected from either depressive disorder or bipolar disorder, and the bipolar disorder is selected from the group consisting of bipolar type-I disorder or bipolar type-II disorder. Still further, examples of the disease in the present invention include insomnia, sleep-related breathing disorder, central hypersomnia, circadian rhythm sleep disorder, parasomnia, sleep-related movement disorder, and sleep disorder caused by other reasons.

In the present specification, insomnia includes psychophysiologic insomnia caused by stress or the like, insomnia caused by medical disease, and the like. Sleep-related breathing disorder includes central sleep apnea syndrome, obstructive sleep apnea syndrome, sleep-related hypoventilation/anoxemia syndrome, and the like. Central hypersomnia includes narcolepsy, idiopathic hypersomnia, recurrent hypersomnia, and the like. Circadian rhythm sleep disorder includes shift work sleep disorder, jet lag syndrome, advanced sleep phase syndrome, delayed sleep phase syndrome, and the like. Parasomnia includes sleep walking, REM sleep behavior disorder, and the like. Sleep-related movement disorder includes restless legs syndrome, periodic limb movement disorder, and the like.

In the present specification, the type of neurodegenerative disease is not limited, Examples of central neurodegenerative disease include: neurodegenerative disease caused by Alzheimer's disease, Parkinson's disease or Down's syndrome; nerve degeneration caused by physical nerve damage (brain tissue damage such as brain contusion, and nerve damage caused by head injury and the like); and nerve degeneration caused by nerve damage occurred after ischemia or ischemic reperfusion include: stroke, cerebral infarction, cerebral hemorrhage, cerebral ischemia, subarachnoid hemorrhage, aneurysmal hemorrhage, myocardial infarction, hypoxia, anoxia and nerve damage caused by grand mal/cerebral ischemia.

The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(III), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(III) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(III) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; antiangiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0] heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxonorleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formulae (I)-(III) compounds of the invention are of interest for their antiproliferative effects. More specifically, the compounds of Formulae (I)-(III) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formulae (I)-(III) are especially useful in treatment of tumors having a high incidence of serine/threonine kinase activity, such as prostate, colon, lung, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formulae (I)-(III) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formulae (I)-(III) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(III) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(III) within the dosage range described above and the dosage of another anti-cancer agent/treatment within the approved dosage range for such known anti-cancer agent/treatment. If a combination product is inappropriate, the compounds of Formulae (I)-(III) and the other anti-cancer agent/treatment can, for example, be administered simultaneously or sequentially. If administered sequentially, the present invention is not limited to any particular sequence of administration. For example, compounds of Formulae (I)-(III) can be administered either prior to, or after, administration of the known anti-cancer agent or treatment.

BIOLOGICAL ASSAYS

CK1ε and CK1δ Kinase Assays

The kinase assay was performed in V-bottom 384-well plates. The final assay volume was 30 μl prepared from 15 μl additions of enzyme, substrates (fluoresceinated peptide FL-AHA-KRRRAL-PSER-VASLPGL-OH and ATP) and test compounds in assay buffer (20 mM HEPES pH 7.4, 30 mM $MgCl_2$, 0.015% Brij35 and 4 mM DTT). The reaction was incubated at room temperature for 22 hours and terminated by adding 45 μl of 35 mM EDTA to each sample. The reaction mixture was analyzed on the Caliper LABCHIP®3000 (Caliper, Hopkinton, Mass.) by electrophoretic separation of the unphosphorylated substrate and phosphorylated product Inhibition data were calculated by comparison of the no enzyme control reactions for 100% inhibition and vehicle-only reactions for 0% inhibition. The final concentration of reagents in the assay were 200 pM CK1ε or CK1δ, 50 μM ATP, 1.5 μM FL-AHA-KRRRAL-PSER-VASLPGL-OH, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

The following compounds were found to have the $IC_{50}$ described in Table A when measured in the assays described above.

TABLE A

| Example No. | CK1ε ($IC_{50}$, μM) | CK1δ ($IC_{50}$, μM) |
| --- | --- | --- |
| 1 | 0.0074 | 0.0052 |
| 2 | 0.0192 | 0.0013 |
| 3 | 0.0154 | 0.0011 |
| 4 | 0.0137 | 0.0037 |
| 5 | 0.0178 | 0.0012 |
| 6 | 0.0173 | 0.0043 |
| 7 | 0.0341 | 0.0083 |
| 8 | 0.0314 | 0.0054 |
| 9 | — | — |
| 10 | 0.1041 | 0.0077 |
| 11 | 0.8986 | 0.0246 |
| 12 | 0.0288 | 0.0073 |
| 13 | 0.0229 | 0.0026 |
| 14 | 0.0234 | 0.0046 |
| 15 | 0.0081 | 0.0017 |
| 16 | 0.0233 | 0.0017 |
| 17 | 0.0269 | 0.0005 |
| 18 | 0.0239 | 0.0004 |
| 19 | 0.0220 | 0.0010 |
| 20 | 0.0092 | 0.0043 |
| 21 | 0.0726 | 0.0095 |
| 22 | 0.0152 | 0.0037 |
| 23 | 0.0086 | 0.0026 |
| 24 | 0.0162 | 0.0063 |
| 25 | 0.0145 | 0.0074 |
| 26 | 0.0200 | 0.0038 |
| 27 | 0.0769 | 0.0078 |
| 28 | 0.0066 | 0.0031 |
| 29 | 0.0481 | 0.0160 |
| 30 | 0.0079 | 0.0058 |
| 31 | 0.0063 | 0.0039 |
| 32 | 0.0983 | 0.0101 |
| 33 | 0.4541 | 0.0304 |
| 34 | 0.0187 | 0.0036 |
| 35 | 0.0091 | 0.0028 |
| 36 | 0.0137 | 0.0073 |
| 37 | 0.1155 | 0.0305 |
| 38 | 0.0434 | 0.0107 |
| 39 | 0.0757 | 0.0102 |
| 40 | 0.0180 | 0.0054 |
| 41 | 0.0115 | 0.0040 |
| 42 | 0.0137 | 0.0023 |
| 43 | 0.0158 | 0.0048 |
| 44 | 0.0212 | 0.0056 |
| 45 | 0.0068 | 0.0019 |
| 46 | 0.0102 | 0.0041 |
| 47 | 0.0199 | 0.0052 |
| 48 | 0.0234 | 0.0057 |
| 49 | 0.0136 | 0.0061 |
| 50 | 0.0999 | 0.0204 |
| 51 | 0.0229 | 0.0063 |
| 52 | 0.0178 | 0.0076 |
| 53 | 0.0214 | 0.0058 |
| 54 | 0.0140 | 0.0045 |
| 55 | 0.0121 | 0.0041 |
| 56 | 0.0449 | 0.0144 |
| 57 | 0.0223 | 0.0089 |
| 58 | 0.0409 | 0.0069 |
| 59 | 0.0221 | 0.0078 |
| 60 | 0.0131 | 0.0055 |
| 61 | 0.0187 | 0.0057 |
| 62 | 0.0281 | 0.0072 |
| 63 | 0.0348 | 0.0080 |
| 64 | 0.0385 | 0.0071 |
| 65 | 0.1575 | 0.0247 |
| 66 | 0.0066 | 0.0028 |
| 67 | 0.0133 | 0.0142 |
| 68 | 0.0281 | 0.0044 |
| 69 | 0.0048 | 0.0023 |
| 70 | 0.0047 | 0.0020 |
| 71 | 0.0173 | 0.0038 |
| 72 | 0.0278 | 0.0100 |
| 73 | 0.0064 | 0.0026 |
| 74 | 0.2323 | 0.0346 |
| 75 | 0.3630 | 0.0410 |
| 76 | 0.0640 | 0.0119 |
| 77 | 0.0602 | 0.0106 |
| 78 | 0.0110 | 0.0033 |
| 79 | — | — |
| 80 | — | — |
| 81 | 0.0056 | 0.0054 |
| 82 | 0.0715 | 0.0033 |
| 83 | 0.0083 | 0.0019 |
| 84 | 1.0210 | 0.4350 |
| 85 | 0.0501 | 0.0070 |
| 86 | 0.0157 | 0.0056 |
| 87 | 0.0113 | 0.0051 |
| 88 | 0.0105 | 0.0042 |
| 89 | 0.0258 | 0.0071 |
| 90 | 0.1349 | 0.0239 |
| 91 | 0.0138 | 0.0074 |
| 92 | 0.0105 | 0.0055 |
| 93 | 0.0060 | 0.0041 |
| 94 | 0.0344 | 0.0083 |
| 95 | 0.0172 | 0.0065 |
| 96 | 0.0420 | 0.0118 |
| 97 | 0.0101 | 0.0064 |
| 98 | 0.0061 | 0.0026 |
| 99 | 0.0473 | 0.0103 |
| 100 | 0.0288 | 0.0094 |
| 101 | 0.1702 | 0.0281 |
| 102 | 0.0099 | 0.0030 |
| 103 | 0.0749 | 0.0085 |
| 104 | 0.0152 | 0.0032 |
| 105 | 0.0465 | 0.0048 |
| 106 | 0.0140 | 0.0035 |
| 107 | 0.0452 | 0.0031 |
| 108 | 0.0326 | 0.0020 |
| 109 | 0.0123 | 0.0025 |
| 110 | 0.0288 | 0.0055 |
| 111 | 0.0350 | 0.0062 |
| 112 | 0.0635 | 0.0060 |
| 113 | 0.0023 | 0.0006 |
| 114 | 0.0316 | 0.0033 |
| 115 | 0.0039 | 0.0004 |
| 116 | 0.0093 | 0.0007 |
| 117 | 0.0018 | 0.0001 |
| 118 | 0.0036 | 0.0008 |
| 119 | 0.0101 | 0.0003 |
| 120 | 0.0186 | 0.00073 |
| 121 | 0.0144 | 0.0012 |
| 122 | — | 0.0005 |
| 123 | 0.0002 | 0.0001 |
| 124 | 0.0013 | 0.0002 |
| 125 | 0.0046 | 0.0006 |
| 126 | 0.1240 | 0.0029 |
| 127 | 0.0062 | 0.0010 |
| 128 | 0.0106 | 0.0015 |
| 129 | 0.0033 | 0.0009 |
| 130 | 0.0235 | 0.0014 |
| 131 | 0.0031 | 0.0003 |
| 132 | 0.0067 | 0.0006 |
| 133 | 0.0081 | 0.0010 |
| 134 | 0.0018 | 0.0008 |
| 135 | 0.0350 | 0.0016 |
| 136 | 0.0120 | 0.0008 |
| 137 | 0.0101 | 0.0010 |
| 138 | 0.0093 | 0.0016 |
| 139 | 0.0093 | 0.0014 |
| 140 | 0.0024 | 0.0025 |
| 141 | 0.0320 | 0.0025 |
| 142 | 0.0022 | 0.0003 |
| 143 | — | 0.0020 |
| 144 | 0.0037 | 0.00074 |
| 145 | 0.0228 | 0.0014 |
| 146 | 0.0049 | 0.0005 |
| 147 | 0.0079 | 0.0007 |
| 148 | 0.0026 | 0.0021 |
| 149 | 0.0105 | 0.0007 |

TABLE A-continued

| Example No. | CK1ε (IC$_{50}$, μM) | CK1δ (IC$_{50}$, μM) |
|---|---|---|
| 150 | 0.0010 | 0.0011 |
| 151 | 0.0057 | 0.0005 |
| 152 | 0.0027 | 0.0003 |
| 153 | 0.0022 | 0.0003 |
| 154 | 0.0003 | 0.0003 |
| 155 | 0.0074 | 0.0004 |
| 156 | 0.0026 | 0.0004 |
| 157 | 0.0013 | 0.0003 |
| 158 | 0.0003 | 0.0002 |
| 159 | 0.0014 | 0.0004 |
| 160 | 0.0010 | 0.0015 |
| 161 | 0.0229 | 0.0017 |
| 162 | 0.0175 | 0.0005 |
| 163 | 0.0006 | 0.0004 |
| 164 | 0.0033 | 0.0009 |
| 165 | 0.0050 | 0.00270 |
| 166 | 0.0019 | 0.0014 |
| 167 | 0.0077 | 0.0024 |
| 168 | 0.0015 | 0.0013 |
| 169 | 0.0008 | 0.0014 |
| 170 | 0.0074 | 0.0026 |
| 171 | 0.0117 | 0.0036 |
| 172 | 0.0104 | 0.0045 |
| 173 | 0.0064 | 0.0015 |
| 174 | 0.0018 | 0.0025 |
| 175 | 0.0040 | 0.0030 |
| 176 | 0.0004 | 0.0010 |
| 177 | 0.0122 | 0.0007 |
| 178 | 0.0013 | 0.0002 |
| 179 | 0.0015 | 0.0014 |
| 180 | 0.0071 | 0.0021 |
| 181 | 0.0143 | 0.0011 |
| 182 | 0.0009 | 0.0017 |
| 183 | 0.0024 | 0.0004 |
| 184 | 0.0012 | 0.0003 |
| 185 | 0.0480 | 0.0160 |
| 186 | 0.1140 | 0.0146 |
| 187 | >2.0000 | 0.0515 |
| 188 | >2.0000 | 0.8710 |
| 189 | 0.2570 | 0.0388 |
| 190 | 0.0145 | 0.0042 |
| 191 | 0.1530 | 0.0245 |
| 192 | 0.0233 | 0.0056 |
| 193 | 0.1020 | 0.0170 |
| 194 | 0.5540 | 0.0970 |
| 195 | 0.1370 | 0.0540 |
| 196 | 0.0020 | 0.0002 |
| 197 | 0.0018 | 0.0003 |
| 198 | 0.0048 | 0.0005 |
| 199 | 0.0019 | 0.0002 |
| 200 | 0.0030 | 0.0003 |
| 201 | 0.0023 | 0.0003 |
| 202 | 0.0081 | 0.0005 |
| 203 | 0.0079 | 0.0009 |
| 204 | 0.0032 | 0.0004 |
| 205 | 0.0098 | 0.0009 |

METHODS OF PREPARATION

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature* 1982-1995: *The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

For ease of reference, the following abbreviations are used herein:

| | |
|---|---|
| AcOH | acetic acid |
| AcCl | acetyl chloride |
| Boc$_2$O | di t-butyl dicarbonate |
| CDI | carbonyldiimidazole |
| CH$_2$Cl$_2$ or DCM | dichloromethane |
| CHCl$_3$ | chloroform |
| DMAP | dimethylaminopyridine |
| DME | dimethoxyethane |
| DIEA or Hunig's base | diisopropylethylamine |
| DMA | dimethylacetamide |
| DMF | dimethylformamide |
| DMSO | dimethylsulfoxide |
| EDC | 1-ethyl-3-[3-dimethylaminopropyl]carbodiimide hydrochloride |
| Et | ethyl |
| Et$_2$O | diethyl ether |
| EtOAc | ethyl acetate |
| EtOH | ethanol |
| Et$_3$N or TEA | triethylamine |
| HATU | 2-(1H-7-azabenzotriazol-1-yl)-1,1,3,3-tetramethyluroniumhexafluorophosphate |
| HCl | hydrochloric acid |
| iPr | isopropyl |
| iPrOH | isopropanol |
| LDA | lithium diisopropylamide |
| Me | methyl |
| MeI | methyl iodide |
| MeOH | methanol |
| MS | molecular sieves |
| NaH | sodium hydride |
| NBS | N-bromosuccinimide |
| n-BuLi | n-butyl lithium |
| NaOMe | sodium methoxide |
| NaOH | sodium hydroxide |
| Pd(Ph$_3$P)$_4$ | tetrakis(triphenylphosphine)palladium(0) |
| PdCl$_2$(dppf) | bis(diphenylphosphino)ferrocene]dichloropalladium(II) dichloromethane |
| CH$_2$Cl$_2$ | adduct |
| TFA | trifluoroacetic acid |
| THF | tetrahydrofuran |
| h | hour(s) |
| min | minute(s) |
| L | liter |
| mL | milliliter |
| μL | microliter |
| g | gram(s) |
| mg | milligram(s) |
| mol | mole(s) |
| mmol | millimole(s) |
| rt | room temperature |
| ret time | HPLC retention time |
| sat or sat'd | saturated |
| aq. | aqueous |
| TLC | thin layer chromatography |

| | |
|---|---|
| HPLC | high performance liquid chromatography |
| Prep HPLC | preparative reverse phase HPLC |
| LC/MS | liquid chromatography/mass spectrometry |
| MS | mass spectrometry |
| NMR | nuclear magnetic resonance |

Analytical HPLC/LC-MS retention time reported for each example and intermediate uses one of the following general Analytical HPLC/LC-MS Methods:

Method A: PHENOMENEX® Luna C18, 50×2 mm, 3μ column; flow rate 0.8 mL/min; gradient time 4 min; 100% Solvent A to 100% Solvent B and holding 100% Solvent B for 1 min; monitoring at 250 nm (Solvent A: 5% MeOH, 95% H₂O, 10 mM ammonium acetate; Solvent B: 95% MeOH, 5% H₂O, 10 mM ammonium acetate).

Method B: PHENOMENEX® Luna 2.0×50 mm 3μ column; flow rate 0.8 mL/min; gradient time 4 min; 100% Solvent A to 100% Solvent B and holding 100% Solvent B for 1 min; monitoring at 220 nm (Solvent A: 10% MeOH, 90% H₂O, 0.1% TFA; Solvent B: 90% MeOH, 10% H₂O, 0.1% TFA).

Method C: Waters BEH C18, 2.0×50 mm, 1.7-μm particles column; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0.5 min hold at 0% B, 0-100% B over 4 minutes, then a 0.5-minute hold at 100% B; Flow: 1 mL/min.

Method D: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow rate: 0.5 mL/min.

Method E: SUPELCO® Ascentis Express 4.6×50 mm 2.7 μm C18; flow rate 4 mL/min, gradient time 4 min; 100% Solvent A to 100% Solvent B and holding 100% Solvent B for 1 min; monitoring at 220 nm Solvent A: 5% acetonitrile, 95% H₂O, 10 mM ammonium acetate; Solvent B: 95% acetonitrile, 5% H₂O, 10 mM ammonium acetate.

Method F: SUPELCO® Ascentis Express 4.6×50 mm 2.7 μm C18; flow rate 4 mL, gradient time 4 min; 100% Solvent A to 100% Solvent B and holding 100% Solvent B for 1 min; monitoring at 220 nm Solvent A: 5% acetonitrile, 95% H₂O, 0.1% TFA; Solvent B: 95% acetonitrile, 5% H₂O, 0.1% TFA.

Method G: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method H: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Method I: SunFire 4.6 mm×50 mm, 5 μm particle size; flow rate 4 mL/min; gradient time 4 min; 100% Solvent A to 100% Solvent B and holding 100% Solvent B for 1 min; monitoring at 220 nm Solvent A: 10% MeOH, 90% H₂O, 0.1% TFA; Solvent B: 90% MeOH, 10% H₂O, 0.1% TFA.

Method J: SunFire C18, 4.6 mm×150 mm, 3.5μ column; flow rate 1 mL/min; gradient time 15 min; 10% Solvent B to 100% Solvent B; monitoring at 254 nm and 220 nm (Solvent A: 5% acetonitrile, 95% water, 0.05% TFA; Solvent B: 95% acetonitrile, 5% water, 0.05% TFA).

Method K: XBridge Phenyl, 4.6 mm×150 mm, 3.5μ column; flow rate 1 ml/min; gradient time 15 min; 10% Solvent B to 100% Solvent B; monitoring at 254 nm and 220 nm (Solvent A: 5% acetonitrile, 95% water, 0.05% TFA; Solvent B: 95% acetonitrile, 5% water, 0.05% TFA)

Scheme 1

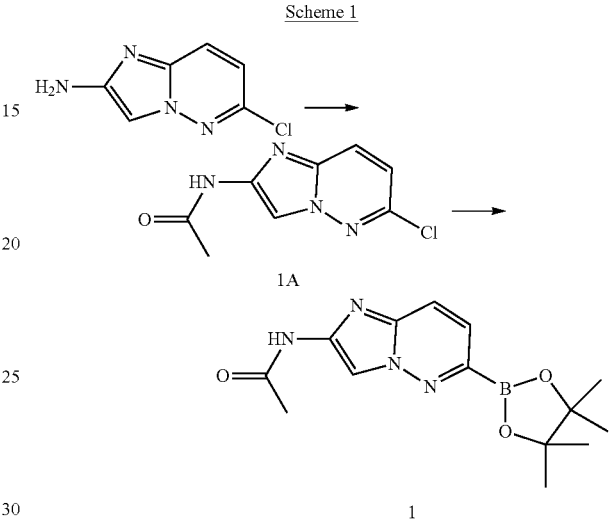

Intermediate 1

N-(6-(4,4,5,5-Tetramethyl-1,3,2-dioxaborolan-2-yl)imidazo[1,2-b]pyridazin-2-yl)acetamide

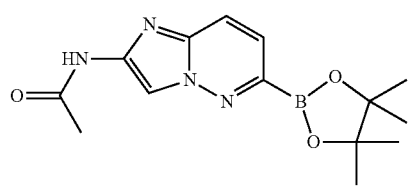 [SMILES: CC(=O)Nc1cn2nc(B3OC(C)(C)C(C)(C)O3)ccc2n1]

Intermediate 1A:
N-(6-Chloroimidazo[1,2-b]pyridazin-2-yl)acetamide

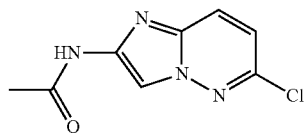

To a solution of 6-chloroimidazo[1,2-b]pyridazin-2-amine (5.09 g, 30.2 mmol) in DMA (25 mL) was added AcCl (2.58 mL, 36.2 mmol). The reaction mixture was stirred at rt for 2 h. After about 30 min, the reaction mixture turned to a suspension. The reaction mixture was carefully quenched with sodium bicarbonate (sat'd) and water. The precipitate was filtered, washed with water, and air dried with high vacuum to give Intermediate 1A (5.5 g, 86%) as a white powder. MS(ES): m/z=211.10/213.10 [M+H]⁺. HPLC Ret time (Method B): 2.68 min. ¹H NMR (400 MHz, DMSO-d₆) δ 10.99 (s, NH, 1H), 8.27 (s, 1H), 8.08 (dd, J=9.4, 0.6 Hz, 1H), 7.35 (d, J=9.5 Hz, 1H), 2.11 (s, 3H).

Intermediate 1: N-(6-(4,4,5,5-Tetramethyl-1,3,2-dioxaborolan-2-yl)imidazo[1,2-b]pyridazin-2-yl)acetamide

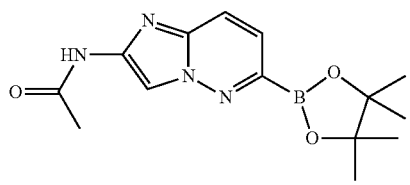 [SMILES: CC(=O)Nc1cn2nc(B3OC(C)(C)C(C)(C)O3)ccc2n1]

To a pressure bottle were added N-(6-chloroimidazo[1,2-b]pyridazin-2-yl)acetamide, Intermediate 1A (5.5 g, 26.1 mmol), 4,4,4',4',5,5,5',5'-octamethyl-2,2'-bi(1,3,2-dioxaborolane) (8 g, 31.3 mmol), potassium acetate (6.5 g, 66.3 mmol), PdCl₂(dppf)-CH₂Cl₂ adduct (1.06 g, 2.31 mmol), and dioxane (100 mL). The reaction mixture was bubbled with nitrogen for 2 min and then heated at 100° C. for 10 h. The reaction mixture was cooled to rt and passed through a pad of CELITE® and the CELITE® cake was washed with MeOH. To the filtrate was added charcoal and stirred for 5 min. The dark mixture was filtered again. The filtrate was concentrated, diluted with EtOAc/MeOH, treated with charcoal again, and filtered. This was repeated for three times until the reaction mixture is a light brown solution. The filtrate was concentrated and the residue was triturated with EtOAc. The solid was collected by filtration, washed with EtOAc, and air-dried by air to give Intermediate 1 (7.8 g, 89% yield) as a tan powder. ¹H NMR (400 MHz, DMSO-d₆) δ 10.61 (s, NH, 1H), 8.17 (s, 1H), 7.51 (d, J=9.3 Hz, 1H), 7.12 (d, J=9.0 Hz, 1H), 2.08 (s, 3H), 1.01 (s, 12H).

Scheme 2

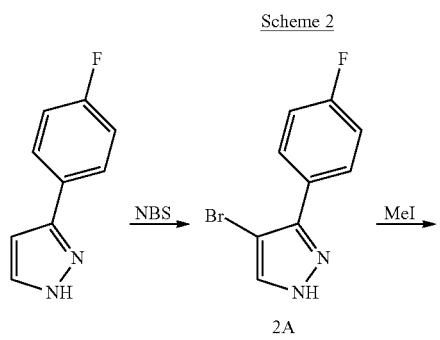

Intermediate 2

4-Bromo-3-(4-fluorophenyl)-1-methyl-1H-pyrazole

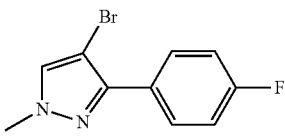

Intermediate 2A: 4-Bromo-3-(4-fluorophenyl)-1H-pyrazole

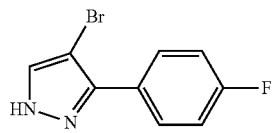 [SMILES: Fc1ccc(-c2n[nH]cc2Br)cc1]

To a solution of 3-(4-fluorophenyl)-1H-pyrazole (10 g, 61.7 mmol) in DMF (50 ml) was added NBS (11 g, 61.7 mmol). The reaction mixture was stirred at rt for 1 h, quenched with water, extracted with EtOAc. The organic layer was washed with brine, dried over anhydrous sodium sulfate, filtered, and concentrated under reduced pressure to give the crude product Intermediate 2A (14.47 g, 99%) as a white solid. MS(ES): m/z=240.89/242.89 [M+H]⁺. HPLC Ret time (Method B): 3.56 min. ¹H NMR (400 MHz, chloroform-d) δ 7.86-7.74 (m, 2H), 7.66 (s, 1H), 7.20-7.11 (m, 2H).

To a solution of 4-bromo-3-(4-fluorophenyl)-1H-pyrazole (14.47 g, 60.0 mmol) in DMF (100 mL) was added 60% NaH dispersion in mineral oil (2.88 g, 72.0 mmol) in portions at 0° C. under nitrogen. The reaction mixture was stirred at rt for 30 min. The reaction mixture was cooled to 0° C. and MeI (4.88 mL, 78 mmol) was added slowly. The reaction mixture was stirred at rt for 1 h and diluted with EtOAc and water. The layers were separated. The aqueous layer was extracted with EtOAc (2×40 mL). The combined organic layer was washed with water and brine, dried over anhydrous sodium sulfate, filtered, and concentrated under reduced pressure. The crude product was purified by BIOTAGE® (300 g Thomson, 50% CH₂Cl₂/hexane equilibration, 50-80% CH₂Cl₂/hexane, 3 L, then 80-85% 0.7 L) to give Intermediate 2 (8.4 g, 54.9%) as a white solid. MS(ES): m/z=254.88/256.88 [M+H]⁺. HPLC Ret time (Method B): 3.68 min. ¹H NMR (400 MHz, chloroform-d) δ 7.92-7.82 (m, 2H), 7.47 (s, 1H), 7.13 (t, J=8.8 Hz, 2H), 3.94 (s, 3H).

Scheme 3

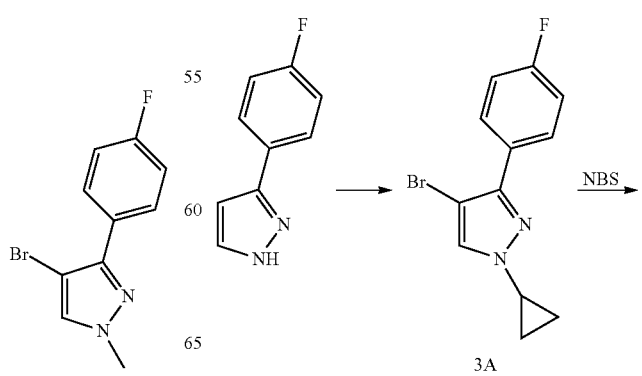

Intermediate 3

4-Bromo-1-cyclopropyl-3-(4-fluorophenyl)-1H-pyrazole

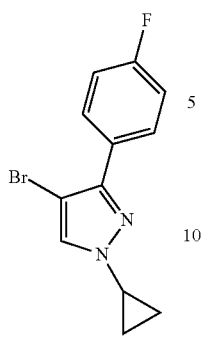

3

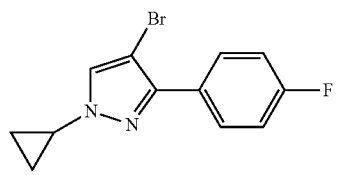 [SMILES: Fc1ccc(-c2nn(C3CC3)cc2Br)cc1]

Intermediate 3A:
1-Cyclopropyl-3-(4-fluorophenyl)-1H-pyrazole

Intermediate 3A was prepared according to the procedures described in *Org. Lett.*, 1653-1655 (2008). To a solution of 3-(4-fluorophenyl)-1H-pyrazole (6.5 g, 40.1 mmol) in dioxane (80 mL) were added cyclopropylboronic acid (7.26 g, 85 mmol), DMAP (14.7 g, 120 mmol), diacetoxycopper (7.28 g, 40.1 mmol), and pyridine 3.24 mL, 40.1 mmol). The reaction mixture was heated at 100° C. overnight. The reaction mixture was cooled to rt, quenched with water, and extracted with EtOAt. The combined organic layer was washed with brine, dried over anhydrous sodium sulfate, filtered, and concentrated under reduced pressure. The crude product was purified by BIOTAGE® (90 g Thomson, 0-40% EtOAc/hex) to give Intermediate 3A (3.2 g, 39.5%) as a tan oil. MS(ES): m/z=203.13 [M+H]$^+$. HPLC Ret time (Method B): 3.52 min. $^1$H NMR (400 MHz, chloroform-d) δ 7.84-7.72 (m, 2H), 7.13-7.01 (m, 2H), 6.46 (d, J=2.3 Hz, 1H), 3.63 (dt, J=7.2, 3.5 Hz, 1H), 1.21-1.11 (m, 2H), 1.11-0.90 (m, 2H).

Intermediate 3:
1-Cyclopropyl-3-(4-fluorophenyl)-1H-pyrazole

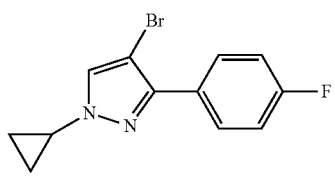 [SMILES: Fc1ccc(-c2nn(C3CC3)cc2Br)cc1]

To a solution of 1-cyclopropyl-3-(4-fluorophenyl)-1H-pyrazole, Intermediate 3A (3.2 g, 15.82 mmol) in DMF (40 mL) was added NBS (2.76 g, 15.51 mmol) in portions over 30 min at rt. The reaction mixture was stirred at rt for 3 h, quenched with water, extracted with EtOAc. The organic layer was washed with brine, dried over anhydrous sodium sulfate, filtered, and concentrated under reduced pressure. The crude product was purified by BIOTAGE® (90 g Thomson, 0-30% EtOAc/hex) to give Intermediate 3 (4 g, 90%) as a tan oil. MS(ES): m/z=281.0/283.0 [M+H]$^+$. HPLC Ret time (Method B): 3.89 min. $^1$H NMR (400 MHz, chloroform-d) δ 7.97-7.80 (m, 2H), 7.56 (s, 1H), 7.19-7.03 (m, 2H), 3.64 (dt, J=7.3, 3.6 Hz, 1H), 1.24-1.03 (m, 4H).

Scheme 4

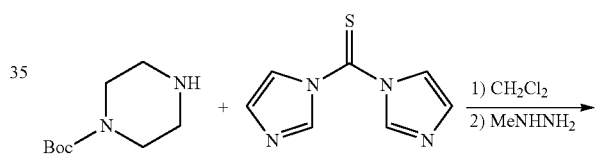

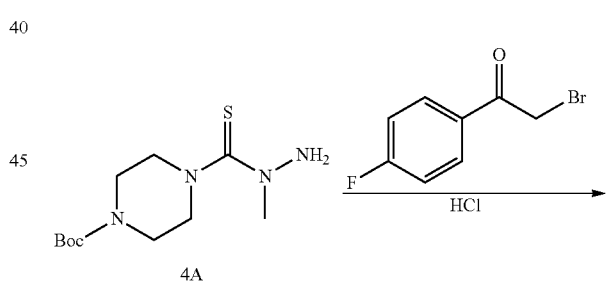

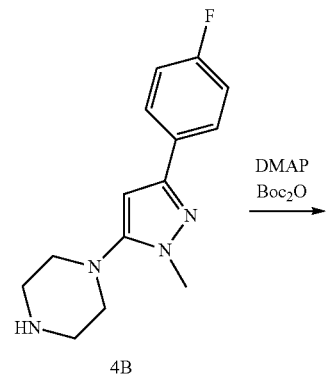

-continued

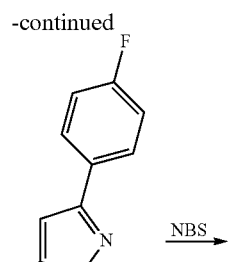

4C

→ NBS

Intermediate 4 tert-Butyl 4-(4-bromo-3-(4-fluorophenyl)-1-methyl-1H-pyrazol-5-yl)piperazine-1-carboxylate

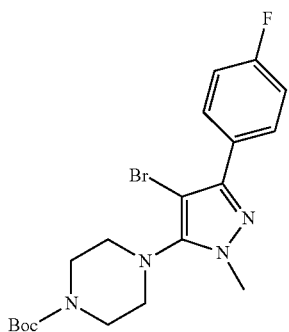 [SMILES: Cn1nc(-c2ccc(F)cc2)c(Br)c1N1CCN(C(=O)OC(C)(C)C)CC1]

4

Intermediate 4A: tert-Butyl 4-(1-methylhydrazinecarbonothioyl)piperazine-1-carboxylate

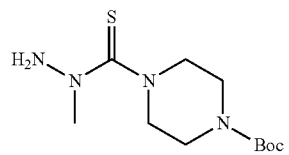 [SMILES: CN(N)C(=S)N1CCN(C(=O)OC(C)(C)C)CC1]

To a stirring solution of di(1H-imidazol-1-yl)methanethione (6.1 g, 34.2 mmol) in dichloromethane (100 mL) was added tert-butyl piperazine-1-carboxylate (6.38 g, 34.2 mmol). The reaction mixture was allowed to stir at rt for 2 h. Methylhydrazine (1.892 g, 41.1 mmol) was then added to the reaction mixture, which was stirred at rt for 6 h and concentrated. The residue was diluted with ether. The ether solution was washed with 0.1N HCl solution, water, and brine. The organic layer was dried over anhydrous sodium sulfate, filtered, and concentrated under reduced pressure. The crude material (tan oil) was suspended in ether/hexane. Filtration gave Intermediate 4A (6.8 g, 72.6% two steps) as a white solid. $^1$H NMR (500 MHz, chloroform-d) δ 3.43 (s, 8H), 3.21 (s, 3H), 1.42-1.48 (s, 9H). MS(ES): m/z=273.2 [M−1]$^+$. HPLC Ret time (Method A): 2.43 min.

Intermediate 4B: 1-(3-(4-Fluorophenyl)-1-methyl-1H-pyrazol-5-yl)piperazine

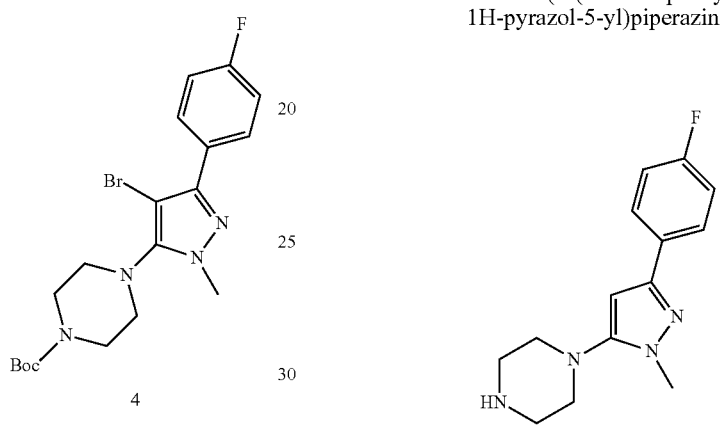

To a solution of tert-butyl 4-(1-methylhydrazinecarbonothioyl)piperazine-1-carboxylate, Intermediate 4A (5.7 g, 20.77 mmol) in ethanol (60 mL) was added 2-bromo-1-(4-fluorophenyl)ethanone (4.3 g, 19.81 mmol) at 0° C. The reaction mixture was stirred at rt for 2 h. Then HCl (4.0 M dioxane solution) (10 mL, 40.0 mmol) was added to the reaction mixture, which was heated at 80° C. overnight. The reaction mixture was then concentrated and the residue was dissolved in 20% MeOH/CHCl$_3$, washed with sodium bicarbonate, water, and dried over anhydrous sodium sulfate, filtered, and concentrated under reduced pressure. The crude product was purified by BIOTAGE® (80-100% B/CH$_2$Cl$_2$, B: 10% MeOH/CH$_2$Cl$_2$) to yield Intermediate 4B (3 g, 55.5%) as a brown oil. $^1$H NMR (500 MHz, chloroform-d) δ 7.71 (dd, J=8.9, 5.4 Hz, 2H), 7.05 (t, J=8.8 Hz, 2H), 6.06 (s, 1H), 3.75 (s, 3H), 3.07-2.97 (m, 4H), 2.95-2.86 (m, 4H). MS(ES): m/z=261.1 [M+H]$^+$. HPLC Ret time (Method B): 2.43 min.

Intermediate 4C: tert-Butyl 4-(3-(4-fluorophenyl)-1-methyl-1H-pyrazol-5-yl)piperazine-1-carboxylate

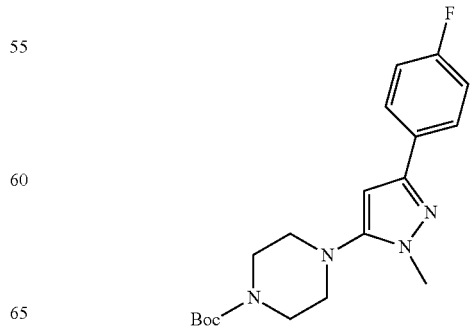

To a solution of 1-(3-(4-fluorophenyl)-1-methyl-1H-pyrazol-5-yl)piperazine, Intermediate 4B (3 g, 11.52 mmol) and DMAP (0.141 g, 1.152 mmol) in CH$_2$Cl$_2$ (50 mL) was added (Boc)$_2$O (2.68 mL, 11.52 mmol). The reaction mixture was stirred at rt for 30 min. The reaction mixture was quenched with sodium bicarbonate and the layers were separated. The organic layer was washed with brine, dried over anhydrous sodium sulfate, filtered, and concentrated under reduced pressure. The crude product was used in the next step without further purification. MS(ES): m/z=361.2 [M+H]$^+$. HPLC Ret time (Method B): 4.18 min.

Intermediate 4: tert-Butyl 4-(4-bromo-3-(4-fluorophenyl)-1-methyl-1H-pyrazol-5-yl)piperazine-1-carboxylate

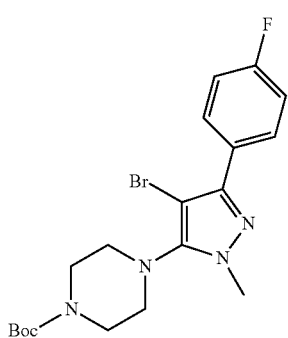 [SMILES: Cn1nc(-c2ccc(F)cc2)c(Br)c1N1CCN(C(=O)OC(C)(C)C)CC1]

To a solution of the crude material tert-butyl 4-(3-(4-fluorophenyl)-1-methyl-1H-pyrazol-5-yl)piperazine-1-carboxylate, Intermediate 4B (11.52 mmol) in CH$_2$Cl$_2$ (40 ml) was added NBS (2.26 g, 12.67 mmol). The reaction mixture was stirred at rt for 1 h. The reaction mixture was washed with water and brine, dried over anhydrous sodium sulfate, filtered, and concentrated under reduced pressure. The crude product was purified by BIOTAGE® (10-60% hex/EtOAc, 1.2 L) to give Intermediate 4 (3.4 g, 67.2% combined yield for two steps) as a white solid. MS(ES): m/z=439.1/441.1 [M+H]$^+$. HPLC Ret time (Method B): 4.3243 min. $^1$H NMR (400 MHz, chloroform-d) δ 7.80 (dd, J=8.9, 5.4 Hz, 2H), 7.12 (t, J=8.8 Hz, 2H), 3.81 (s, 3H), 3.58 (br. s., 4H), 3.22 (t, J=4.9 Hz, 4H), 1.52 (s, 9H).

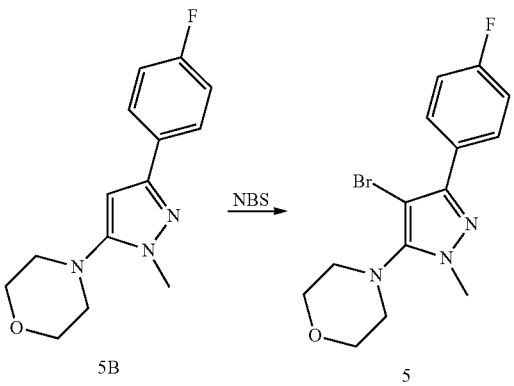

Intermediate 5

4-(4-Bromo-3-(4-fluorophenyl)-1-methyl-1H-pyrazol-5-yl)morpholine

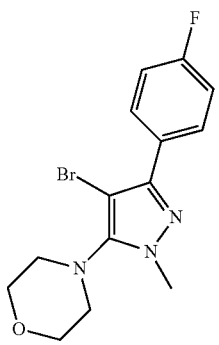 [SMILES: Cn1nc(-c2ccc(F)cc2)c(Br)c1N1CCOCC1]

Intermediate 5 was prepared by the procedures described for the preparation of Intermediates 4A and 4B using morpholine. MS(ES): m/z=340.1/342.1 [M+H]$^+$. HPLC Ret time (Method A): 3.89 min. $^1$H NMR (400 MHz, chloroform-d) δ 7.80 (dd, J=9.0, 5.5 Hz, 2H), 7.11 (t, J=8.8 Hz, 2H), 3.88-3.80 (m, 7H), 3.34-3.21 (m, 4H).

Scheme 5

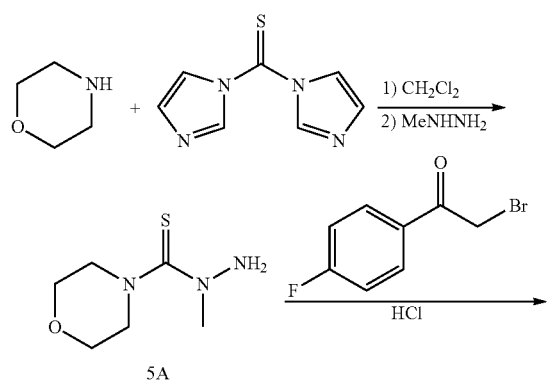

Scheme 6

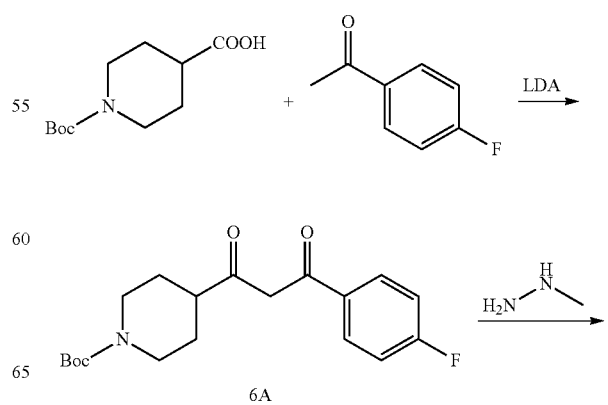

Intermediate 6 tert-Butyl 4-(4-bromo-3-(4-fluorophenyl)-1-methyl-1H-pyrazol-5-yl)piperidine-1-carboxylate

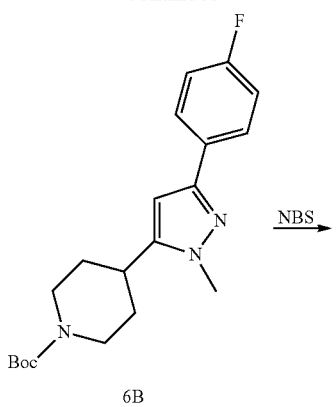

6B

NBS →

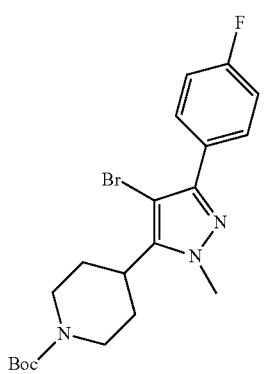 [SMILES: Cn1nc(-c2ccc(F)cc2)c(Br)c1C1CCN(C(=O)OC(C)(C)C)CC1]

6

Intermediate 6A: tert-Butyl 4-(3-(4-fluorophenyl)-3-oxopropanoyl)piperidine-1-carboxylate

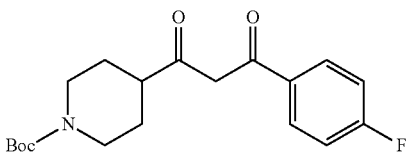 [SMILES: CC(C)(C)OC(=O)N1CCC(C(=O)CC(=O)c2ccc(F)cc2)CC1]

Intermediate 6A was prepared according to the procedures described in *J. Med. Chem.,* 47:3693 (2004). To a solution of 1-(4-fluorophenyl)ethanone (9.04 g, 65.4 mmol) in THF (80 ml) was added LDA (36.0 mL, 72.0 mmol) at −78° C. under nitrogen. The resulting yellow solution was stirred at −78° C. for 30 min. In another flask, to a solution of 1-(tert-butoxycarbonyl)piperidine-4-carboxylic acid (15 g, 65.4 mmol) in THF (60 mL) was added CDI (10.61 g, 65.4 mmol) in portions. The reaction mixture was stirred at rt for 40 min. The resulting solution was added to the first reaction mixture dropwise in 30 min at −78° C. under nitrogen. The reaction mixture was stirred at rt over night and quenched with 60 mL of 10% citric acid. The resulting solution was taken up in EtOAc, washed with brine, dried over anhydrous sodium sulfate, filtered, and concentrated under reduced pressure. The crude product was purified by BIOTAGE® (30-50% hex/EtOAc) to give Intermediate 6A (18 g, 79%) as a white solid. MS(ES): m/z=250.09 [M+H]$^+$. HPLC Ret time (Method B): 4.32 min.

Intermediate 6B: tert-Butyl 4-(3-(4-fluorophenyl)-1-methyl-1H-pyrazol-5-yl)piperidine-1-carboxylate

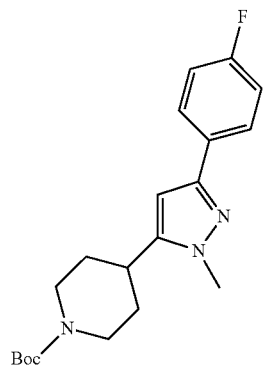 [SMILES: Cn1nc(-c2ccc(F)cc2)cc1C1CCN(C(=O)OC(C)(C)C)CC1]

To a solution of tert-butyl 4-(3-(4-fluorophenyl)-3-oxopropanoyl)piperidine-1-carboxylate, Intermediate 6A (18 g, 51.5 mmol) in MeOH (80 mL) was added methylhydrazine (2.373 g, 51.5 mmol). The reaction mixture was heated at 50° C. for 2 h and concentrated under reduced pressure. The residue was used for the next step without purification. MS(ES): m/z=360.13 [M+H]$^+$. HPLC Ret time (Method B): 4.47 min.

Intermediate 6: tert-Butyl 4-(4-bromo-3-(4-fluorophenyl)-1-methyl-1H-pyrazol-5-yl)piperidine-1-carboxylate

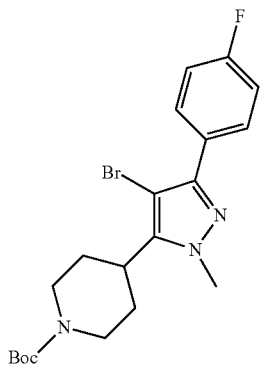 [SMILES: Cn1nc(-c2ccc(F)cc2)c(Br)c1C1CCN(C(=O)OC(C)(C)C)CC1]

To a solution of crude tert-butyl 4-(3-(4-fluorophenyl)-1-methyl-1H-pyrazol-5-yl)piperidine-1-carboxylate, Intermediate 6B (51.5 mmol) in $CH_2Cl_2$ (60 mL) was added NBS (9.17 g, 51.5 mmol) in portions. The reaction mixture was stirred at rt for 6 h. The reaction mixture was washed with water and brine, dried over anhydrous sodium sulfate, filtered, and concentrated under reduced pressure. The crude product was purified by BIOTAGE® (10-60% hex/EtOAc) to give Intermediate 6 (8 g, 35.4% combined yield for two steps) as a white solid. The desired regioisomer is the more polar spot. The undesired regioisomer (less polar spot on TLC) was not isolated. MS(ES): m/z=438.02/440.02 [M+H]$^+$. HPLC Ret time (Method B): 4.37 min. $^1$H NMR (400 MHz, chloroform-d) δ 7.87-7.74 (m, 2H), 7.20-7.04 (m, 2H), 4.31 (br. s., 1H), 3.95 (s, 3H), 3.12-2.94 (m, 1H), 2.81 (br. s., 2H), 2.19 (qd, J=12.8, 4.3 Hz, 2H), 1.75 (d, J=12.5 Hz, 2H), 1.62 (br. s., 1H), 1.54-1.46 (m, 9H).

Scheme 7

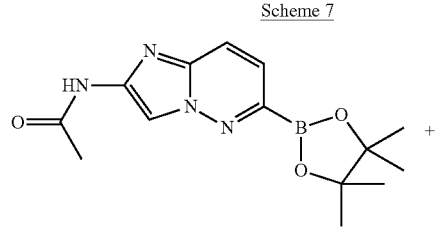

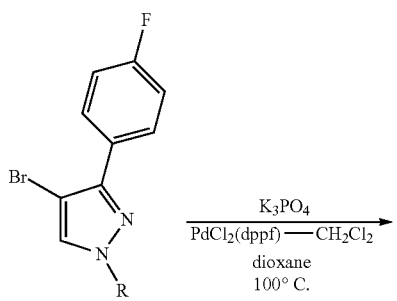

2: R = Me
3: R = Cyclopropyl

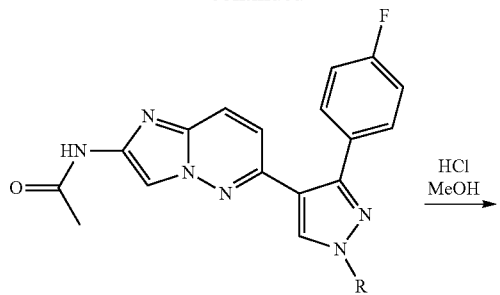

7A: R = Me
8A: R = Cyclopropyl

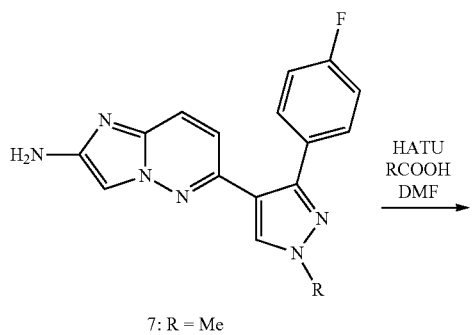

7: R = Me
8: R = Cyclopropyl

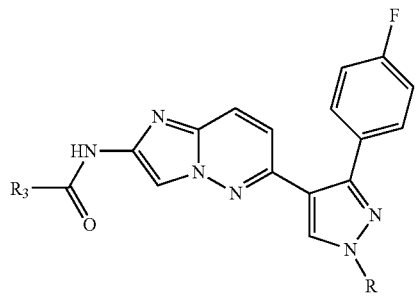

Intermediate 7

6-(3-(4-Fluorophenyl)-1-methyl-1H-pyrazol-4-yl)imidazo[1,2-b]pyridazin-2-amine

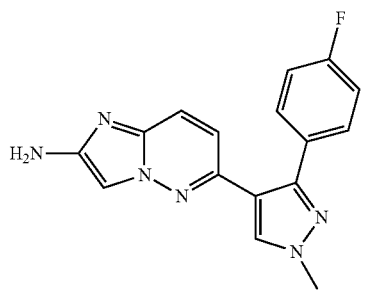 [SMILES: Cn1cc(-c2ccc3nc(N)cn3n2)c(-c2ccc(F)cc2)n1]

Intermediate 7A: N-(6-(3-(4-Fluorophenyl)-1-methyl-1H-pyrazol-4-yl)imidazo[1,2-b]pyridazin-2-yl)acetamide

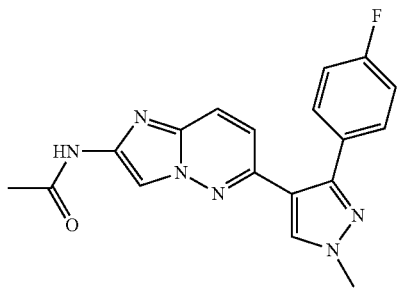 [SMILES: CC(=O)Nc1cn2nc(-c3cn(C)nc3-c3ccc(F)cc3)ccc2n1]

To a pressure bottle were added 4-bromo-3-(4-fluorophenyl)-1-methyl-1H-pyrazole, Intermediate 2 (2.95 g, 11.8 mmol), N-(6-(4,4,5,5-tetramethyl-1,3,2-dioxaborolan-2-yl)imidazo[1,2-b]pyridazin-2-yl)acetamide, Intermediate 1 (3.5 g, 11.8 mmol), potassium phosphate tribasic (2.0 M water solution, 17.4 mL, 34.8 mmol), PdCl$_2$(dppf)-CH$_2$Cl$_2$ adduct (0.95 g, 1.16 mmol), and dioxane (60 mL). The reaction mixture was bubbled with nitrogen for 2 min, capped, and heated at 100° C. overnight. The reaction mixture was cooled to rt, diluted with CH$_2$Cl$_2$, and washed with water and brine, dried over anhydrous sodium sulfate, filtered, and concentrated under reduced pressure. The crude product was purified by BIOTAGE® (90 g Thomson, 20-60% B/CH$_2$Cl$_2$, B:10% MeOH/CH$_2$Cl$_2$) to give Intermediate 7A (1.6 g, 39.4%) as a brown foam. MS(ES): m/z=351.2 [M+H]$^+$. HPLC Ret time (Method B): 3.19 min. $^1$H NMR (400 MHz, DMSO-d$_6$) δ 10.87 (s, NH, 1H), 8.31 (s, 1H), 8.10 (s, 1H), 7.90 (d, J=8.9 Hz, 1H), 7.62-7.49 (m, 2H), 7.30-7.20 (m, 2H), 7.05 (d, J=9.4 Hz, 1H), 3.96 (s, 3H), 2.10 (s, 3H).

Intermediate 7: 6-(3-(4-Fluorophenyl)-1-methyl-1H-pyrazol-4-yl)imidazo[1,2-b]pyridazin-2-amine

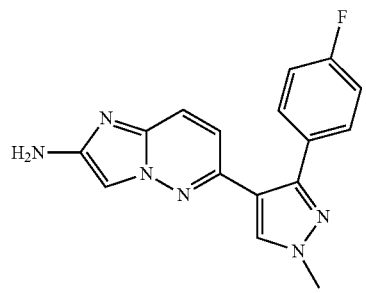 [SMILES: Cn1cc(-c2ccc3nc(N)cn3n2)c(-c2ccc(F)cc2)n1]

To a solution of N-(6-(3-(4-fluorophenyl)-1-methyl-1H-pyrazol-4-yl)imidazo[1,2-b]pyridazin-2-yl)acetamide, Intermediate 7A, (1.6 g, 4.57 mmol) in MeOH (25 mL) was added hydrogen chloride (8 mL, excess, 4.0 M dioxane solution). The reaction mixture was stirred at rt overnight and concentrated. The residue was dissolved in 20% MeOH/CHCl$_3$ (120 mL), washed with saturated sodium bicarbonate and brine, dried over anhydrous sodium sulfate, filtered, and concentrated under reduced pressure. The crude product was purified by BIOTAGE® (90 g Thomson, 50-100% B/CH$_2$Cl$_2$, B: 10% MeOH/CH$_2$Cl$_2$ to give Intermediate 7 (1.2 g, 85%) as a brown foam. MS(ES): m/z=309.2 [M+H]$^+$. HPLC Ret time (Method A): 3.00 min. $^1$H NMR (500 MHz, methanol-d$_4$) δ 7.94 (s, 1H), 7.60 (s, including NH$_2$, 4H), 7.53-7.41 (m, 2H), 7.08 (t, J=8.7 Hz, 2H), 6.80 (d, J=9.4 Hz, 1H), 4.00 (s, 3H).

Intermediate 8

6-(1-Cyclopropyl-3-(4-fluorophenyl)-1H-pyrazol-4-yl)imidazo[1,2-b]pyridazin-2-amine

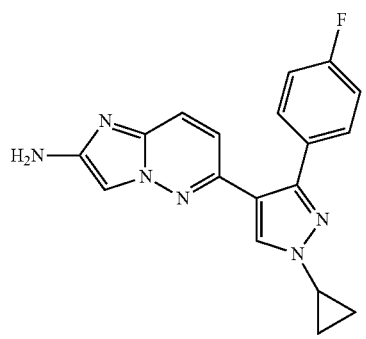 [SMILES: Nc1cn2nc(-c3cn(C4CC4)nc3-c3ccc(F)cc3)ccc2n1]

Intermediate 8A: N-(6-(1-Cyclopropyl-3-(4-fluorophenyl)-1H-pyrazol-4-yl)imidazo[1,2-b]pyridazin-2-yl)acetamide

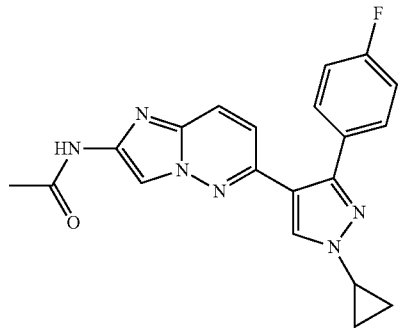 [SMILES: CC(=O)Nc1cn2nc(-c3cn(C4CC4)nc3-c3ccc(F)cc3)ccc2n1]

To a pressure bottle were added 4-bromo-1-cyclopropyl-3-(4-fluorophenyl)-1H-pyrazole, Intermediate 3 (2.9 g, 10.32 mmol), N-(6-(4,4,5,5-tetramethyl-1,3,2-dioxaborolan-2-yl)imidazo[1,2-b]pyridazin-2-yl)acetamide, Intermediate 1, (4.7 g, 15.48 mmol), potassium phosphate tribasic (2.0 M water solution, 15 mL, 30.9 mmol), and PdCl$_2$(dppf)-CH$_2$Cl$_2$ adduct (0.84 g, 1.03 mmol) in dioxane (60 mL). The reaction mixture was bubbled with nitrogen for 2 min, capped, and heated at 100° C. overnight. The reaction mixture was cooled to rt, diluted with CH$_2$Cl$_2$, and washed with water and brine, dried over anhydrous sodium sulfate, filtered, and concentrated under reduced pressure. The crude product was purified by BIOTAGE® (90 g Thomson, 20-60% B/CH$_2$Cl$_2$, B:10% MeOH/CH$_2$Cl$_2$) to give Intermediate 8A (2.8 g, 54.8%) as a tan solid. MS(ES): m/z=377.24 [M+H]$^+$. HPLC Ret time (Method B): 3.45 min. $^1$H NMR (400 MHz, DMSO-d$_6$) δ 10.90 (s, NH, 1H), 8.42 (s, 1H), 8.09 (s, 1H), 7.92 (d, J=9.5 Hz, 1H), 7.68-7.49 (m, 2H), 7.23 (t, J=8.7 Hz, 2H), 7.12 (d, J=9.3 Hz, 1H), 3.98-3.77 (m, 1H), 2.10 (s, 3H), 1.19 (br. s., 2H), 1.05 (d, J=5.8 Hz, 2H).

Intermediate 8: 6-(1-Cyclopropyl-3-(4-fluorophenyl)-1H-pyrazol-4-yl)imidazo[1,2-b]pyridazin-2-amine

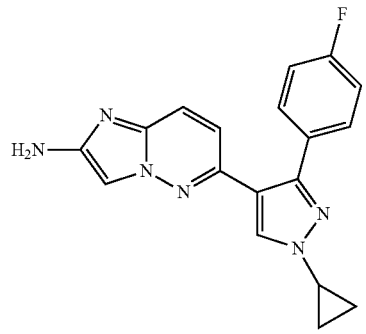 [SMILES: Nc1cn2nc(-c3cn(C4CC4)nc3-c3ccc(F)cc3)ccc2n1]

To a solution of N-(6-(1-cyclopropyl-3-(4-fluorophenyl)-1H-pyrazol-4-yl)imidazo[1,2-b]pyridazin-2-yl)acetamide, Intermediate 8A (2 g, 5.31 mmol), in MeOH (25 mL) was added hydrogen chloride (8 mL, excess, 4.0 M dioxane solution). The reaction mixture was stirred at rt overnight and concentrated. The residue was dissolved in 20% MeOH/CHCl$_3$ (120 mL), washed with saturated sodium bicarbonate and brine, dried over anhydrous sodium sulfate, filtered, and concentrated under reduced pressure. The crude product (1.8 g, 49.6%) was used in the next step without further purification. Small amount of crude product was purified by prep. HPLC to get the analytical data for the product. MS(ES): m/z=335.21 [M+H]$^+$. HPLC Ret time (Method B): 2.91 min. $^1$H NMR (400 MHz, DMSO-d$_6$) δ 8.42 (s, NH, 1H), 7.92 (d, J=9.3 Hz, 1H), 7.56 (dd, J=8.9, 5.6 Hz, 2H), 7.36 (s, 1H), 7.29-7.09 (m, 3H), 3.88 (td, J=7.3, 3.6 Hz, H), 1.28-1.13 (m, 2H), 1.13-0.92 (m, 2H).

Scheme 8

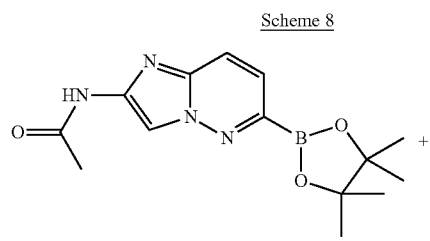

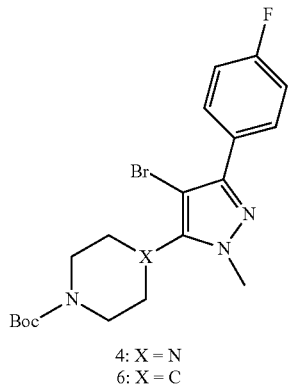

4: X = N
6: X = C

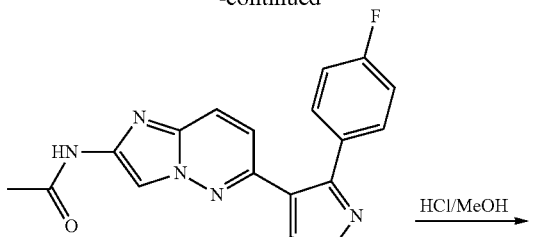

9A: X = N
10A: X = C

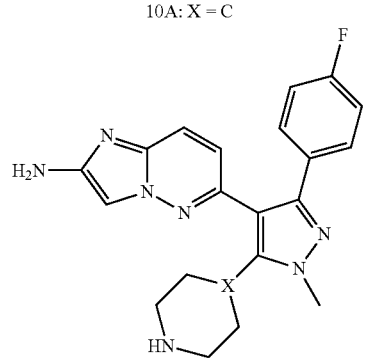

9B: X = N
10B: X = C

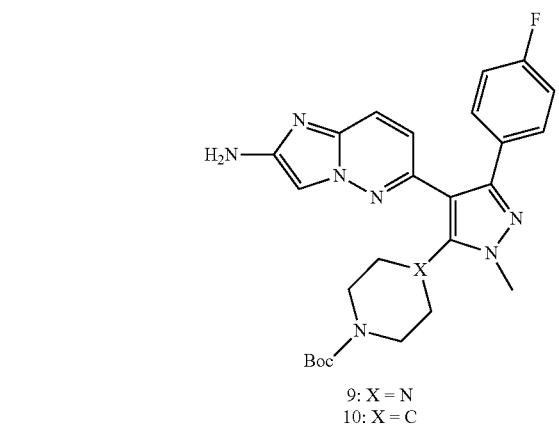

9: X = N
10: X = C

Intermediate 9 tert-Butyl 4-(4-(2-aminoimidazo[1,2-b]pyridazin-6-yl)-3-(4-fluorophenyl)-1-methyl-1H-pyrazol-5-yl)piperazine-1-carboxylate

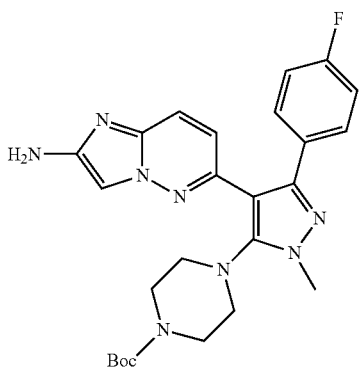 [SMILES: Cn1nc(-c2ccc(F)cc2)c(-c2ccc3nc(N)cn3n2)c1N1CCN(C(=O)OC(C)(C)C)CC1]

Intermediate 9A: tert-Butyl 4-(4-(2-acetamidoimidazo[1,2-b]pyridazin-6-yl)-3-(4-fluorophenyl)-1-methyl-1H-pyrazol-5-yl)piperazine-1-carboxylate

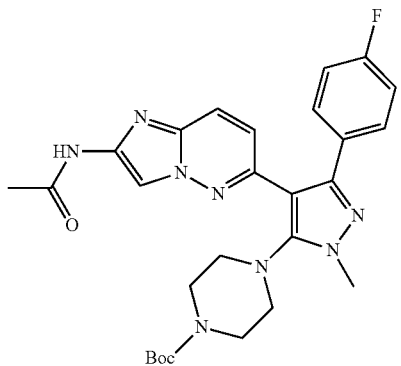 [SMILES: CC(=O)Nc1cn2nc(-c3c(-c4ccc(F)cc4)nn(C)c3N3CCN(C(=O)OC(C)(C)C)CC3)ccc2n1]

To a pressure bottle were added tert-butyl 4-(4-bromo-3-(4-fluorophenyl)-1-methyl-1H-pyrazol-5-yl)piperazine-1-carboxylate, Intermediate 4 (1.3 g, 2.96 mmol), N-(6-(4,4,5,5-tetramethyl-1,3,2-dioxaborolan-2-yl)imidazo[1,2-b]pyridazin-2-yl)acetamide, Intermediate 1, (1.34 g, 4.4 mmol), potassium phosphate tribasic (2.0 M water solution, 4.54 mL, 8.88 mmol), PdCl$_2$(dppf)-CH$_2$Cl$_2$ adduct (0.25 g, 0.3 mmol) in dioxane (40 mL). The reaction mixture was bubbled with nitrogen for 2 min, capped, and heated at 100° C. overnight. The reaction mixture was cooled to RT, diluted with CH$_2$Cl$_2$, and washed with water and brine, dried over anhydrous sodium sulfate, filtered, and concentrated under reduced pressure. The crude product was purified by BIOTAGE® (90 g Thomson, 20-60% B/CH$_2$Cl$_2$, B:10% MeOH/CH$_2$Cl$_2$) to give Intermediate 9A (1 g, 37.9%) as a tan oil. MS(ES): m/z=533.3 [M–H]$^+$. HPLC Ret time (Method A): 3.96 min.

Intermediate 9B: tert-Butyl 4-(4-(2-acetamidoimidazo[1,2-b]pyridazin-6-yl)-3-(4-fluorophenyl)-1-methyl-1H-pyrazol-5-yl)piperazine-1-carboxylate

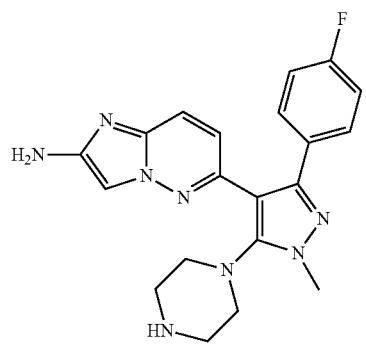 [SMILES: Cn1nc(-c2ccc(F)cc2)c(-c2ccc3nc(N)cn3n2)c1N1CCNCC1]

To a solution of tert-butyl 4-(4-(2-acetamidoimidazo[1,2-b]pyridazin-6-yl)-3-(4-fluorophenyl)-1-methyl-1H-pyrazol-5-yl)piperazine-1-carboxylate, Intermediate 9A (1 g, 1.87 mmol) in MeOH (25 mL) was added 4M hydrogen chloride (8 mL) in dioxane solution. The reaction mixture was stirred at RT overnight and concentrated. The residue was dissolved in 20% MeOH/CHCl$_3$ (120 mL), washed with saturated sodium bicarbonate and brine, dried over anhydrous sodium sulfate, filtered, and concentrated under reduced pressure. The crude product was used in the next step without further purification. MS(ES): m/z=393.09 [M+H]$^+$. HPLC Ret time (Method A): 2.28 min.

Intermediate 9: tert-Butyl 4-(4-(2-aminoimidazo[1,2-b]pyridazin-6-yl)-3-(4-fluorophenyl)-1-methyl-1H-pyrazol-5-yl)piperazine-1-carboxylate

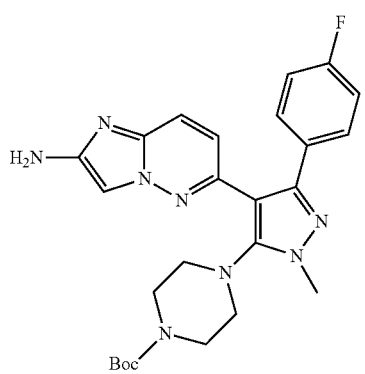

To a solution of 6-(3-(4-fluorophenyl)-1-methyl-5-(piperazin-1-yl)-1H-pyrazol-4-yl)imidazo[1,2-b]pyridazin-2-amine, Intermediate 9B (550 mg, 0.841 mmol) and Hunig's Base (0.176 mL, 1.009 mmol) in CH$_2$Cl$_2$ (40 mL) was added Boc$_2$O (0.156 mL, 0.673 mmol). The reaction mixture was stirred at RT for 4 h, washed with water and brine, dried over anhydrous sodium sulfate, filtered, and concentrated under reduced pressure. The crude product was purified by BIOTAGE® (40-80% B/CH$_2$Cl$_2$, B: 10% MeOH/CH$_2$Cl$_2$) to give Intermediate 9 (280 mg, 67.6%) as a tan oil. MS(ES): m/z=493.2 [M+H]$^+$. HPLC Ret time (Method A): 3.82 min.

Intermediate 10 tert-Butyl 4-(4-(2-aminoimidazo[1,2-b]pyridazin-6-yl)-3-(4-fluorophenyl)-1-methyl-1H-pyrazol-5-yl)piperidine-1-carboxylate

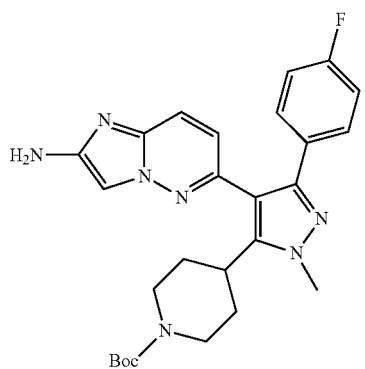 [SMILES: Cn1nc(-c2ccc(F)cc2)c(-c2ccc3nc(N)cn3n2)c1C1CCN(C(=O)OC(C)(C)C)CC1]

Intermediate 10A: tert-Butyl 4-(4-(2-acetamidoimidazo[1,2-b]pyridazin-6-yl)-3-(4-fluorophenyl)-1-methyl-1H-pyrazol-5-yl)piperidine-1-carboxylate

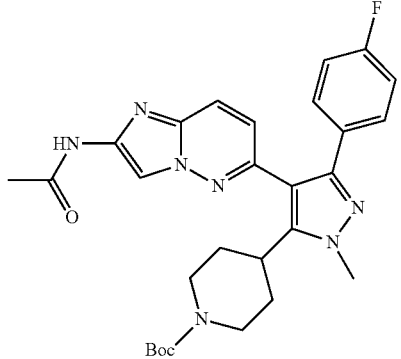 [SMILES: CC(=O)Nc1cn2nc(-c3c(-c4ccc(F)cc4)nn(C)c3C3CCN(C(=O)OC(C)(C)C)CC3)ccc2n1]

Intermediate 10A was prepared by the procedure described for the preparation of Intermediate 9A using Intermediates 1 and 6. MS(ES): m/z=534.56 [M+H]+. HPLC Ret time (Method A): 3.73 min. ¹H NMR (400 MHz, DMSO-d₆) δ 10.93 (s, NH, 1H), 8.23 (s, 1H), 7.99-7.85 (m, 1H), 7.39-7.26 (m, 2H), 7.21-7.05 (m, 2H), 6.92 (d, J=9.0 Hz, 1H), 4.05-3.76 (m, 2H), 3.97 (s, 3H), 3.24-3.06 (m, 1H), 2.75 (m, 2H), 2.11 (s, 3H), 1.72 (d, J=11.3 Hz, 2H), 1.50 (m., 2H), 1.25 (s, 9H).

Intermediate 10B: 6-(3-(4-Fluorophenyl)-1-methyl-5-(piperidin-4-yl)-1H-pyrazol-4-yl)imidazo[1,2-b]pyridazin-2-amine

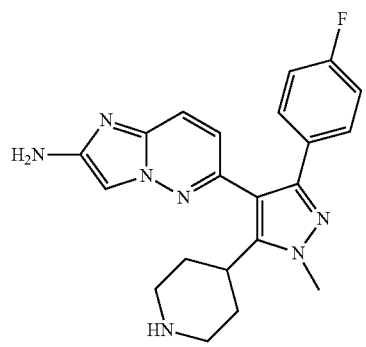

Intermediate 10B was prepared by the procedure described for the preparation of Intermediate 9B using Intermediate 10A. MS(ES): m/z=392.23 [M+H]+. HPLC Ret time (Method B): 2.36 min.

Intermediate 10: tert-Butyl 4-(4-(2-aminoimidazo[1,2-b]pyridazin-6-yl)-3-(4-fluorophenyl)-1-methyl-1H-pyrazol-5-yl)piperidine-1-carboxylate

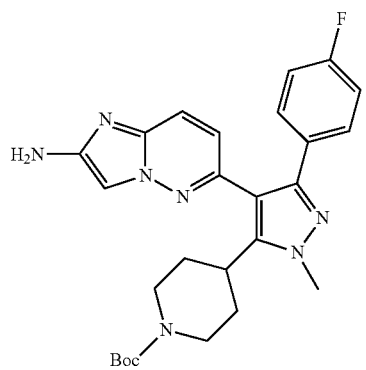

Intermediate 10 was prepared by the procedure described for the preparation of Intermediate 9 using Intermediate 10B. MS(ES): m/z=492.29 [M-Boc]+. HPLC Ret time (Method B): 3.17 min.

Scheme 9

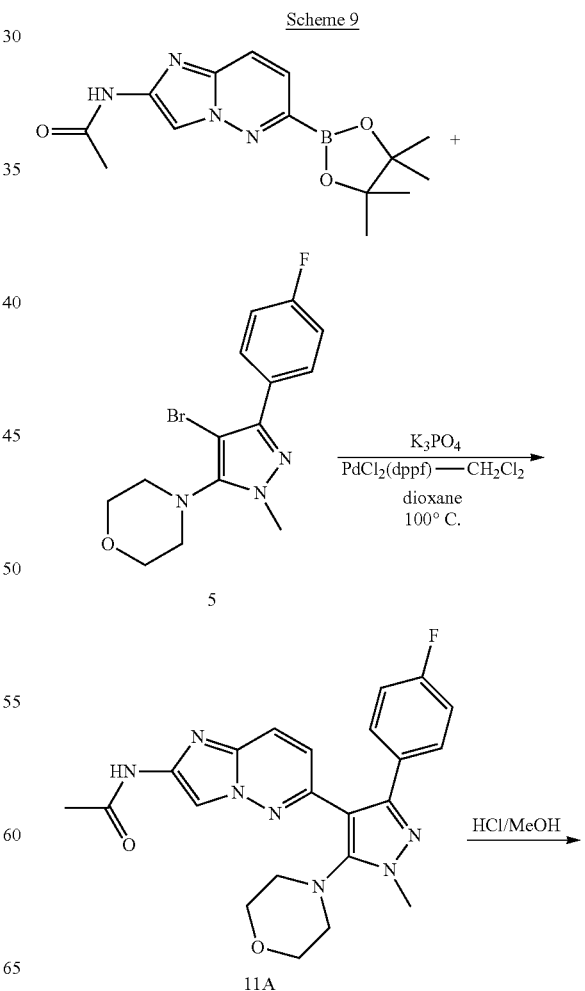

-continued

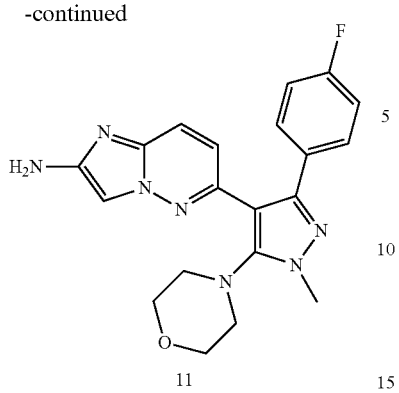

Intermediate 11

6-(3-(4-Fluorophenyl)-1-methyl-5-morpholino-1H-pyrazol-4-yl)imidazo[1,2-b]pyridazin-2-amine

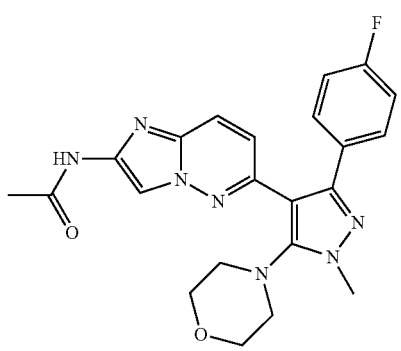 [SMILES: CC(=O)Nc1cn2nc(-c3c(-c4ccc(F)cc4)nn(C)c3N3CCOCC3)ccc2n1]

Intermediate 11A: N-(6-(3-(4-Fluorophenyl)-1-methyl-5-morpholino-1H-pyrazol-4-yl)imidazo[1,2-b]pyridazin-2-yl)acetamide Intermediate 11A was prepared by the procedure described for the preparation of Intermediate 9 using Intermediates 1 and 5. MS(ES): m/z=436.2 [M+H]$^+$. HPLC Ret time (Method A): 3.35 min. $^1$H NMR (400 MHz, DMSO-d$_6$) δ 10.97 (s, 1H), 8.28 (s, 1H), 7.93 (dd, J=9.3, 0.8 Hz, 1H), 7.38 (dd, J=9.0, 5.5 Hz, 2H), 7.15 (t, J=9.0 Hz, 2H), 6.98 (d, J=9.3 Hz, 1H), 3.82 (s, 3H), 3.69-3.55 (m, 4H), 3.00-2.86 (m, 4H), 2.13 (s, 3H).

Intermediate 11: 6-(3-(4-Fluorophenyl)-1-methyl-5-morpholino-1H-pyrazol-4-yl)imidazo[1,2-b]pyridazin-2-amine

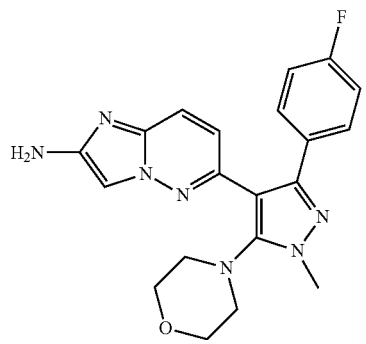 [SMILES: Cn1nc(-c2ccc(F)cc2)c(-c2ccc3nc(N)cn3n2)c1N1CCOCC1]

Intermediate 11 was prepared by the procedure described for the preparation of Intermediate 8 using Intermediate 11A. MS(ES): m/z=394.2 [M+H]$^+$. HPLC Ret time (Method A): 3.13 min.

Examples

The invention is further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

Compound 1

N-(6-(3-(4-Fluorophenyl)-1-methyl-1H-pyrazol-4-yl)imidazo[1,2-b]pyridazin-2-yl)isonicotinamide

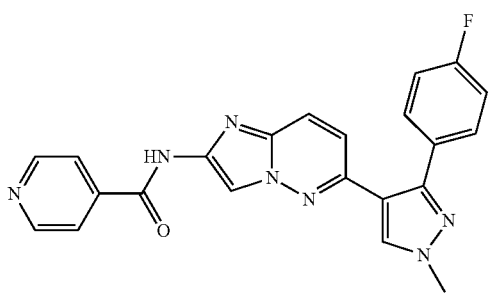 [SMILES: Cn1cc(-c2ccc3nc(NC(=O)c4ccncc4)cn3n2)c(-c2ccc(F)cc2)n1]

To a solution of 6-(3-(4-fluorophenyl)-1-methyl-1H-pyrazol-4-yl)imidazo[1,2-b]pyridazin-2-amine, 7 (50 mg, 0.162 mmol) in DMF (1 mL) was added isonicotinic acid (40 mg, 0.325 mmol), HATU (125 mg, 0.325 mmol), and Hunig's Base (85 mg, 0.65 mmol). The reaction mixture was stirred at rt overnight and purified by prep. HPLC to give Compound 1 (28 mg, 42%) as a tan powder. MS(ES): m/z=414.3 [M+H]$^+$. HPLC Ret time (Method E): 3.49 min. $^1$H NMR (400 MHz, DMSO-d$_6$) δ 11.84 (s, NH, 1H), 8.99-8.78 (m, 2H), 8.36 (d, J=2.5 Hz, 2H), 8.08 (dd, J=4.6, 1.6 Hz, 2H), 8.01 (dd, J=9.4, 0.6 Hz, 1H), 7.70-7.53 (m, 2H), 7.34-7.19 (m, 2H), 7.14 (d, J=9.5 Hz, 1H), 3.98 (s, 3H).

The following compounds in Table 1 were prepared by the procedure described for the preparation of compound 1 using Intermediate 7 and the corresponding acids.

TABLE 1

| Compound No. | Structure | Name | [M + H]⁺ | Ret time | HPLC Method |
|---|---|---|---|---|---|
| 2 | 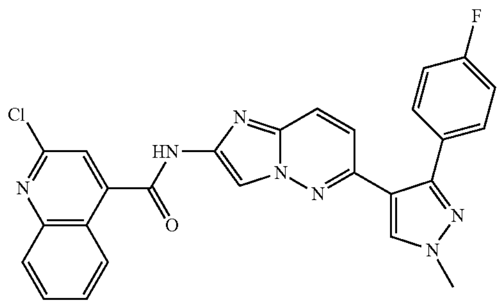 [SMILES: Cn1cc(-c2ccc3nc(NC(=O)c4cc(Cl)nc5ccccc45)cn3n2)c(-c2ccc(F)cc2)n1] | 2-chloro-N-(6-(3-(4-fluorophenyl)-1-methyl-1H-pyrazol-4-yl)imidazo[1,2-b]pyridazin-2-yl)quinoline-4-carboxamide | 498.07 | 4.08 | B |
| 3 | 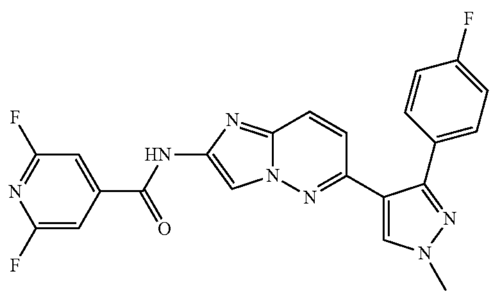 [SMILES: Cn1cc(-c2ccc3nc(NC(=O)c4cc(F)nc(F)c4)cn3n2)c(-c2ccc(F)cc2)n1] | 2,6-difluoro-N-(6-(3-(4-fluorophenyl)-1-methyl-1H-pyrazol-4-yl)imidazo[1,2-b]pyridazin-2-yl)isonicotinamide | 449.12 | 2.86/ 4.02 | C/D |
| 4 | 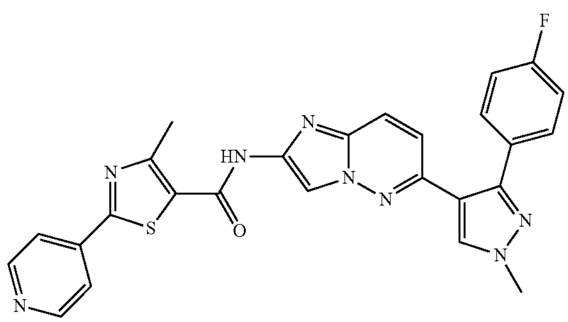 [SMILES: Cc1nc(-c2ccncc2)sc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methyl-2-(pyridin-4-yl)thiazol-5-carboxamide | 511.24 | 3.54 | B |
| 5 | 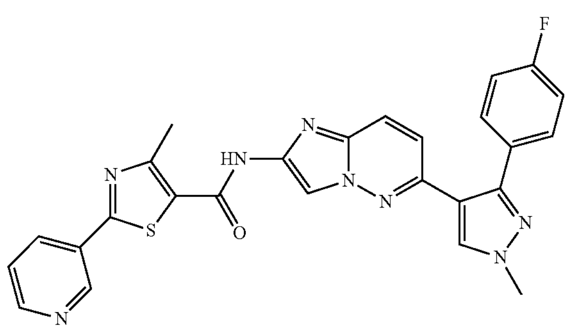 [SMILES: Cc1nc(-c2cccnc2)sc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methyl-2-(pyridin-3-yl)thiazol-5-carboxamide | 510.14 | 2.51/ 3.76 | C/D |

TABLE 1-continued

| Compound No. | Structure | Name | [M + H]⁺ | Ret time | HPLC Method |
|---|---|---|---|---|---|
| 6 | 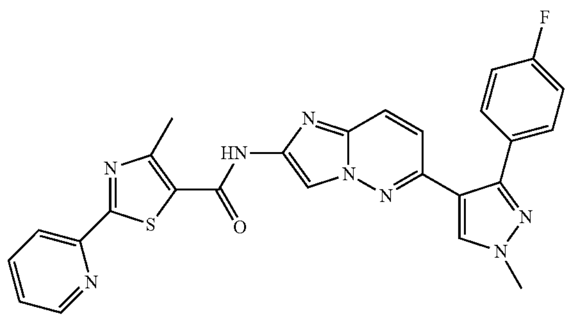 [SMILES: Cc1nc(-c2ccccn2)sc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methyl-2-(pyridin-2-yl)thiazol-5-carboxamide | 511.2 | 4.01 | A |
| 7 | 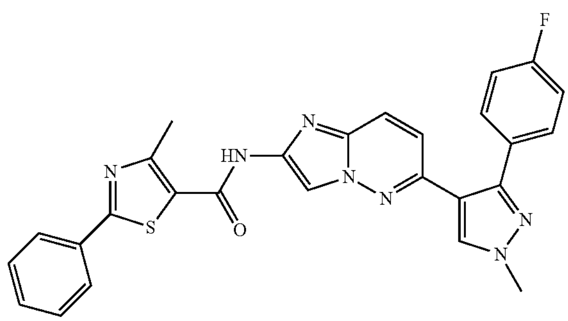 [SMILES: Cc1nc(-c2ccccc2)sc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methyl-2-phenylthiazol-5-carboxamide | 510.3 | 4.18 | A |
| 8 | 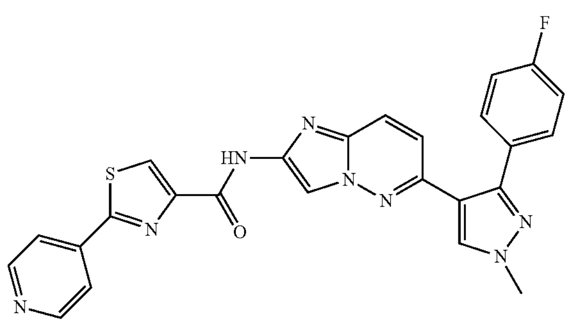 [SMILES: Cn1cc(-c2ccc3nc(NC(=O)c4csc(-c5ccncc5)n4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-2-(pyridin-4-yl)thiazole-4-carboxamide | 497.16 | 3.44 | B |
| 9 | 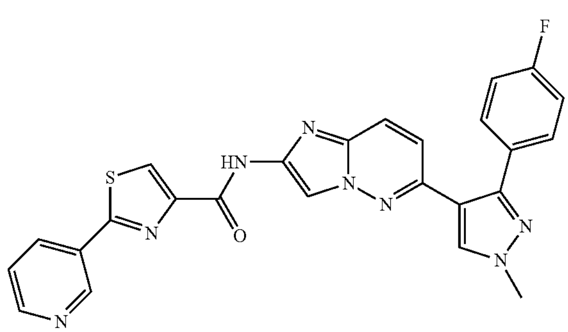 [SMILES: Cn1cc(-c2ccc3nc(NC(=O)c4csc(-c5cccnc5)n4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-2-(pyridin-3-yl)thiazol-4-carboxamide | 497.16 | 3.54 | B |

TABLE 1-continued

| Compound No. | Name | [M + H]+ | Ret time | HPLC Method |
|---|---|---|---|---|
| 10 | N-(6-(3-(4-fluorophenyl)-1-methyl-1H-pyrazol-4-yl)imidazo[1,2-b]pyridazin-2-yl)-2-phenylthiazole-2-carboxamide | 495.13 | 3.09/4.39 | C/D |
| 11 | 2-(4-chlorophenyl)-N-(6-(3-(4-fluorophenyl)-1-methyl-1H-pyrazol-4-yl)imidazo[1,2-b]pyridazin-2-yl)thiazol-4-carboxamide | 530.13 | 4.36 | B |
| 12 | N-(6-(3-(4-fluorophenyl)-1-methyl-1H-pyrazol-4-yl)imidazo[1,2-b]pyridazin-2-yl)-3-methylisoxazole-4-carboxamide | 418.18 | 3.59 | B |
| 13 | 2-bromo-N-(6-(3-(4-fluorophenyl)-1-methyl-1H-pyrazol-4-yl)imidazo[1,2-b]pyridazin-2-yl)thiazole-4-carboxamide | 498.07/500.07 | 3.94 | B |
| 14 | N-(6-(3-(4-fluorophenyl)-1-methyl-1H-pyrazol-4-yl)imidazo[1,2-b]pyridazin-2-yl)thiazole-4-carboxamide | 419.10 | 2.15/3.41 | C/D |

TABLE 1-continued

| Compound No. | Structure | Name | [M + H]⁺ | Ret time | HPLC Method |
|---|---|---|---|---|---|
| 15 | 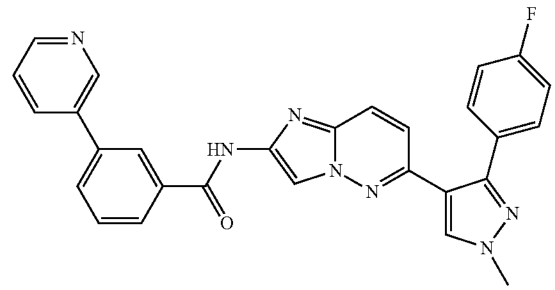 [SMILES: Cn1cc(-c2ccc3nc(NC(=O)c4cccc(-c5cccnc5)c4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-3-(pyridin-3-yl)benzamide | 489.17 | 2.67/ 3.97 | C/D |
| 16 | 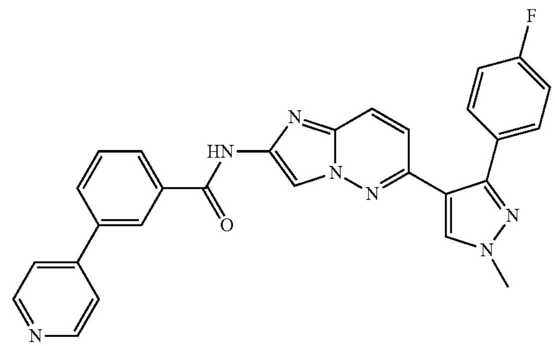 [SMILES: Cn1cc(-c2ccc3nc(NC(=O)c4cccc(-c5ccncc5)c4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-3-(pyridin-4-yl)benzamide | 489.17 | 2.71/ 4.00 | C/D |
| 17 | 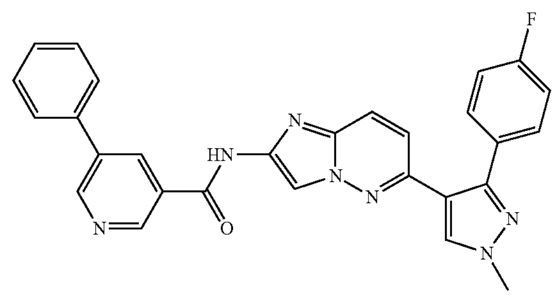 [SMILES: Cn1cc(-c2ccc3nc(NC(=O)c4cncc(-c5ccccc5)c4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-5-phenylnicotinamide | 489.17 | 2.89/ 4.23 | C/D |
| 18 | 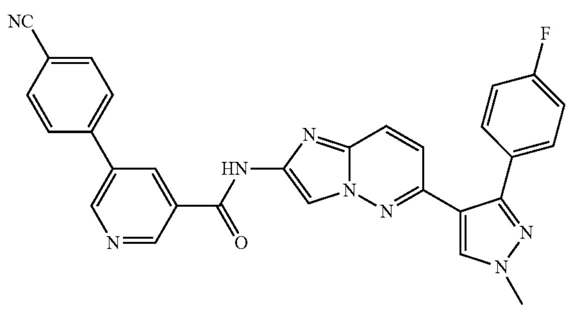 [SMILES: Cn1cc(-c2ccc3nc(NC(=O)c4cncc(-c5ccc(C#N)cc5)c4)cn3n2)c(-c2ccc(F)cc2)n1] | 5-(4-cyanophenyl)-N-(6-(3-(4-fluorophenyl)-1-methyl-1H-pyrazol-4-yl)imidazo[1,2-b]pyridazin-2-yl)nicotinamide | 514.17 | 2.76/ 4.01 | C/D |
| 19 | 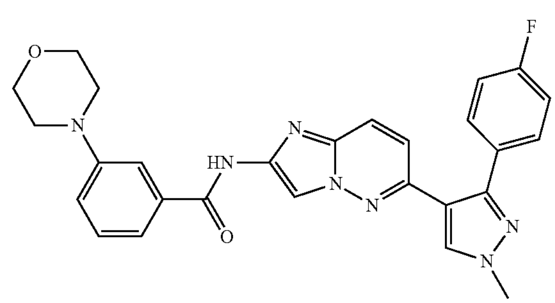 [SMILES: Cn1cc(-c2ccc3nc(NC(=O)c4cccc(N5CCOCC5)c4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-3-morpholinobenzamide | 497.20 | 2.55/ 3.92 | C/D |

TABLE 1-continued

| Compound No. | Name | [M + H]+ | Ret time | HPLC Method |
|---|---|---|---|---|
| 20 | 2-fluoro-N-(6-(3-(4-fluorophenyl)-1-methyl-1H-pyrazol-4-yl)imidazo[1,2-b]pyridazin-2-yl)benzamide | 431.15 | 2.37 | F |
| 21 | N-(6-(3-(4-fluorophenyl)-1-methyl-1H-pyrazol-4-yl)imidazo[1,2-b]pyridazin-2-yl)pyrimidine-2-carboxamide | 415.15 | 2.01 | F |
| 22 | N-(6-(3-(4-fluorophenyl)-1-methyl-1H-pyrazol-4-yl)imidazo[1,2-b]pyridazin-2-yl)isoxazole-5-carboxamide | 404.16 | 1.95 | F |
| 23 | 3-fluoro-N-(6-(3-(4-fluorophenyl)-1-methyl-1H-pyrazol-4-yl)imidazo[1,2-b]pyridazin-2-yl)benzamide | 431.13 | 2.41 | F |
| 24 | 4-chloro-2-fluoro-N-(6-(3-(4-fluorophenyl)-1-methyl-1H-pyrazol-4-yl)imidazo[1,2-b]pyridazin-2-yl)benzamide | 465.08 | 2.62 | F |

TABLE 1-continued

| Compound No. | Structure | Name | [M + H]+ | Ret time | HPLC Method |
|---|---|---|---|---|---|
| 25 | 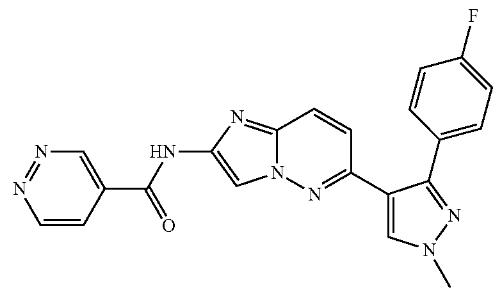 [SMILES: Cn1cc(-c2ccc3nc(NC(=O)c4ccnnc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)pyridazine-4-carboxamide | 415.16 | 1.77 | F |
| 26 | 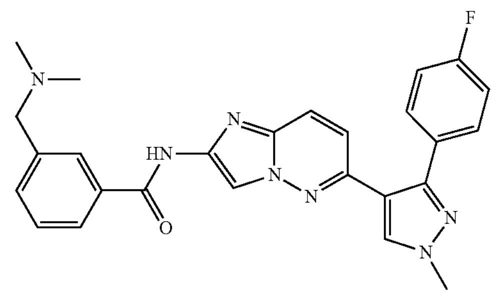 [SMILES: CN(C)Cc1cccc(C(=O)Nc2cn3nc(-c4cn(C)nc4-c4ccc(F)cc4)ccc3n2)c1] | 3-((dimethylamino)methyl)-N-(6-(3-(4-fluorophenyl)-1-methyl-1H-pyrazol-4-yl)imidazo[1,2-b]pyridazin-3-yl)benzamide | 470.19 | 1.85 | F |
| 27 | 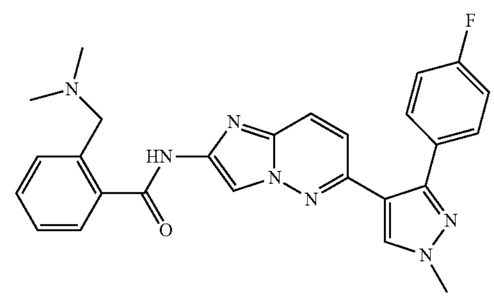 [SMILES: CN(C)Cc1ccccc1C(=O)Nc1cn2nc(-c3cn(C)nc3-c3ccc(F)cc3)ccc2n1] | 2-((dimethylamino)methyl)-N-(6-(3-(4-fluorophenyl)-1-methyl-1H-pyrazol-4-yl)imidazo[1,2-b]pyridazin-2-yl)benzamide | 470.20 | 2.20 | F |
| 28 | 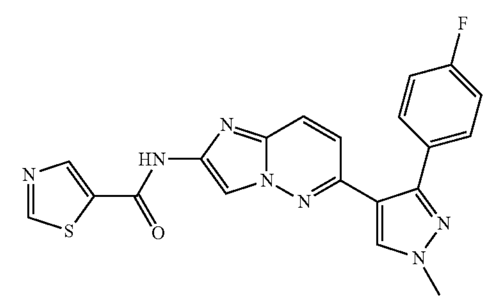 [SMILES: Cn1cc(-c2ccc3nc(NC(=O)c4cncs4)cn3n2)c(-c2ccc(F)cc2)n1] | N-(6-(3-(4-fluorophenyl)-1-methyl-1H-pyrazol-4-yl)imidazo[1,2-b]pyridazin-2-yl)thiazole-5-carboxamide | 420.04 | 1.96 | F |
| 29 | 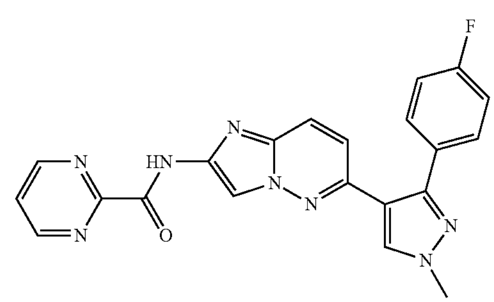 [SMILES: Cn1cc(-c2ccc3nc(NC(=O)c4ncccn4)cn3n2)c(-c2ccc(F)cc2)n1] | N-(6-(3-(4-fluorophenyl)-1-methyl-1H-pyrazol-4-yl)imidazo[1,2-b]pyridazin-2-yl)pyrimidine-2-carboxamide | 415.19 | 1.78 | F |

TABLE 1-continued

| Compound No. | Structure | Name | [M + H]⁺ | Ret time | HPLC Method |
|---|---|---|---|---|---|
| 30 | 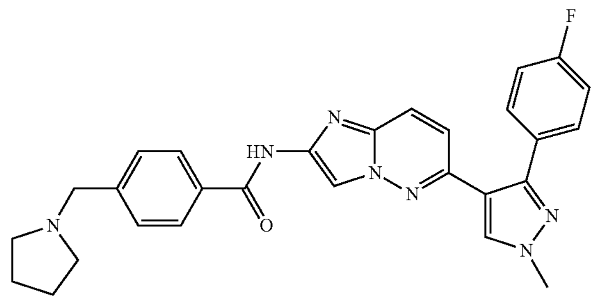 [SMILES: Cn1cc(-c2ccc3nc(NC(=O)c4ccc(CN5CCCC5)cc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-4-(pyrrolidin-1-ylmethyl)benzamide | 496.19 | 1.79 | F |
| 31 | 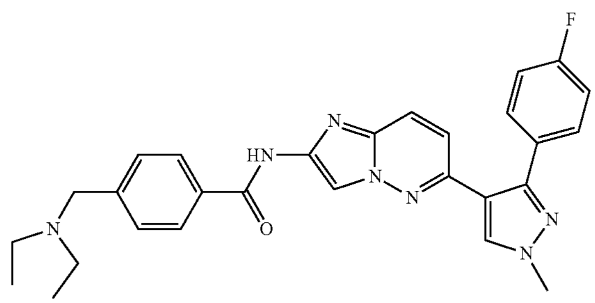 [SMILES: CCN(CC)Cc1ccc(C(=O)Nc2cn3nc(-c4cn(C)nc4-c4ccc(F)cc4)ccc3n2)cc1] | 4-((diethylamino)methyl)-N-(6-(3-(4-fluorophenyl)-1-methyl-1H-pyrazol-4-yl)imidazo[1,2-b]pyridazin-2-yl)benzamide | 498.22 | 1.91 | F |
| 32 | 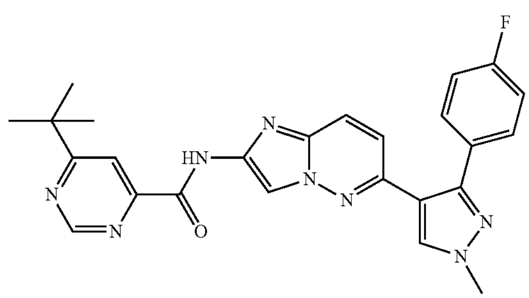 [SMILES: Cn1cc(-c2ccc3nc(NC(=O)c4cc(C(C)(C)C)ncn4)cn3n2)c(-c2ccc(F)cc2)n1] | 6-(tert-butyl)-N-(6-(3-(4-fluorophenyl)-1-methyl-1H-pyrazol-4-yl)imidazo[1,2-b]pyridazin-2-yl)pyrimidine-4-carboxamide | 471.18 | 2.85 | F |
| 33 | 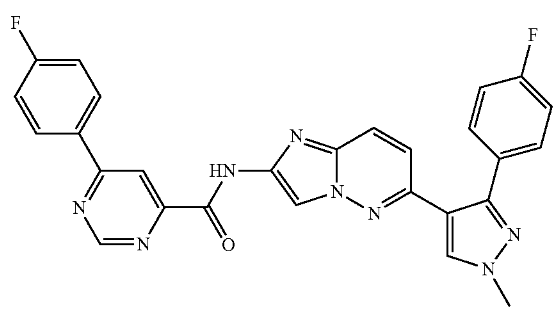 [SMILES: Cn1cc(-c2ccc3nc(NC(=O)c4cc(-c5ccc(F)cc5)ncn4)cn3n2)c(-c2ccc(F)cc2)n1] | 6-(4-fluorophenyl)-N-(6-(3-(4-fluorophenyl)-1-methyl-1H-pyrazol-4-yl)imidazo[1,2-b]pyridazin-2-yl)pyrimidine-4-carboxamide | 509.12 | 2.91 | F |
| 34 | 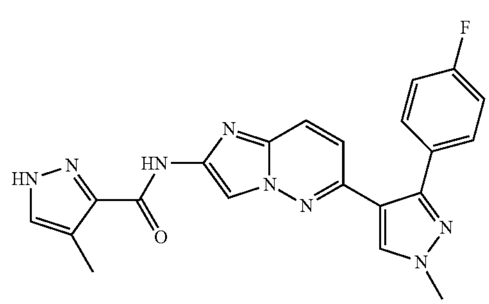 [SMILES: Cc1c[nH]nc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methyl-1H-pyrazol-3-carboxamide | 417.17 | 1.95 | F |

TABLE 1-continued

| Compound No. | Structure | Name | [M + H]+ | Ret time | HPLC Method |
|---|---|---|---|---|---|
| 35 | 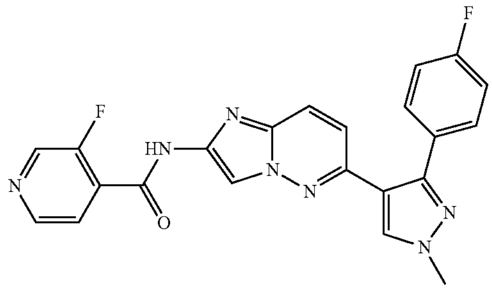 [SMILES: Cn1cc(-c2ccc3nc(NC(=O)c4ccncc4F)cn3n2)c(-c2ccc(F)cc2)n1] | 3-fluoro-N-(6-(3-(4-fluorophenyl)-1-methyl-1H-pyrazol-4-yl)imidazo[1,2-b]pyridazin-2-yl)isonicotinamide | 432.14 | 1.96 | F |
| 36 | 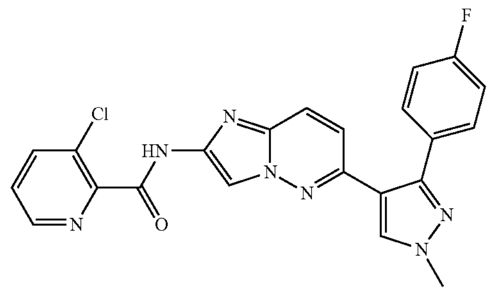 [SMILES: Cn1cc(-c2ccc3nc(NC(=O)c4ncccc4Cl)cn3n2)c(-c2ccc(F)cc2)n1] | 3-chloro-N-(6-(3-(4-fluorophenyl)-1-methyl-1H-pyrazol-4-yl)imidazo[1,2-b]pyridazin-2-yl)picolinamide | 448.10 | 1.99 | F |
| 37 | 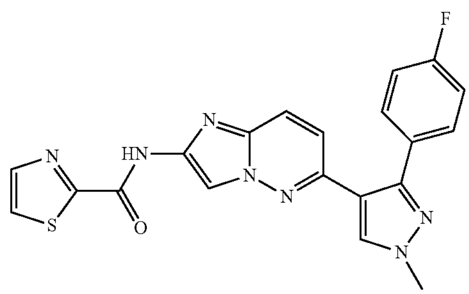 [SMILES: Cn1cc(-c2ccc3nc(NC(=O)c4nccs4)cn3n2)c(-c2ccc(F)cc2)n1] | N-(6-(3-(4-fluorophenyl)-1-methyl-1H-pyrazol-4-yl)imidazo[1,2-b]pyridazin-2-yl)thiazole-2-carboxamide | 420.12 | 1.93 | F |
| 38 | 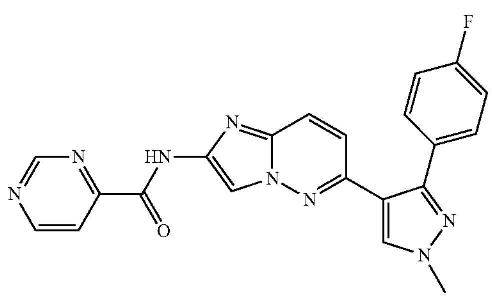 [SMILES: Cn1cc(-c2ccc3nc(NC(=O)c4ccncn4)cn3n2)c(-c2ccc(F)cc2)n1] | N-(6-(3-(4-fluorophenyl)-1-methyl-1H-pyrazol-4-yl)imidazo[1,2-b]pyridazin-2-yl)pyrimidine-4-carboxamide | 415.16 | 2.00 | F |
| 39 | 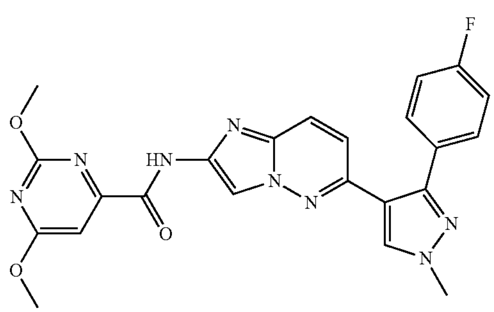 [SMILES: COc1cc(C(=O)Nc2cn3nc(-c4cn(C)nc4-c4ccc(F)cc4)ccc3n2)nc(OC)n1] | N-(6-(3-(4-fluorophenyl)-1-methyl-1H-pyrazol-4-yl)imidazo[1,2-b]pyridazin-2-yl)-2,6-dimethoxypyrimidine-4-carboxamide | 475.1 | 2.54 | F |

TABLE 1-continued

| Compound No. | Structure | Name | [M + H]+ | Ret time | HPLC Method |
|---|---|---|---|---|---|
| 40 | 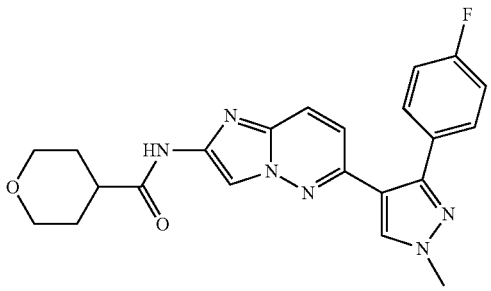 [SMILES: Cn1cc(-c2ccc3nc(NC(=O)C4CCOCC4)cn3n2)c(-c2ccc(F)cc2)n1] | N-(6-(3-(4-fluorophenyl)-1-methyl-1H-pyrazol-4-yl)imidazo[1,2-b]pyridazin-2-yl)tetrahydro-2H-pyran-4-carboxamide | 421.1 | 1.31 | C |
| 41 | 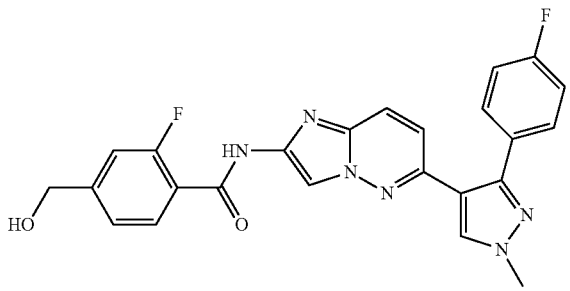 [SMILES: Cn1cc(-c2ccc3nc(NC(=O)c4ccc(CO)cc4F)cn3n2)c(-c2ccc(F)cc2)n1] | 2-fluoro-N-(6-(3-(4-fluorophenyl)-1-methyl-1H-pyrazol-4-yl)imidazo[1,2-b]pyridazin-2-yl)-4-(hydroxymethyl)benzamide | 461.15 | 1.98 | F |
| 42 | 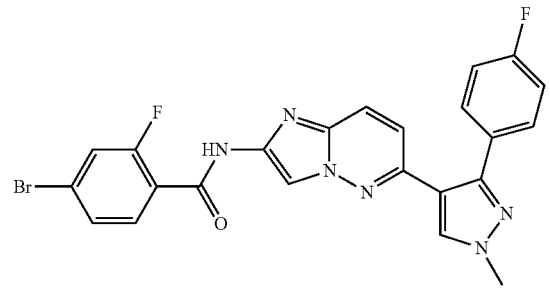 | 4-bromo-2-fluoro-N-(6-(3-(4-fluorophenyl)-1-methyl-1H-pyrazol-4-yl)imidazo[1,2-b]pyridazin-2-yl)benzamide | 509.09 | 2.60 | F |
| 43 | 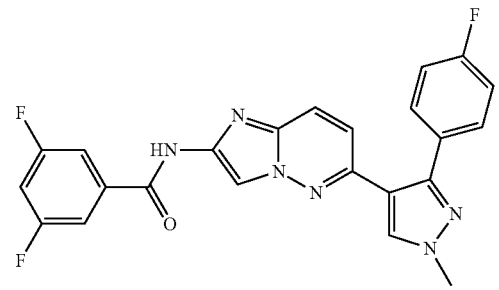 | 3,5-difluoro-N-(6-(3-(4-fluorophenyl)-1-methyl-1H-pyrazol-4-yl)imidazo[1,2-b]pyridazin-2-yl)benzamide | 448.93 | 1.82/ 1.80 | G/H |
| 44 | 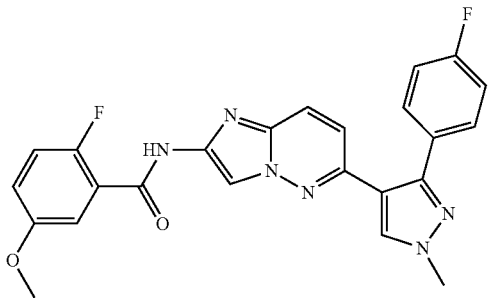 [SMILES: COc1ccc(F)c(C(=O)Nc2cn3nc(-c4cn(C)nc4-c4ccc(F)cc4)ccc3n2)c1] | 2-fluoro-N-(6-(3-(4-fluorophenyl)-1-methyl-1H-pyrazol-4-yl)imidazo[1,2-b]pyridazin-2-yl)-5-methoxybenzamide | 460.95 | 1.76/ 1.73 | G/H |

TABLE 1-continued

| Compound No. | Structure | Name | [M + H]+ | Ret time | HPLC Method |
|---|---|---|---|---|---|
| 45 | 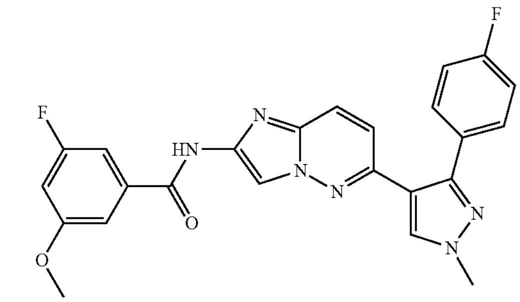 [SMILES: COc1cc(F)cc(C(=O)Nc2cn3nc(-c4cn(C)nc4-c4ccc(F)cc4)ccc3n2)c1] | 3-fluoro-N-(6-(3-(4-fluorophenyl)-1-methyl-1H-pyrazol-4-yl)imidazo[1,2-b]pyridazin-2-yl)-5-methoxybenzamide | 460.98 | 1.81/ 1.78 | G/H |
| 46 | 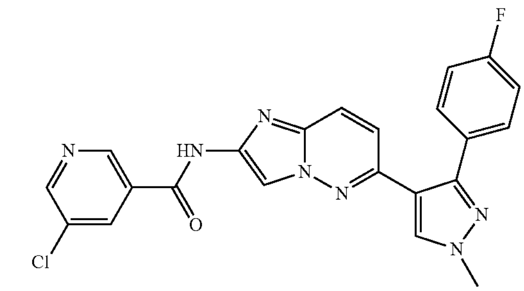 [SMILES: Cn1cc(-c2ccc3nc(NC(=O)c4cncc(Cl)c4)cn3n2)c(-c2ccc(F)cc2)n1] | 5-chloro-N-(6-(3-(4-fluorophenyl)-1-methyl-1H-pyrazol-4-yl)imidazo[1,2-b]pyridazin-2-yl)nicotinamide | 447.91 | 1.61/ 1.58 | G/H |
| 47 | 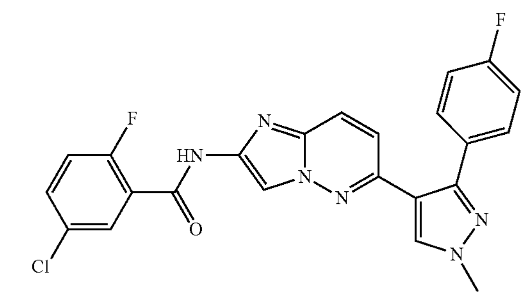 [SMILES: Cn1cc(-c2ccc3nc(NC(=O)c4cc(Cl)ccc4F)cn3n2)c(-c2ccc(F)cc2)n1] | 5-chloro-2-fluoro-N-(6-(3-(4-fluorophenyl)-1-methyl-1H-pyrazol-4-yl)imidazo[1,2-b]pyridazin-2-yl)benzamide | 464.91 | 1.88/ 1.86 | G/H |
| 48 | 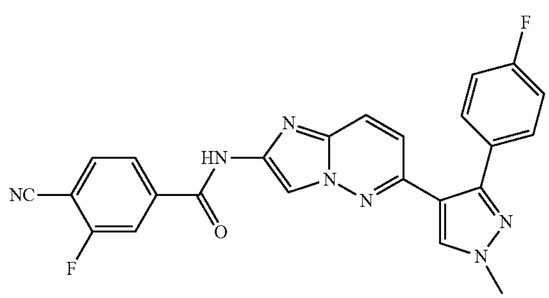 [SMILES: Cn1cc(-c2ccc3nc(NC(=O)c4ccc(C#N)c(F)c4)cn3n2)c(-c2ccc(F)cc2)n1] | 4-cyano-3-fluoro-N-(6-(3-(4-fluorophenyl)-1-methyl-1H-pyrazol-4-yl)imidazo[1,2-b]pyridazin-2-yl)benzamide | 455.95 | 1.72/ 1.71 | G/H |
| 49 | 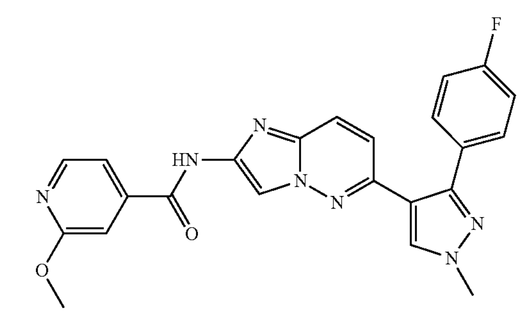 [SMILES: COc1cc(C(=O)Nc2cn3nc(-c4cn(C)nc4-c4ccc(F)cc4)ccc3n2)ccn1] | N-(6-(3-(4-fluorophenyl)-1-methyl-1H-pyrazol-4-yl)imidazo[1,2-b]pyridazin-2-yl)-2-methoxyisonicotinamide | 443.96 | 1.59/ 1.55 | G/H |

TABLE 1-continued

| Compound No. | Structure | Name | [M + H]+ | Ret time | HPLC Method |
|---|---|---|---|---|---|
| 50 | 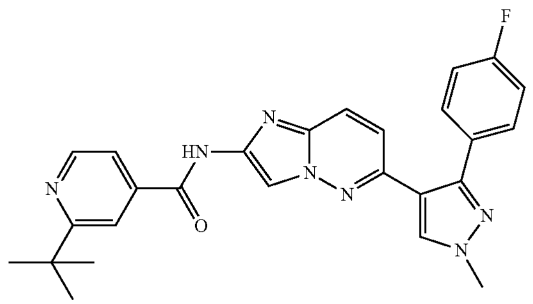 [SMILES: Cn1cc(-c2ccc3nc(NC(=O)c4ccnc(C(C)(C)C)c4)cn3n2)c(-c2ccc(F)cc2)n1] | 2-(tert-butyl)-N-(6-(3-(4-fluorophenyl)-1-methyl-1H-pyrazol-4-yl)imidazo[1,2-b]pyridazin-2-yl)isonicotinamide | 470.01 | 1.88/ 1.47 | G/H |
| 51 | 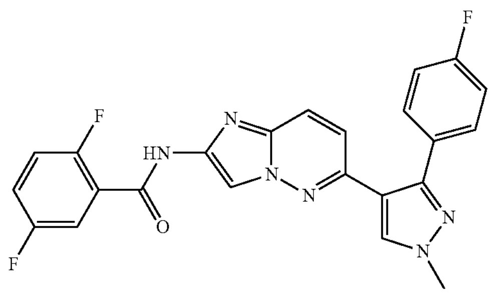 [SMILES: Cn1cc(-c2ccc3nc(NC(=O)c4cc(F)ccc4F)cn3n2)c(-c2ccc(F)cc2)n1] | 2,5-difluoro-N-(6-(3-(4-fluorophenyl)-1-methyl-1H-pyrazol-4-yl)imidazo[1,2-b]pyridazin-2-yl)benzamide | 448.94 | 1.75/ 1.73 | G/H |
| 52 | 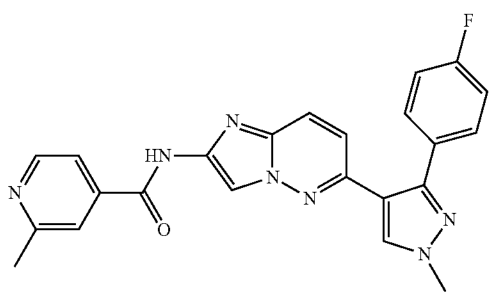 [SMILES: Cc1cc(C(=O)Nc2cn3nc(-c4cn(C)nc4-c4ccc(F)cc4)ccc3n2)ccn1] | N-(6-(3-(4-fluorophenyl)-1-methyl-1H-pyrazol-4-yl)imidazo[1,2-b]pyridazin-2-yl)-2-methylisonicotinamide | 427.99 | 1.43/ 1.11 | G/H |
| 53 | 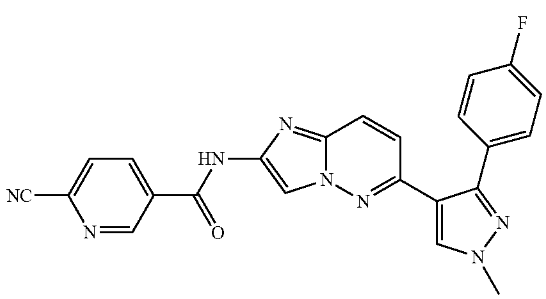 [SMILES: Cn1cc(-c2ccc3nc(NC(=O)c4ccc(C#N)nc4)cn3n2)c(-c2ccc(F)cc2)n1] | 6-cyano-N-(6-(3-(4-fluorophenyl)-1-methyl-1H-pyrazol-4-yl)imidazo[1,2-b]pyridazin-2-yl)nicotinamide | 438.96 | 1.50/ 1.49 | G/H |
| 54 | 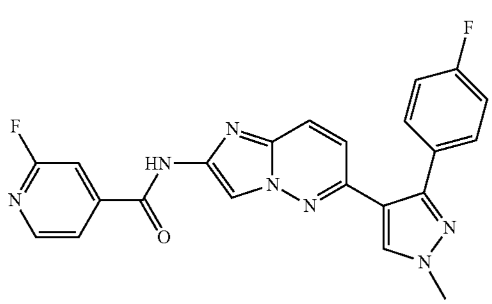 [SMILES: Cn1cc(-c2ccc3nc(NC(=O)c4ccnc(F)c4)cn3n2)c(-c2ccc(F)cc2)n1] | 2-fluoro-N-(6-(3-(4-fluorophenyl)-1-methyl-1H-pyrazol-4-yl)imidazo[1,2-b]pyridazin-2-yl)isonicotinamide | 431.93 | 1.53/ 1.52 | G/H |

TABLE 1-continued

| Compound No. | Structure | Name | [M + H]+ | Ret time | HPLC Method |
|---|---|---|---|---|---|
| 55 | 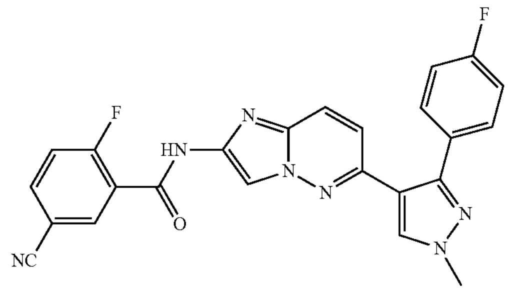 [SMILES: Cn1cc(-c2ccc3nc(NC(=O)c4cc(C#N)ccc4F)cn3n2)c(-c2ccc(F)cc2)n1] | 5-cyano-2-fluoro-N-(6-(3-(4-fluorophenyl)-1-methyl-1H-pyrazol-4-yl)imidazo[1,2-b]pyridazin-2-yl)benzamide | 455.94 | 1.61/1.60 | G/H |
| 56 | 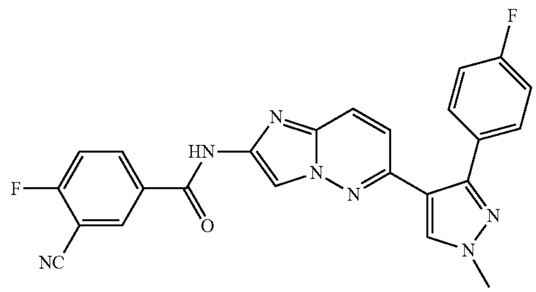 [SMILES: Cn1cc(-c2ccc3nc(NC(=O)c4ccc(F)c(C#N)c4)cn3n2)c(-c2ccc(F)cc2)n1] | 3-cyano-4-fluoro-N-(6-(3-(4-fluorophenyl)-1-methyl-1H-pyrazol-4-yl)imidazo[1,2-b]pyridazin-2-yl)benzamide | 455.93 | 1.70/1.68 | G/H |
| 57 | 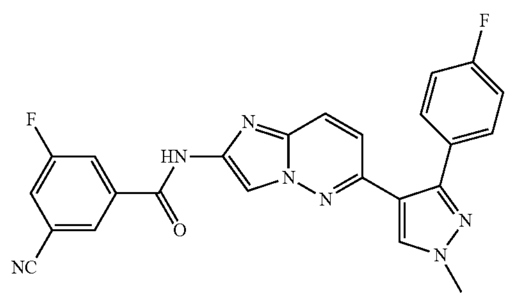 [SMILES: Cn1cc(-c2ccc3nc(NC(=O)c4cc(F)cc(C#N)c4)cn3n2)c(-c2ccc(F)cc2)n1] | 3-cyano-5-fluoro-N-(6-(3-(4-fluorophenyl)-1-methyl-1H-pyrazol-4-yl)imidazo[1,2-b]pyridazin-2-yl)benzamide | 455.94 | 1.73/1.71 | G/H |
| 58 | 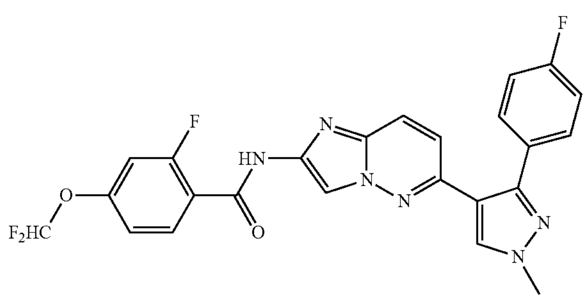 [SMILES: Cn1cc(-c2ccc3nc(NC(=O)c4ccc(OC(F)F)cc4F)cn3n2)c(-c2ccc(F)cc2)n1] | 4-(difluoromethoxy)-2-fluoro-N-(6-(3-(4-fluorophenyl)-1-methyl-1H-pyrazol-4-yl)imidazo[1,2-b]pyridazin-2-yl)benzamide | 496.95 | 1.83/1.81 | G/H |
| 59 | 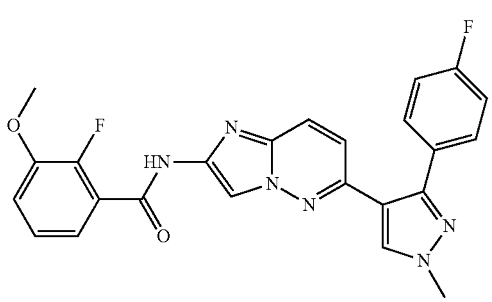 [SMILES: COc1cccc(C(=O)Nc2cn3nc(-c4cn(C)nc4-c4ccc(F)cc4)ccc3n2)c1F] | 2-fluoro-N-(6-(3-(4-fluorophenyl)-1-methyl-1H-pyrazol-4-yl)imidazo[1,2-b]pyridazin-2-yl)-3-methoxybenzamide | 460.96 | 1.69/1.67 | G/H |

TABLE 1-continued

| Compound No. | Structure | Name | [M + H]+ | Ret time | HPLC Method |
|---|---|---|---|---|---|
| 60 | 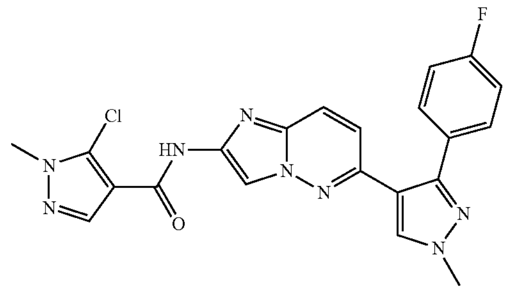 [SMILES: Cn1cc(-c2ccc3nc(NC(=O)c4cnn(C)c4Cl)cn3n2)c(-c2ccc(F)cc2)n1] | 5-chloro-N-(6-(3-(4-fluorophenyl)-1-methyl-1H-pyrazol-4-yl)imidazo[1,2-b]pyridazin-2-yl)-1-methyl-1H-pyrazole-4-carboxamide | 450.94 | 1.45/ 1.42 | G/H |
| 61 | 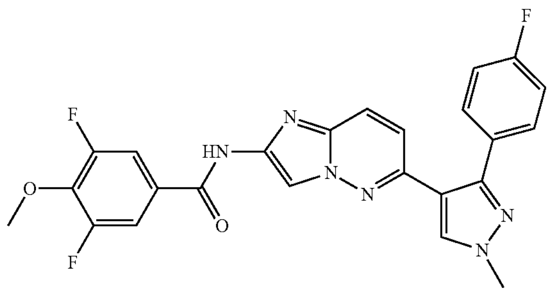 [SMILES: COc1c(F)cc(C(=O)Nc2cn3nc(-c4cn(C)nc4-c4ccc(F)cc4)ccc3n2)cc1F] | 3,5-difluoro-N-(6-(3-(4-fluorophenyl)-1-methyl-1H-pyrazol-4-yl)imidazo[1,2-b]pyridazin-2-yl)-4-methoxybenzamide | 478.95 | 1.78/ 1.76 | G/H |
| 62 | 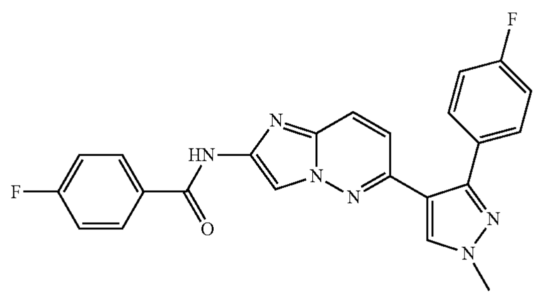 [SMILES: Cn1cc(-c2ccc3nc(NC(=O)c4ccc(F)cc4)cn3n2)c(-c2ccc(F)cc2)n1] | 4-fluoro-N-(6-(3-(4-fluorophenyl)-1-methyl-1H-pyrazol-4-yl)imidazo[1,2-b]pyridazin-2-yl)benzamide | 430.95 | 1.70/ 1.66 | G/H |
| 63 | 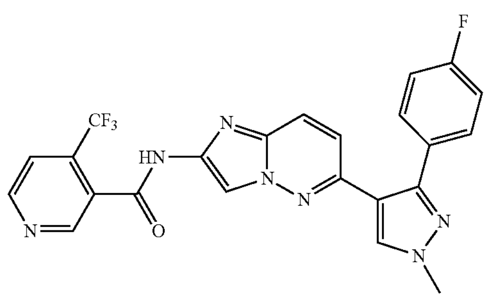 [SMILES: Cn1cc(-c2ccc3nc(NC(=O)c4cnccc4C(F)(F)F)cn3n2)c(-c2ccc(F)cc2)n1] | N-(6-(3-(4-fluorophenyl)-1-methyl-1H-pyrazol-4-yl)imidazo[1,2-b]pyridazin-2-yl)-4-(trifluoromethyl)nicotinamide | 481.94 | 1.54/ 1.54 | G/H |
| 64 | 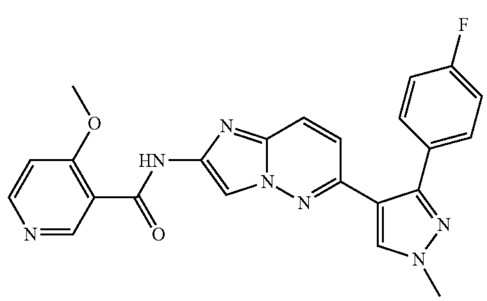 [SMILES: COc1ccncc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methoxynicotinamide | 444.12 | 1.40/ 1.10 | G/H |

TABLE 1-continued

| Compound No. | Structure | Name | [M + H]+ | Ret time | HPLC Method |
|---|---|---|---|---|---|
| 65 | 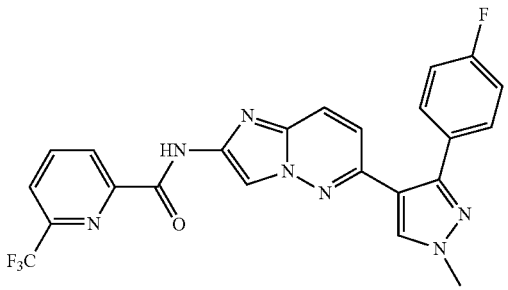 [SMILES: Cn1cc(-c2ccc3nc(NC(=O)c4cccc(C(F)(F)F)n4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-6-(trifluoromethyl)picolinamide | 482.10 | 1.91/ 1.88 | G/H |
| 66 | 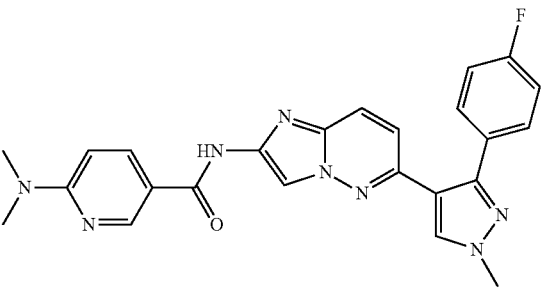 [SMILES: CN(C)c1ccc(C(=O)Nc2cn3nc(-c4cn(C)nc4-c4ccc(F)cc4)ccc3n2)cn1] | 6-(dimethylamino)-N-(6-(3-(4-fluorophenyl)-1-methyl-1H-pyrazol-4-yl)imidazo[1,2-b]pyridazin-2-yl)nicotinamide | 457.16 | 1.57/ 1.14 | G/H |
| 67 | 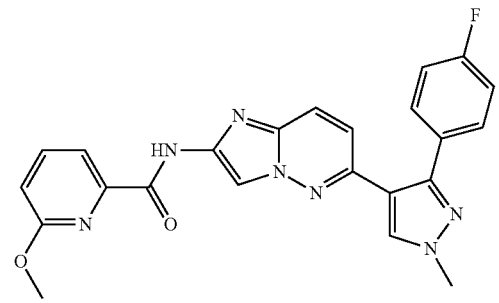 [SMILES: COc1cccc(C(=O)Nc2cn3nc(-c4cn(C)nc4-c4ccc(F)cc4)ccc3n2)n1] | N-(6-(3-(4-fluorophenyl)-1-methyl-1H-pyrazol-4-yl)imidazo[1,2-b]pyridazin-2-yl)-6-methoxypicolinamide | 444.11 | 1.82/ 1.78 | G/H |
| 68 | 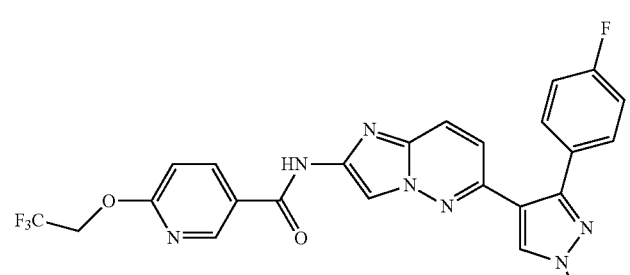 | N-(6-(3-(4-fluorrophenyl)-1-methyl-1H-pyrazol-4-yl)imidazo[1,2-b]pyridazin-2-yl)-6-(2,2,2-trifluoroethoxy)nicotinamide | 512.11 | 1.89/ 1.86 | G/H |
| 69 | 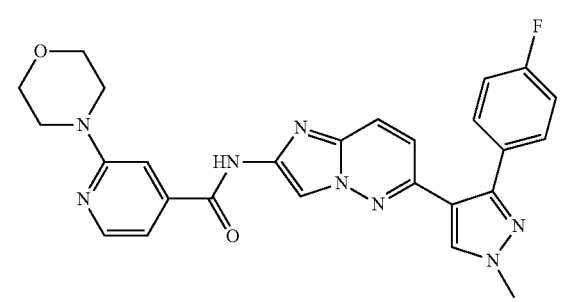 | N-(6-(3-(4-fluorophenyl)-1-methyl-1H-pyrazol-4-yl)imidazo[1,2-b]pyridazin-2-yl)-2-morpholinoisonicotinamide | 499.17 | 1.58/ 1.24 | G/H |

TABLE 1-continued

| Compound No. | Structure | Name | [M + H]+ | Ret time | HPLC Method |
|---|---|---|---|---|---|
| 70 | 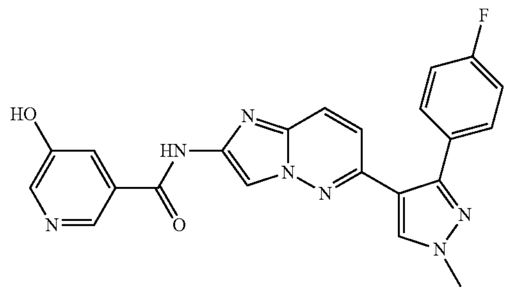 [SMILES: Cn1cc(-c2ccc3nc(NC(=O)c4cncc(O)c4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-5-hydroxynicotinamide | 430.11 | 1.26/ 1.13 | G/H |
| 71 | 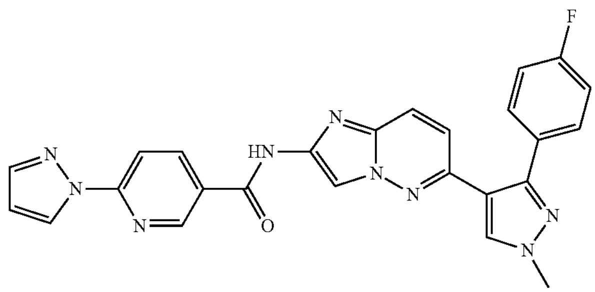 [SMILES: Cn1cc(-c2ccc3nc(NC(=O)c4ccc(-n5cccn5)nc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-6-(1H-pyrazol-1-yl)nicotinamide | 480.13 | 1.69/ 1.66 | G/H |
| 72 | 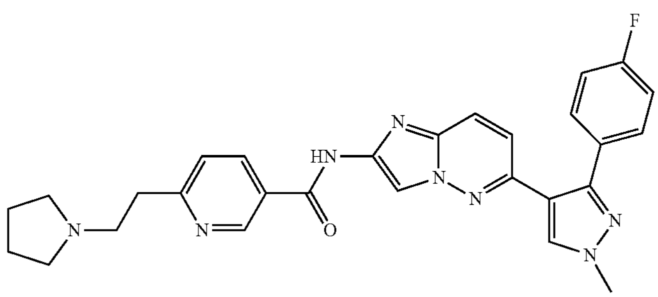 [SMILES: Cn1cc(-c2ccc3nc(NC(=O)c4ccc(CCN5CCCC5)nc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-6-(2-(pyrrolidin-1-yl)ethyl)nicotinamide | 511.18 | 1.28/ 1.17 | G/H |
| 73 | 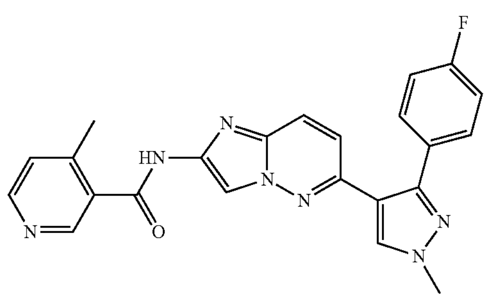 [SMILES: Cc1ccncc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-4-methylnicotinamide | 428.13 | 1.40/ 1.13 | G/H |
| 74 | 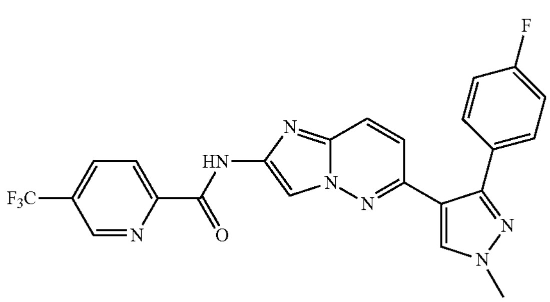 [SMILES: Cn1cc(-c2ccc3nc(NC(=O)c4ccc(C(F)(F)F)cn4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-5-(trifluoromethyl)picolinamide | 482.09 | 1.94/ 1.91 | G/H |

TABLE 1-continued

| Compound No. | Structure | Name | [M + H]+ | Ret time | HPLC Method |
|---|---|---|---|---|---|
| 75 | 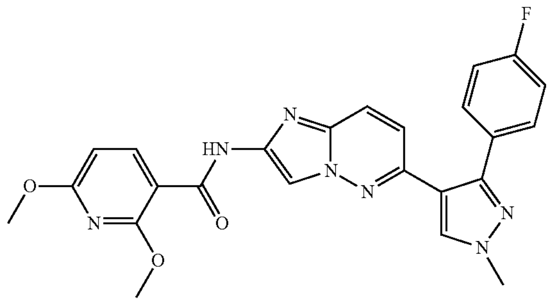 [SMILES: COc1ccc(C(=O)Nc2cn3nc(-c4cn(C)nc4-c4ccc(F)cc4)ccc3n2)c(OC)n1] | N-(6-(3-(4-fluorophenyl)-1-methyl-1H-pyrazol-4-yl)imidazo[1,2-b]pyridazin-2-yl)-2,6-dimethoxynicotinamide | 474.13 | 1.91/ 1.87 | G/H |
| 76 | 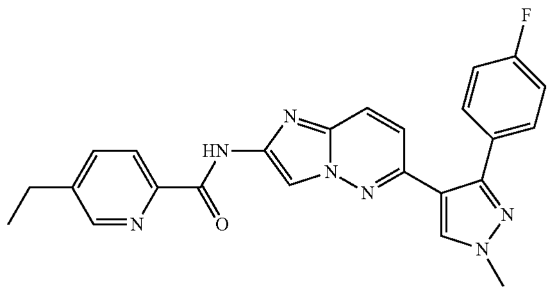 [SMILES: CCc1ccc(C(=O)Nc2cn3nc(-c4cn(C)nc4-c4ccc(F)cc4)ccc3n2)nc1] | 5-ethyl-N-(6-(3-(4-fluorrophenyl)-1-methyl-1H-pyrazol-4-yl)imidazo[1,2-b]pyridazin-2-yl)picolinamide | 442.14 | 1.91/ 1.86 | G/H |
| 77 | 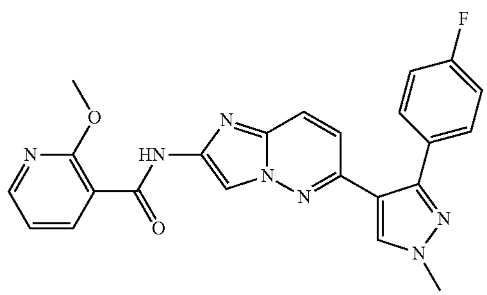 [SMILES: COc1ncccc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-2-methoxynicotinamide | 444.12 | 1.70/ 1.67 | G/H |
| 78 | 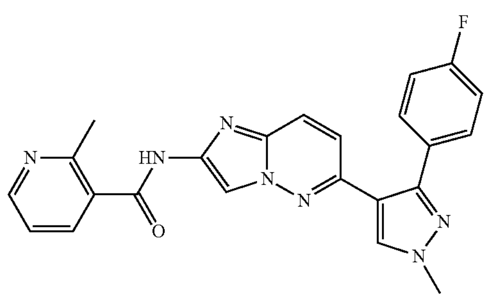 [SMILES: Cc1ncccc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-2-methylnicotinamide | 428.13 | 1.35/ 1.08 | G/H |
| 79 | 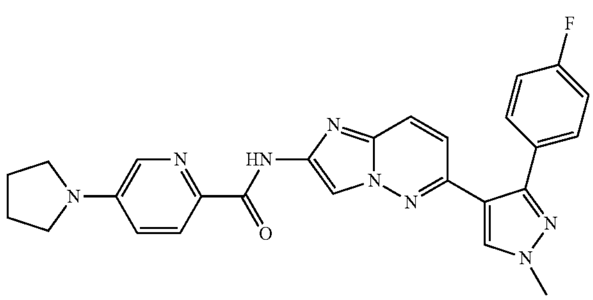 [SMILES: Cn1cc(-c2ccc3nc(NC(=O)c4ccc(N5CCCC5)cn4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-5-(pyrrolidin-1-yl)picolinamide | 483.15 | 1.96/ 1.80 | G/H |

TABLE 1-continued

| Compound No. | Structure | Name | [M + H]+ | Ret time | HPLC Method |
|---|---|---|---|---|---|
| 80 | 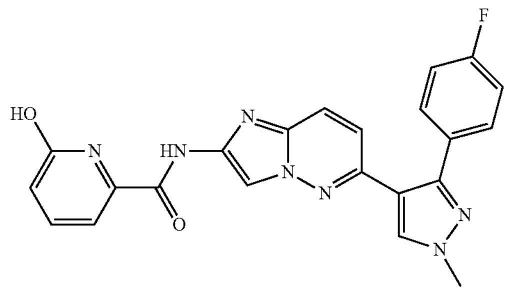 [SMILES: Cn1cc(-c2ccc3nc(NC(=O)c4cccc(O)n4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-6-hydroxypicolinamide | 430.10 | 1.75/1.74 | G/H |
| 81 | 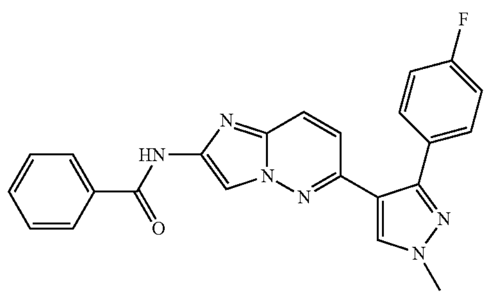 [SMILES: Cn1cc(-c2ccc3nc(NC(=O)c4ccccc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)benzamide | 412.80 | 2.233/2.187 | E/F |
| 82 | 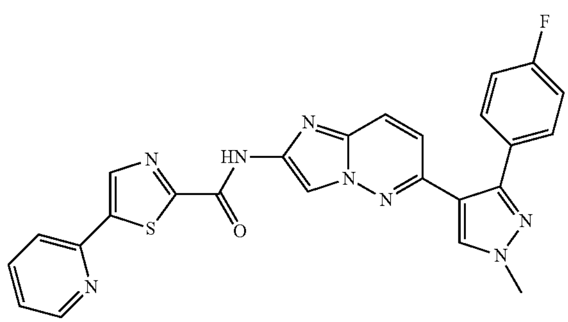 [SMILES: Cn1cc(-c2ccc3nc(NC(=O)c4ncc(-c5ccccn5)s4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-5-(pyridin-2-yl)thiazole-2-carboxamide | 497.09 | 1.801 | C |
| 83 | 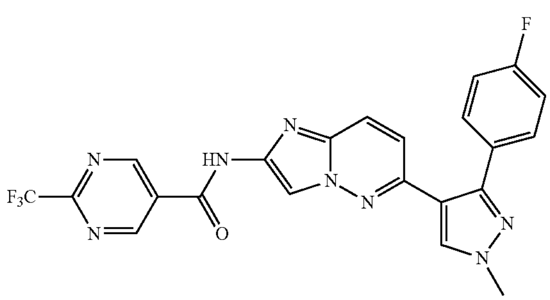 [SMILES: Cn1cc(-c2ccc3nc(NC(=O)c4cnc(C(F)(F)F)nc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-6-(trifluoromethyl)nicotinamide | 438.08 | 1.71 | C |
| 84 | 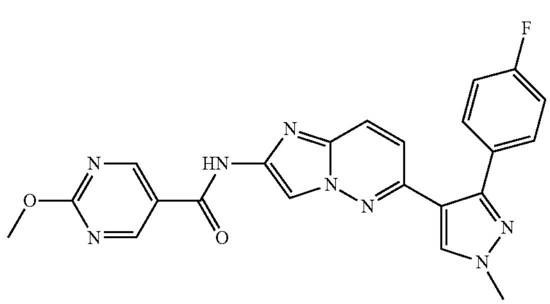 [SMILES: COc1ncc(C(=O)Nc2cn3nc(-c4cn(C)nc4-c4ccc(F)cc4)ccc3n2)cn1] | N-(6-(3-(4-fluorophenyl)-1-methyl-1H-pyrazol-4-yl)imidazo[1,2-b]pyridazin-2-yl)-2-methoxypyrimidine-5-carboxamide | 445.11 | 1.40 | C |

TABLE 1-continued

| Compound No. | Structure | Name | [M + H]+ | Ret time | HPLC Method |
|---|---|---|---|---|---|
| 85 | 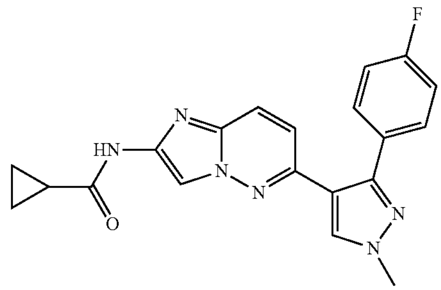 [SMILES: Cn1cc(-c2ccc3nc(NC(=O)C4CC4)cn3n2)c(-c2ccc(F)cc2)n1] | N-(6-(3-(4-fluorophenyl)-1-methyl-1H-pyrazol-4-yl)imidazo[1,2-b]pyridazin-2-yl)cyclopropanecarboxamide | 377.16 | 1.35 | C |
| 86 | 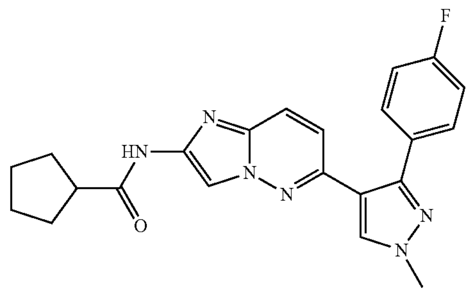 [SMILES: Cn1cc(-c2ccc3nc(NC(=O)C4CCCC4)cn3n2)c(-c2ccc(F)cc2)n1] | N-(6-(3-(4-fluorophenyl)-1-methyl-1H-pyrazol-4-yl)imidazo[1,2-b]pyridazin-2-yl)cyclopentanecarboxamide | 405.16 | 1.66 | C |
| 87 | 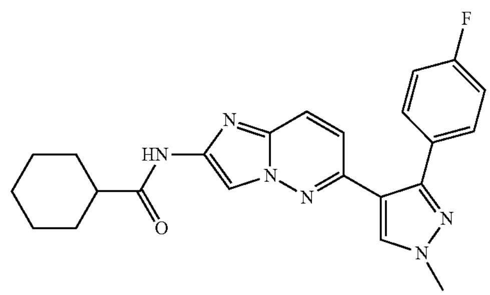 [SMILES: Cn1cc(-c2ccc3nc(NC(=O)C4CCCCC4)cn3n2)c(-c2ccc(F)cc2)n1] | N-(6-(3-(4-fluorophenyl)-1-methyl-1H-pyrazol-4-yl)imidazo[1,2-b]pyridazin-2-yl)cyclohexanecarboxamide | 419.18 | 1.72 | C |
| 88 | 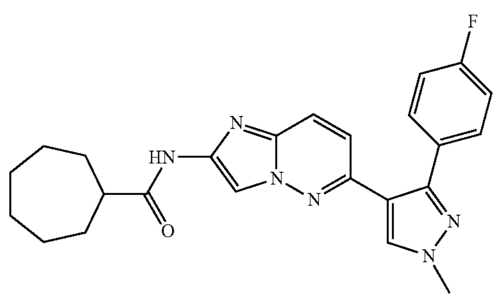 [SMILES: Cn1cc(-c2ccc3nc(NC(=O)C4CCCCCC4)cn3n2)c(-c2ccc(F)cc2)n1] | N-(6-(3-(4-fluorophenyl)-1-methyl-1H-pyrazol-4-yl)imidazo[1,2-b]pyridazin-2-yl)cyclopentanecarboxamide | 433.19 | 1.84 | C |
| 89 | 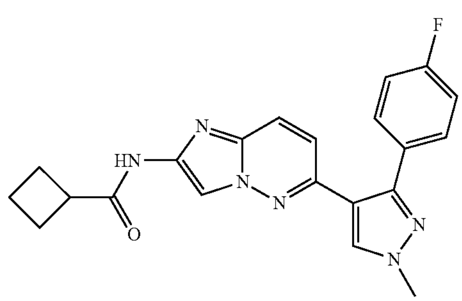 [SMILES: Cn1cc(-c2ccc3nc(NC(=O)C4CCC4)cn3n2)c(-c2ccc(F)cc2)n1] | N-(6-(3-(4-fluorophenyl)-1-methyl-1H-pyrazol-4-yl)imidazo[1,2-b]pyridazin-2-yl)cyclobutanecarboxamide | 391.18 | 1.53 | C |

TABLE 1-continued

| Compound No. | Structure | Name | [M + H]+ | Ret time | HPLC Method |
|---|---|---|---|---|---|
| 90 | 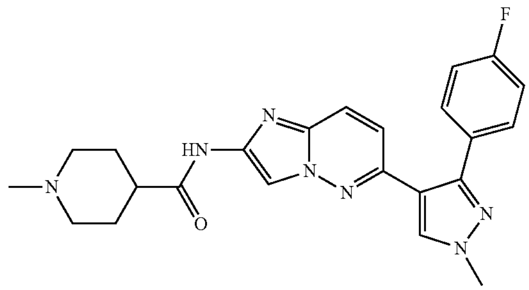 [SMILES: CN1CCC(C(=O)Nc2cn3nc(-c4cn(C)nc4-c4ccc(F)cc4)ccc3n2)CC1] | N-(6-(3-(4-fluorophenyl)-1-methyl-1H-pyrazol-4-yl)imidazo[1,2-b]pyridazin-2-yl)-1-methylpiepridine-4-carboxamide | 434.18 | 1.12 | C |
| 91 | 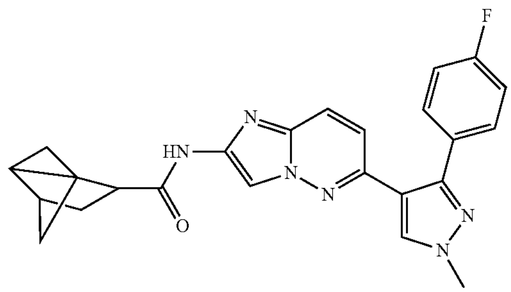 [SMILES: Cn1cc(-c2ccc3nc(NC(=O)C4CC5CC46CC56)cn3n2)c(-c2ccc(F)cc2)n1] | N-(6-(3-(4-fluorophenyl)-1-methyl-1H-pyrazol-4-yl)imidazo[1,2-b]pyridazin-2-yl)tricyclo[3.2.0.03,6]heptane-5-carboxamide | 457.18 | 1.99 | C |
| 92 | 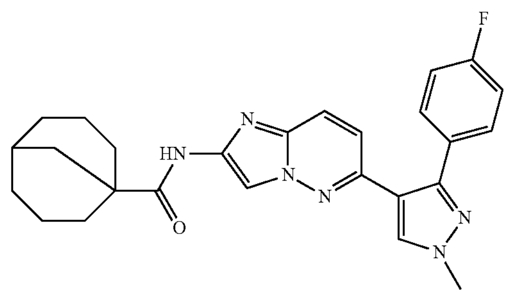 [SMILES: Cn1cc(-c2ccc3nc(NC(=O)C45CCCC(CCC4)C5)cn3n2)c(-c2ccc(F)cc2)n1] | N-(6-(3-(4-fluorophenyl)-1-methyl-1H-pyrazol-4-yl)imidazo[1,2-b]pyridazin-2-yl)bicyclo[3.3.1]nonane-1-carboxamide | 459.21 | 2.08 | C |
| 93 | 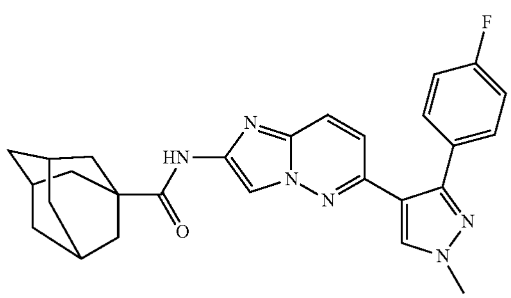 [SMILES: Cn1cc(-c2ccc3nc(NC(=O)C45CC6CC(CC(C6)C4)C5)cn3n2)c(-c2ccc(F)cc2)n1] | (3,5,7)-N-(6-(3-(4-fluorophenyl)-1-methyl-1H-pyrazol-4-yl)imidazo[1,2-b]pyridazin-2-yl)adamantane-1-carboxamide | 471.21 | 2.11 | C |
| 94 | 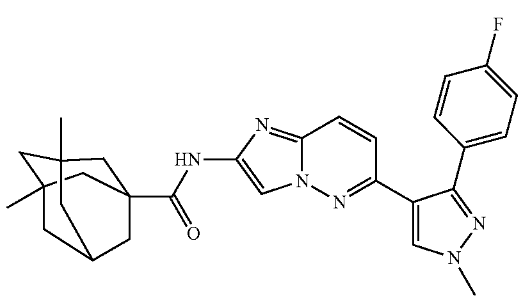 [SMILES: Cn1cc(-c2ccc3nc(NC(=O)C45CC6CC(C)(CC(C)(C6)C4)C5)cn3n2)c(-c2ccc(F)cc2)n1] | (1,3,5S7)-N-(6-(3-(4-fluorophenyl)-1-methyl-1H-pyrazol-4-yl)imidazo[1,2-b]pyridazin-2-yl)-3,5-dimethyladamantane-1-carboxamide | 499.29 | 2.38 | C |

TABLE 1-continued

| Compound No. | Structure | Name | [M + H]⁺ | Ret time | HPLC Method |
|---|---|---|---|---|---|
| 95 | 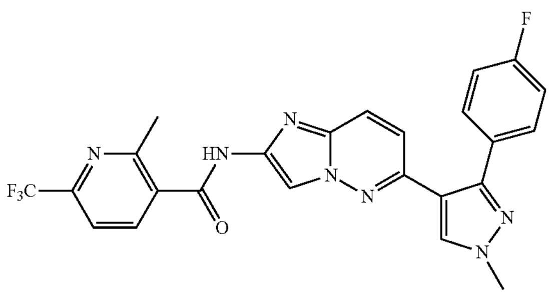 [SMILES: Cc1nc(C(F)(F)F)ccc1C(=O)Nc1cn2nc(-c3cn(C)nc3-c3ccc(F)cc3)ccc2n1] | N-(6-(3-(4-fluorophenyl)-1-methyl-1H-pyrazol-4-yl)imidazo[1,2-b]pyridazin-2-yl)-2-methyl-6-(trifluoromethyl)nicotinamide | 495.88 | 1.82 | C |
| 96 | 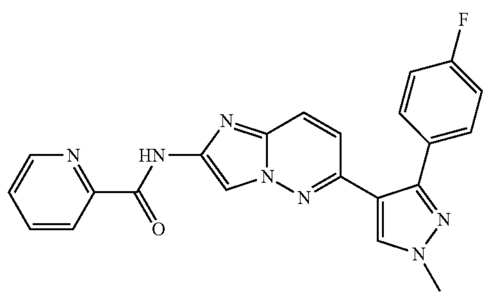 [SMILES: Cn1cc(-c2ccc3nc(NC(=O)c4ccccn4)cn3n2)c(-c2ccc(F)cc2)n1] | N-(6-(3-(4-fluorophenyl)-1-methyl-1H-pyrazol-4-yl)imidazo[1,2-b]pyridazin-2-yl)picolinamide | 414.00 | 3.55 | I |
| 97 | 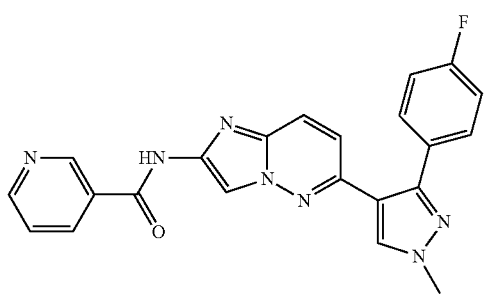 [SMILES: Cn1cc(-c2ccc3nc(NC(=O)c4cccnc4)cn3n2)c(-c2ccc(F)cc2)n1] | N-(6-(3-(4-fluorophenyl)-1-methyl-1H-pyrazol-4-yl)imidazo[1,2-b]pyridazin-2-yl)nicotinamide | 414.86 | 2.85 | I |
| 98 | 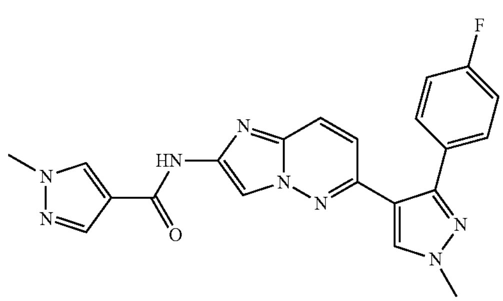 [SMILES: Cn1cc(C(=O)Nc2cn3nc(-c4cn(C)nc4-c4ccc(F)cc4)ccc3n2)cn1] | N-(6-(3-(4-fluorophenyl)-1-methyl-1H-pyrazol-4-yl)imidazo[1,2-b]pyridazin-2-yl)-1-methyl-1H-pyrazole-4-carboxamide | 417.00 | 0.77 | F |

TABLE 1-continued

| Compound No. | Structure | Name | [M + H]+ | Ret time | HPLC Method |
|---|---|---|---|---|---|
| 99 | 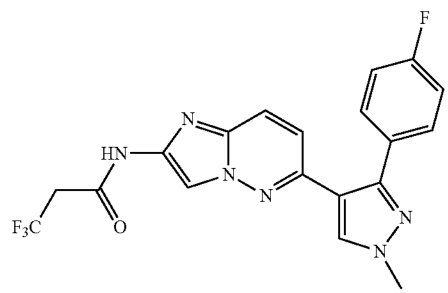 [SMILES: Cn1cc(-c2ccc3nc(NC(=O)CC(F)(F)F)cn3n2)c(-c2ccc(F)cc2)n1] | 3,3,3-trifluoro-N-(6-(3-(4-fluorophenyl)-1-methyl-1H-pyrazol-4-yl)imidazo[1,2-b]pyridazin-2-yl)propanamide | 419.12 | 1.69 | G/H |
| 100 | 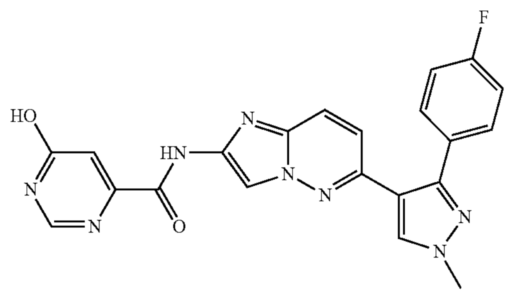 [SMILES: Cn1cc(-c2ccc3nc(NC(=O)c4cc(O)ncn4)cn3n2)c(-c2ccc(F)cc2)n1] | N-(6-(3-(4-fluorophenyl)-1-methyl-1H-pyrazol-4-yl)imidazo[1,2-b]pyridazin-2-yl)-6-hydroxypyrimidine-4-carboxamide | 431.07 | 1.21 | C |

Compound 101

N-(6-(1-Cyclopropyl-3-(4-fluorophenyl)-1H-pyrazol-4-yl)imidazo[1,2-b]pyridazin-2-yl)cyclopropanecarboxamide Compound 102

N-(6-(1-Cyclopropyl-3-(4-fluorophenyl)-1H-pyrazol-4-yl)imidazo[1,2-b]pyridazin-2-yl)isonicotinamide To a solution of 6-(1-cyclopropyl-3-(4-fluorophenyl)-1H-pyrazol-4-yl)imidazo[1,2-b]pyridazin-2-amine, 8 (50 mg, 0.15 mmol) in DMA (1 mL) was added cyclopropanecarbonyl chloride (30 mg, 0.3 mmol). The reaction mixture was diluted with MeOH and purified by prep. HPLC to give Compound 101 (44.8 mg, 45.6%) as a tan solid (2TFA salt). MS(ES): m/z=403.21 [M+H]+. HPLC Ret time (Method B): 3.65 min. $^1$H NMR (500 MHz, DMSO-$d_6$) δ 11.15 (s, 1H), 8.40 (s, 1H), 8.06 (s, 1H), 7.91 (dd, J=9.5, 0.6 Hz, 1H), 7.72-7.49 (m, 2H), 7.33-7.16 (m, 2H), 7.11 (d, J=9.3 Hz, 1H), 3.85 (dt, J=7.3, 3.7 Hz, 1H), 2.12-1.90 (m, 1H), 1.33-1.11 (m, 2H), 1.11-0.98 (m, 2H), 0.93-0.72 (m, 4H).

To a solution of 6-(1-cyclopropyl-3-(4-fluorophenyl)-1H-pyrazol-4-yl)imidazo[1,2-b]pyridazin-2-amine, Intermediate 8 (40 mg, 0.12 mmol) in DMA (1 mL) were added isonicotinoyl chloride, HCl (42.6 mg, 0.24 mmol) and pyridine (0.04 mL, 0.48 mmol). The reaction mixture was stirred at rt overnight, diluted with MeOH, and purified by prep. HPLC to give Compound 102 (38.8 mg, 47.1%) as a tan solid (2TFA salt). MS(ES): m/z=440.19 [M+H]+. HPLC Ret time (Method B): 3.42 min. $^1$H NMR (400 MHz, DMSO-$d_6$) δ 11.83 (s, 1H), 8.96-8.79 (m, 2H), 8.46 (s, 1H), 8.34 (s, 1H), 8.11-7.88 (m, 3H), 7.59 (dd, J=8.9, 5.6 Hz, 2H), 7.33-7.07 (m, 3H), 3.88 (s, 1H), 1.31-1.14 (m, 2H), 1.06 (dd, J=7.4, 2.4 Hz, 2H).

Compound 103

N-(6-(1-Cyclopropyl-3-(4-fluorophenyl)-1H-pyrazol-4-yl)imidazo[1,2-b]pyridazin-2-yl)-2-(pyridin-4-yl)thiazole-4-carboxamide

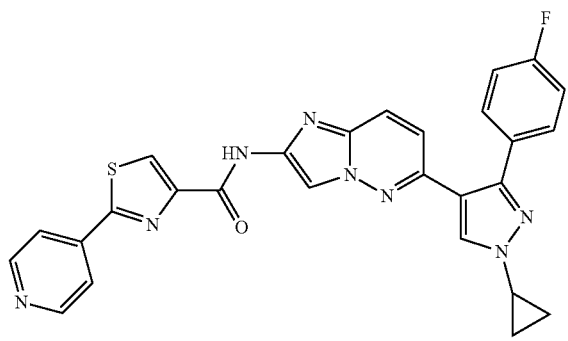 [SMILES: O=C(Nc1cn2nc(-c3cn(C4CC4)nc3-c3ccc(F)cc3)ccc2n1)c1csc(-c2ccncc2)n1]

To a solution of 6-(1-cyclopropyl-3-(4-fluorophenyl)-1H-pyrazol-4-yl)imidazo[1,2-b]pyridazin-2-amine, Intermediate 8 (50 mg, 0.15 mmol) in DMF (1 mL) were added 2-(pyridin-4-yl)thiazole-4-carboxylic acid (67.6 mg, 0.299 mmol), HATU (114 mg, 0.299 mmol), and Hunig's Base (0.104 mL, 0.589 mmol). The reaction mixture was stirred at rt overnight, diluted with MeOH, and purified by prep. HPLC to give Compound 103 (45.8 mg, 35.1%) as a white solid (3 TFA salt). MS(ES): m/z=523.24 [M+H]⁺. HPLC Ret time (Method B): 3.60 min. $^1$H NMR (400 MHz, DMSO-d$_6$) δ 11.31 (s, NH, 1H), 9.10-8.85 (m, 2H), 8.81 (s, 1H), 8.53-8.37 (m, 3H), 8.34 (s, 1H), 8.01 (dd, J=9.4, 0.6 Hz, 1H), 7.60 (dd, J=8.9, 5.6 Hz, 2H), 7.39-7.17 (m, 3H), 3.89 (m, 1H), 1.33-1.14 (m, 2H), 1.14-0.98 (m, 2H).

The following compounds in Table 2 were prepared by the procedure described for the preparation of compound 1 using Intermediate 8 and the corresponding acids.

TABLE 2

| Compound No. | Structure | Name | [M + H]⁺ | Ret time | HPLC Method |
|---|---|---|---|---|---|
| 104 | 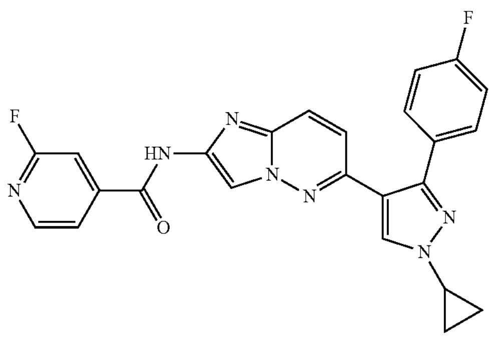 [SMILES: O=C(Nc1cn2nc(-c3cn(C4CC4)nc3-c3ccc(F)cc3)ccc2n1)c1ccnc(F)c1] | N-(6-(1-cyclopropyl-3-(4-fluorophenyl)-1H-pyrazol-4-yl)imidazo[1,2-b]pyridazin-2-yl)-2-fluoroisonicotinamide | 458.2 | 3.87 | A |
| 105 | 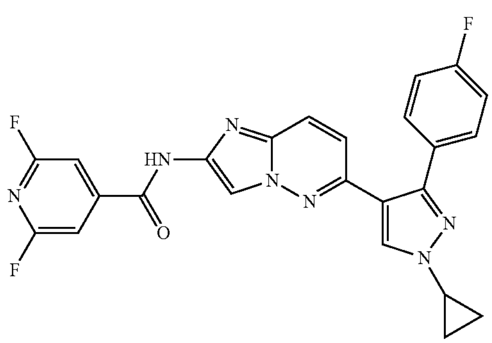 [SMILES: O=C(Nc1cn2nc(-c3cn(C4CC4)nc3-c3ccc(F)cc3)ccc2n1)c1cc(F)nc(F)c1] | N-(6-(1-cyclopropyl-3-(4-fluorophenyl)-1H-pyrazol-4-yl)imidazo[1,2-b]pyridazin-2-yl)-2,6-difluoroisonicotinamide | 476.3 | 4.08 | A |

TABLE 2-continued

| Compound No. | Structure | Name | [M + H]+ | Ret time | HPLC Method |
|---|---|---|---|---|---|
| 106 | 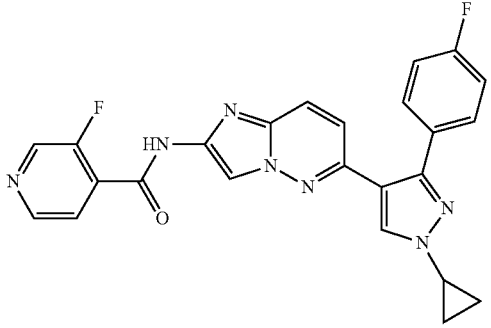 [SMILES: O=C(Nc1cn2nc(-c3cn(C4CC4)nc3-c3ccc(F)cc3)ccc2n1)c1ccncc1F] | N-(6-(1-cyclopropyl-3-(4-fluorophenyl)-1H-pyrazol-4-yl)imidazo[1,2-b]pyridazin-2-yl)-3-fluoroisonicotinamide | 458.17 | 3.73 | B |
| 107 | 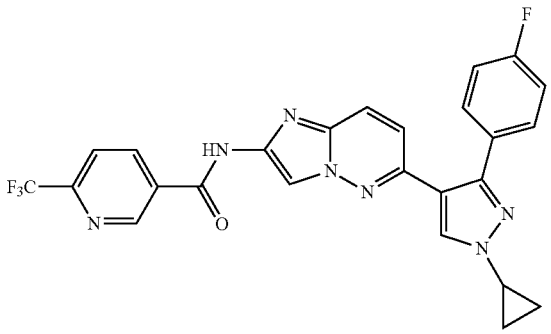 [SMILES: O=C(Nc1cn2nc(-c3cn(C4CC4)nc3-c3ccc(F)cc3)ccc2n1)c1ccc(C(F)(F)F)nc1] | N-(6-(1-cyclopropyl-3-(4-fluorophenyl)-1H-pyrazol-4-yl)imidazo[1,2-b]pyridazin-2-yl)-6-(trifluoromethyl)nicotinamide | 508.3 | 4.06 | A |
| 108 | 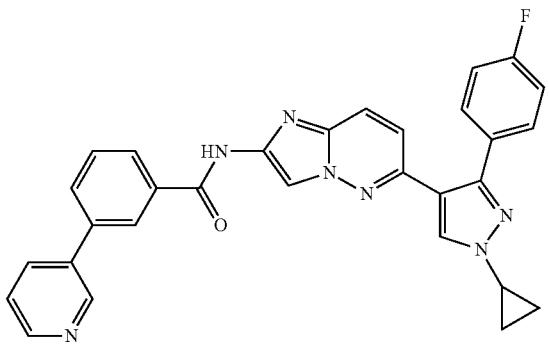 [SMILES: O=C(Nc1cn2nc(-c3cn(C4CC4)nc3-c3ccc(F)cc3)ccc2n1)c1cccc(-c2cccnc2)c1] | N-(6-(1-cyclopropyl-3-(4-fluorophenyl)-1H-pyrazol-4-yl)imidazo[1,2-b]pyridazin-2-yl)-3-(pyridin-3-yl)benzamide | 516.3 | 4.29 | A |
| 109 | 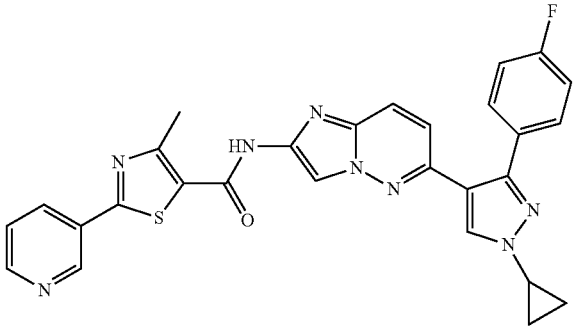 [SMILES: Cc1nc(-c2cccnc2)sc1C(=O)Nc1cn2nc(-c3cn(C4CC4)nc3-c3ccc(F)cc3)ccc2n1] | N-(6-(1-cyclopropyl-3-(4-fluorophenyl)-1H-pyrazol-4-yl)imidazo[1,2-b]pyridazin-2-yl)-4-methyl-2-(pyridin-3-yl)thiazole-5-carboxamide | 537.2 | 4.08 | A |

TABLE 2-continued

| Compound No. | Structure | Name | [M + H]+ | Ret time | HPLC Method |
|---|---|---|---|---|---|
| 110 | 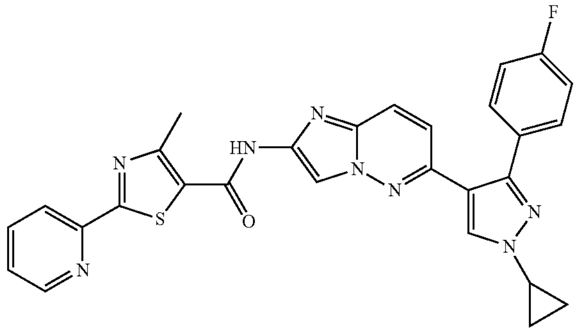 [SMILES: Cc1nc(-c2ccccn2)sc1C(=O)Nc1cn2nc(-c3cn(C4CC4)nc3-c3ccc(F)cc3)ccc2n1] | N-(6-(1-cyclopropyl-3-(4-fluorophenyl)-1H-pyrazol-4-yl)imidazo[1,2-b]pyridazin-2-yl)-4-methyl-2-(pyridin-2-yl)thiazole-5-carboxamide | 537.2 | 4.18 | A |
| 111 | 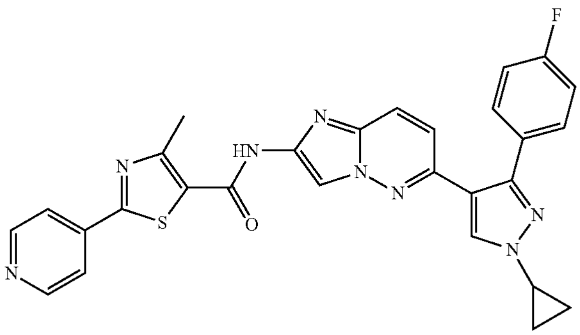 [SMILES: Cc1nc(-c2ccncc2)sc1C(=O)Nc1cn2nc(-c3cn(C4CC4)nc3-c3ccc(F)cc3)ccc2n1] | N-(6-(1-cyclopropyl-3-(4-fluorophenyl)-1H-pyrazol-4-yl)imidazo[1,2-b]pyridazin-2-yl)-4-methyl-2-(pyridin-4-yl)thiazole-5-carboxamide | 535.3 (M − H)+ | 4.10 | A |
| 112 | 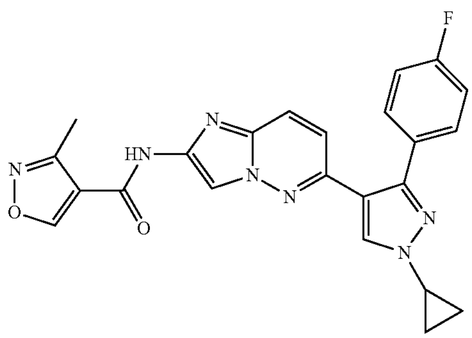 [SMILES: Cc1nocc1C(=O)Nc1cn2nc(-c3cn(C4CC4)nc3-c3ccc(F)cc3)ccc2n1] | N-(6-(1-cyclopropyl-3-(4-fluorophenyl)-1H-pyrazol-4-yl)imidazo[1,2-b]pyridazin-2-yl)-3-methylisoxazole-4-carboxamide | 440.20 | 3.84 | B |

Compound 113 tert-Butyl 4-(4-(2-(2-fluoroisonicotinamido)imidazo[1,2-b]pyridazin-6-yl)-3-(4-fluorophenyl)-1-methyl-1H-pyrazol-5-yl)piperazine-1-carboxylate

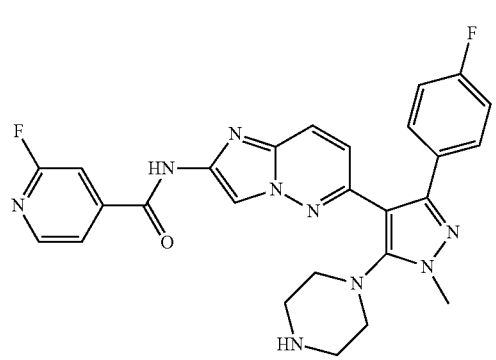

Compound 113A: tert-Butyl 4-(4-(2-(2-fluoroisonicotinamido)imidazo[1,2-b]pyridazin-6-yl)-3-(4-fluorophenyl)-1-methyl-1H-pyrazol-5-yl)piperazine-1-carboxylate

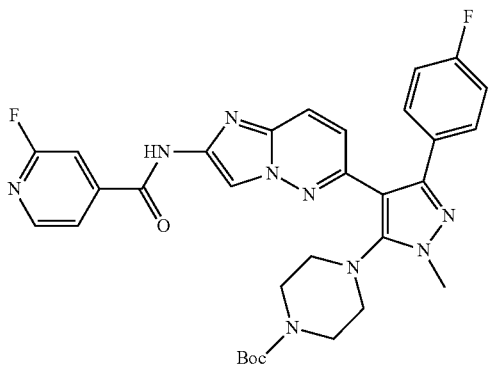 [SMILES: Cn1nc(-c2ccc(F)cc2)c(-c2ccc3nc(NC(=O)c4ccnc(F)c4)cn3n2)c1N1CCN(C(=O)OC(C)(C)C)CC1]

To a solution of 2-fluoroisonicotinic acid (160 mg, 1.137 mmol) and tert-butyl 4-(4-(2-aminoimidazo[1,2-b]pyridazin-6-yl)-3-(4-fluorophenyl)-1-methyl-1H-pyrazol-5-yl)piperazine-1-carboxylate 9 (280 mg, 0.568 mmol) in DMF (5 mL) was added Hunig's Base (0.397 mL, 2.274 mmol) and HATU (432 mg, 1.137 mmol). The reaction mixture was stirred at rt overnight, quenched with water and the precipitate was collected by filtration. Intermediate 9A was obtained as a tan powder (250 mg, 71.4%), which was used for the next step without further purification. MS(ES): m/z=614.3 [M−H]+. HPLC Ret time (Method A): 4.27 min.

Compound 113: tert-Butyl 4-(4-(2-(2-fluoroisonicotinamido)imidazo[1,2-b]pyridazin-6-yl)-3-(4-fluorophenyl)-1-methyl-1H-pyrazol-5-yl)piperazine-1-carboxylate

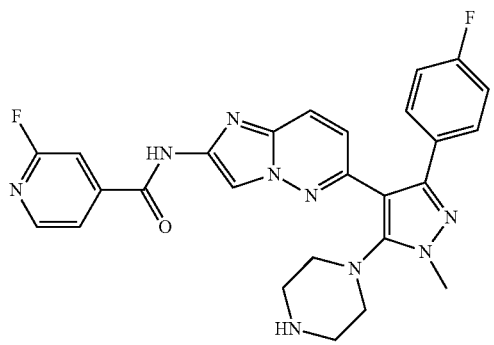 [SMILES: Cn1nc(-c2ccc(F)cc2)c(-c2ccc3nc(NC(=O)c4ccnc(F)c4)cn3n2)c1N1CCNCC1]

To a solution of tert-butyl 4-(4-(2-(2-fluoroisonicotinamido)imidazo[1,2-b]pyridazin-6-yl)-3-(4-fluorophenyl)-1-methyl-1H-pyrazol-5-yl)piperazine-1-carboxylate, Compound 113A (250 mg, 0.406 mmol) in CH$_2$Cl$_2$ (10 ml) was added TFA (2 ml). The reaction mixture was stirred at rt overnight and concentrated. The residue was dissolved in 20% MeOH/CHCl$_3$, washed with sodium bicarbonate, water, dried over anhydrous sodium sulfate, filtered, and concentrated under reduced pressure. The crude product was purified by BIOTAGE® (80-100% B/CH$_2$Cl$_2$, B: 10% MeOH/CH$_2$Cl$_2$) to yield Compound 113 (144 mg, 69%) as a brown oil. MS(ES): m/z=516.09 [M+H]+. HPLC Ret time (Method B): 3.26 min. $^1$H NMR (400 MHz, DMSO-d$_6$) δ 11.95 (s, NH, 1H), 8.78-8.60 (m, 3H including NH), 8.49 (d, J=5.0 Hz, 1H), 8.12-7.90 (m, 2H), 7.82 (s, 1H), 7.46-7.33 (m, 2H), 7.23-7.09 (m, 2H), 6.96 (d, J=9.3 Hz, 1H), 3.85 (s, 3H), 3.26-3.07 (m, 8H).

Compound 114

2-Fluoro-N-(6-(3-(4-fluorophenyl)-1-methyl-5-(4-(3,3,3-trifluoropropyl)piperazin-1-yl)-1H-pyrazol-4-yl)imidazo[1,2-b]pyridazin-2-yl)isonicotinamide

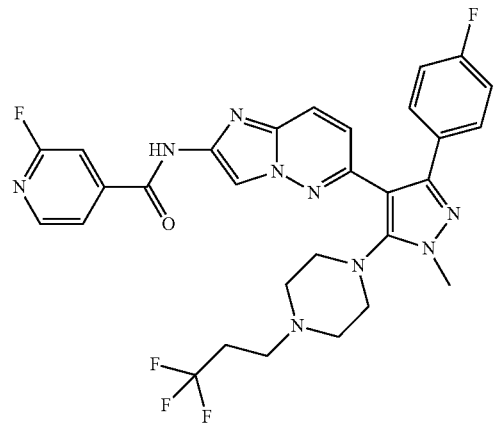 [SMILES: Cn1nc(-c2ccc(F)cc2)c(-c2ccc3nc(NC(=O)c4ccnc(F)c4)cn3n2)c1N1CCN(CCC(F)(F)F)CC1]

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113, (30 mg, 0.058 mmol), and 3,3,3-trifluoropropanal (13 mg, 0.116 mmol) in MeOH was added sodium cyanoborohydride (0.18 mL, 0.18 mmol, 1M THF solution). The reaction mixture was stirred at rt overnight and concentrated under reduced pressure. The residue was dissolved in DMF and purified by prep HPLC to give Compound 114 (11.5 mg, 24%). MS(ES): m/z=678.32 [M+H]+. HPLC Ret time (Method B): 3.08 min. $^1$H NMR (500 MHz, DMSO-d$_6$) δ 11.68 (s, NH, 1H), 8.49 (s, 1H), 8.31 (d, J=5.2 Hz, 1H), 8.00 (d, J=9.2 Hz, 1H), 7.51 (s, 1H), 7.38-7.29 (m, 2H), 7.25 (d, J=5.2 Hz, 1H), 7.12 (t, J=9.0 Hz, 2H), 7.04 (d, J=9.2 Hz, 1H), 3.97 (s, 3H), 3.82-3.70 (m, 4H), 3.66-3.50 (m, 4H), 2.11-1.94 (m, 2H), 1.84-1.71 (m, 2H).

The following compounds in Table 3 were prepared by the procedure described for the preparation of Compound 114 using Compound 113 and the corresponding aldehydes.

TABLE 3

| Compound No. | Structure | Name | [M + H]+ | Ret time | HPLC Method |
|---|---|---|---|---|---|
| 115 | 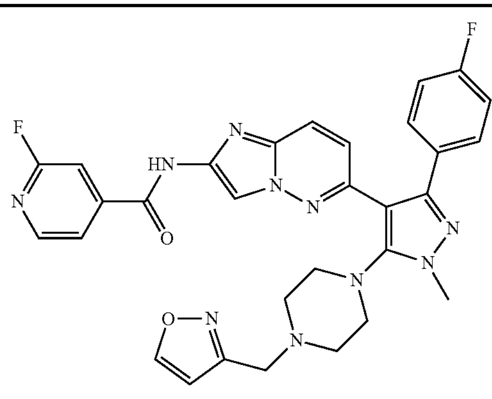 | 2-fluoro-N-(6-(3-(4-fluorophenyl)-5-(4-(isoxazol-3-ylmethyl)piperazin-1-yl)-1-methyl-1H-pyrazol-4-yl)imidazo[1,2-b]pyridazin-2-yl)isonicotinamide | 596.2 | 2.68/3.90 | C/D |

| Compound No. | Structure | Name | [M+H]+ | Ret time | HPLC Method |
|---|---|---|---|---|---|
| 116 | 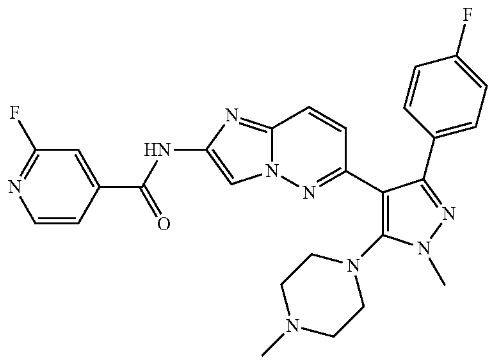 [SMILES: CN1CCN(c2c(-c3ccc4nc(NC(=O)c5ccnc(F)c5)cn4n3)c(-c3ccc(F)cc3)nn2C)CC1] | 2-fluoro-N-(6-(3-(4-fluorophenyl)-1-methyl-5-(4-methylpiperazin-1-yl)-1H-pyrazol-4-yl)imidazo[1,2-b]pyridazin-2-yl)isonicotinamide | 530.12 | 3.24 | B |
| 117 | 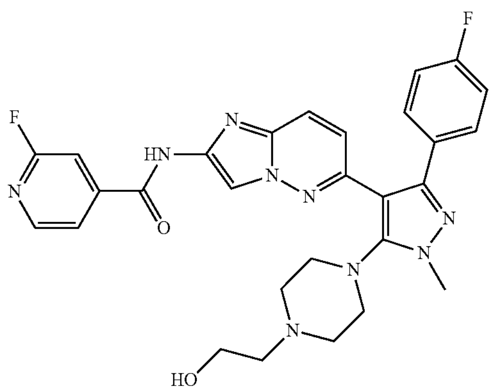 [SMILES: Cn1nc(-c2ccc(F)cc2)c(-c2ccc3nc(NC(=O)c4ccnc(F)c4)cn3n2)c1N1CCN(CCO)CC1] | 2-fluoro-N-(6-(3-(4-fluorophenyl)-5-(4-(2-hydroxyethyl)piperazin-1-yl)-1-methyl-1H-pyrazol-4-yl)imidazo[1,2-b]pyridazin-2-yl)isonicotinamide | 559.23 | 2.19/ 3.70 | C/D |

Compound 118

N-(6-(3-(4-Fluorophenyl)-1-methyl-5-(piperazin-1-yl)-1H-pyrazol-4-yl)imidazo[1,2-b]pyridazin-2-yl)-2-methoxyisonicotinamide

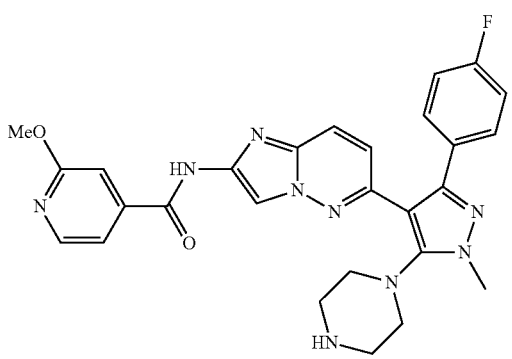 [SMILES: COc1cc(C(=O)Nc2cn3nc(-c4c(-c5ccc(F)cc5)nn(C)c4N4CCNCC4)ccc3n2)ccn1]

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113, (30 mg, 0.058 mmol) in MeOH (5 mL) was added HCl (1 mL, excess, 4.0 M dioxane solution). The reaction mixture was concentrated and purified by prep. HPLC to give Compound 118 (14 mg, 45.9%) as a tan power. MS(ES): m/z=527.22 M+. HPLC Ret time (Method D): 3.53 min. $^1$H NMR (500 MHz, DMSO-$d_6$) δ 8.52 (s, 1H), 8.37 (d, J=5.5 Hz, 1H), 8.00 (d, J=9.2 Hz, 1H), 7.68-7.52 (m, 1H), 7.46 (s, 1H), 7.43-7.34 (m, 2H), 7.15 (t, J=8.9 Hz, 2H), 7.06 (d, J=9.5 Hz, 1H), 3.94 (s, 3H), 3.80 (s, 3H), 2.88-2.79 (m, 4H), 2.79-2.69 (m, 4H).

Compound 119

2-Fluoro-N-(6-(3-(4-fluorophenyl)-5-(4-(3-fluoropropyl)piperazin-1-yl)-1-methyl-1H-pyrazol-4-yl)imidazo[1,2-b]pyridazin-2-yl)isonicotinamide

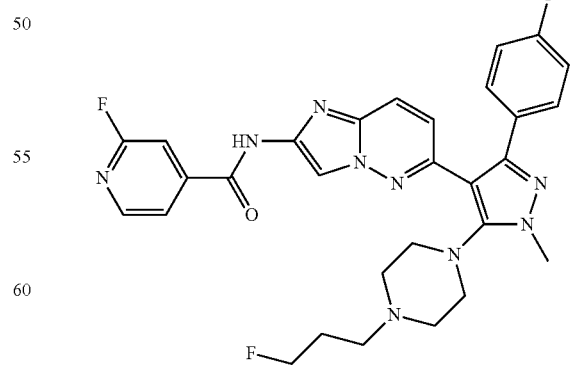

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113, (30 mg, 0.058 mmol) in EtOH (5 mL) was added 1-bromo-3-fluoropropane (32.6 mg, 0.233 mmol) and Et$_3$N (0.1 mL, 0.29 mmol). The reaction mixture was heated at 70° C. overnight and concentrated. The residue was purified by prep. HPLC to give Compound 119 (19.5 mg, 58.5%). MS(ES): m/z=575.24 M$^+$. HPLC Ret time (Method D): 3.99 min. $^1$H NMR (500 MHz, DMSO-d$_6$) δ 8.57-8.39 (m, 2H), 8.03 (d, J=9.2 Hz, 1H), 7.97 (d, J=5.2 Hz, 1H), 7.81 (s, 1H), 7.46-7.33 (m, 2H), 7.15 (t, J=8.9 Hz, 2H), 7.08 (d, J=9.2 Hz, 1H), 4.49 (t, J=6.0 Hz, 1H), 4.39 (t, J=6.0 Hz, 1H), 3.80 (s, 3H), 2.94 (m, 4H), 2.45 (m., 4H), 2.38 (m, 2H), 1.87-1.68 (m, 2H).

Compound 120

2-Fluoro-N-(6-(3-(4-fluorophenyl)-5-(4-(2-methoxyethyl)piperazin-1-yl)-1-methyl-1H-pyrazol-4-yl)imidazo[1,2-b]pyridazin-2-yl)isonicotinamide

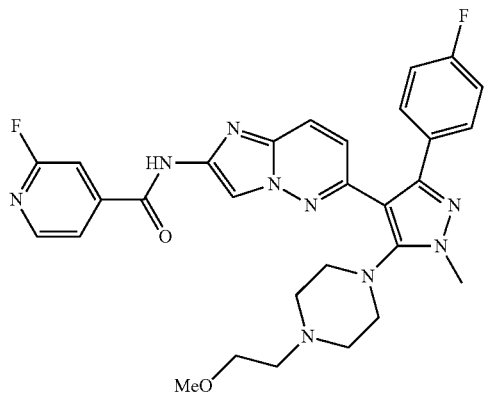 [SMILES: COCCN1CCN(c2c(-c3ccc4nc(NC(=O)c5ccnc(F)c5)cn4n3)c(-c3ccc(F)cc3)nn2C)CC1]

Compound 120 was prepared by the procedure described for the preparation of Compound 119 using Compound 113 and bromo and 1-bromo-2-methoxyethane. MS(ES): m/z=573.24 M$^+$. HPLC Ret time (Method D): 3.93 min. $^1$H NMR (500 MHz, DMSO-d$_6$) δ 8.55-8.45 (m, 2H), 8.03 (d, J=9.5 Hz, 1H), 7.97 (d, J=4.9 Hz, 1H), 7.81 (s, 1H), 7.39 (dd, J=8.9, 5.5 Hz, 2H), 7.15 (t, J=9.0 Hz, 2H), 7.08 (d, J=9.2 Hz, 2H), 3.80 (s, 3H), 3.47-3.39 (m, 2H), 3.25-3.17 (m, 2H), 2.97-2.87 (m, 4H), 2.50-2.39 (m, 4H).

Compound 121

2-Fluoro-N-(6-(3-(4-fluorophenyl)-1-methyl-5-(4-(3,3,3-trifluoropropanoyl)piperazin-1-yl)-1H-pyrazol-4-yl)imidazo[1,2-b]pyridazin-2-yl)isonicotinamide

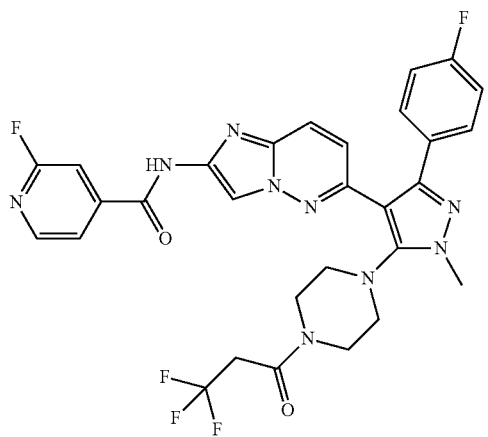 [SMILES: Cn1nc(-c2ccc(F)cc2)c(-c2ccc3nc(NC(=O)c4ccnc(F)c4)cn3n2)c1N1CCN(C(=O)CC(F)(F)F)CC1]

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113 (30 mg, 0.058 mmol) in DMF were added 3,3,3-trifluoropropanoic acid (15 mg, 0.116 mmol), HATU (60 mg, 0.116 mmol), and Hunig's Base (0.1 mL, 0.232 mmol). The reaction mixture was stirred at rt overnight and purified by prep. HPLC to furnish Compound 121. MS(ES): m/z=625.20 M$^+$. HPLC Ret time (Method C): 2.65 min and (Method D): 3.80 min. $^1$H NMR (500 MHz, DMSO-d$_6$) δ 8.59-8.43 (m, 2H), 8.06-7.92 (m, 2H), 7.80 (s, 1H), 7.39 (dd, J=8.5, 5.5 Hz, 2H), 7.16 (t, J=8.9 Hz, 2H), 7.04 (d, J=9.2 Hz, 1H), 3.85 (s, 3H), 3.65-3.51 (m., 6H), 3.07-2.92 (m, 4H).

Compound 122

N-(6-(5-(4-(Cyclopropanecarbonyl)piperazin-1-yl)-3-(4-fluorophenyl)-1-methyl-1H-pyrazol-4-yl)imidazo[1,2-b]pyridazin-2-yl)-2-fluoroisonicotinamide

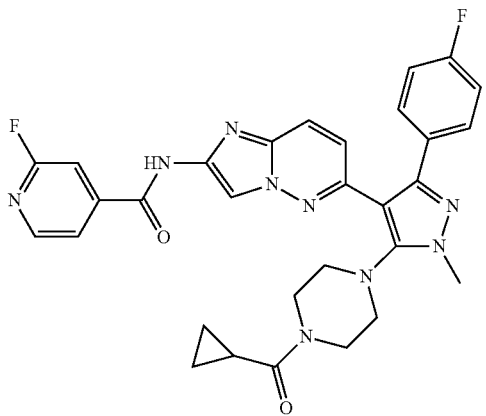 [SMILES: Cn1nc(-c2ccc(F)cc2)c(-c2ccc3nc(NC(=O)c4ccnc(F)c4)cn3n2)c1N1CCN(C(=O)C2CC2)CC1]

Compound 122 was prepared by the procedure described for the preparation of Compound 121 using Compound 113 and cyclopropanecarboxylic acid. MS(ES): m/z=584.17 (M+H)$^+$. HPLC Ret time (Method D): 3.77 min. $^1$H NMR (500 MHz, DMSO-d$_6$) δ 11.91 (s, NH, 1H), 8.62-8.43 (m, 2H), 8.08-7.92 (m, 2H), 7.81 (s, 1H), 7.56-7.32 (m, 2H), 7.28-7.09 (m, 2H), 7.03 (d, J=9.3 Hz, 1H), 3.76 (br. s., 3H), 3.55-2.91 (m., 8H), 2.05-1.81 (m, 1H), 0.79-0.54 (m, 4H).

Compound 123

N-(6-(5-(4-(2-Aminoacetyl)piperazin-1-yl)-3-(4-fluorophenyl)-1-methyl-1H-pyrazol-4-yl)imidazo[1,2-b]pyridazin-2-yl)-2-fluoroisonicotinamide

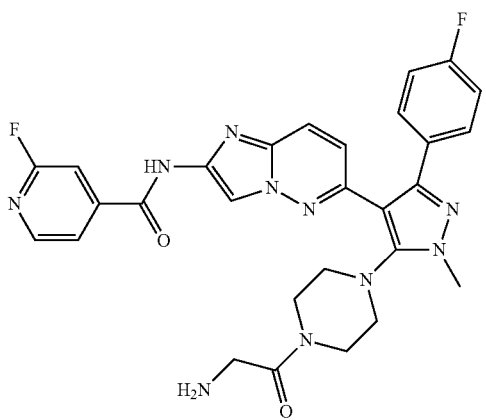 [SMILES: Cn1nc(-c2ccc(F)cc2)c(-c2ccc3nc(NC(=O)c4ccnc(F)c4)cn3n2)c1N1CCN(C(=O)CN)CC1]

113

Compound 123A: tert-Butyl (2-(4-(4-(2-(2-fluoroisonicotinamido)imidazo[1,2-b]pyridazin-6-yl)-3-(4-fluorophenyl)-1-methyl-1H-pyrazol-5-yl)piperazin-1-yl)-2-oxoethyl)carbamate

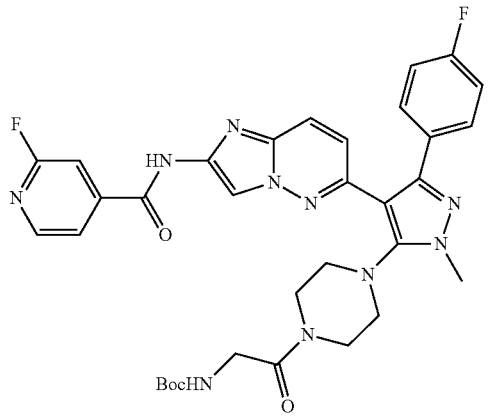 [SMILES: Cn1nc(-c2ccc(F)cc2)c(-c2ccc3nc(NC(=O)c4ccnc(F)c4)cn3n2)c1N1CCN(C(=O)CNC(=O)OC(C)(C)C)CC1]

Compound 123A was prepared by the procedure described for the preparation of Compound 121 using Compound 113 and 2-((tert-butoxycarbonyl)amino)acetic acid. MS(ES): m/z=673.15 (M+H)⁺. HPLC Ret time (Method B): 3.95 min.

Compound 123: N-(6-(5-(4-(2-Aminoacetyl)piperazin-1-yl)-3-(4-fluorophenyl)-1-methyl-1H-pyrazol-4-yl)imidazo[1,2-b]pyridazin-2-yl)-2-fluoroisonicotinamide

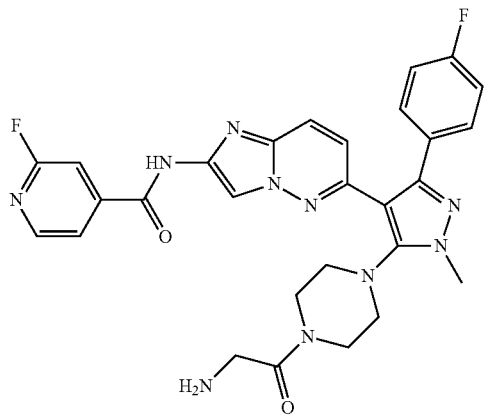 [SMILES: Cn1nc(-c2ccc(F)cc2)c(-c2ccc3nc(NC(=O)c4ccnc(F)c4)cn3n2)c1N1CCN(C(=O)CN)CC1]

To a solution of tert-butyl (2-(4-(4-(2-(2-fluoroisonicotinamido)imidazo[1,2-b]pyridazin-6-yl)-3-(4-fluorophenyl)-1-methyl-1H-pyrazol-5-yl)piperazin-1-yl)-2-oxoethyl)carbamate, Compound 123A (0.058 mmol) in CH₂Cl₂ (5 mL) was added TFA (1 mL, excess). The reaction mixture was stirred at rt for 3 h and concentrated. The residue was dissolved in DMF and purified by prep. HPLC to give Compound 123 (11 mg, 33% two steps) as a tan powder. MS(ES): m/z=572.22 M⁺. HPLC Ret time (Method C): 2.06 min and (Method D): 3.54 min. ¹H NMR (500 MHz, DMSO-d₆) δ 8.56-8.42 (m, 2H), 8.07-7.90 (m, 2H), 7.80 (s, 1H), 7.39 (dd, J=8.7, 5.6 Hz, 2H), 7.16 (t, J=8.9 Hz, 2H), 7.03 (d, J=9.2 Hz, 1H), 3.85 (s, 3H), 3.55-3.31 (m, 6H), 2.94 (m., 4H).

114

Compound 124

N-(6-(5-(4-(2-Amino-2-oxoethyl)piperazin-1-yl)-3-(4-fluorophenyl)-1-methyl-1H-pyrazol-4-yl)imidazo[1,2-b]pyridazin-2-yl)-2-fluoroisonicotinamide

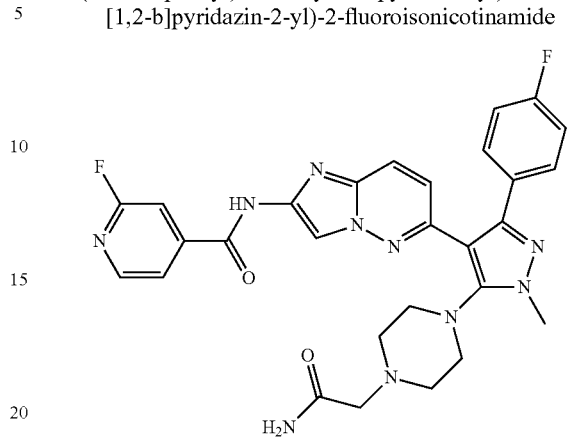

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113 (35 mg, 0.068 mmol) in DMF (1 mL) was added 2-bromoacetamide (18.7 mg, 0.136 mmol). The reaction mixture was stirred at rt overnight and purified by prep. HPLC to give Compound 124 (20.4 mg, 52.4%) as a tan powder. MS(ES): m/z=572.22 M⁺. HPLC Ret time (Method C): 2.31 min and (Method D): 3.77 min. ¹H NMR (500 MHz, DMSO-d₆) δ 8.49 (s, NH, 1H), 8.56-8.42 (m, H), 8.07-7.90 (m, 3H), 7.80 (s, 1H), 7.39 (dd, J=8.7, 5.6 Hz, 2H), 7.16 (t, J=8.9 Hz, 2H), 7.03 (d, J=9.2 Hz, 1H), 3.85 (s, 3H), 3.55-3.31 (m, 6H), 2.94 (m, 4H).

Compound 125

N-(6-(5-(4-(2-Cyanoethyl)piperazin-1-yl)-3-(4-fluorophenyl)-1-methyl-1H-pyrazol-4-yl)imidazo[1,2-b]pyridazin-2-yl)-2-fluoroisonicotinamide

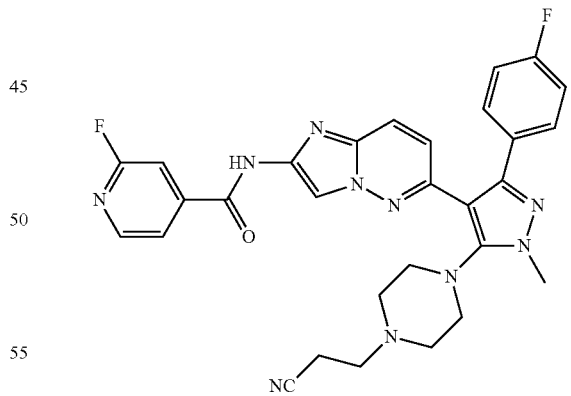

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113 (35 mg, 0.068 mmol) in DMF (1 mL) was added acrylonitrile (10 mg, 0.175 mmol). The reaction mixture was stirred at rt overnight and purified by prep. HPLC to give Compound 125 (22.1 mg, 67.7%) as a tan powder. MS(ES): m/z=568.23 M⁺. HPLC Ret time (Method C): 2.58 min and (Method D): 3.83 min.

Compound 126

2-Fluoro-N-(6-(3-(4-fluorophenyl)-1-methyl-5-(4-(2-(methylsulfonyl)ethyl)piperazin-1-yl)-1H-pyrazol-4-yl)imidazo[1,2-b]pyridazin-2-yl)isonicotinamide

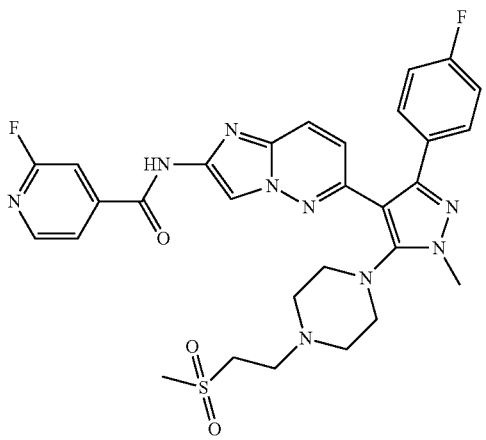 [SMILES: Cn1nc(-c2ccc(F)cc2)c(-c2ccc3nc(NC(=O)c4ccnc(F)c4)cn3n2)c1N1CCN(CCS(C)(=O)=O)CC1]

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113 (25 mg, 0.048 mmol) in DMF (1 mL) was added (methylsulfonyl)ethene (10 mg, 0.097 mmol). The reaction mixture was stirred at rt overnight and purified by prep. HPLC to give Compound 126 (18.5 mg, 61.6%) as a tan powder. MS(ES): m/z=621.21 M+. HPLC Ret time (Method C): 2.41 min and (Method D): 3.69 min.

Compound 127

(R)-2-Fluoro-N-(6-(3-(4-fluorophenyl)-1-methyl-5-(4-(3,3,3-trifluoro-2-hydroxypropyl)piperazin-1-yl)-1H-pyrazol-4-yl)imidazo[1,2-b]pyridazin-2-yl)isonicotinamide

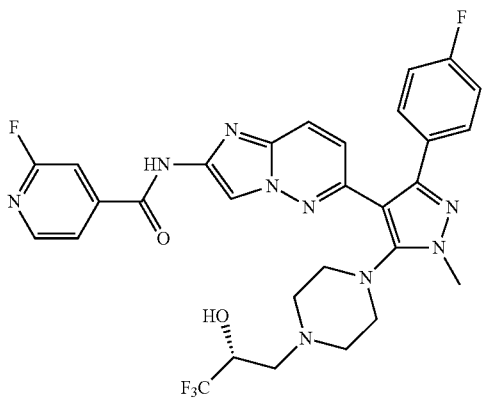 [SMILES: Cn1nc(-c2ccc(F)cc2)c(-c2ccc3nc(NC(=O)c4ccnc(F)c4)cn3n2)c1N1CCN(C[C@@H](O)C(F)(F)F)CC1]

To a solution of 2-fluoro-N-(6-(3-(4-fluorophenyl)-1-methyl-5-(piperazin-1-yl)-1H-pyrazol-4-yl)imidazo[1,2-b]pyridazin-2-yl)isonicotinamide, Compound 113 (30 mg, 0.058 mmol) in dichloroethylene (1 mL) was added (R)-2-(trifluoromethyl)oxirane (65.2 mg, 0.582 mmol). The reaction mixture was stirred at rt overnight, concentrated, the residue was dissolved in DMF and purified by prep. HPLC to give the Compound 127 (10.8 mg, 19.1%) as a tan powder. MS(ES): m/z=627.21 M+. HPLC Ret time (Method C): 2.80 min and (Method D): 4.04 min.

Compound 128

(S)-2-Fluoro-N-(6-(3-(4-fluorophenyl)-1-methyl-5-(4-(3,3,3-trifluoro-2-hydroxypropyl)piperazin-1-yl)-1H-pyrazol-4-yl)imidazo[1,2-b]pyridazin-2-yl)isonicotinamide

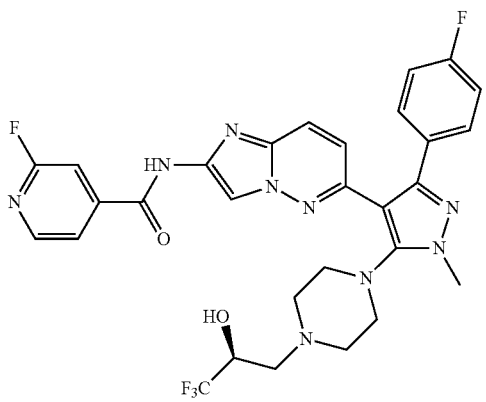 [SMILES: Cn1nc(-c2ccc(F)cc2)c(-c2ccc3nc(NC(=O)c4ccnc(F)c4)cn3n2)c1N1CCN(C[C@H](O)C(F)(F)F)CC1]

Compound 128 was prepared by the procedure described for the preparation of Compound 128 using Compound 113 and (S)-2-(trifluoromethyl)oxirane. MS(ES): m/z=627.21 M+. HPLC Ret time (Method C): 2.78 min and (Method D): 4.02 min.

Compound 129

N-(6-(3-(4-Fluorophenyl)-1-methyl-5-(piperazin-1-yl)-1H-pyrazol-4-yl)imidazo[1,2-b]pyridazin-2-yl)isonicotinamide

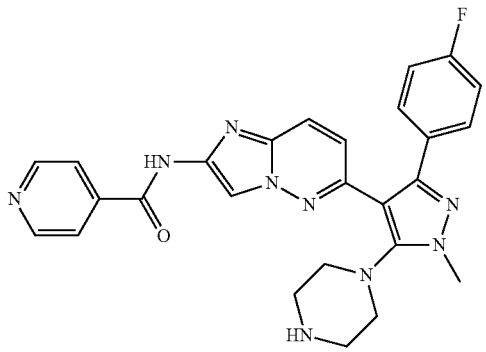 [SMILES: Cn1nc(-c2ccc(F)cc2)c(-c2ccc3nc(NC(=O)c4ccncc4)cn3n2)c1N1CCNCC1]

Compound 129 was prepared by the procedures described for the preparation of Compound 113A and Compound 113 using Intermediate 9 and isonicotinic acid. MS(ES): m/z=497.21 M+. HPLC Ret time (Method C): 1.85 min and (Method D): 3.21 min. $^1$H NMR (500 MHz, DMSO-d$_6$) δ 8.88-8.77 (m, 2H), 8.53 (s, 1H), 8.06-7.93 (m, 3H), 7.50-7.35 (m, 2H), 7.15 (t, J=8.9 Hz, 2H), 7.06 (d, J=9.2 Hz, 1H), 3.80 (s, 3H), 2.89-2.79 (m, 4H), 2.79-2.69 (m, 4H).

Compound 130

N-(6-(3-(4-Fluorophenyl)-1-methyl-5-(4-(3,3,3-trifluoropropyl)piperazin-1-yl)-1H-pyrazol-4-yl)imidazo[1,2-b]pyridazin-2-yl)isonicotinamide

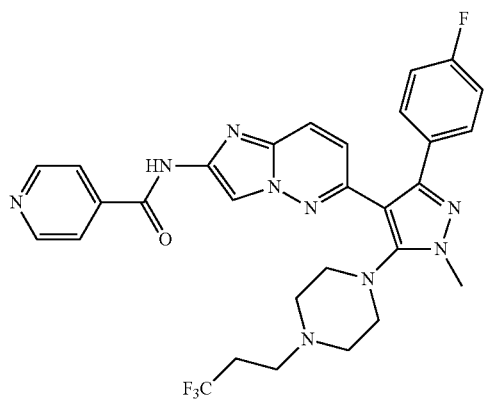 [SMILES: Cn1nc(-c2ccc(F)cc2)c(-c2ccc3nc(NC(=O)c4ccncc4)cn3n2)c1N1CCN(CCC(F)(F)F)CC1]

Compound 130 was prepared by the procedure described for the preparation of Compound 114 using Compound 129 and 3,3,3-trifluoropropanal. MS(ES): m/z=593.23 M+. HPLC Ret time (Method C): 2.74 min and (Method D): 4.03 min. $^1$H NMR (500 MHz, DMSO-d$_6$) δ 11.83 (br. s., NH, 1H), 8.89-8.70 (m, 2H), 8.51 (s, 1H), 8.15-7.95 (m, 3H), 7.48-7.34 (m, 2H), 7.15 (t, J=9.0 Hz, 2H), 7.07 (d, J=9.2 Hz, 1H), 3.80 (s, 3H), 2.93 (m, 4H), 2.54 (br. s., 1H), 2.50-2.27 (m, 8H).

Compound 131

N-(6-(3-(4-Fluorophenyl)-5-(4-(isoxazol-3-ylmethyl)piperazin-1-yl)-1-methyl-1H-pyrazol-4-yl)imidazo[1,2-b]pyridazin-2-yl)isonicotinamide

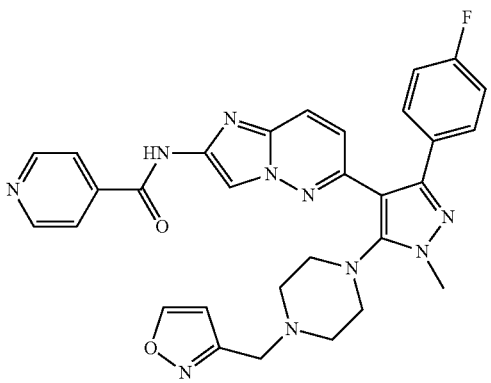

Compound 131 was prepared by the procedure described for the preparation of Compound 114 using Compound 129 and isoxazole-3-carbaldehyde. MS(ES): m/z=578.23 M+. HPLC Ret time (Method C): 2.43 min and (Method D): 3.75 min. $^1$H NMR (500 MHz, DMSO-d$_6$) δ 8.88-8.77 (m, 3H), 8.52 (s, 1H), 8.05-7.92 (m, 3H), 7.43-7.33 (m, 2H), 7.15 (t, J=8.9 Hz, 2H), 7.06 (d, J=9.2 Hz, 1H), 6.52 (d, J=1.5 Hz, 1H), 3.79 (s, 3H), 3.62 (s, 2H), 2.95 (t, J=4.6 Hz, 4H), 2.49 (m, 4H).

Compound 132

N-(6-(3-(4-Fluorophenyl)-1-methyl-5-(4-(3,3,3-trifluoropropanoyl)piperazin-1-yl)-1H-pyrazol-4-yl)imidazo[1,2-b]pyridazin-2-yl)isonicotinamide

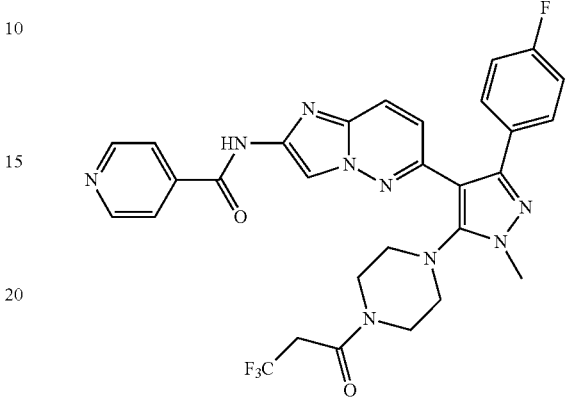

Compound 132 was prepared by the procedure described for the preparation of Compound 121 using Compound 129 and 3,3,3-trifluoropropanoic acid. MS(ES): m/z=607.21 M+. HPLC Ret time (Method C): 2.39 min and (Method D): 3.63 min. $^1$H NMR (500 MHz, DMSO-d$_6$) δ 8.87-8.76 (m, 2H), 8.50 (s, 1H), 8.07-7.92 (m, 3H), 7.47-7.29 (m, 2H), 7.25-7.09 (m, 2H), 7.03 (d, J=9.5 Hz, 1H), 3.85 (s, 3H), 3.65 (q, J=11.2 Hz, 2H), 3.57 (br. s., 2H), 3.54-3.45 (m, 2H), 3.04-2.91 (m, 4H).

Compound 133

N-(6-(3-(4-Fluorophenyl)-5-(4-(isoxazole-3-carbonyl)piperazin-1-yl)-1-methyl-1H-pyrazol-4-yl)imidazo[1,2-b]pyridazin-2-yl)isonicotinamide

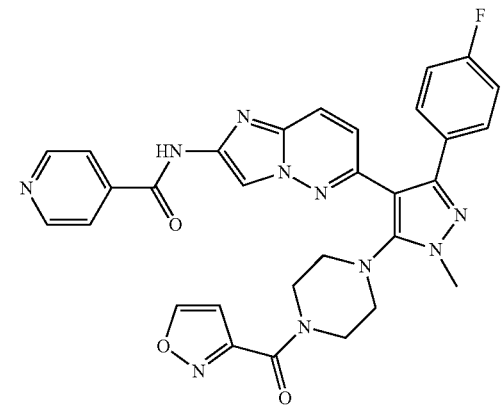 [SMILES: Cn1nc(-c2ccc(F)cc2)c(-c2ccc3nc(NC(=O)c4ccncc4)cn3n2)c1N1CCN(C(=O)c2ccon2)CC1]

Compound 133 was prepared by the procedure described for the preparation of Compound 121 using Compound 129 and isoxazole-3-carboxylic acid. MS(ES): m/z=592.21 M+. HPLC Ret time (Method C): 2.34 min and (Method D): 3.65 min. $^1$H NMR (500 MHz, DMSO-d$_6$) δ 9.08 (d, J=1.5 Hz, 1H), 8.86-8.75 (m, 2H), 8.50 (s, 1H), 8.07-7.94 (m, 3H), 7.48-7.36 (m, 2H), 7.24-7.09 (m, 2H), 7.02 (d, J=9.2 Hz, 1H), 6.81 (d, J=1.8 Hz, 1H), 3.87 (s, 3H), 3.76-3.60 (m, 4H), 3.04 (m, 4H).

Compound 134

N-(6-(3-(4-Fluorophenyl)-1-methyl-5-(piperazin-1-yl)-1H-pyrazol-4-yl)imidazo[1,2-b]pyridazin-2-yl)-2-morpholinoisonicotinamide

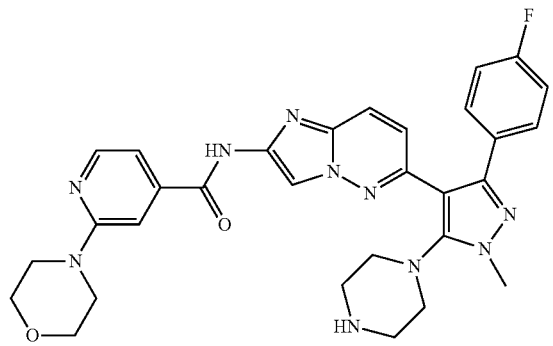 [SMILES: Cn1nc(-c2ccc(F)cc2)c(-c2ccc3nc(NC(=O)c4ccnc(N5CCOCC5)c4)cn3n2)c1N1CCNCC1]

Compound 134 was prepared by the procedures described for the preparation of Compounds 113A and 113 using Intermediate 9 and 2-morpholinoisonicotinic acid. MS(ES): m/z=583.15 [M+H]$^+$. HPLC Ret time (Method B): 3.06 min. $^1$H NMR (500 MHz, DMSO-d$_6$) δ 8.80-8.61 (m, 1H), 8.30-8.12 (m, 1H), 7.98-7.77 (m, 2H), 7.54-7.30 (m, 3H), 7.10 (t, J=8.8 Hz, 2H), 6.96 (d, J=9.3 Hz, 1H), 3.98-3.88 (m, 8H), 3.94 (s, 3H), 3.46-3.28 (m, 8H).

Compound 135

N-(6-(3-(4-Fluorophenyl)-1-methyl-5-(4-(3,3,3-trifluoropropyl)piperazin-1-yl)-1H-pyrazol-4-yl)imidazo[1,2-b]pyridazin-2-yl)-2-morpholinoisonicotinamide

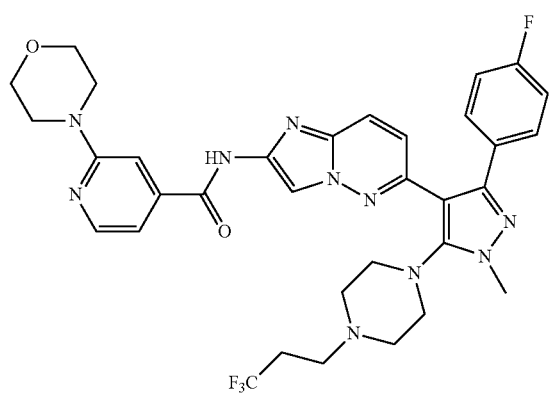 [SMILES: Cn1nc(-c2ccc(F)cc2)c(-c2ccc3nc(NC(=O)c4ccnc(N5CCOCC5)c4)cn3n2)c1N1CCN(CCC(F)(F)F)CC1]

Compound 135 was prepared by the procedures described for the preparation of Compound 114 using Compound 134 and 3,3,3-trifluoropropanal. MS(ES): m/z=678.28 M$^+$. HPLC Ret time (Method C): 3.08 min and (Method D): 4.23 min. $^1$H NMR (500 MHz, DMSO-d$_6$) δ 11.68 (s, NH, 1H), 8.50 (s, 1H), 8.31 (d, J=4.9 Hz, 1H), 8.00 (d, J=9.2 Hz, 1H), 7.52 (s, 1H), 7.39 (dd, J=8.5, 5.5 Hz, 2H), 7.25 (d, J=5.2 Hz, 1H), 7.15 (t, J=8.9 Hz, 2H), 7.06 (d, J=9.2 Hz, 1H), 3.80 (s, 3H), 3.86-3.69 (m, 4H), 3.64-3.51 (m, 4H), 3.03-2.85 (m, 4H), 2.58-2.34 (m, 12H).

Compound 136

N-(6-(3-(4-Fluorophenyl)-5-(4-(isoxazol-3-ylmethyl)piperazin-1-yl)-1-methyl-1H-pyrazol-4-yl)imidazo[1,2-b]pyridazin-2-yl)-2-morpholinoisonicotinamide

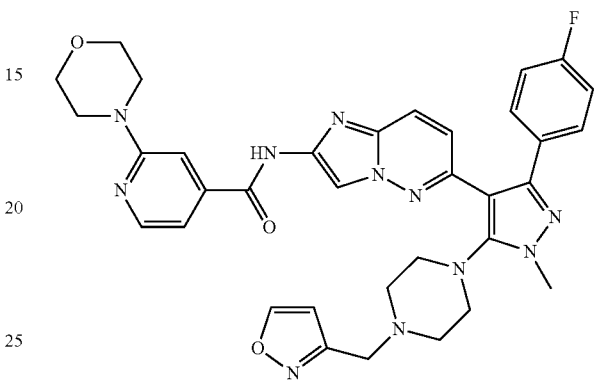

Compound 136 was prepared by the procedure described for the preparation of Compound 114 using Compound 134 and isoxazole-3-carbaldehyde. MS(ES): m/z=663.28 M$^+$. HPLC Ret time (Method C): 2.65 min and (Method D): 4.01 min. $^1$H NMR (500 MHz, DMSO-d$_6$) δ 11.66 (s, NH, 1H), 8.83 (s, 1H), 8.50 (s, 1H), 8.31 (d, J=5.2 Hz, 1H), 8.12-7.92 (m, 1H), 7.52 (s, 1H), 7.39 (dd, J=8.7, 5.6 Hz, 2H), 7.25 (d, J=5.2 Hz, 1H), 7.14 (t, J=8.9 Hz, 2H), 7.05 (d, J=9.5 Hz, 1H), 6.51 (s, 1H), 3.79 (s, 3H), 3.82-3.70 (m, 4H), 3.67-3.52 (m, 6H), 3.02-2.91 (m, 4H), 2.44-2.49 (m, 4H).

Compound 137

N-(6-(3-(4-Fluorophenyl)-5-(4-(isoxazole-3-carbonyl)piperazin-1-yl)-1-methyl-1H-pyrazol-4-yl)imidazo[1,2-b]pyridazin-2-yl)-2-morpholinoisonicotinamide

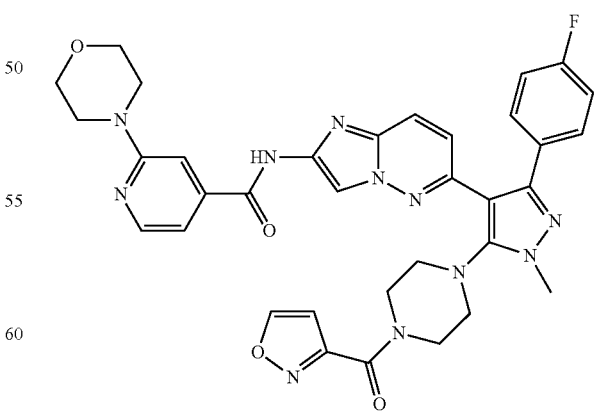

Compound 137 was prepared by the procedure described for the preparation of Compound 121 using Compound 134 and isoxazole-3-carboxylic acid. MS(ES): m/z=677.26 M$^+$.

HPLC Ret time (Method C): 2.64 min and (Method D): 3.88 min. ¹H NMR (500 MHz, DMSO-d₆) δ ¹H NMR (500 MHz, DMSO-d₆) δ 11.64 (s, NH, 1H), 9.07 (d, J=1.5 Hz, 1H), 8.48 (s, 1H), 8.30 (d, J=5.2 Hz, 1H), 7.97 (d, J=9.2 Hz, 1H), 7.51 (s, 1H), 7.41 (dd, J=8.5, 5.8 Hz, 2H), 7.25 (d, J=5.2 Hz, 1H), 7.16 (t, J=8.9 Hz, 2H), 7.01 (d, J=9.2 Hz, 1H), 6.81 (d, J=1.5 Hz, 1H), 3.87 (s, 3H), 3.81-3.47 (m, 12H), 3.04 (m, 4H).

Compound 138

N-(6-(3-(4-Fluorophenyl)-1-methyl-5-(4-(3,3,3-trifluoropropanoyl)piperazin-1-yl)-1H-pyrazol-4-yl)imidazo[1,2-b]pyridazin-2-yl)-2-morpholinoisonicotinamide

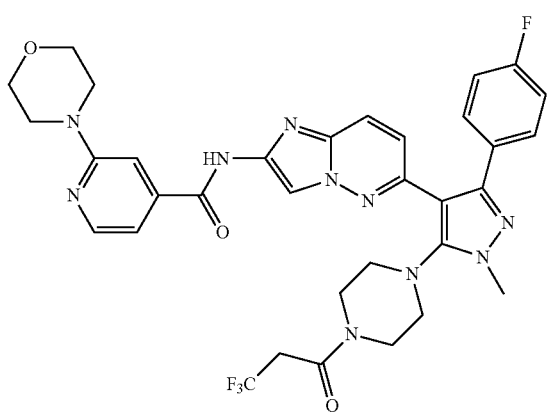 [SMILES: Cn1nc(-c2ccc(F)cc2)c(-c2ccc3nc(NC(=O)c4ccnc(N5CCOCC5)c4)cn3n2)c1N1CCN(C(=O)CC(F)(F)F)CC1]

Compound 138 was prepared by the procedure described for the preparation of Compound 121 using Compound 134 and 3,3,3-trifluoropropanoic acid. MS(ES): m/z=692.26 M⁺. HPLC Ret time (Method C): 2.63 min and (Method D): 3.86 min. ¹H NMR (500 MHz, DMSO-d₆) δ 11.66 (s, 1H), 8.49 (s, 1H), 8.31 (d, J=4.9 Hz, 1H), 7.98 (d, J=9.2 Hz, 1H), 7.51 (s, 1H), 7.47-7.31 (m, 2H), 7.31-7.20 (m, 1H), 7.16 (t, J=9.0 Hz, 2H), 7.03 (d, J=9.2 Hz, 1H), 3.85 (s, 3H), 3.77-3.72 (m, 4H), 3.72-3.53 (m, 8H), 3.53-3.45 (m, 2H), 2.99-2.91 (m, 4H).

Compound 139

N-(6-(3-(4-Fluorophenyl)-5-(4-(3-fluoropropyl)piperazin-1-yl)-1-methyl-1H-pyrazol-4-yl)imidazo[1,2-b]pyridazin-2-yl)-2-morpholinoisonicotinamide

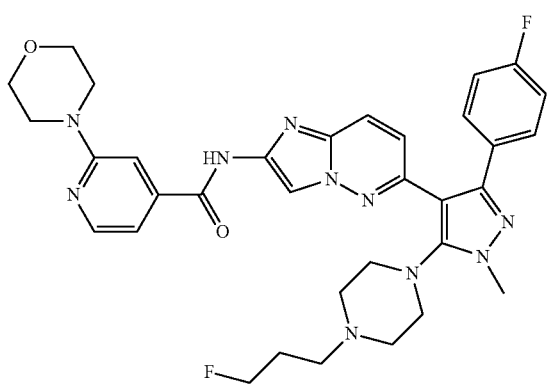 [SMILES: Cn1nc(-c2ccc(F)cc2)c(-c2ccc3nc(NC(=O)c4ccnc(N5CCOCC5)c4)cn3n2)c1N1CCN(CCCF)CC1]

Compound 139 was prepared by the procedure described for the preparation of Compound 119 using Compound 134 and 1-fluoro-3-iodopropane. MS(ES): m/z=642.30 M⁺. HPLC Ret time (Method L): 2.41 min and (Method K): 3.69 min.

Compound 140

2-Amino-N-(6-(3-(4-fluorophenyl)-1-methyl-5-(piperazin-1-yl)-1H-pyrazol-4-yl)imidazo[1,2-b]pyridazin-2-yl)isonicotinamide

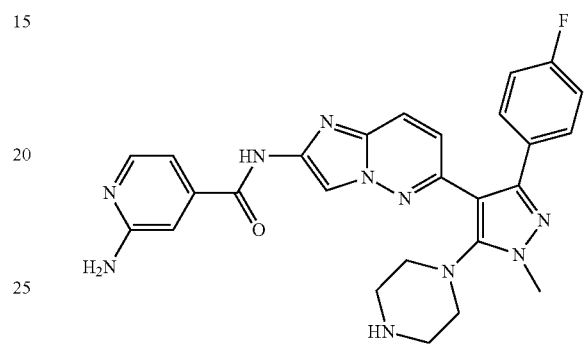

Compound 140 was prepared by the procedure described for the preparations of Compound 113A and Compound 113 using Intermediates 9 and 2-(tert-butoxycarbonyl)aminoisonicotinic acid. MS(ES): m/z=512.22 M⁺. HPLC Ret time (Method C): 1.89 min and (Method D): 3.16 min. ¹H NMR (500 MHz, DMSO-d₆) δ 11.50 (s, NH, 1H), 8.52 (s, 1H), 8.07 (d, J=5.2 Hz, 1H), 7.98 (d, J=9.2 Hz, 1H), 7.39 (dd, J=8.5, 5.5 Hz, 2H), 7.15 (t, J=9.0 Hz, 2H), 7.09 (dd, J=5.3, 1.4 Hz, 1H), 7.05-6.90 (m, 2H), 6.24 (s, NH2, 2H), 3.81 (s, 3H), 2.98-2.78 (m, 8H).

Compound 141

2-Amino-N-(6-(3-(4-fluorophenyl)-1-methyl-5-(4-(3,3,3-trifluoropropyl)piperazin-1-yl)-1H-pyrazol-4-yl)imidazo[1,2-b]pyridazin-2-yl)isonicotinamide

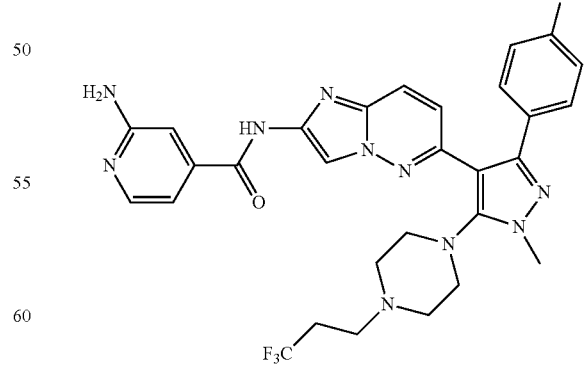

Compound 141 was prepared by the procedure described for the preparation of Compound 114 using Compound 140 and 3,3,3-trifluoropropanal. MS(ES): m/z=608.24 M⁺. HPLC Ret time (Method C): 2.68 min and (Method D): 3.95 min. ¹H NMR (500 MHz, DMSO-d₆) δ 11.51 (s, NH, 1H), 8.47 (s, 1H), 8.07 (d, J=5.5 Hz, 1H), 8.00 (d, J=9.2 Hz, 1H), 7.38 (dd, J=8.7, 5.6 Hz, 2H), 7.21-7.01 (m, 4H), 6.99 (s, 1H), 6.24 (s, NH2 2H), 3.80 (s, 3H), 3.03-2.87 (m, 4H), 2.58-2.47 (m, 4H).

8.84 (d, J=1.5 Hz, 1H), 8.48 (s, 1H), 8.07 (d, J=5.2 Hz, 1H), 7.99 (d, J=9.5 Hz, 1H), 7.48-7.32 (m, 2H), 7.17-6.97 (m, 5H), 6.52 (d, J=1.5 Hz, 1H), 6.24 (s, NH2, 2H), 3.79 (s, 3H), 3.62 (s, 2H), 3.00-2.80 (m, 4H), 2.53-2.44 (m, 4H).

Compound 142

2-Amino-N-(6-(3-(4-fluorophenyl)-5-(4-(isoxazol-3-ylmethyl)piperazin-1-yl)-1-methyl-1H-pyrazol-4-yl)imidazo[1,2-b]pyridazin-2-yl)isonicotinamide

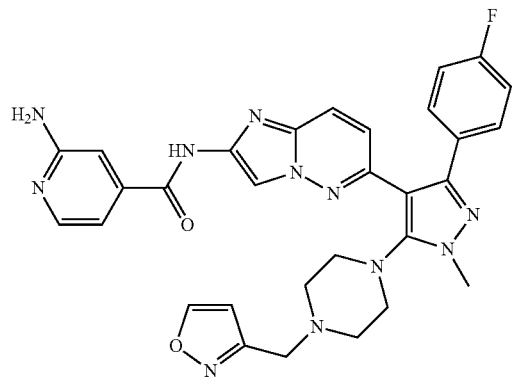 [SMILES: Cn1nc(-c2ccc(F)cc2)c(-c2ccc3nc(NC(=O)c4ccnc(N)c4)cn3n2)c1N1CCN(Cc2ccon2)CC1]

Compound 142 was prepared by the procedure described for the preparation of Compound 114 using Compound 140 and isoxazole-3-carbaldehyde. MS(ES): m/z=593.24 M⁺. HPLC Ret time (Method C): 2.35 min and (Method D): 3.66 min. ¹H NMR (500 MHz, DMSO-d₆) δ 11.50 (s, NH, 1H), Compound 143

2-Fluoro-N-(6-(3-(4-fluorophenyl)-1-methyl-5-morpholino-1H-pyrazol-4-yl)imidazo[1,2-b]pyridazin-2-yl)isonicotinamide

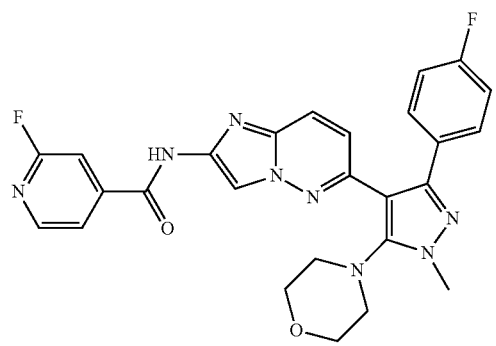 [SMILES: Cn1nc(-c2ccc(F)cc2)c(-c2ccc3nc(NC(=O)c4ccnc(F)c4)cn3n2)c1N1CCOCC1]

Compound 143 was prepared by the procedure described for the preparation of Compound 1 using Intermediate 11 and 2-fluoroisonicotinic acid. MS(ES): m/z=516.18 M⁺. HPLC Ret time (Method C): 2.45 min and (Method D): 3.88 min. ¹H NMR (500 MHz, DMSO-d₆) δ 8.54 (s, 1H), 8.47 (d, J=5.2 Hz, 1H), 8.07-7.92 (m, 2H), 7.81 (s, 1H), 7.40 (dd, J=8.7, 5.6 Hz, 2H), 7.16 (t, J=8.9 Hz, 2H), 7.04 (d, J=9.2 Hz, 1H), 3.84 (s, 3H), 3.73-3.61 (m, 4H), 3.00-2.91 (m, 4H).

The following compounds in Table 4 were prepared by the procedure described for the preparation of Compound 1 using Intermediate 11 and the corresponding acids.

TABLE 4

| Compound No. | Structure | Name | [M + H]⁺ | Ret time | HPLC Method |
|---|---|---|---|---|---|
| 144 | 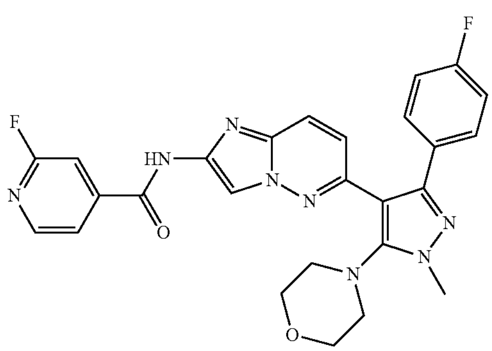 [SMILES: Cn1nc(-c2ccc(F)cc2)c(-c2ccc3nc(NC(=O)c4ccnc(F)c4)cn3n2)c1N1CCOCC1] | 2-fluoro-N-(6-(3-(4-fluorophenyl)-1-methyl-5-morpholino-1H-pyrazol-4-yl)imidazo[1,2-b]pyridazin-2-yl)isonicotinamide | 499.3 | 3.59 | A |

TABLE 4-continued

| Compound No. | Structure | Name | [M + H]+ | Ret time | HPLC Method |
|---|---|---|---|---|---|
| 145 | 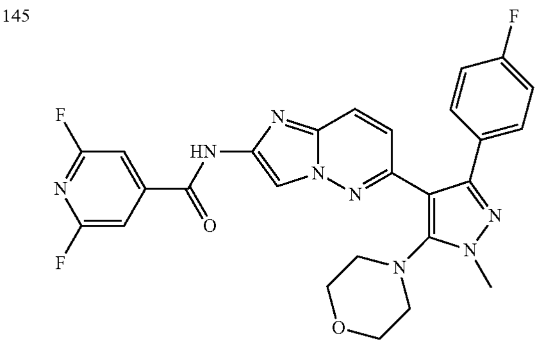 | 2,6-difluoro-N-(6-(3-(4-fluorophenyl)-1-methyl-5-morpholino-1H-pyrazol-4-yl)imidazo[1,2-b]pyridazin-2-yl)isonicotinamide | 535.2 | 3.96 | A |
| 146 | 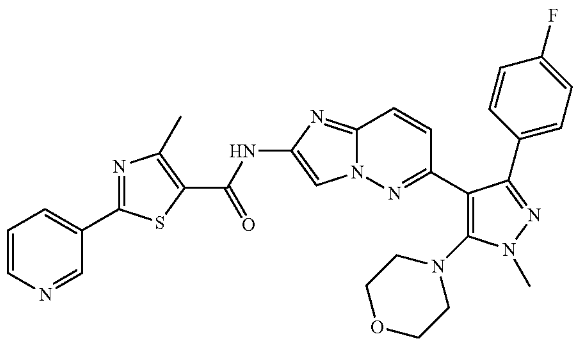 [SMILES: Cc1nc(-c2cccnc2)sc1C(=O)Nc1cn2nc(-c3c(-c4ccc(F)cc4)nn(C)c3N3CCOCC3)ccc2n1] | N-(6-(3-(4-fluorophenyl)-1-methyl-5-morpholino-1H-pyrazol-4-yl)imidazo[1,2-b]pyridazin-2-yl)-4-methyl-2-(pyridin-3-yl)thiazole-5-carboxamide | 596.3 | 3.94 | A |
| 147 | 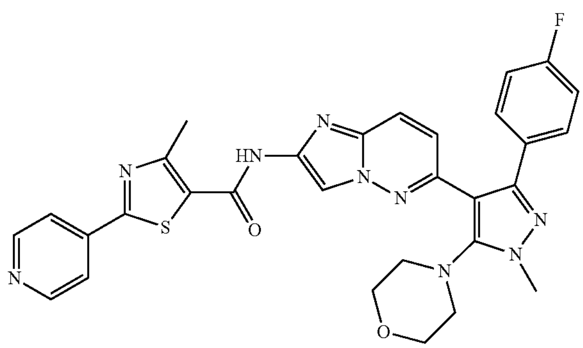 [SMILES: Cc1nc(-c2ccncc2)sc1C(=O)Nc1cn2nc(-c3c(-c4ccc(F)cc4)nn(C)c3N3CCOCC3)ccc2n1] | N-(6-(3-(4-fluorophenyl)-1-methyl-5-morpholino-1H-pyrazol-4-yl)imidazo[1,2-b]pyridazin-2-yl)-4-methyl-2-(pyridin-4-yl)thiazole-5-carboxamide | 596.3 | 3.99 | A |

Compound 148

2-Fluoro-N-(6-(3-(4-fluorophenyl)-1-methyl-5-(piperidin-4-yl)-1H-pyrazol-4-yl)imidazo[1,2-b]pyridazin-2-yl)isonicotinamide

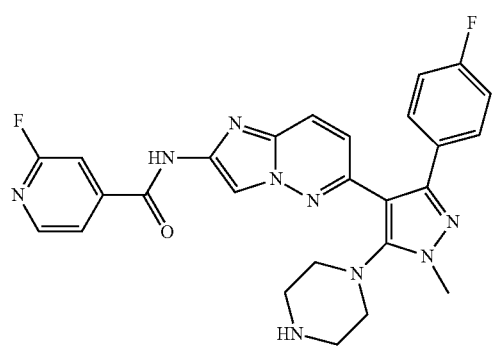

Compound 148A: tert-Butyl 4-(4-(2-(2-fluoroisonicotinamido)imidazo[1,2-b]pyridazin-6-yl)-3-(4-fluorophenyl)-1-methyl-1H-pyrazol-5-yl)piperidine-1-carboxylate

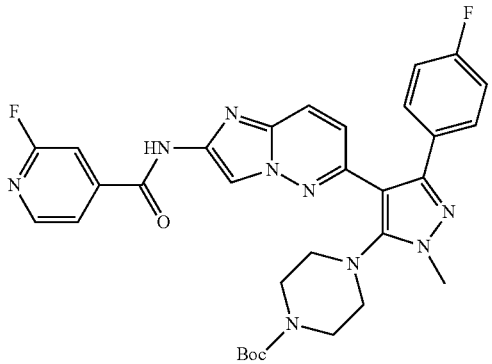 [SMILES: Cn1nc(-c2ccc(F)cc2)c(-c2ccc3nc(NC(=O)c4ccnc(F)c4)cn3n2)c1N1CCN(C(=O)OC(C)(C)C)CC1]

Compound 148A was prepared by the procedure described for the preparation of Compound 113A using Intermediate 10 and 2-fluoroisonicotinic acid. MS(ES): m/z=394.2 [M+H]⁺. HPLC Ret time (Method A): 3.13 min.

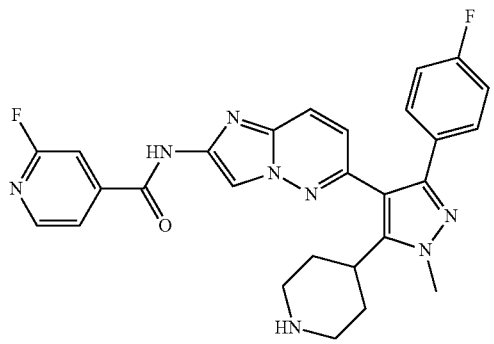 [SMILES: Cn1nc(-c2ccc(F)cc2)c(-c2ccc3nc(NC(=O)c4ccnc(F)c4)cn3n2)c1C1CCNCC1]

Compound 148 was prepared by the procedure described for the preparation of Compound 113 using Compound 148A. MS(ES): m/z=514.20 M⁺. HPLC Ret time (Method C): 2.12 min and (Method D): 3.47 min.

Compound 149

2-Fluoro-N-(6-(3-(4-fluorophenyl)-1-methyl-5-(4-(3,3,3-trifluoropropyl)piperazin-1-yl)-1H-pyrazol-4-yl)imidazo[1,2-b]pyridazin-2-yl)isonicotinamide

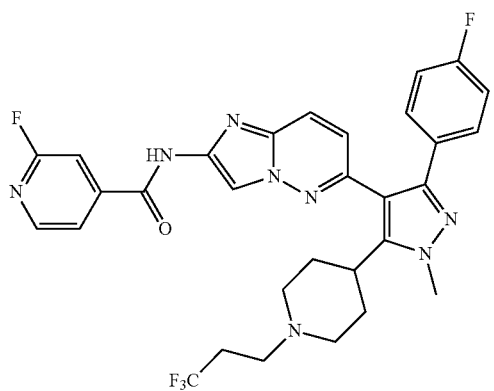 [SMILES: Cn1nc(-c2ccc(F)cc2)c(-c2ccc3nc(NC(=O)c4ccnc(F)c4)cn3n2)c1C1CCN(CCC(F)(F)F)CC1]

Compound 149 was prepared by the procedure described for the preparation of Compound 114 using Compound 148 and 3,3,3-trifluoropropanal. MS(ES): m/z=610.22 M⁺. HPLC Ret time (Method C): 2.82 min and (Method D): 4.06 min. $^1$H NMR (500 MHz, DMSO-$d_6$) δ 11.91 (br. s., NH, 1H), 8.59-8.43 (m, 2H), 8.03 (d, J=9.2 Hz, 1H), 7.96 (d, J=4.9 Hz, 1H), 7.81 (s, 1H), 7.33 (dd, J=8.7, 5.6 Hz, 2H), 7.13 (t, J=8.9 Hz, 2H), 7.05 (d, J=9.2 Hz, 1H), 3.97 (s, 3H), 2.94-2.79 (m, 3H), 2.51-2.27 (m, 4H), 2.00 (t, J=11.0 Hz, 2H), 1.78-1.72 (m, 2H), 1.72-1.56 (m, 2H).

Compound 150

2-Fluoro-N-(6-(3-(4-fluorophenyl)-5-(1-(isoxazol-3-ylmethyl)piperidin-4-yl)-1-methyl-1H-pyrazol-4-yl)imidazo[1,2-b]pyridazin-2-yl)isonicotinamide

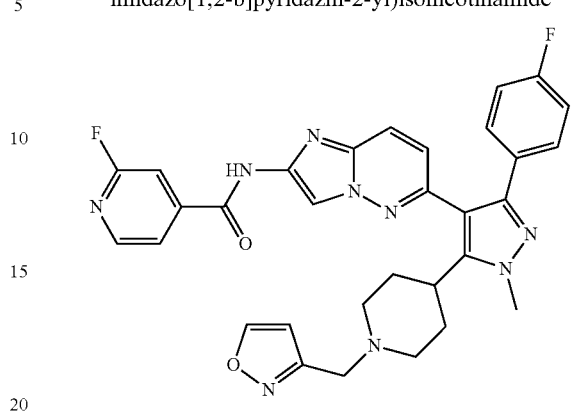

Compound 150 was prepared by the procedure described for the preparation of Compound 114 using Compound 148 and isoxazole-3-carbaldehyde. MS(ES): m/z=595.23 M⁺. HPLC Ret time (Method A): 2.65 min and (Method B): 3.89 min. $^1$H NMR (500 MHz, DMSO-$d_6$) δ 8.83 (d, J=1.5 Hz, 1H), 8.61-8.42 (m, 2H), 8.10-7.89 (m, 2H), 7.82 (s, 1H), 7.43-7.24 (m, 2H), 7.13 (t, J=9.0 Hz, 2H), 7.02 (d, J=9.2 Hz, 1H), 6.47 (d, J=1.5 Hz, 1H), 3.96 (s, 3H), 3.56 (s, 2H), 3.00-2.86 (m, 2H), 2.82 (d, J=11.3 Hz, 2H), 2.08 (td, J=11.2, 3.5 Hz, 2H), 1.89-1.67 (m, 3H).

Compound 151

2-Fluoro-N-(6-(3-(4-fluorophenyl)-1-methyl-5-(1-(3,3,3-trifluoropropanoyl)piperidin-4-yl)-1H-pyrazol-4-yl)imidazo[1,2-b]pyridazin-2-yl)isonicotinamide

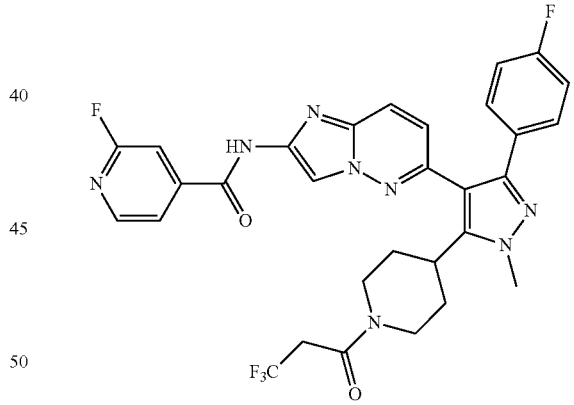

Compound 151 was prepared by the procedure described for the preparation of Compound 121 using Compound 148 and 3,3,3-trifluoropropanoic acid. MS(ES): m/z=624.20 M⁺. HPLC Ret time (Method C): 2.55 min and (Method D): 3.69 min. $^1$H NMR (500 MHz, DMSO-$d_6$) δ 11.88 (br. s., NH, 1H), 8.64-8.41 (m, 2H), 8.02-7.94 (m, 2H), 7.80 (s, 1H), 7.34 (dd, J=8.7, 5.6 Hz, 2H), 7.14 (t, J=8.9 Hz, 2H), 6.98 (d, J=9.2 Hz, 1H), 4.42 (d, J=12.2 Hz, 1H), 3.99 (s, 3H), 3.92-3.84 (m, 1H), 3.67-3.45 (m, 2H), 3.29-3.17 (m, 1H), 3.09 (t, J=12.1 Hz, 1H), 2.62 (t, J=11.9 Hz, 1H), 1.82 (d, J=12.5 Hz, 2H), 1.72 (dd, J=12.4, 3.8 Hz, 1H), 1.51 (dd, J=12.8, 4.0 Hz, 1H).

The following compounds in Table 5 were prepared by the procedure described for the preparation of Compound 21 using Compound 50 and corresponding acids.

TABLE 5

| Compound No. | Structure | Name | M⁺ | Ret time | HPLC Method |
|---|---|---|---|---|---|
| 152 | 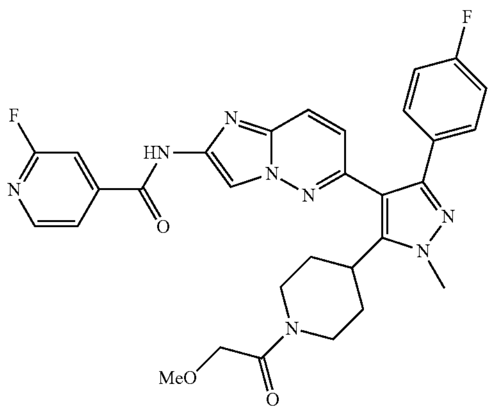 [SMILES: COCC(=O)N1CCC(c2c(-c3ccc4nc(NC(=O)c5ccnc(F)c5)cn4n3)c(-c3ccc(F)cc3)nn2C)CC1] | 2-fluoro-N-(6-(3-(4-fluorophenyl)-5-(1-(2-methoxyacetyl)piperidin-4-yl)-1-methyl-1H-pyrazol-4-yl)imidazo[1,2-b]pyridazin-2-yl)isonicotinamide | 586.23 | 2.32/ 3.91 | C/D |
| 153 | 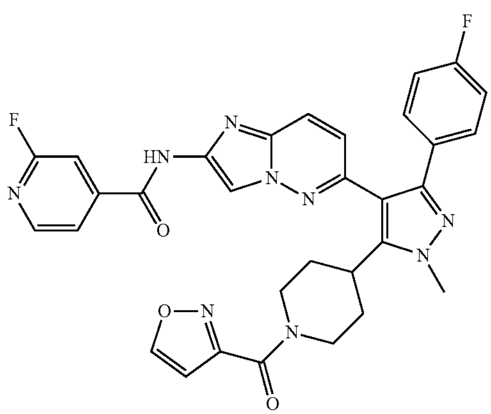 [SMILES: Cn1nc(-c2ccc(F)cc2)c(-c2ccc3nc(NC(=O)c4ccnc(F)c4)cn3n2)c1C1CCN(C(=O)c2ccon2)CC1] | 2-fluoro-N-(6-(3-(4-fluorophenyl)-5-(1-(isoxazole-3-carbonyl)piperidin-4-yl)-1-methyl-1H-pyrazol-4-yl)imidazo[1,2-b]pyridazin-2-yl)isonicotinamide | 609.20 | 2.51/ 3.72 | C/D |
| 154 | 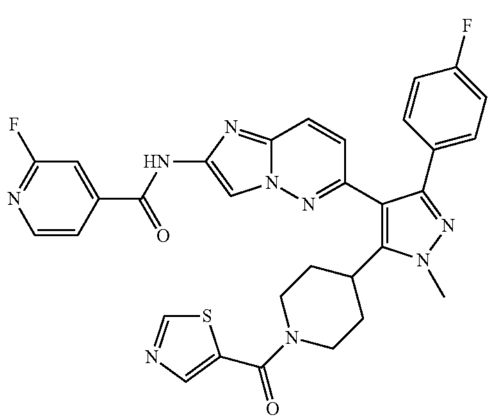 [SMILES: Cn1nc(-c2ccc(F)cc2)c(-c2ccc3nc(NC(=O)c4ccnc(F)c4)cn3n2)c1C1CCN(C(=O)c2cncs2)CC1] | 2-fluoro-N-(6-(3-(4-fluorophenyl)-1-methyl-5-(1-(thiazole-5-carbonyl)piperidin-4-yl)-1H-pyrazol-4-yl)imidazo[1,2-b]pyridazin-2-yl)isonicotinamide | 625.18 | 2.40/ 2.76 | C/D |

Compound 155

2-Fluoro-N-(6-(3-(4-fluorophenyl)-5-(1-(3-fluoropropyl)piperidin-4-yl)-1-methyl-1H-pyrazol-4-yl)imidazo[1,2-b]pyridazin-2-yl)isonicotinamide

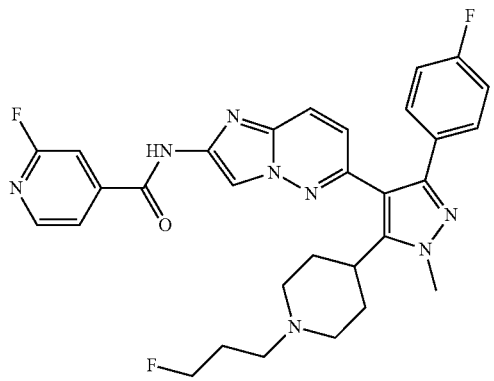 [SMILES: Cn1nc(-c2ccc(F)cc2)c(-c2ccc3nc(NC(=O)c4ccnc(F)c4)cn3n2)c1C1CCN(CCCF)CC1]

To a solution of N-(6-(3-(4-fluorophenyl)-1-methyl-5-(piperidin-4-yl)-1H-pyrazol-4-yl)imidazo[1,2-b]pyridazin-2-yl)-2-morpholinoisonicotinamide, Compound 148 (30 mg, 0.052 mmol) in EtOH were added 1-fluoro-3-iodopropane (29.1 mg, 0.155 mmol) and Et$_3$N (28.8 µl, 0.206 mmol). The reaction mixture was heated at 50° C. for 5 h, cooled, concentrated and the residue was purified by prep. HPLC to afford Compound 155. MS(ES): m/z=641.30 M$^+$. HPLC Ret time (Method C): 2.21 min and (Method D): 3.83 min. $^1$H NMR (500 MHz, DMSO-d$_6$) δ 8.51 (s, 1H), 8.33 (d, J=4.9 Hz, 1H), 8.01 (d, J=9.2 Hz, 1H), 7.52 (s, 1H), 7.36 (dd, J=8.4, 5.6 Hz, 2H), 7.26 (d, J=4.9 Hz, 1H), 7.14 (t, J=8.9 Hz, 2H), 7.04 (d, J=9.5 Hz, 1H), 4.47 (t, J=6.0 Hz, 1H), 4.38 (t, J=5.8 Hz, 1H), 3.99 (s, 3H), 3.00-2.82 (m, 3H), 2.34 (t, J=7.2 Hz, 2H), 2.04-1.61 (m, 8H).

Compound 156

N-(6-(5-(1-(2-Cyanoethyl)piperidin-4-yl)-3-(4-fluorophenyl)-1-methyl-1H-pyrazol-4-yl)imidazo[1,2-b]pyridazin-2-yl)-2-fluoroisonicotinamide

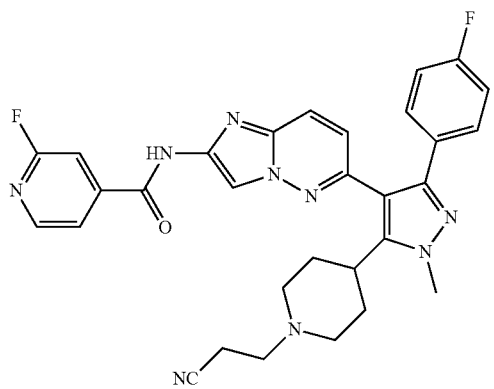 [SMILES: Cn1nc(-c2ccc(F)cc2)c(-c2ccc3nc(NC(=O)c4ccnc(F)c4)cn3n2)c1C1CCN(CCC#N)CC1]

Compound 156 was prepared by the procedure described for the preparation of Compound 125 using Compound 148 and acrylonitrile. MS(ES): m/z=567.23 M$^+$. HPLC Ret time (Method C): 2.50 min and (Method D): 2.70 min. $^1$H NMR (500 MHz, DMSO-d$_6$) δ 11.90 (br. s., NH, 1H), 8.52-8.46 (m, 2H), 8.03 (d, J=9.5 Hz, 1H), 7.96 (d, J=4.9 Hz, 1H), 7.80 (s, 1H), 7.40-7.23 (m, 2H), 7.13 (t, J=9.0 Hz, 2H), 7.06 (d, J=9.5 Hz, 1H), 3.97 (s, 3H), 3.00-2.84 (m, 3H), 2.67-2.48 (m, 4H), 2.06 (t, J=10.8 Hz, 2H), 1.84-1.72 (m, 2H), 1.72-1.52 (m, 2H).

Compound 157

N-(6-(5-(1-(2-Amino-2-oxoethyl)piperidin-4-yl)-3-(4-fluorophenyl)-1-methyl-1H-pyrazol-4-yl)imidazo[1,2-b]pyridazin-2-yl)-2-fluoroisonicotinamide

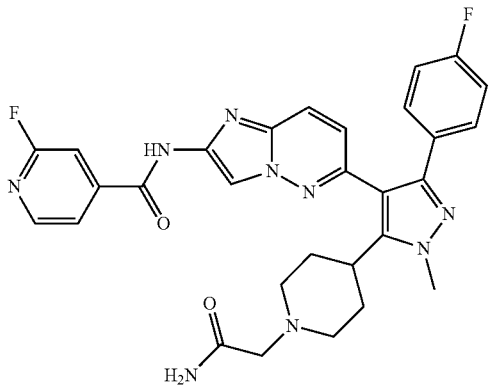 [SMILES: Cn1nc(-c2ccc(F)cc2)c(-c2ccc3nc(NC(=O)c4ccnc(F)c4)cn3n2)c1C1CCN(CC(N)=O)CC1]

Compound 157 was prepared by the procedure described for the preparation of Compound 124 using Compound 148 and bromoacetamide. MS(ES): m/z=571.23 M$^+$. HPLC Ret time (Method C): 2.28 min and (Method D): 3.66 min. $^1$H NMR (500 MHz, DMSO-d$_6$) δ 11.90 (br. s., NH, 1H), 8.54-8.45 (m, 2H), 8.04-7.95 (m, 2H), 7.81 (s, 1H), 7.35 (dd, J=8.5, 5.5 Hz, 2H), 7.20-6.96 (m, 5H including NH$_2$), 4.00 (s, 3H), 3.00-2.77 (m, 3H), 2.82 (s, 2H), 2.12 (t, J=10.8 Hz, 2H), 1.92-1.77 (m, 2H), 1.77-1.68 (m, 2H).

Compound 158

(R)-2-Fluoro-N-(6-(3-(4-fluorophenyl)-1-methyl-5-(1-(3,3,3-trifluoro-2-hydroxypropyl)piperidin-4-yl)-1H-pyrazol-4-yl)imidazo[1,2-b]pyridazin-2-yl)isonicotinamide

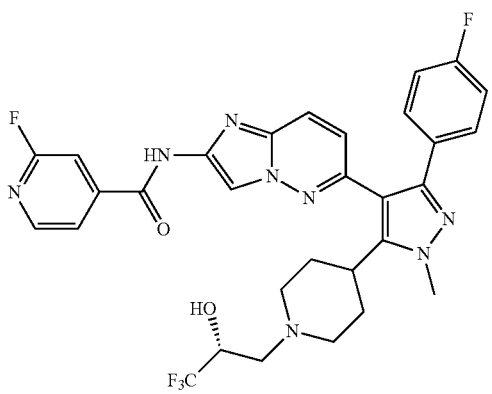

Compound 158 was prepared by the procedure described for the preparation of Compound 127 using Compound 148 and (R)-2-(trifluoromethyl)oxirane. MS(ES): m/z=626.22 M$^+$. HPLC Ret time (Method C): 2.55 min and (Method D): 2.68 min. $^1$H NMR (500 MHz, DMSO-d$_6$) δ 8.57-8.43 (m, 2H), 8.03 (d, J=9.2 Hz, 1H), 7.96 (d, J=5.2 Hz, 1H), 7.81 (s, 1H), 7.40-7.29 (m, 2H), 7.17-7.00 (m, 3H), 4.07 (m, 1H), 3.97 (s, 3H), 2.98-2.82 (m, 3H), 2.48-2.37 (m, 2H), 2.21-2.01 (m, 2H), 1.79-1.71 (m, 2H), 1.71-1.58 (m, 2H).

Compound 159

(S)-2-Fluoro-N-(6-(3-(4-fluorophenyl)-1-methyl-5-(1-(3,3,3-trifluoro-2-hydroxypropyl)piperidin-4-yl)-1H-pyrazol-4-yl)imidazo[1,2-b]pyridazin-2-yl)isonicotinamide

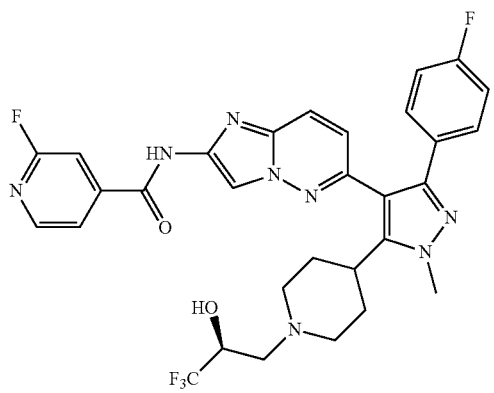 [SMILES: Cn1nc(-c2ccc(F)cc2)c(-c2ccc3nc(NC(=O)c4ccnc(F)c4)cn3n2)c1C1CCN(C[C@H](O)C(F)(F)F)CC1]

Compound 159 was prepared by the procedure described for the preparation of Compound 127 using Compound 148 and (S)-2-(trifluoromethyl)oxirane. MS(ES): m/z=626.22 M+. HPLC Ret time (Method C): 2.52 min and (Method D): 2.65 min. $^1$H NMR (500 MHz, DMSO-$d_6$) δ 11.91 (br. s., NH, 1H), 8.53-8.46 (m, 2H), 8.04 (d, J=9.2 Hz, 1H), 8.00-7.90 (m, 1H), 7.81 (s, 1H), 7.33 (dd, J=8.9, 5.5 Hz, 2H), 7.22-6.99 (m, 3H), 4.07 (m, 1H), 3.97 (s, 3H), 3.00-2.84 (m, 4H), 2.48-2.31 (m, 1H), 2.18-1.98 (m, 2H), 1.81-1.71 (m, 2H), 1.71-1.58 (m, 2H).

Compound 160

N-(6-(3-(4-Fluorophenyl)-1-methyl-5-(piperidin-4-yl)-1H-pyrazol-4-yl)imidazo[1,2-b]pyridazin-2-yl)-2-morpholinoisonicotinamide

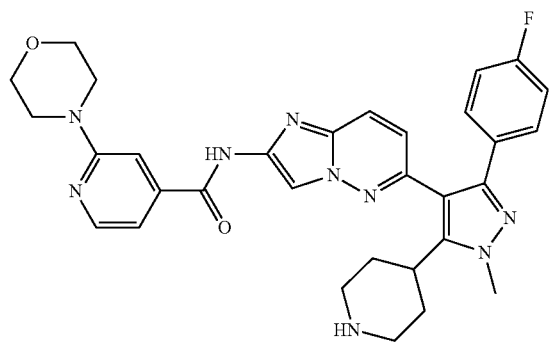 [SMILES: Cn1nc(-c2ccc(F)cc2)c(-c2ccc3nc(NC(=O)c4ccnc(N5CCOCC5)c4)cn3n2)c1C1CCNCC1]

Compound 160 was prepared by the procedures described for the preparation of Compound 113A and Compound 113 using Intermediate 11 and 2-morpholinoisonicotinic acid. MS(ES): m/z=581.27 M+. HPLC Ret time (Method C): 2.17 min and (Method D): 3.58 min. $^1$H NMR (500 MHz, DMSO-$d_6$) δ 8.50 (s, NH, 1H), 8.31 (d, J=4.9 Hz, 1H), 7.99 (d, J=9.5 Hz, 1H), 7.52 (s, 1H), 7.34 (dd, J=8.7, 5.6 Hz, 3H), 7.25 (d, J=4.9 Hz, 1H), 7.13 (t, J=8.9 Hz, 3H), 7.01 (d, J=9.2 Hz, 1H), 3.98 (s, 3H), 3.81-3.68 (m, 4H), 3.65-3.56 (m, 2H), 3.08-2.85 (m, 3H), 2.61-2.53 (m, 2H), 1.74-1.65 (m, 3H), 1.65-1.51 (m, 3H).

Compound 161

N-(6-(3-(4-Fluorophenyl)-1-methyl-5-(1-(3,3,3-trifluoropropyl)piperidin-4-yl)-1H-pyrazol-4-yl)imidazo[1,2-b]pyridazin-2-yl)-2-morpholinoisonicotinamide

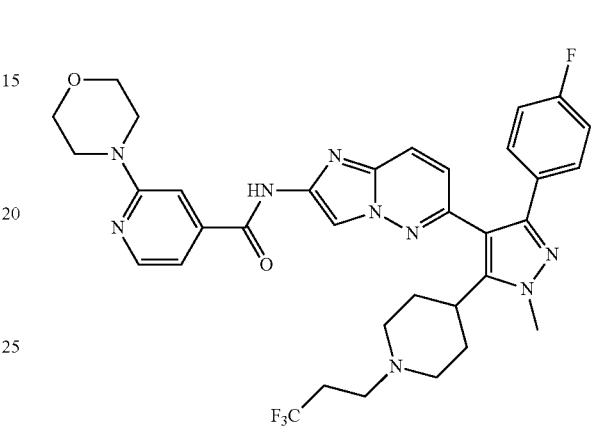

Compound 161 was prepared by the procedure described for the preparation of Compound 114 using Compound 160 and 3,3,3-trifluoropropanal. MS(ES): m/z=677.28 M+. HPLC Ret time (Method C): 2.80 min and (Method D): 4.18 min. $^1$H NMR (500 MHz, DMSO-$d_6$) δ 11.68 (s, NH, 1H), 8.49 (s, 1H), 8.31 (d, J=5.2 Hz, 1H), 8.00 (d, J=9.2 Hz, 1H), 7.51 (s, 1H), 7.43-7.29 (m, 2H), 7.25 (d, J=5.2 Hz, 1H), 7.12 (t, J=9.0 Hz, 2H), 7.04 (d, J=9.2 Hz, 1H), 3.97 (s, 3H), 3.82-3.70 (m, 4H), 3.66-3.49 (m, 4H), 2.99-2.81 (m, 3H), 2.52-2.29 (m, 4H), 2.07-1.95 (m, 2H), 1.83-1.71 (m, 2H), 1.71-1.59 (m, 2H).

Compound 162

N-(6-(3-(4-Fluorophenyl)-5-(1-(3-fluoropropyl)piperidin-4-yl)-1-methyl-1H-pyrazol-4-yl)imidazo[1,2-b]pyridazin-2-yl)-2-morpholinoisonicotinamide

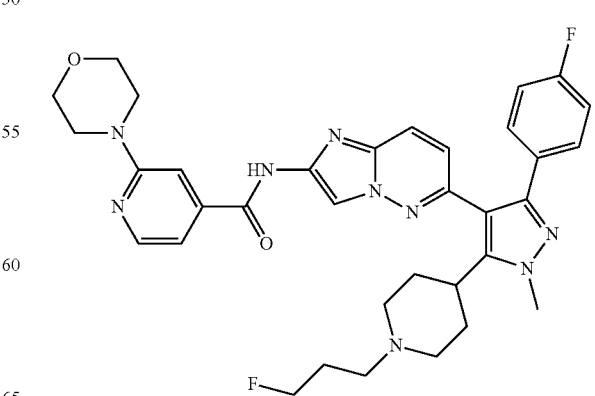

Compound 162 was prepared by the procedure described for the preparation of Compound 119 using Compound 160 and 1-fluoro-3-iodopropane. MS(ES): m/z=641.30 M+. HPLC Ret time (Method C): 2.21 min and (Method D): 3.83 min. $^1$H NMR (500 MHz, DMSO-d$_6$) δ 11.68 (s, NH, 1H), 8.49 (s, 1H), 8.31 (d, J=5.2 Hz, 1H), 8.00 (d, J=9.2 Hz, 1H), 7.52 (s, 1H), 7.34 (dd, J=8.7, 5.6 Hz, 2H), 7.25 (d, J=5.2 Hz, 1H), 7.13 (t, J=8.9 Hz, 2H), 7.02 (d, J=9.2 Hz, 1H), 4.45 (t, J=6.0 Hz, 1H), 4.36 (t, J=6.0 Hz, 1H), 3.97 (s, 3H), 3.84-3.70 (m, 4H), 3.66-3.48 (m, 4H), 2.87 (d, J=11.3 Hz, 3H), 2.32 (t, J=7.3 Hz, 2H), 1.99-1.87 (m, 2H), 1.85-1.61 (m, 6H).

Compound 163

N-(6-(5-(1-(2-Amino-2-oxoethyl)piperidin-4-yl)-3-(4-fluorophenyl)-1-methyl-1H-pyrazol-4-yl)imidazo[1,2-b]pyridazin-2-yl)-2-morpholinoisonicotinamide

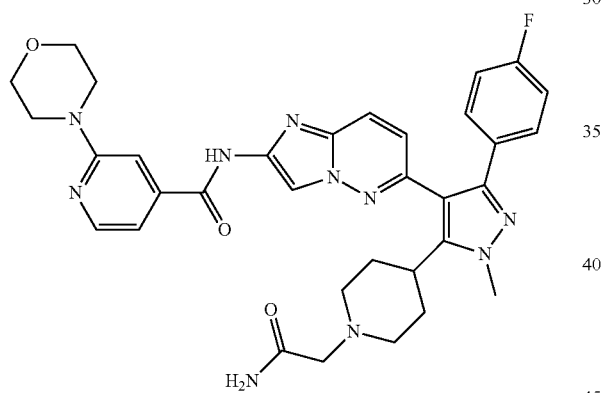

Compound 163 was prepared by the procedure described for the preparation of Compound 124 using Compound 160 and 2-bromoacetamide. MS(ES): m/z=638.29 M+. HPLC Ret time (Method L): 2.26 min and (Method K): 3.77 min. $^1$H NMR (500 MHz, DMSO-d$_6$) δ 11.67 (s, NH, 1H), 8.49 (s, 1H), 8.31 (d, J=5.2 Hz, 1H), 7.99 (d, J=9.2 Hz, 1H), 7.52 (s, 1H), 7.35 (dd, J=8.9, 5.5 Hz, 2H), 7.25 (d, J=5.2 Hz, 1H), 7.20-7.09 (m, 2H), 7.09-6.96 (m, 1H), 4.00 (s, 3H), 3.84-3.69 (m, 4H), 3.64-3.51 (m, 4H), 2.92 (s, 2h), 2.97-2.76 (m, 3H), 2.12 (t, J=10.8 Hz, 2H), 1.86-1.77 (m, 2H), 1.77-1.64 (m, 2H).

Compound 164

N-(6-(3-(4-Fluorophenyl)-1-methyl-5-(piperidin-4-yl)-1H-pyrazol-4-yl)imidazo[1,2-b]pyridazin-2-yl)isonicotinamide

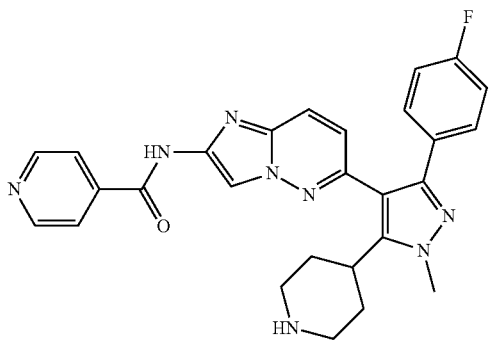 [SMILES: Cn1nc(-c2ccc(F)cc2)c(-c2ccc3nc(NC(=O)c4ccncc4)cn3n2)c1C1CCNCC1]

Compound 164 was prepared by the procedures described for the preparation of Compounds 113A and 113 using Intermediate 11 and isonicotinic acid. MS(ES): m/z=496.21 M+. HPLC Ret time (Method C): 1.70 min and (Method D): 2.98 min. $^1$H NMR (500 MHz, DMSO-d$_6$) δ 8.88-8.79 (m, 2H), 8.59-8.47 (m, 1H), 8.05-7.92 (m, 3H), 7.40-7.28 (m, 2H), 7.17-7.07 (m, 2H), 7.02 (d, J=9.2 Hz, 1H), 3.98 (s, 3H), 3.08-2.92 (m, 5H), 2.90 (s, 3H), 1.72-1.65 (m, 2H), 1.65-1.51 (m, 2H).

Compound 165

N-(6-(3-(4-Fluorophenyl)-1-methyl-5-(1-methylpiperidin-4-yl)-1H-pyrazol-4-yl)imidazo[1,2-b]pyridazin-2-yl)isonicotinamide

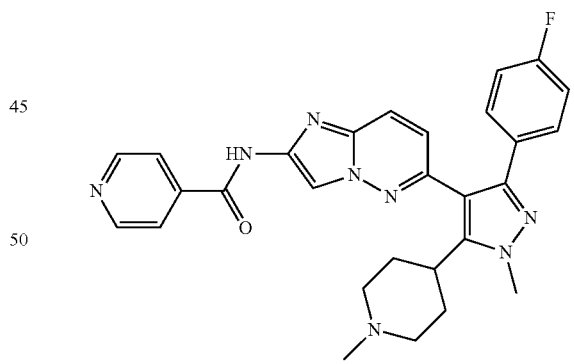

Compound 165 was prepared by the procedure described for the preparation of Compound 114 using Compound 164 and formaldehyde. MS(ES): m/z=510.23 M+. HPLC Ret time (Method C): 75 min and (Method D): 3.06 min. $^1$H NMR (500 MHz, DMSO-d$_6$) δ 8.87-8.77 (m, 2H), 8.51 (s, 1H), 8.06-7.95 (m, 3H), 7.39-7.30 (m, 2H), 7.18-7.07 (m, 2H), 7.03 (d, J=9.5 Hz, 1H), 3.96 (s, 3H), 2.88-2.80 (m, 1H), 2.80-2.68 (m, 2H), 2.10 (s, 3H), 1.66-1.91 (m, 6H).

The following compounds in Table 6 were prepared by the procedure described for the preparation of Compound 114 using Compound 164 and the corresponding aldehydes.

TABLE 6

| Compound No. | Structure | Name | [M + H]+ | Ret time | HPLC Method |
|---|---|---|---|---|---|
| 166 | 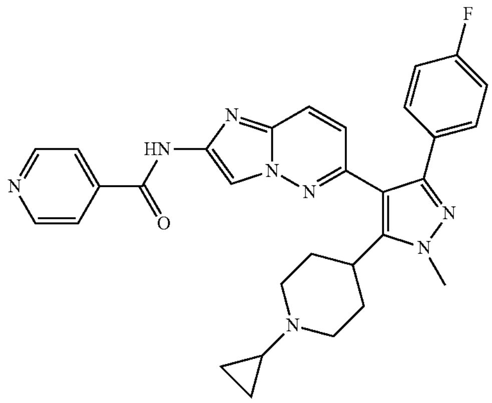 [SMILES: Cn1nc(-c2ccc(F)cc2)c(-c2ccc3nc(NC(=O)c4ccncc4)cn3n2)c1C1CCN(C2CC2)CC1] | N-(6-(5-(1-cyclopropylpiperidin-4-yl)-3-(4-fluorophenyl)-1-methyl-1H-pyrazol-4-yl)imidazo[1,2-b]pyridazin-2-yl)isonicotinamide | 537.40 | 2.06, 3.60 | C, D |
| 167 | 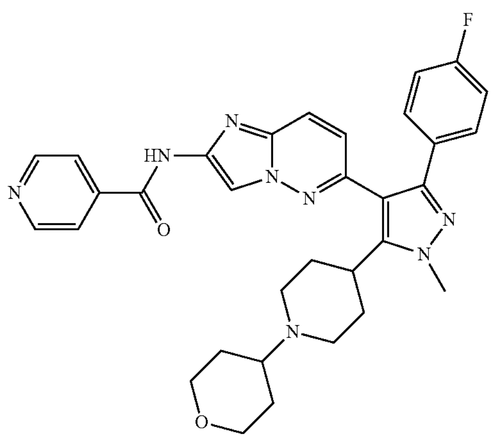 [SMILES: Cn1nc(-c2ccc(F)cc2)c(-c2ccc3nc(NC(=O)c4ccncc4)cn3n2)c1C1CCN(C2CCOCC2)CC1] | N-(6-(3-(4-fluorophenyl)-1-methyl-5-(1-(tetrahydro-2H-pyran-4-yl)piperidin-4-yl)-1H-pyrazol-4-yl)imidazo[1,2-b]pyridazin-2-yl)isonicotinamide | 581.40 | 1.78, 3.23 | C, D |
| 168 | 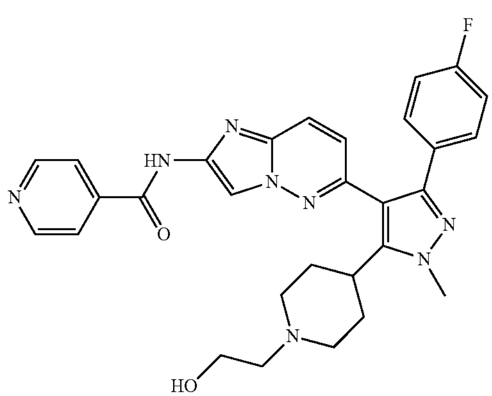 [SMILES: Cn1nc(-c2ccc(F)cc2)c(-c2ccc3nc(NC(=O)c4ccncc4)cn3n2)c1C1CCN(CCO)CC1] | N-(6-(3-(4-fluorophenyl)-5-(1-(2-hydroxyethyl)piperidin-4-yl)-1-methyl-1H-pyrazol-4-yl)imidazo[1,2-b]pyridazin-2-yl)isonicotinamide | 541.31 | 2.90 | A |

TABLE 6-continued

| Compound No. | Structure | Name | [M + H]+ | Ret time | HPLC Method |
|---|---|---|---|---|---|
| 169 | 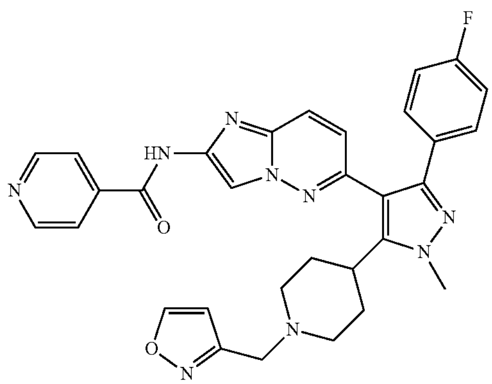 [SMILES: Cn1nc(-c2ccc(F)cc2)c(-c2ccc3nc(NC(=O)c4ccncc4)cn3n2)c1C1CCN(Cc2ccon2)CC1] | N-(6-(3-(4-fluorophenyl)-5-(1-(isoxazol-3-ylmethyl)piperidin-4-yl)-1-methyl-1H-pyrazol-4-yl)imidazo[1,2-b]pyridazin-2-yl)isonicotinamide | 578.30 | 2.14, 3.46 | C, D |
| 170 | 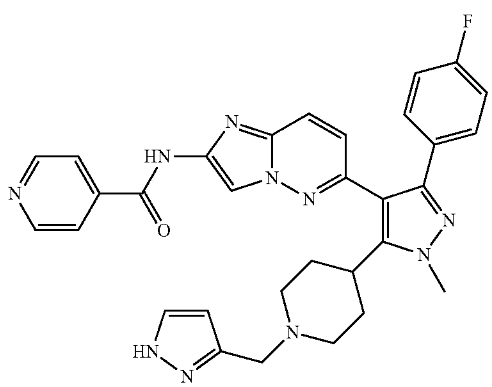 [SMILES: Cn1nc(-c2ccc(F)cc2)c(-c2ccc3nc(NC(=O)c4ccncc4)cn3n2)c1C1CCN(Cc2cc[nH]n2)CC1] | N-(6-(5-(1-((1H-pyrazol-3-yl)methyl)piperidin-4-yl)-3-(4-fluorophenyl)-1-methyl-1H-pyrazol-4-yl)imidazo[1,2-b]pyridazin-2-yl)isonicotinamide | 577.40 | 2.02, 3.56 | C, D |
| 171 | 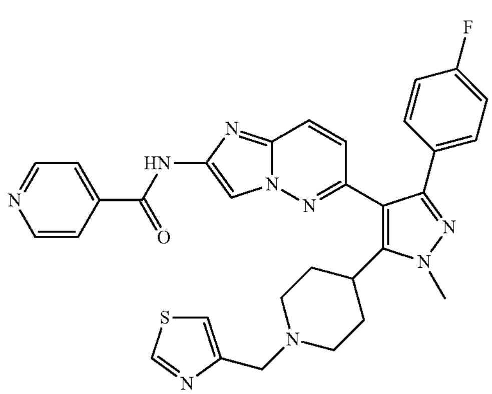 | N-(6-(3-(4-fluorophenyl)-1-methyl-5-(1-(thiazol-4-ylmethyl)piperidin-4-yl)-1H-pyrazol-4-yl)imidazo[1,2-b]pyridazin-2-yl)isonicotinamide | 594.30 | 2.16, 3.70 | C, D |

TABLE 6-continued

| Compound No. | Structure | Name | [M + H]+ | Ret time | HPLC Method |
|---|---|---|---|---|---|
| 172 | 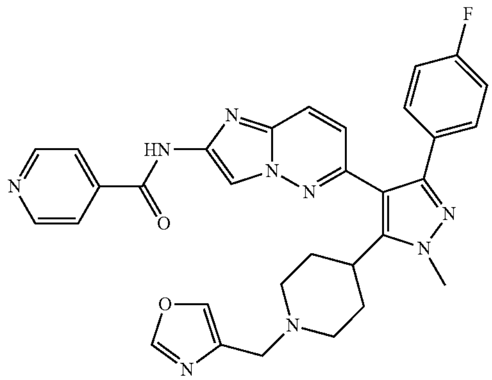 [SMILES: Cn1nc(-c2ccc(F)cc2)c(-c2ccc3nc(NC(=O)c4ccncc4)cn3n2)c1C1CCN(Cc2cscn2)CC1] | N-(6-(3-(4-fluorophenyl)-1-methyl-5-(1-(oxazol-4-ylmethyl)piperidin-4-yl)-1H-pyrazol-4-yl)imidazo[1,2-b]pyridazin-2-yl)isonicotinamide | 578.40 | 2.14, 3.64 | C, D |
| 173 | 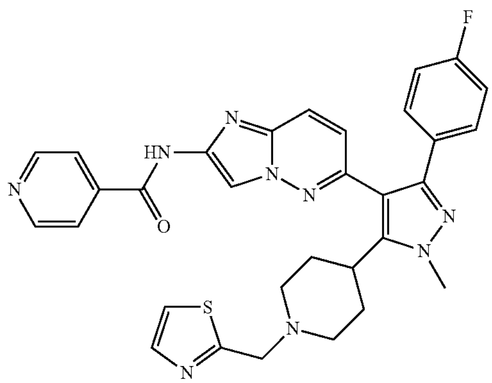 [SMILES: Cn1nc(-c2ccc(F)cc2)c(-c2ccc3nc(NC(=O)c4ccncc4)cn3n2)c1C1CCN(Cc2nccs2)CC1] | N-(6-(3-(4-fluorophenyl)-1-methyl-5-(1-(thiazol-2-ylmethyl)piperidin-4-yl)-1H-pyrazol-4-yl)imidazo[1,2-b]pyridazin-2-yl)isonicotinamide | 594.40 | 2.46, 3.87 | C, D |

Compound 174

N-(6-(3-(4-Fluorophenyl)-1-methyl-5-(piperidin-4-yl)-1H-pyrazol-4-yl)imidazo[1,2-b]pyridazin-2-yl)-4-methyl-2-(pyridin-3-yl)thiazole-5-carboxamide

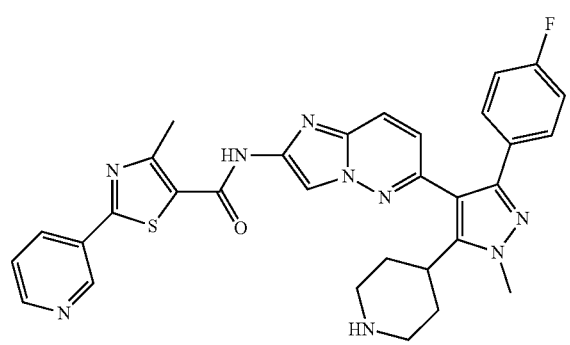 [SMILES: Cc1nc(-c2cccnc2)sc1C(=O)Nc1cn2nc(-c3c(-c4ccc(F)cc4)nn(C)c3C3CCNCC3)ccc2n1]

Compound 175

N-(6-(3-(4-Fluorophenyl)-1-methyl-5-(1-methylpiperidin-4-yl)-1H-pyrazol-4-yl)imidazo[1,2-b]pyridazin-2-yl)-4-methyl-2-(pyridin-3-yl)thiazole-5-carboxamide

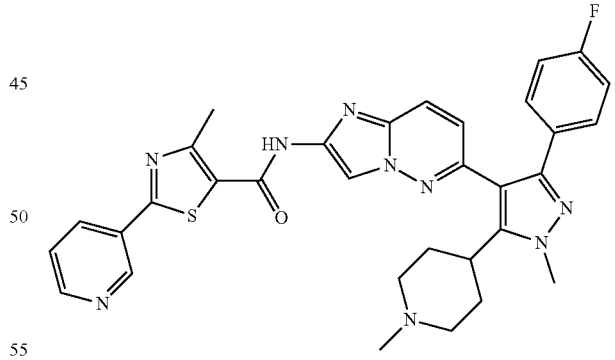

Compound 174 was prepared by the procedure described for the preparation of Compounds 113A and 113 using Intermediates 11 and 4-methyl-2-(pyridin-3-yl)thiazole-5-carboxylic acid. MS(ES): m/z=593.21 M+. HPLC Ret time (Method C): 2.27 min and (Method D): 3.72 min. $^1$H NMR (500 MHz, DMSO-$d_6$) δ 9.19 (d, J=2.1 Hz, 1H), 8.74 (d, J=4.6 Hz, 1H), 8.46 (s, 1H), 8.37 (d, J=8.2 Hz, 1H), 8.04-7.90 (m, 2H), 7.61 (dd, J=7.9, 4.9 Hz, 1H), 7.34 (dd, J=8.5, 5.5 Hz, 2H), 7.13 (t, J=9.0 Hz, 2H), 7.01 (d, J=9.2 Hz, 1H), 3.98 (s, 3H), 3.06-2.93 (m, 3H), 2.91 (s, 3H), 2.66-2.45 (m, 2H), 1.71 (m, 2H), 1.66-1.52 (m, 2H).

Compound 175 was prepared by the procedure described for the preparation of Compound 114 using Compound 174 and formaldehyde. MS(ES): m/z=607.23 M+. HPLC Ret time (Method C): 2.24 min and (Method D): 3.81 min. $^1$H NMR (500 MHz, DMSO-$d_6$) δ 9.19 (d, J=2.1 Hz, 1H), 8.75 (dd, J=4.7, 1.4 Hz, 1H), 8.45 (s, 1H), 8.37 (dt, J=8.1, 1.9 Hz, 1H), 8.09-7.91 (m, 2H), 7.61 (dd, J=7.9, 4.9 Hz, 1H), 7.44-7.30 (m, 2H), 7.13 (t, J=8.9 Hz, 2H), 7.02 (d, J=9.5 Hz, 1H), 3.97 (s, 3H), 2.91 (s, 3H), 2.88-2.77 (m, 5H), 2.75 (s, 3H), 1.82-1.60 (m, 4H).

The following compounds in Table 7 were prepared by the procedure described for the preparation of Compound 114 using Compound 174 and the corresponding aldehydes.

TABLE 7

| Compound No. | Structure | Name | M+ | Ret time | HPLC Method |
|---|---|---|---|---|---|
| 176 | 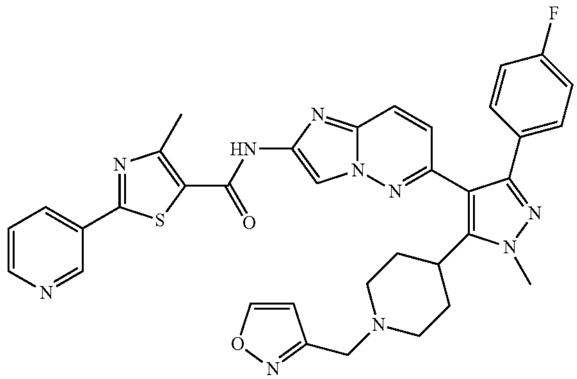 [SMILES: Cc1nc(-c2cccnc2)sc1C(=O)Nc1cn2nc(-c3c(-c4ccc(F)cc4)nn(C)c3C3CCN(Cc4ccon4)CC3)ccc2n1] | N-(6-(3-(4-fluorophenyl)-5-(1-(isoxazol-3-ylmethyl)piperidin-4-yl)-1-methyl-1H-pyrazol-4-yl)imidazo[1,2-b]pyridazin-2-yl)-4-methyl-2-(pyridin-3-yl)thiazole-5-carboxamide | 675.50 | 2.71/ 4.07 | C, D |
| 177 | 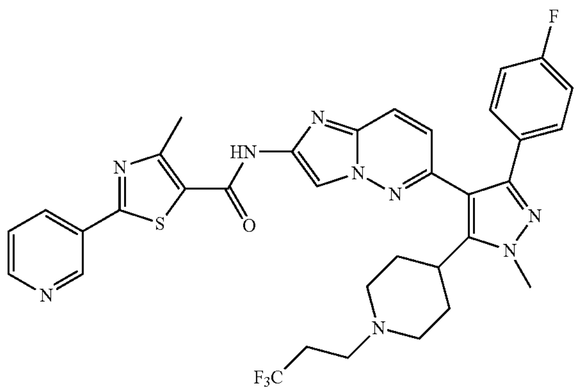 [SMILES: Cc1nc(-c2cccnc2)sc1C(=O)Nc1cn2nc(-c3c(-c4ccc(F)cc4)nn(C)c3C3CCN(CCC(F)(F)F)CC3)ccc2n1] | N-(6-(3-(4-fluorophenyl)-1-methyl-5-(1-(3,3,3-trifluoropropyl)piperidin-4-yl)-1H-pyrazol-4-yl)imidazo[1,2-b]pyridazin-2-yl)-4-methyl-2-(pyridin-3-yl)thiazole-5-carboxamide | 690.51 | 2.90/ 4.26 | C, D |

Compound 178

N-(6-(5-(1-(2-Amino-2-oxoethyl)piperidin-4-yl)-3-(4-fluorophenyl)-1-methyl-1H-pyrazol-4-yl)imidazo[1,2-b]pyridazin-2-yl)-4-methyl-2-(pyridin-3-yl)thiazole-5-carboxamide

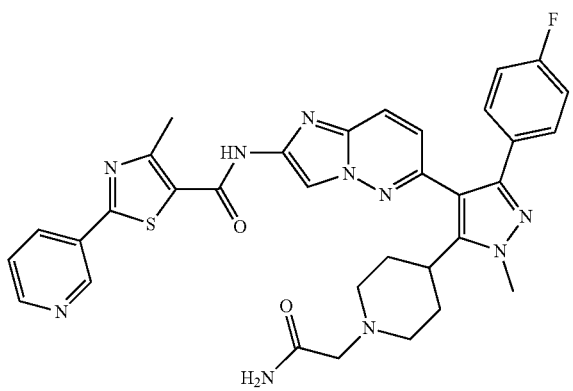 [SMILES: Cc1nc(-c2cccnc2)sc1C(=O)Nc1cn2nc(-c3c(-c4ccc(F)cc4)nn(C)c3C3CCN(CC(N)=O)CC3)ccc2n1]

Compound 178 was prepared by the procedure described for the preparation of Compound 124 using Compound 174 and 2-bromoacetamide. MS(ES): m/z=650.23 M+. HPLC Ret time (Method C): 2.35 min and (Method D): 3.93 min. ¹H NMR (500 MHz, DMSO-d₆) δ 9.19 (d, J=1.8 Hz, 1H), 8.74 (dd, J=4.9, 1.5 Hz, 1H), 8.45 (s, 1H), 8.37 (dt, J=8.1, 1.9 Hz, 1H), 8.09-7.89 (m, 1H), 7.60 (dd, J=7.8, 5.0 Hz, 1H), 7.45-7.30 (m, 2H), 7.23-7.09 (m, 3H), 7.09-6.95 (m, 2H), 4.00 (s, 3H), 2.98-2.79 (m, 3H), 2.83 (s, 2H), 2.74 (s, 3H), 2.79-1.65 (m, 6H).

Compound 179

N-(6-(3-(4-Fluorophenyl)-1-methyl-5-(piperidin-4-yl)-1H-pyrazol-4-yl)imidazo[1,2-b]pyridazin-2-yl)-4-methyl-2-(pyridin-4-yl)thiazole-5-carboxamide

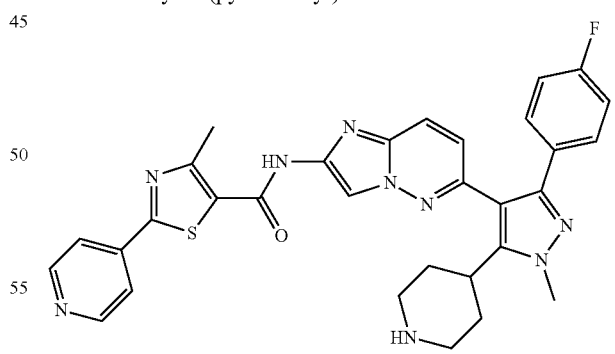

Compound 179 was prepared by the procedures described for the preparation of Compounds 113A and 113 using Intermediate 11 and 4-methyl-2-(pyridin-4-yl)thiazole-5-carboxylic acid. MS(ES): m/z=593.21 M+. HPLC Ret time (Method C): 2.23 min and (Method D): 3.73 min. ¹H NMR (500 MHz, DMSO-d₆) δ 8.83-8.73 (m, 2H), 8.47 (s, 1H), 8.05-7.88 (m, 3H), 7.34 (dd, J=8.7, 5.6 Hz, 2H), 7.19-7.07 (m, 2H), 7.01 (d, J=9.2 Hz, 1H), 3.98 (s, 3H), 3.02-2.97 (m, 3H), 2.91 (s, 3H), 1.79-1.51 (m, 6H).

Compound 180

N-(6-(3-(4-Fluorophenyl)-1-methyl-5-(1-methylpiperidin-4-yl)-1H-pyrazol-4-yl)imidazo[1,2-b]pyridazin-2-yl)-4-methyl-2-(pyridin-4-yl)thiazole-5-carboxamide

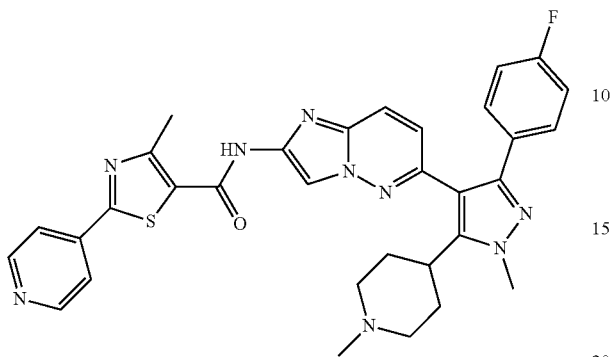

Compound 180 was prepared by the procedure described for the preparation of Compound 114 using Compound 179 and formaldehyde. MS(ES): m/z=607.23 M⁺. HPLC Ret time (Method C): 2.24 min and (Method D): 3.81 min. $^1$H NMR (500 MHz, DMSO-$d_6$) δ 8.83-8.72 (m, 2H), 8.45 (s, 1H), 8.04-7.93 (m, 4H), 7.42-7.30 (m, 2H), 7.21-7.07 (m, 2H), 7.07-6.91 (m, 1H), 3.97 (s, 3H), 2.91 (s, 3H), 22.85-2.76 (m, 3H), 2.11-1.59 (m, 6H).

The following compounds in Table 8 were prepared by the procedure described for the preparation of Compound 114 using Compound 179 and the corresponding aldehydes.

TABLE 8

| Compound No. | Structure | Name | M⁺ | Ret time | HPLC Method |
|---|---|---|---|---|---|
| 181 | 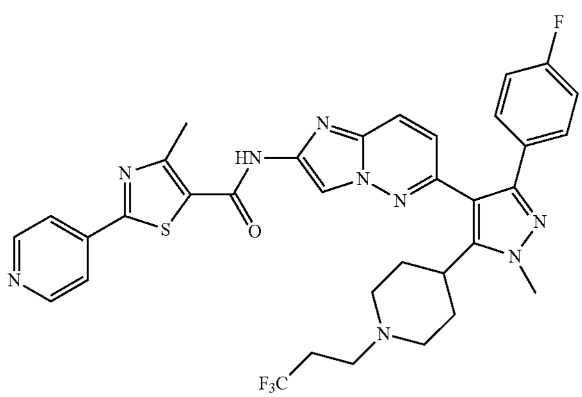 [SMILES: Cc1nc(-c2ccncc2)sc1C(=O)Nc1cn2nc(-c3c(-c4ccc(F)cc4)nn(C)c3C3CCN(CCC(F)(F)F)CC3)ccc2n1] | N-(6-(3-(4-fluorophenyl)-1-methyl-5-(1-(3,3,3-trifluoropropyl)piperidin-4-yl)-1H-pyrazol-4-yl)imidazo[1,2-b]pyridazin-2-yl)-4-methyl-2-(pyridin-4-yl)thiazole-5-carboxamide | 690.46 | 2.91/ 4.28 | C, D |
| 182 | 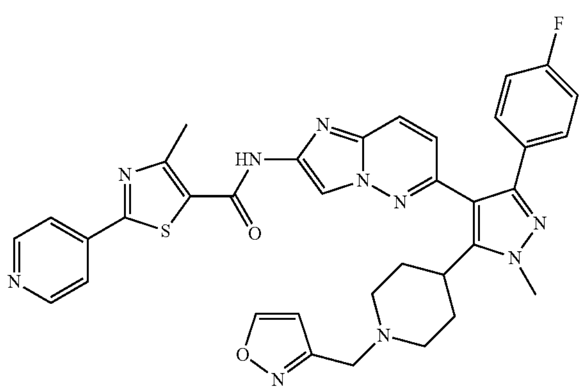 [SMILES: Cc1nc(-c2ccncc2)sc1C(=O)Nc1cn2nc(-c3c(-c4ccc(F)cc4)nn(C)c3C3CCN(Cc4ccon4)CC3)ccc2n1] | N-(6-(3-(4-fluorophenyl)-5-(1-(isoxazol-3-ylmethyl)piperidin-4-yl)-1-methyl-1H-pyrazol-4-yl)imidazo[1,2-b]pyridazin-2-yl)-4-methyl-2-(pyridin-4-yl)thiazole-5-carboxamide | 675.40 | 2.73/ 4.10 | C, D |

Compound 183

N-(6-(5-(1-(2-Cyanoethyl)piperidin-4-yl)-3-(4-fluorophenyl)-1-methyl-1H-pyrazol-4-yl)imidazo[1,2-b]pyridazin-2-yl)-4-methyl-2-(pyridin-4-yl)thiazole-5-carboxamide

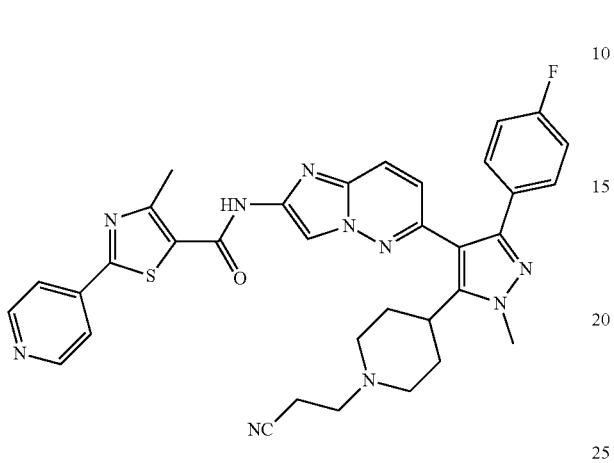

Compound 183 was prepared by the procedure described for the preparation of Compound 125 using compound 179 and acrylnitrile. MS(ES): m/z=647.47 M$^+$. HPLC Ret time (Method C): 2.25 min and (Method D): 3.97 min. $^1$H NMR (500 MHz, DMSO-d$_6$) δ 8.77 (d, J=6.1 Hz, 2H), 8.45 (s, 1H), 8.00 (d, J=9.2 Hz, 1H), 7.97-7.90 (m, 2H), 7.34 (dd, J=8.7, 5.6 Hz, 2H), 7.13 (t, J=8.9 Hz, 2H), 7.04 (d, J=9.2 Hz, 1H), 3.97 (s, 3H), 2.91 (s, 3H), 2.98-2.84 (m, 1H), 2.65-2.49 (m, 6H), 2.06 (t, J=10.8 Hz, 2H), 1.84-1.71 (m, 2H), 1.71-1.58 (m, 2H).

Compound 184

N-(6-(5-(1-(2-Amino-2-oxoethyl)piperidin-4-yl)-3-(4-fluorophenyl)-1-methyl-1H-pyrazol-4-yl)imidazo[1,2-b]pyridazin-2-yl)-4-methyl-2-(pyridin-4-yl)thiazole-5-carboxamide

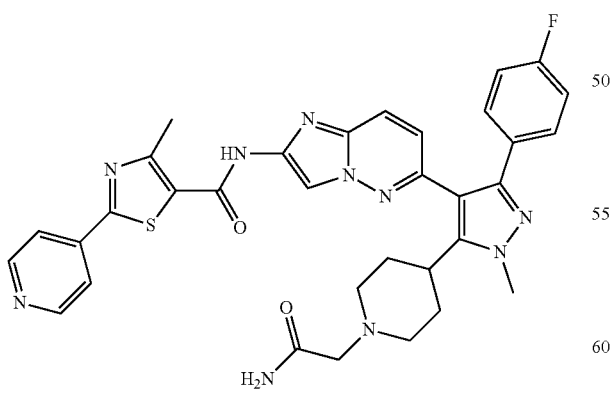

Compound 184 was prepared by the procedure described for the preparation of Compound 124 using Compound 179 and 2-bromoacetamide. MS(ES): m/z=650.23 M$^+$. HPLC Ret time (Method C): 2.35 min and (Method D): 3.96 min.

Scheme 10

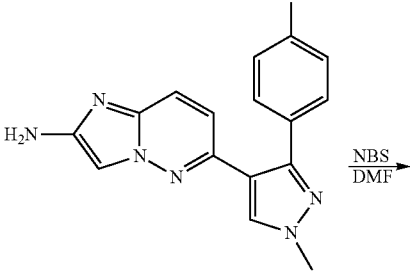

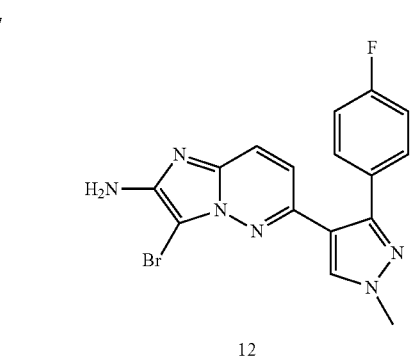

Intermediate 12

3-Bromo-6-(3-(4-fluorophenyl)-1-methyl-1H-pyrazol-4-yl)imidazo[1,2-b]pyridazin-2-amine

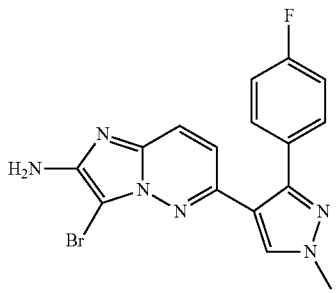 [SMILES: Cn1cc(-c2ccc3nc(N)c(Br)n3n2)c(-c2ccc(F)cc2)n1]

To a solution of Intermediate 7 (0.085 g, 0.276 mmol) in DMF (1.5 mL) was added NBS (0.049 g, 0.276 mmol). The reaction mixture was stirred at rt for 1 h and diluted with water. The solid was filtered off to provide Intermediate 12 (5.5 mg, 22% yield) as a yellowish solid. $^1$H NMR (400 MHz, methanol-d$_4$) δ ppm 8.11 (s, 1H), 7.67-7.56 (m, 2H), 7.51 (d, J=9.0 Hz, 1H), 7.19-7.07 (m, 2H), 7.00 (d, J=9.0 Hz, 1H), 4.00 (s, 3H).

Compound 185

6-(3-(4-Fluorophenyl)-1-methyl-1H-pyrazol-4-yl)-N-(pyrimidin-2-yl)imidazo[1,2-b]pyridazin-2-amine

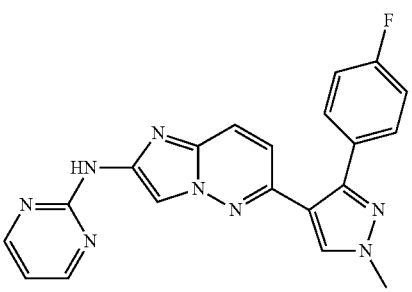 [SMILES: Cn1cc(-c2ccc3nc(Nc4ncccn4)cn3n2)c(-c2ccc(F)cc2)n1]

To a degassed mixture of Intermediate 7 (0.019 g, 0.062 mmol), 2-bromopyrimidine (0.020 g, 0.123 mmol), Pd$_2$(dba)$_3$ (0.0056 g, 6.16 μmol) and BINAP (0.012 g, 0.018 mmol) in toluene (0.62 mL) was added LiHMDS (0.185 mL, 0.185 mmol). The reaction was degassed again and heated at 100° C. for 30 minutes. It was quenched with water and the volatiles were evaporated under reduced pressure. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to provide compound 185 (0.0016 g, 15% yield). HPLC Ret. Time: 1.00 min. and 1.23 min. (Methods G and H respectively). MS(ES): m/z=387 [M+H]$^+$. $^1$H NMR (500 MHz, methanol-d$_4$) δ ppm 8.55 (d, J=4.5 Hz, 1H), 8.50 (s, 1H), 8.02 (s, 1H), 7.66 (d, J=8.9 Hz, 1H), 7.60 (s, 2H), 7.56-7.49 (m, 2H), 7.16-7.07 (m, 2H), 6.94 (d, J=9.4 Hz, 1H), 6.89 (t, J=5.0 Hz, 1H), 4.04 (s, 3H).

Compound 186

1-(6-(3-(4-Fluorophenyl)-1-methyl-1H-pyrazol-4-yl)imidazo[1,2-b]pyridazin-2-yl)-3-phenylurea

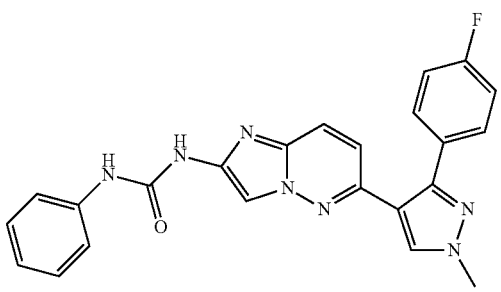 [SMILES: Cn1cc(-c2ccc3nc(NC(=O)Nc4ccccc4)cn3n2)c(-c2ccc(F)cc2)n1]

To a solution of Intermediate 7 (0.017 g, 0.055 mmol) in CH$_2$Cl$_2$ (0.28 mL) was added phenyl isocynate (0.013 g, 0.113 mmol). The reaction mixture was stirred at rt for 30 minutes, followed by heating at 40° C. for 1 h. The volatiles were evaporated under reduced pressure and the crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give compound 186 (0.018 g, 60% yield). HPLC Ret. Time: 2.232 min. and 2.152 min. (Methods G and H respectively). MS(ES): m/z=428 [M+H]$^+$. $^1$H NMR (500 MHz, methanol-d$_4$) δ ppm 8.11-8.08 (m, 1H), 8.02 (s, 1H), 7.63 (d, J=9.4 Hz, 1H), 7.51 (dd, J=8.4, 5.4 Hz, 2H), 7.47 (d, J=7.4 Hz, 2H), 7.35-7.28 (m, 2H), 7.14-7.03 (m, 3H), 6.93 (d, J=8.9 Hz, 1H), 4.02 (s, 3H).

Compound 187

Benzyl 6-(3-(4-fluorophenyl)-1-methyl-1H-pyrazol-4-yl)imidazo[1,2-b]pyridazin-2-ylcarbamate

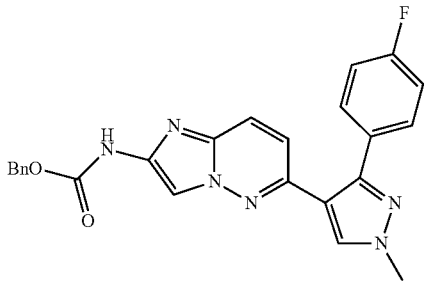 [SMILES: Cn1cc(-c2ccc3nc(NC(=O)OCc4ccccc4)cn3n2)c(-c2ccc(F)cc2)n1]

To a solution of Intermediate 7 in CH$_2$Cl$_2$ (0.28 mL) was added benzyl carbonochloridate (0.0094 g, 0.055 mmol). The reaction mixture was stirred at rt for 30 minutes, followed by heating at 40° C. for 1 h. The volatiles were then evaporated under reduced pressure and the crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give compound 187 (0.0021 g, 6.1% yield). HPLC Ret. Time: 2.40 min. and 2.35 min. (Methods G and H respectively). MS(ES): m/z=443 [M+H]$^+$. $^1$H NMR (500 MHz, DMSO-d$_6$) δ ppm 10.69-10.54 (m, 1H), 8.31 (s, 1H), 7.96-7.84 (m, 2H), 7.56 (dd, J=8.9, 5.4 Hz, 2H), 7.48-7.32 (m, 5H), 7.22 (t, J=8.9 Hz, 2H), 7.04 (d, J=9.4 Hz, 1H), 5.21 (s, 2H), 3.96 (s, 3H).

Compound 188

3-Bromo-6-(3-(4-fluorophenyl)-1-methyl-1H-pyrazol-4-yl)-N-(pyrimidin-2-yl)imidazo[1,2-b]pyridazin-2-amine

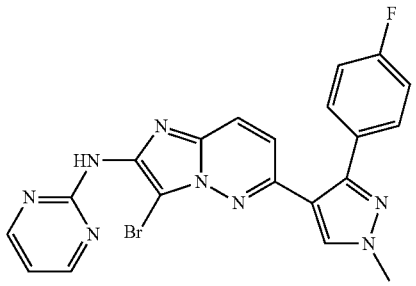 [SMILES: Cn1cc(-c2ccc3nc(Nc4ncccn4)c(Br)n3n2)c(-c2ccc(F)cc2)n1]

To a solution of Intermediate 12 (0.011 g, 0.028 mmol) in DMF (1 mL) was added NaH (60% dispersion in mineral oil, 0.0034 g, 0.142 mmol) and the reaction mixture was stirred at rt for 30 minutes, followed by the addition of 2-bromopyrimidine (0.009 g, 0.057 mmol). The resultant mixture was stirred at rt for 40 minutes and then diluted with water and DMSO (1 mL) and purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate;

Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give compound 188 (0.0013 g, 10% yield). HPLC Ret. Time: 1.85 min. and 1.73 min. (Methods G and H respectively). MS(ES): m/z=466 [M+H]$^+$. $^1$H NMR (500 MHz, methanol-d$_4$) δ ppm 8.45 (d, J=4.5 Hz, 2H), 8.13 (s, 1H), 7.77 (d, J=9.4 Hz, 1H), 7.63-7.57 (m, 4H), 7.16-7.07 (m, 3H), 4.05 (s, 3H).

Scheme 11

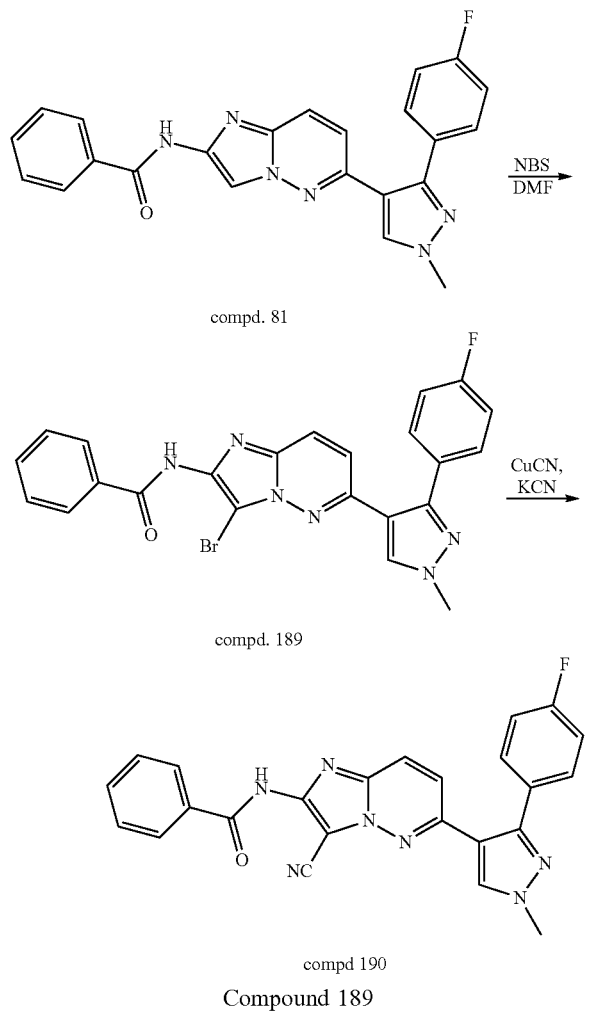

compd. 81 compd. 189 compd 190

Compound 189

N-(3-Bromo-6-(3-(4-fluorophenyl)-1-methyl-1H-pyrazol-4-yl)imidazo[1,2-b]pyridazin-2-yl)benzamide To a solution of compound 81 (0.357 g, 0.866 mmol) in DMF (3 mL) was added NBS (0.162 g, 0.909 mmol) and the reaction was stirred at rt for 15 minutes. The reaction was diluted with water (40 mL) and the generated precipitate was filtered off. It was purified by silica gel chromatography (12 g ISCO column, eluting with a solution of 10% MeOH in CH$_2$Cl$_2$) to provide compound 189 (0.41 g, 96% yield) as a light yellow solid. HPLC Ret. Time: 1.60 min. (Method G). MS(ES): m/z=491 [M+H]$^+$. $^1$H NMR (500 MHz, DMSO-d$_6$) δ ppm 10.69 (s, 1H), 8.44 (s, 1H), 8.09 (d, J=9.4 Hz, 1H), 8.06-8.01 (m, 2H), 7.96 (s, 1H), 7.76-7.69 (m, 2H), 7.67-7.61 (m, 1H), 7.59-7.53 (m, 2H), 7.29 (d, J=9.4 Hz, 1H), 7.27-7.21 (m, 2H), 3.99 (s, 3H), 2.74 (s, 2H).

Compound 190

N-(3-Cyano-6-(3-(4-fluorophenyl)-1-methyl-1H-pyrazol-4-yl)imidazo[1,2-b]pyridazin-2-yl)benzamide

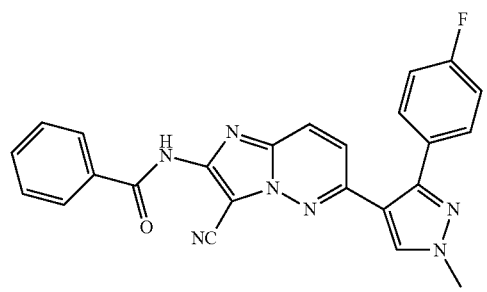

A vial containing compound 189 (0.04 g, 0.081 mmol), CuCN (0.011 g, 0.122 mmol) and KCN (0.011 g, 0.163 mmol) was purged with nitrogen, to which was added DMF (0.4 mL) and the reaction mixture was heated at 120° C. for 20 h. It was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give compound 190 (0.01 g, 27.8% yield). HPLC Ret. Time: 1.59 min. (Method G). MS(ES): m/z=438 [M+H]$^+$. $^1$H NMR (500 MHz, methanol-d$_4$) δ ppm 8.22 (s, 1H), 8.04 (d, J=7.4 Hz, 2H), 7.84 (d, J=9.4 Hz, 1H), 7.67 (s, 1H), 7.66-7.60 (m, 3H), 7.58-7.51 (m, 2H), 7.28 (d, J=9.4 Hz, 1H), 7.15 (t, J=8.7 Hz, 2H), 4.04 (s, 3H).

Compound 191

N-(3-Chloro-6-(3-(4-fluorophenyl)-1-methyl-1H-pyrazol-4-yl)imidazo[1,2-b]pyridazin-2-yl)benzamide

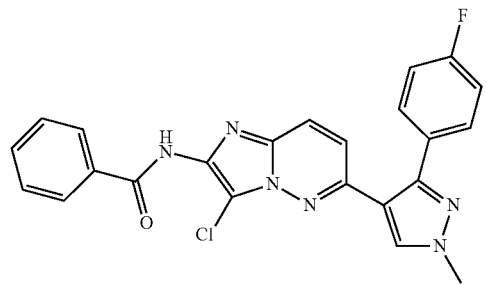 [SMILES: Cn1cc(-c2ccc3nc(NC(=O)c4ccccc4)c(Br)n3n2)c(-c2ccc(F)cc2)n1]

Compound 191 was prepared analogous to compound 189 by reacting compound 81 with NCS. It was purified via preparative LC/MS with the following the conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 5-100% B over 25 minutes, then a 5-minute hold at 100% B; Flow: 20 mL/min. Fractions containing the desired product were combined and dried via centrifugal evaporation to provide compound 191 (0.0054 g, 25% yield). HPLC Ret. Time: 1.62 min. (Method G). MS(ES): m/z=447 [M+H]⁺.

Compound 192

N-(3-Fluoro-6-(3-(4-fluorophenyl)-1-methyl-1H-pyrazol-4-yl)imidazo[1,2-b]pyridazin-2-yl)benzamide

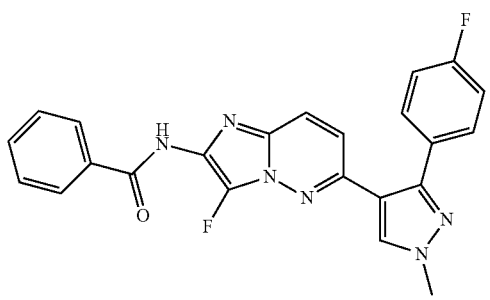 [SMILES: Cn1cc(-c2ccc3nc(NC(=O)c4ccccc4)c(F)n3n2)c(-c2ccc(F)cc2)n1]

To a solution of compound 81 (0.02 g, 0.048 mmol) in CH₃CN (0.24 mL) was added SELECTFLUOR® (0.017 g, 0.048 mmol) and the reaction was stirred at rt for 15 minutes. It was quenched with water (0.2 mL) and purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give compound 192 (0.0037 g, 14% yield). HPLC Ret. Time: 2.14 min and 2.13 min. (Methods G and H respectively) MS(ES): m/z=431 [M+H]⁺. ¹H NMR (500 MHz, methanol-d₄) δ ppm 8.12 (s, 1H), 8.02 (d, J=7.4 Hz, 2H), 7.69 (dd, J=9.7, 1.2 Hz, 1H), 7.61 (s, 2H), 7.57-7.50 (m, 4H), 7.16-7.09 (m, 2H), 6.98 (d, J=9.4 Hz, 1H), 4.03 (s, 3H).

Scheme 12

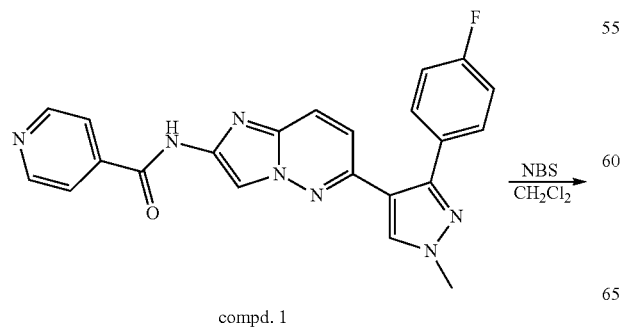

compd. 1

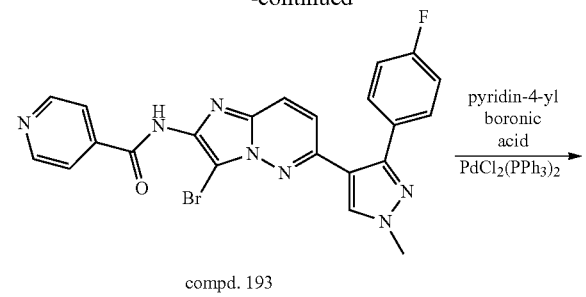

compd. 193

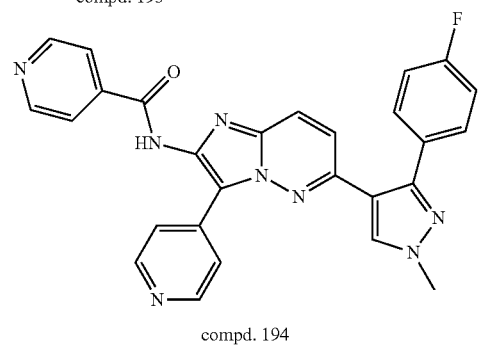

compd. 194

Compound 193

N-(3-Bromo-6-(3-(4-fluorophenyl)-1-methyl-1H-pyrazol-4-yl)imidazo[1,2-b]pyridazin-2-yl)isonicotinamide

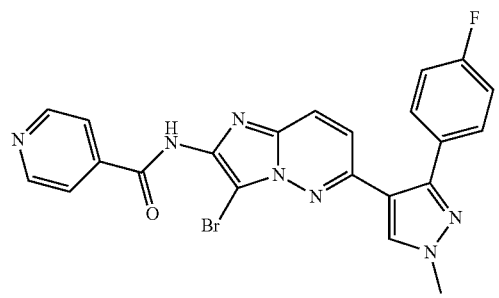 [SMILES: Cn1cc(-c2ccc3nc(NC(=O)c4ccncc4)c(Br)n3n2)c(-c2ccc(F)cc2)n1]

Compound 193 was synthesized analogous to compound 189 by reacting Compound 1 with N-bromosuccinimide. HPLC Ret. Time: 1.31 min. and 1.12 min. (Methods G and H respectively). MS(ES): m/z=493.9 [M+H]⁺.

Compound 194

N-(6-(3-(4-Fluorophenyl)-1-methyl-1H-pyrazol-4-yl)-3-(pyridin-4-yl)imidazo[1,2-b]pyridazin-2-yl)isonicotinamide, 2 TFA

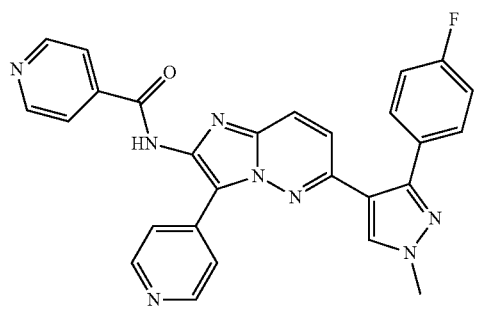 [SMILES: Cn1cc(-c2ccc3nc(NC(=O)c4ccncc4)c(-c4ccncc4)n3n2)c(-c2ccc(F)cc2)n1]

To a microwave reaction vial was added compound 193 (0.02 g, 0.041 mmol), pyridin-4-ylboronic acid (0.0075 g, 0.061 mmol), PdCl$_2$(PPh$_3$)$_2$ (0.0143 g, 0.020 mmol) and Na$_2$CO$_3$ (0.0129 g, 0.122 mmol). The vial was capped and purged with nitrogen followed by the addition of DME (0.5 mL) and water (0.01 mL). The vial was purged (×3) with nitrogen and irradiated in a microwave oven at 120° C. for 2 h. The reaction mixture was concentrated under reduced pressure and purified via preparative HPLC using the following conditions: gradient 30-90% MeOH/water, Solvent A (90% water, 10% methanol, 0.1% TFA), Solvent B (10% water, 90% methanol, 0.1% TFA), gradient time 10 min., run time 15 min. at 25 mL/min) Concentration of the desired fractions under reduced pressure afforded compound 194 (di TFA salt, 0.0010 g, 3.4% yield) as a white solid. HPLC Ret. Time: 1.96 min. and 8.41 min. (Methods K and J respectively). $^1$H NMR (400 MHz, methanol-d$_4$) δ ppm 8.87-8.81 (m, 2H), 8.55 (d, J=7.0 Hz, 2H), 8.38 (s, 1H), 8.20-8.12 (m, 3H), 8.05-7.99 (m, 2H), 7.71 (d, J=9.5 Hz, 1H), 7.59-7.51 (m, 2H), 7.14-7.04 (m, 2H), 4.06 (s, 3H).

Scheme 13

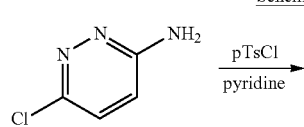

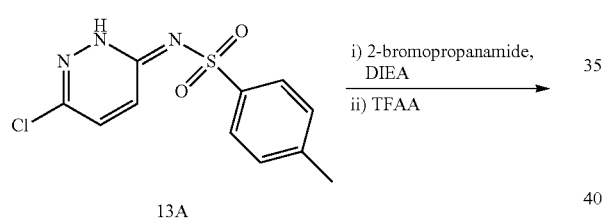

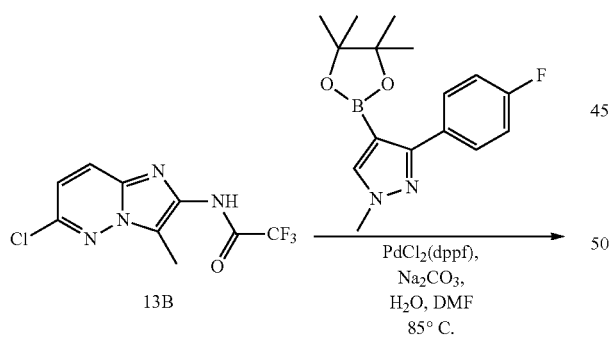

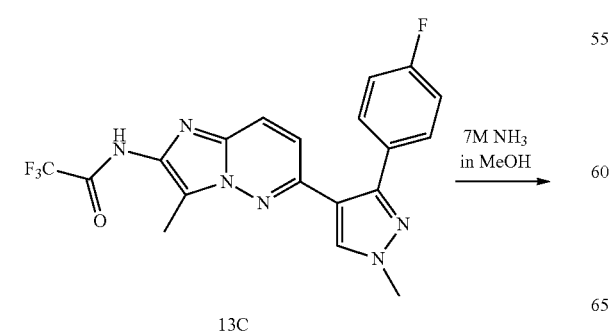

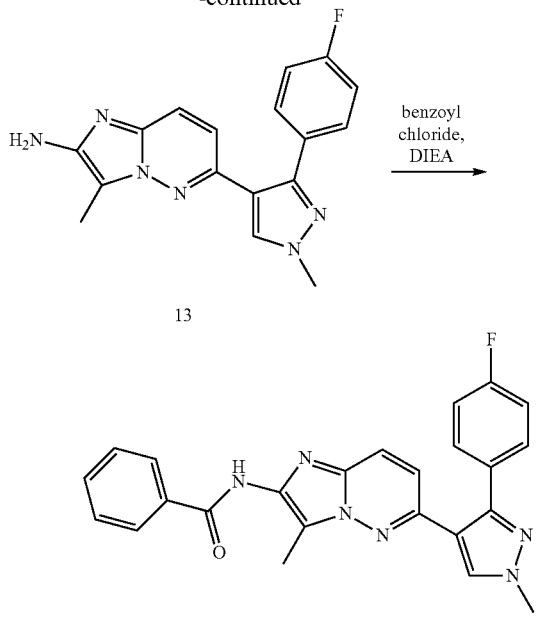

Intermediate 13

6-(3-(4-Fluorophenyl)-1-methyl-1H-pyrazol-4-yl)-3-methylimidazo[1,2-b]pyridazin-2-amine, 2 TFA

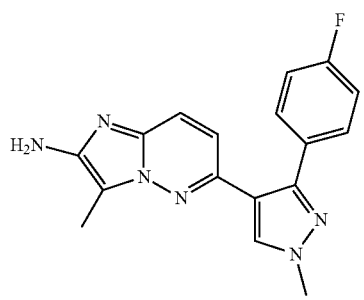 [SMILES: Cc1c(N)nc2ccc(-c3cn(C)nc3-c3ccc(F)cc3)nn12]

Intermediate 13A: (E)-N-(6-Chloropyridazin-3(2H)-ylidene)-4-methylbenzenesulfonamide

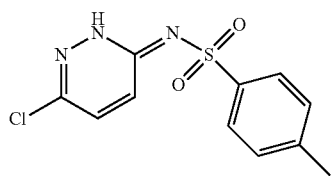 [SMILES: Cc1ccc(S(=O)(=O)/N=c2\ccc(Cl)n[nH]2)cc1]

A solution of 6-chloropyridazin-3-amine (4.00 g, 30.9 mmol) and pTsCl (8.54 g, 44.8 mmol) in pyridine (103 mL, 30.9 mmol) was stirred at rt for 2 h. It was then diluted with water (300 mL) and extracted with EtOAc (3×150 mL). The combined organics were washed with aq. NaHCO$_3$ and brine. The organic phase was dried over anhydrous sodium sulfate and concentrated under reduced pressure. The residue was purified via silica gel chromatography (ISCO column, eluting with a gradient of 5-60% solution of EtOAc in heptane) to provide the Intermediate 13A (7.1 g, 81% yield) as a yellowish solid. MS(ES): m/z=284 [M+H]$^+$.

Intermediate 13B: N-(6-Chloro-3-methylimidazo[1,2-b]pyridazin-2-yl)-2,2,2-trifluoroacetamide

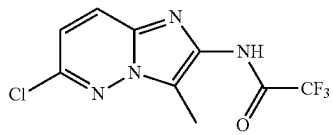 [SMILES: Cc1c(NC(=O)C(F)(F)F)nc2ccc(Cl)nn12]

To a solution of Intermediate 13A (1.00 g, 3.52 mmol) in DMF (2.5 mL) were added 2-bromopropanamide (0.589 g, 3.88 mmol) and Hunig's base (0.74 mL, 4.23 mmol). The reaction was heated at 60° C. for 24 h. It was diluted with water and Et$_2$O (100 mL) and stirred for 30 minutes, followed by filtering off a tan solid. The filter cake was washed with Et$_2$O. To a solution of the above solid (0.7 g) in CH$_2$Cl$_2$ was added TFAA (11.75 mL, 3.52 mmol) and the reaction mixture was stirred at rt for 1 h. It was quenched with satd. aq. NaHCO$_3$ and extracted with EtOAc (3×100 mL). The combined organics were dried over anhydrous sodium sulfate and concentrated under reduced pressure. The residue was purified by silica gel chromatography (24 g ISCO column, eluting with a gradient of 0-10% solution of MeOH in CH$_2$Cl$_2$) to provide Intermediate 13B (0.775 g, 79% yield) as a tan solid. MS(ES): m/z=279 [M+H]$^+$.

Intermediate 13C: 2,2,2-Trifluoro-N-(6-(3-(4-fluorophenyl)-1-methyl-1H-pyrazol-4-yl)-3-methylimidazo[1,2-b]pyridazin-2-yl)acetamide

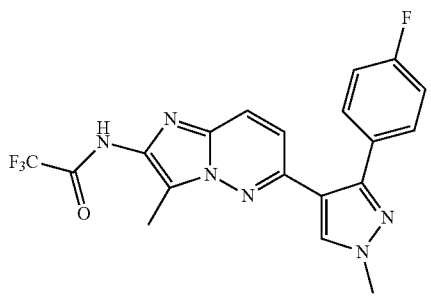 [SMILES: Cc1c(NC(=O)C(F)(F)F)nc2ccc(-c3cn(C)nc3-c3ccc(F)cc3)nn12]

To a purged mixture of Intermediate 13B (0.105 g, 0.377 mmol), 3-(4-fluorophenyl)-1-methyl-4-(4,4,5,5-tetramethyl-1,3,2-dioxaborolan-2-yl)-1H-pyrazole (0.120 g, 0.396 mmol), and PdCl$_2$(dppf) (0.014 g, 0.019 mmol) was added DMF (2.5 mL) and 2M aq. solution of Na$_2$CO$_3$ (0.565 mL, 1.13 mmol). The reaction mixture was purged again and heated at 85° C. for 12 h. It was then diluted with water (10 mL) and extracted with EtOAc (3×10 mL). The combined organics were dried over anhydrous sodium and concentrated under reduced pressure and purified by silica gel chromatography (12 g ISCO column, eluting with a gradient of 0-10% solution of MeOH in CH$_2$Cl$_2$) to provide Intermediate 13C (0.164 g, 61% yield) as a brown oil. HPLC Ret. Time: 2.09 min. and 2.05 min. (Methods G and H respectively). MS(ES): m/z=533 [M+H]$^+$. $^1$H NMR (500 MHz, methanol-d$_4$) δ ppm 8.10 (s, 1H), 7.74 (d, J=9.4 Hz, 1H), 7.61 (s, 1H), 7.58-7.51 (m, 2H), 7.16-7.02 (m, 3H), 4.03 (s, 3H), 2.37 (s, 3H).

Intermediate 13: 6-(3-(4-Fluorophenyl)-1-methyl-1H-pyrazol-4-yl)-3-methylimidazo[1,2-b]pyridazin-2-amine, 2 TFA

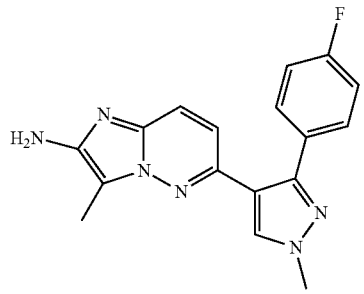 [SMILES: Cc1c(N)nc2ccc(-c3cn(C)nc3-c3ccc(F)cc3)nn12]

A solution of Intermediate 13C (0.140 g, 0.335 mmol) in ammonia (7M solution in MeOH, 1.5 mL, 69.3 mmol) was irradiated in a microwave oven at 80° C. for 40 minutes. The reaction mixture was concentrated and the residue was purified by silica gel chromatography (12 g ISCO column, eluting with a gradient of 0-10% solution of MeOH in CH$_2$Cl$_2$) to provide Intermediate 13 (di TFA salt, 0.160 g, 86% yield) as a tan solid. HPLC Ret. Time: 1.66 min. and 1.43 min. (Methods G and H respectively). MS(ES): m/z=323 [M+H]$^+$.

Compound 195

N-(6-(3-(4-Fluorophenyl)-1-methyl-1H-pyrazol-4-yl)-3-methylimidazo[1,2-b]pyridazin-2-yl)benzamide, 2 TFA

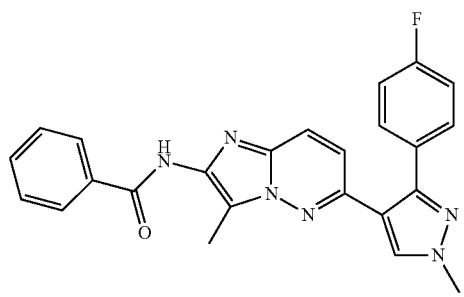 [SMILES: Cc1c(NC(=O)c2ccccc2)nc2ccc(-c3cn(C)nc3-c3ccc(F)cc3)nn12]

To a solution of Intermediate 13C (0.015 g, 0.047 mmol) in CH$_2$Cl$_2$ (3 mL) was added benzoyl chloride (0.0065 g, 0.047 mmol), Hunig's base (0.033 mL, 0.186 mmol) and DMAP (0.057 mg, 0.465 μmol). The reaction mixture was stirred at rt for 1 h and then concentrated under reduced pressure. The residue was purified by preparative HPLC using the following conditions: gradient of 30-90% MeOH/water, Solvent A (90% water, 10% methanol, 0.1% TFA), Solvent B (10% water, 90% methanol, 0.1% TFA), gradient time 10 min., run time 15 min. at 25 mL/min) to provide compound 195 (di TFA salt, 0.009 g, 34% yield) as a white solid. HPLC Ret. Time: 3.076 min. and 10.099 min. (Methods K and J respectively). MS(ES): m/z=427 [M+H]$^+$. $^1$H NMR (400 MHz, DMSO-d$_6$) δ ppm 10.61 (s, 1H), 8.42 (s, 1H), 8.07-8.03 (m, 2H), 8.00 (d, J=9.5 Hz, 1H), 7.68-7.58 (m, 3H), 7.57-7.50 (m, 2H), 7.29-7.17 (m, 3H), 3.98 (s, 3H), 2.27 (s, 3H).

Scheme 14
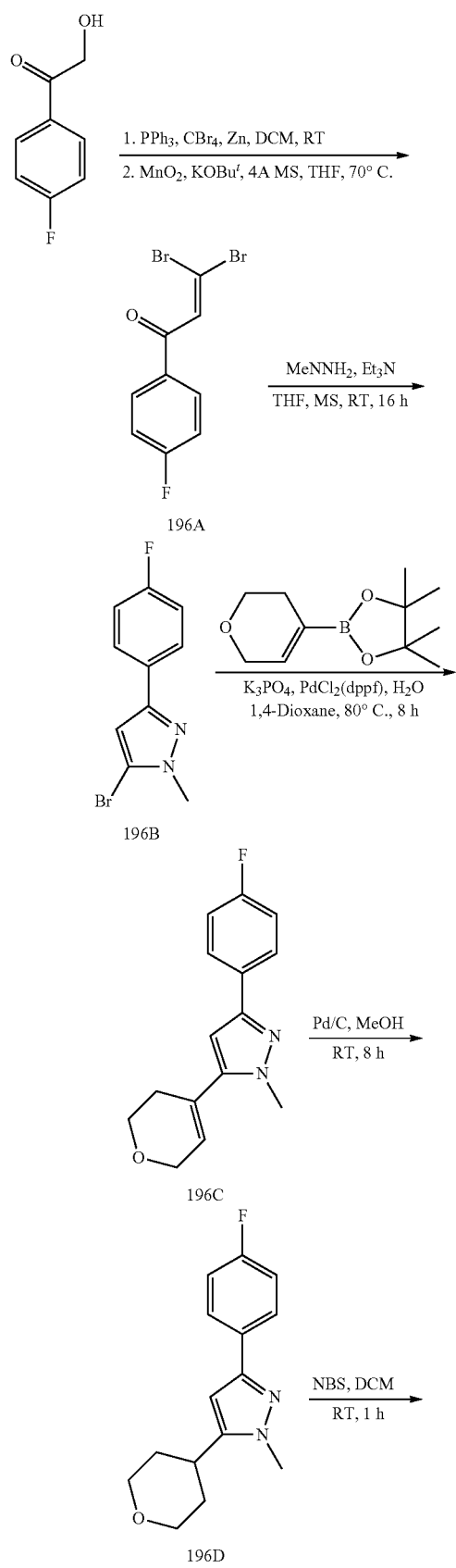
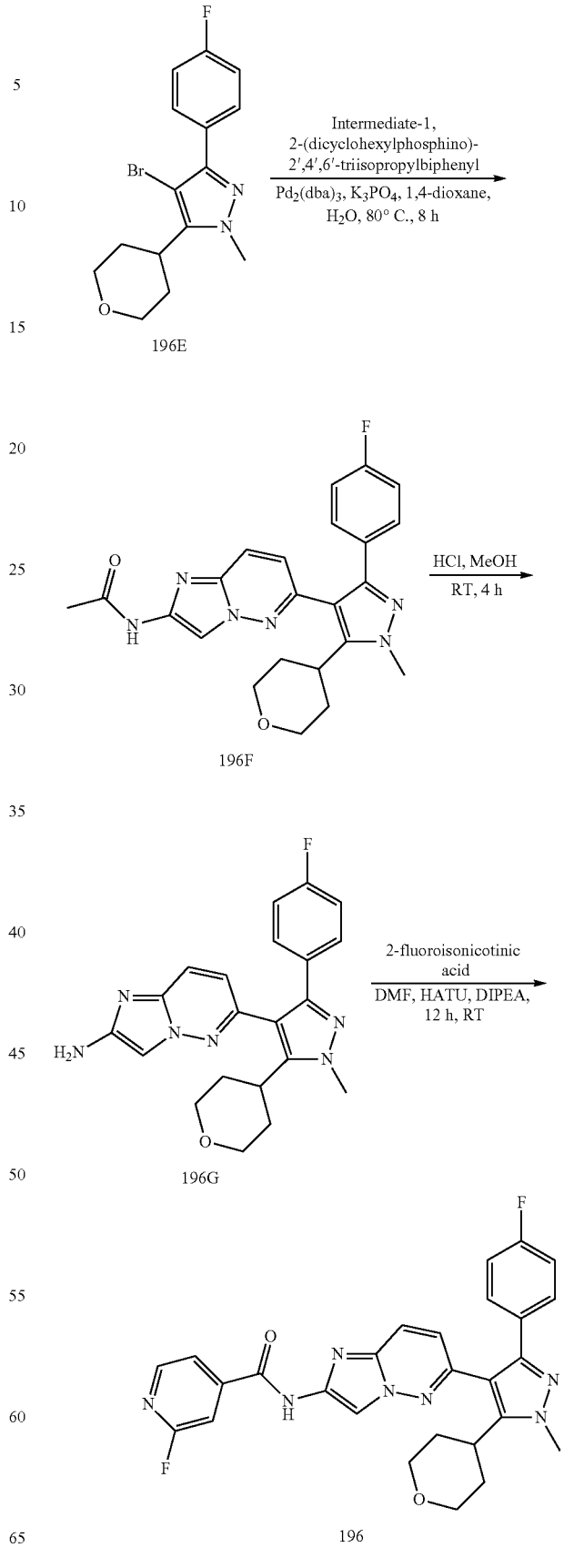

Intermediate 196A 3,3-Dibromo-1-(4-fluorophenyl)prop-2-en-1-one

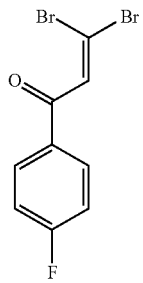 [SMILES: O=C(C=C(Br)Br)c1ccc(F)cc1]

To a solution of triphenylphosphine (60 g, 229 mmol) in dry DCM (600 mL) was added carbon tetrabromide (76 g, 229 mmol) and zinc (14.96 g, 229 mmol) at room temperature and was stirred for 30 h. The reaction mixture was concentrated to afford crude dibromomethylenetriphenylphosphorane (73.8 g, 171 mmol) which was dissolved in dry THF (1200 mL) and added manganese dioxide (33.8 g, 389 mmol) and activated 4A molecular sieves (2 g), potassium tert-butoxide (19.22 g, 171 mmol) followed by 1-(4-fluorophenyl)-2-hydroxyethanone (12 g, 78 mmol) as solution in dry THF (300 mL) and the resulting reaction mixture was refluxed for 8 h. The reaction mixture was cooled to room temperature, diluted with ethyl acetate and filtered through CELITE® pad. The CELITE® pad was washed with ethyl acetate and the combined organic layer was concentrated to obtain the crude product. The residue was purified by silica gel chromatography (40 g REDISEP® column, eluting with 5% EtOAc in hexane). Collected fractions were concentrated together to afford Intermediate 196A (6.5 g, 27%) as a yellow oil. MS(ES): m/z=309 [M+H]$^+$; $^1$H NMR (300 MHz, CDCl$_3$) δ ppm 7.95-8.05 (m, 2H) 7.81 (s, 1H) 7.14-7.24 (m, 2H).

Intermediate 196B:
5-Bromo-3-(4-fluorophenyl)-1-methyl-1H-pyrazole

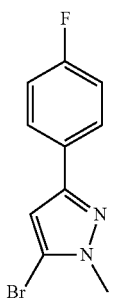

To a solution of Intermediate 196A (1 g, 3.25 mmol), 4A molecular sieves (0.1 g) in dry THF (10 mL) was added methyl hydrazine (0.299 g, 6.49 mmol) in THF (10 mL) followed by triethylamine (0.905 mL, 6.49 mmol) and stirred at RT for 16 h. The reaction mixture was filtered through CELITE® and the CELITE® pad was washed with ethyl acetate. The combined organic layer was concentrated under reduced pressure to afford the crude product. The crude product was purified by silica gel chromatography (40 g REDISEP® column, eluting with 5% EtOAc in hexane). Collected fractions were concentrated together to afford Intermediate 196B (0.69 g, 83%) as an off-white solid. MS(ES): m/z=257 [M+H]$^+$; $^1$H NMR (300 MHz, CDCl$_3$) δ ppm 7.62-7.78 (m, 2H), 7.01-7.14 (m, 2H), 6.53 (s, 1H), 3.92 (s, 3H).

Intermediate 196C: 5-(3,6-Dihydro-2H-pyran-4-yl)-3-(4-fluorophenyl)-1-methyl-1H-pyrazole

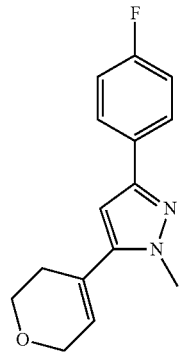 [SMILES: Cn1nc(-c2ccc(F)cc2)cc1C1=CCOCC1]

To a solution of Intermediate 196B (1.0 g, 3.92 mmol), 2-(3,6-dihydro-2H-pyran-4-yl)-4,4,5,5-tetramethyl-1,3,2-dioxaborolane (1.071 g, 5.10 mmol) and K$_3$PO$_4$ (4.90 mL, 9.80 mmol, 2M in water), PdCl$_2$(dppf) (0.172 g, 0.235 mmol) in dioxane (15 mL) was purged with nitrogen for 10 min and stirred at 80° C. for 8 h. Reaction mixture was concentrated to remove dioxane and the crude product obtained was diluted with ethyl acetate and washed with water. The aqueous layer was back extracted with ethyl acetate (2×30 mL) and the combined the organic layer was dried over Na$_2$SO$_4$, filtered and concentrated. The residue was purified by silica gel chromatography (40 g REDISEP® column, eluting with 1% methanol in chloroform). Collected fractions were concentrated together to afford Intermediate 196C (0.9 g, 89%) as an off-white solid. MS(ES): m/z=259 [M+H]$^+$; $^1$H NMR (400 MHz, CDCl$_3$) δ ppm 7.67-7.80 (m, 2H), 7.00-7.15 (m, 2H), 6.39 (s, 1H), 5.92-6.04 (m, 1H), 4.34 (q, J=2.75 Hz, 2H), 3.98 (m, 2H), 3.95 (s, 3H), 2.46 (m, 2H).

Intermediate 196D: 3-(4-Fluorophenyl)-1-methyl-5-(tetrahydro-2H-pyran-4-yl)-1H-pyrazole

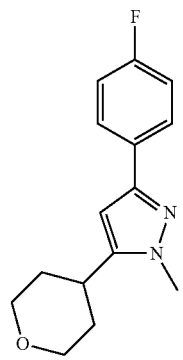 [SMILES: Cn1nc(-c2ccc(F)cc2)cc1C1CCOCC1]

To a solution of Intermediate 196C (1 g, 3.87 mmol) in MeOH (10 mL) was purged with nitrogen and added Pd/C (0.206 g, 1.936 mmol). The reaction mixture was hydrogenated under hydrogen bladder pressure for 8 h. Hydrogen gas was released and reaction mixture was filtered through CELITE® pad. The pad was washed with methanol and combined methanol solution was concentrated to afford Intermediate 196D (1 g, 99%) as a white solid which was taken to the next step without further purification. MS(ES): m/z=261 [M+H]+.

Intermediate 196E: 4-Bromo-3-(4-fluorophenyl)-1-methyl-5-(tetrahydro-2H-pyran-4-yl)-1H-pyrazole

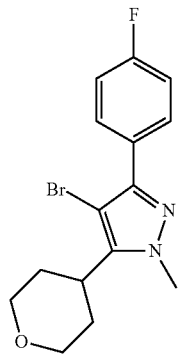 [SMILES: Cn1nc(-c2ccc(F)cc2)c(Br)c1C1CCOCC1]

To a solution of Intermediate 196D (1 g, 3.84 mmol) in DCM (2 ml) was added NBS (0.684 g, 3.84 mmol) and stirred at RT for 1 h. Reaction mixture was diluted with DCM, washed with water, dried over anhydrous Na$_2$SO$_4$, filtered and concentrated to afford Intermediate 196E (0.11 g, 84%) as a pale yellow solid which was taken to the next step without further purification. MS(ES): m/z=340 [M+H]+; $^1$H NMR (400 MHz, CDCl$_3$) δ ppm 7.75-7.82 (m, 2H), 7.07-7.14 (m, 2H), 4.13 (dd, J=11.54, 4.52 Hz, 2H), 3.95 (s, 3H), 3.53 (td, J=11.92, 2.01 Hz, 2H), 3.08-3.20 (m, 1H), 2.37 (qd, J=12.80, 4.52 Hz, 2H), 1.58-1.71 (m, 2H).

Intermediate 196F: N-(6-(3-(4-Fluorophenyl)-1-methyl-5-(tetrahydro-2H-pyran-4-yl)-1H-pyrazol-4-yl)imidazo[1,2-b]pyridazin-2-yl)acetamide

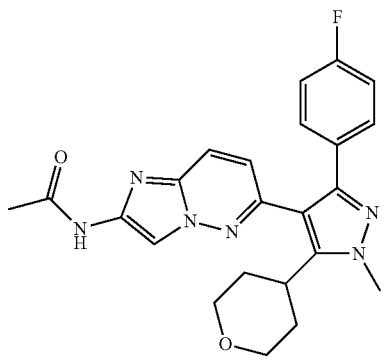 [SMILES: CC(=O)Nc1cn2nc(-c3c(-c4ccc(F)cc4)nn(C)c3C3CCOCC3)ccc2n1]

To a solution of Intermediate 196E (800 mg, 2.36 mmol), Intermediate-1 (2138 mg, 7.08 mmol) and K$_3$PO$_4$ (2.95 mL, 5.90 mmol, 2M in H$_2$O) in dioxane (10 mL) was purged with nitrogen. To this mixture was added 2-(dicyclohexylphosphino)-2',4',6'-triisopropylbiphenyl (135 mg, 0.283 mmol), Pd$_2$(dba)$_3$ (130 mg, 0.142 mmol) and the reaction mixture was stirred at 80° C. for 8 h. The reaction mixture was cooled to room temperature and concentrated to remove volatiles. Crude product was then dissolved in dichloromethane and washed with water, brine, dried over Na$_2$SO$_4$, filtered and concentrated. The residue was purified by silica gel chromatography (40 g REDISEP® column, eluting with 1% methanol in chloroform). Collected fractions were concentrated together to afford Intermediate 196F (0.4 g, crude) as a brown solid and was taken to the next step without further purification. MS(ES): m/z=435 [M+H]+;

Intermediate 196G: 6-(3-(4-Fluorophenyl)-1-methyl-5-(tetrahydro-2H-pyran-4-yl)-1H-pyrazol-4-yl)imidazo[1,2-b]pyridazin-2-amine

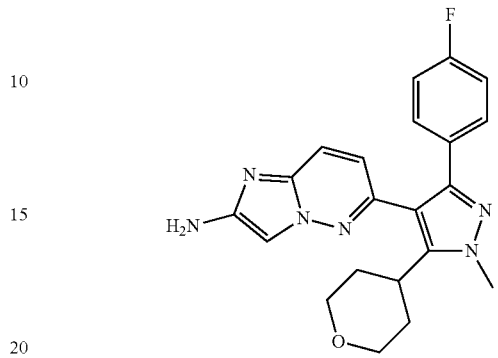

To a solution of Intermediate 196F (360 mg, 0.829 mmol) in methanol (4 mL) was added 4 M HCl in dioxane (4.14 mL, 16.57 mmol). The reaction mixture was stirred at room temperature for 4 h and concentrated. The residue was dissolved in water and basified with saturated NaHCO$_3$ solution and back extracted with ethyl acetate (3×20 mL). The combined organic layer was washed with water (2×50 mL), dried over Na$_2$SO$_4$, filtered and concentrated to afford Intermediate 196G (0.3 g). MS(ES): m/z=393 [M+H]+. The crude product was taken to the next step without further purification Compound 196: 2-Fluoro-N-(6-(3-(4-fluorophenyl)-1-methyl-5-(tetrahydro-2H-pyran-4-yl)-1H-pyrazol-4-yl)imidazo[1,2-b]pyridazin-2-yl)isonicotinamide

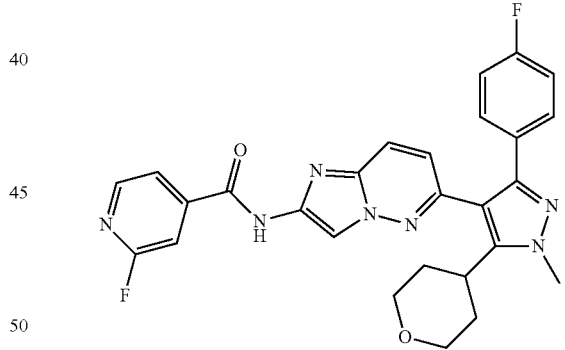

To a solution of Intermediate 196G (50 mg, 0.127 mmol) and 2-fluoroisonicotinic acid (36.0 mg, 0.255 mmol) in DMF (1 mL) was added HATU (121 mg, 0.319 mmol) followed by DIPEA (0.067 mL, 0.382 mmol) and stirred at room temperature for 12 h. Reaction mixture was diluted with saturated NaHCO$_3$ solution and the aqueous layer was back extracted with ethyl acetate (3×10 mL). The combined organic layer was washed with water, dried over Na$_2$SO$_4$, filtered and concentrated. Crude product was purified by reverse phase preparative HPLC to afford compound 196 (0.015 g, 21%) as an off-white solid. MS(ES): m/z=514 [M−H]+; HPLC Ret. Time 9.43 min and 8.86 min. (HPLC Method J and K); $^1$H NMR (400 MHz, DMSO-d$_6$) δ ppm 8.52 (s, 1H), 8.47 (d, J=5.21 Hz, 1H), 8.02 (d, J=9.22 Hz, 1H), 7.96 (dt, J=5.11, 1.65 Hz, 1H), 7.80 (s, 1H), 7.29-7.39

(m, 2H), 7.09-7.18 (m, 2H), 7.02 (d, J=9.22 Hz, 1H), 3.99 (s, 3H), 3.79-3.88 (m, 2H), 3.35-3.44 (m, 2H), 3.14-3.24 (m, 1H), 1.63-1.79 (m, 4H).

The following compounds in Table 9 were prepared by the procedure described for the preparation of Compound 196 using Compound 196G and the corresponding acids.

TABLE 9

| Compound No. | Structure | Name | [M + H]+ | Ret Time | HPLC Method |
|---|---|---|---|---|---|
| 197 | 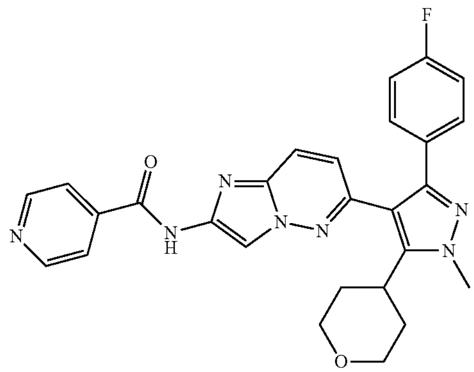 [SMILES: Cn1nc(-c2ccc(F)cc2)c(-c2ccc3nc(NC(=O)c4ccncc4)cn3n2)c1C1CCOCC1] | N-(6-(3-(4-Fluorophenyl)-1-methyl-5-(tetrahydro-2H-pyran-4-yl)-1H-pyrazol-4-yl)imidazo[1,2-b]pyridazin-2-yl)isonicotinamide | 496 | 6.71 7.00 | J K |
| 198 | 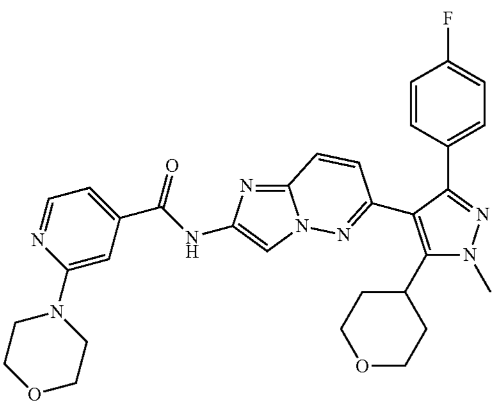 [SMILES: Cn1nc(-c2ccc(F)cc2)c(-c2ccc3nc(NC(=O)c4ccnc(N5CCOCC5)c4)cn3n2)c1C1CCOCC1] | N-(6-(3-(4-Fluorophenyl)-1-methyl-5-(tetrahydro-2H-pyran-4-yl)-1H-pyrazol-4-yl)imidazo[1,2-b]pyridazin-2-yl)-2-morpholinoisonicotinamide | 581 | 6.95 7.21 | J K |
| 199 | 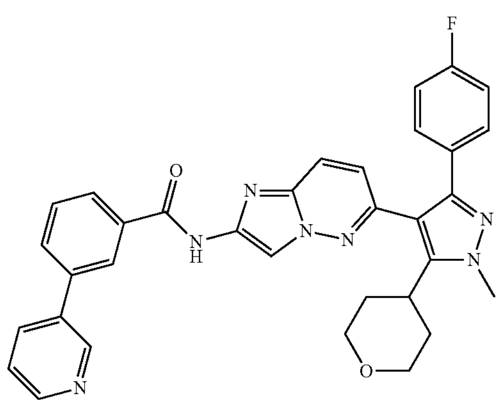 [SMILES: Cn1nc(-c2ccc(F)cc2)c(-c2ccc3nc(NC(=O)c4cccc(-c5cccnc5)c4)cn3n2)c1C1CCOCC1] | N-(6-(3-(4-Fluorophenyl)-1-methyl-5-(tetrahydro-2H-pyran-4-yl)-1H-pyrazol-4-yl)imidazo[1,2-b]pyridazin-2-yl)-3-(pyridin-3-yl)benzamide | 574 | 6.68 7.29 | J K |

TABLE 9-continued
| Compound No. | Structure | Name | [M + H]+ | Ret Time | HPLC Method |
|---|---|---|---|---|---|
| 200 | 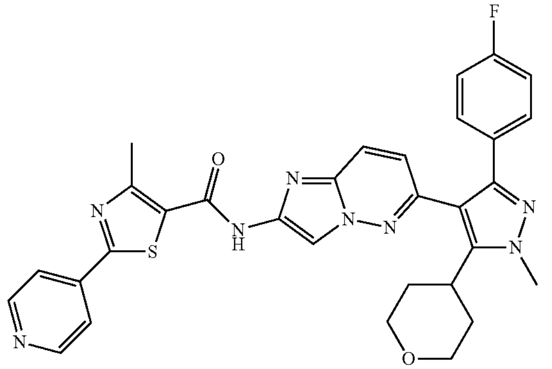 [SMILES: Cc1nc(-c2ccncc2)sc1C(=O)Nc1cn2nc(-c3c(-c4ccc(F)cc4)nn(C)c3C3CCOCC3)ccc2n1] | N-(6-(3-(4-Fluorophenyl)-1-methyl-5-(tetrahydro-2H-pyran-4-yl)-1H-pyrazol-4-yl)imidazo[1,2-b]pyridazin-2-yl)-4-methyl-2-(pyridin-4-yl)thiazole-5-carboxamide | 593 | 6.15 6.25 | J K |
| 201 | 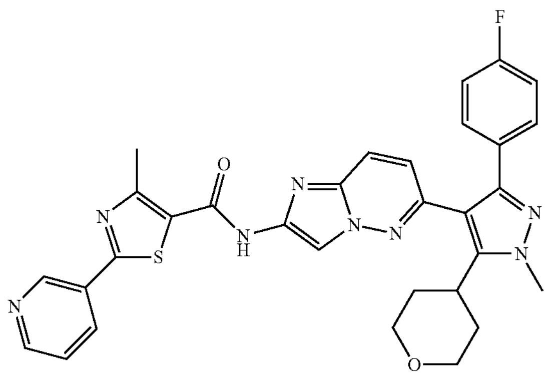 [SMILES: Cc1nc(-c2cccnc2)sc1C(=O)Nc1cn2nc(-c3c(-c4ccc(F)cc4)nn(C)c3C3CCOCC3)ccc2n1] | N-(6-(3-(4-Fluorophenyl)-1-methyl-5-(tetrahydro-2H-pyran-4-yl)-1H-pyrazol-4-yl)imidazo[1,2-b]pyridazin-2-yl)-4-methyl-2-(pyridin-3-yl)thiazole-5-carboxamide | 593 | 12.13 10.99 | J K |
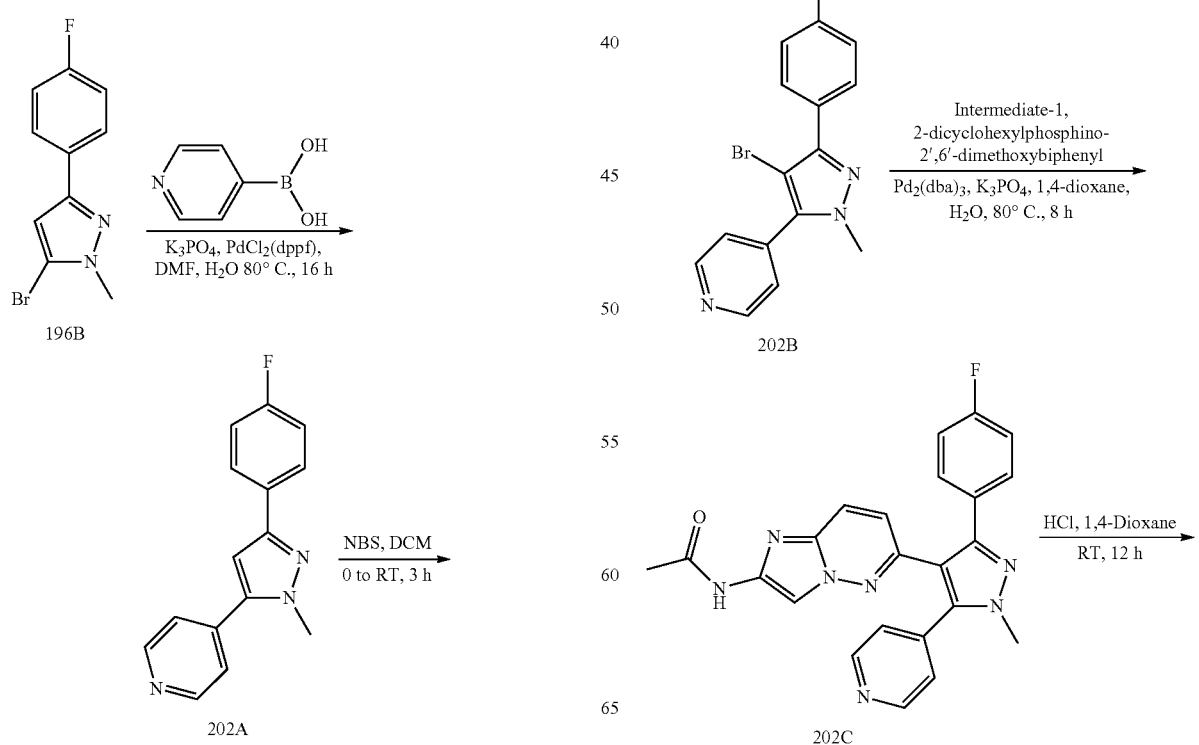
Scheme 15

-continued

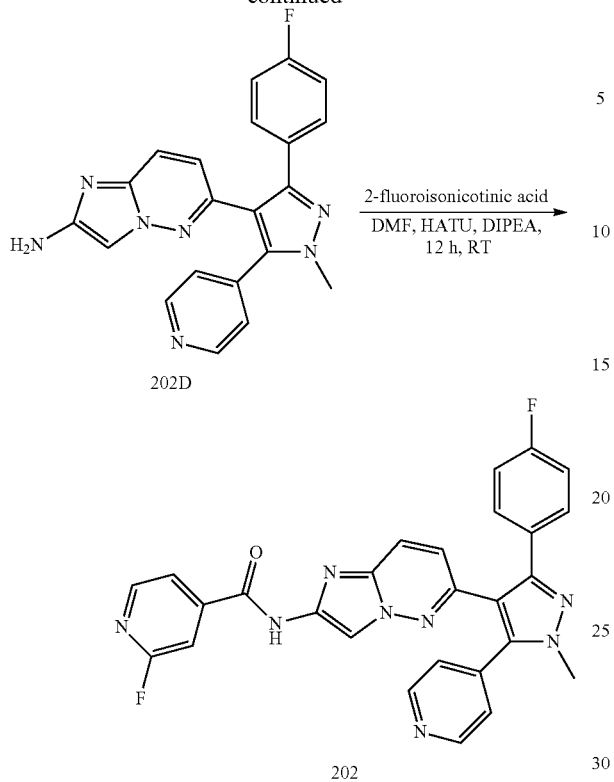

202D

→ 2-fluoroisonicotinic acid
DMF, HATU, DIPEA,
12 h, RT

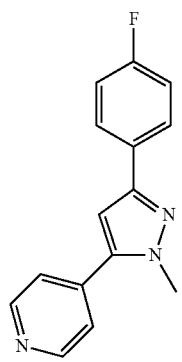 [SMILES: Cn1nc(-c2ccc(F)cc2)cc1-c1ccncc1]

202

Intermediate 202A: 4-(3-(4-Fluorophenyl)-1-methyl-1H-pyrazol-5-yl)pyridine

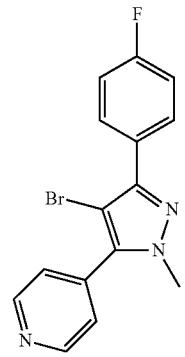 [SMILES: Cn1nc(-c2ccc(F)cc2)c(Br)c1-c1ccncc1]

To a solution of Intermediate 196B (0.69 g, 2.70 mmol), 4-pyridylboronic acid (0.499 g, 4.06 mmol) and potassium phosphate (1.413 g, 8.11 mmol) in DMF (7 mL) and water (0.7 mL) was added $PdCl_2$(dppf)-DCM adduct (0.110 g, 0.135 mmol) and purged with nitrogen gas for 10 min. and stirred at 80° C. for 16 h. The reaction mixture was suspended in ethyl acetate and water, layers separated and the aqueous layer was with EtOAc (3×100 ml). The combined organic layer was washed with water, brine, dried over sodium sulphate and concentrated under reduced pressure to afford crude product, which was purified by silica gel chromatography (40 g REDISEP® column, eluting with 25% EtOAc in hexane). Collected fractions were concentrated together to afford Intermediate 202A (0.41 g, 59%) as an off-white solid. MS(ES): m/z=255 [M+H]$^+$; $^1$H NMR (400 MHz, $CDCl_3$) δ ppm 8.68-8.81 (m, 2H), 7.74-7.89 (m, 2H), 7.36-7.44 (m, 2H), 7.06-7.15 (m, 2H), 6.67 (s, 1H), 3.99 (s, 3H).

Intermediate 202B: 4-(4-Bromo-3-(4-fluorophenyl)-1-methyl-1H-pyrazol-5-yl)pyridine

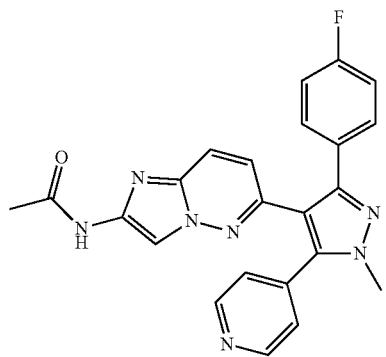 [SMILES: CC(=O)Nc1cn2nc(-c3c(-c4ccc(F)cc4)nn(C)c3-c3ccncc3)ccc2n1]

To a solution of Intermediate 202A (0.4 g, 1.579 mmol) in dry DCM (10 mL) was added NBS (0.309 g, 1.737 mmol) portionwise at 0° C. and stirred for 1 h. Then the temperature was raised to room temperature and stirred further for 2 h. The residue was suspended in ethyl acetate and water, layers separated and the aqueous layer was extracted with EtOAc (3×100 ml). The combined organic layer was washed with water, brine, dried over sodium sulphate and concentrated under reduced pressure to afford Intermediate 202B (0.4 g, 76%) as a pale yellow solid. MS(ES): m/z=332 [M+H]$^+$; $^1$H NMR (400 MHz, $CDCl_3$) δ ppm 8.77-8.86 (m, 2H), 7.83-7.97 (m, 2H), 7.36-7.46 (m, 2H), 7.09-7.19 (m, 2H), 3.90 (s, 3H).

Intermediate 202C: N-(6-(3-(4-Fluorophenyl)-1-methyl-5-(pyridin-4-yl)-1H-pyrazol-4-yl)imidazo[1,2-b]pyridazin-2-yl)acetamide To a degassed solution of Intermediate 202B (0.3 g, 0.903 mmol), Intermediate-1 (0.819 g, 2.71 mmol), potassium phosphate (0.472 g, 2.71 mmol) and in 1,4-dioxane (1 mL) and water (0.1 mL) was added 2-dicyclohexylphosphino-2', 6'-dimethoxybiphenyl (0.074 g, 0.181 mmol) and $Pd_2$(dba)$_3$ (0.083 g, 0.090 mmol) and the reaction was purged with nitrogen gas for 10 min. The reaction was heated to 90° C. and stirred for 16 h. The reaction mixture was cooled to room temperature diluted with water and filtered through CELITE® pad and extracted with EtOAc (3×100 ml). The combined organic layer was washed with water, brine, dried over $Na_2SO_4$, filtered and concentrated. The residue was purified by silica gel chromatography (40 g REDISEP® column, eluting with 5% methanol in chloroform). Collected fractions were concentrated together to afford Intermediate 202C (0.16 g, 41%) as an off-white solid. MS(ES): m/z=428 [M+H]$^+$; $^1$H NMR (300 MHz, DMSO-$d_6$) δ ppm 10.88 (s, 1H), 8.61-8.70 (m, 2H), 8.09 (s, 1H), 7.84 (dd, J=9.25, 0.57 Hz, 1H), 7.45-7.54 (m, 4H), 7.19 (t, J=8.92 Hz, 2H), 6.82 (d, J=9.25 Hz, 1H), 3.90 (s, 3H), 2.08 (s, 3H).

Intermediate 202D: 6-(3-(4-Fluorophenyl)-1-methyl-5-(pyridin-4-yl)-1H-pyrazol-4-yl)imidazo[1,2-b]pyridazin-2-amine

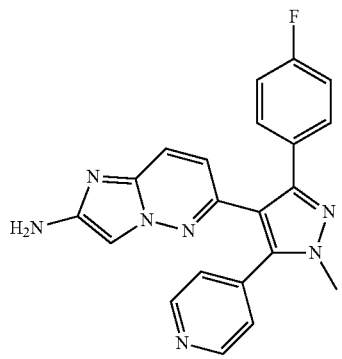 [SMILES: Cn1nc(-c2ccc(F)cc2)c(-c2ccc3nc(N)cn3n2)c1-c1ccncc1]

To a solution of Intermediate 202C (0.16 g, 0.374 mmol) in methanol (1 mL) was added 4 M HCl in dioxane (3 ml, 12.00 mmol) and the reaction was stirred at room temperature for 12 h. Excess of HCl in dioxane was removed under high vacuum. The reaction mixture was quenched with 10% sodium bicarbonate solution and extracted with chloroform (3×80 ml). The combined organic layer was washed with water, brine, dried over sodium sulphate, filtered and concentrated to afford Intermediate 202D (0.12 g, 83%) as a brown solid. MS(ES): m/z=386 [M+H]$^+$; $^1$H NMR (300 MHz, DMSO-d$_6$) δ ppm 8.58-8.70 (m, 2H), 7.38-7.56 (m, 5H), 7.10-7.24 (m, 3H), 6.62 (d, J=8.97 Hz, 1H), 5.50 (s, 2H), 3.90 (s, 3H).

Compound 202: 2-Fluoro-N-(6-(3-(4-fluorophenyl)-1-methyl-5-(pyridin-4-yl)-1H-pyrazol-4-yl)imidazo[1,2-b]pyridazin-2-yl)isonicotinamide

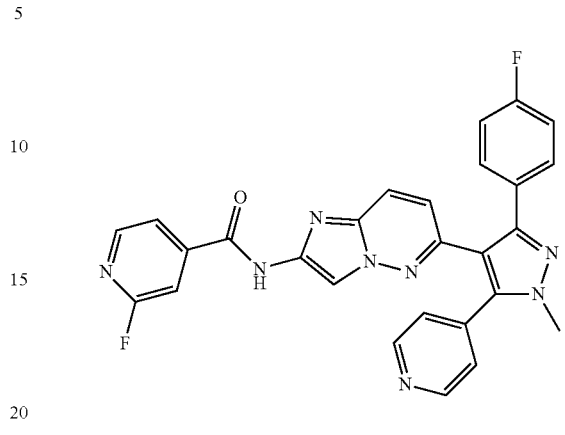

To a solution of Intermediate 202D (0.06 g, 0.156 mmol), HATU (0.118 g, 0.311 mmol) and DIPEA (0.095 mL, 0.545 mmol) in DMF (1 mL) was added 2-fluoroisonicotinic acid (0.044 g, 0.311 mmol) and the reaction mixture was stirred at room temperature for 16 h. DMF was removed under high vacuum and the residue was added 10% sodium bicarbonate solution (10 ml) and extracted with chloroform (3×80 mL). The combined organic layer was washed with water, brine, dried over sodium sulphate, filtered and concentrated. The crude product was purified by reverse phase preparative HPLC to afford compound 202 (0.012 g, 14%) as a white solid. MS(ES): m/z=509 [M+H]$^+$; HPLC Ret. Time 6.63 min and 7.17 min (Method J and K respectively); $^1$H NMR (400 MHz, DMSO-d$_6$) δ ppm 11.90 (bs, 1H), 8.64-8.70 (m, 2H), 8.46 (d, J=5.15 Hz, 1H), 8.34 (d, J=0.56 Hz, 1H), 7.90-7.98 (m, 2H), 7.77 (s, 1H), 7.49-7.55 (m, 4H), 7.21 (t, J=8.97 Hz, 2H), 6.89 (d, J=9.29 Hz, 1H), 3.92 (s, 3H).

The following compounds in Table 10 were prepared by the procedure described for the preparation of Compound 202 using Compound 202D and the corresponding acids.

TABLE 10

| Compound No. | Structure | Name | [M + H]$^+$ | Ret Time | HPLC Method |
|---|---|---|---|---|---|
| 203 | 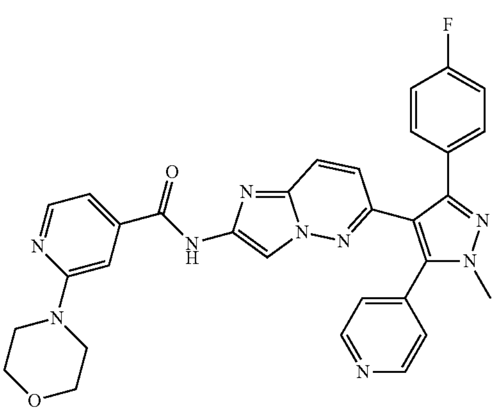 [SMILES: Cn1nc(-c2ccc(F)cc2)c(-c2ccc3nc(NC(=O)c4ccnc(N5CCOCC5)c4)cn3n2)c1-c1ccncc1] | N-(6-(3-(4-Fluorophenyl)-1-methyl-5-(pyridin-4-yl)-1H-pyrazol-4-yl)imidazo[1,2-b]pyridazin-2-yl)-2-morpholinoisonicotinamide | 576 | 5.63<br>6.24 | J<br>K |

TABLE 10-continued

| Compound No. | Structure | Name | [M + H]+ | Ret Time | HPLC Method |
|---|---|---|---|---|---|
| 204 | 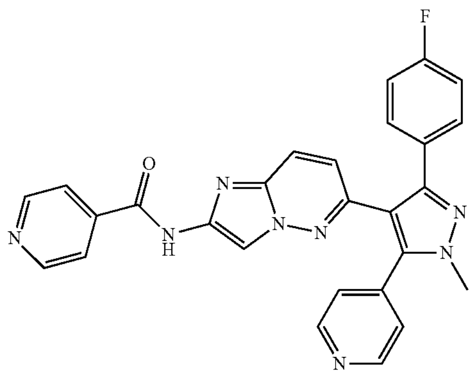 [SMILES: Cn1nc(-c2ccc(F)cc2)c(-c2ccc3nc(NC(=O)c4ccncc4)cn3n2)c1-c1ccncc1] | N-(6-(3-(4-Fluorophenyl)-1-methyl-5-(pyridin-4-yl)-1H-pyrazol-4-yl)imidazo[1,2-b]pyridazin-2-yl)isonicotinamide | 491 | 5.36 5.85 | J K |
| 205 | 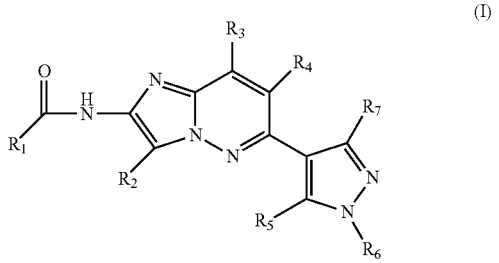 | N-(6-(3-(4-Fluorophenyl)-1-methyl-5-(pyridin-4-yl)-1H-pyrazol-4-yl)imidazo[1,2-b]pyridazin-2-yl)-3-(pyridin-3-yl)benzamide | 567 | 5.53 6.31 | J K |

What is claimed is:

1. A compound according to Formula (I):

(I)

or a pharmaceutically acceptable salt thereof, wherein:

$R_1$ is selected from $C_{1-4}$alkyl (optionally substituted with F, Cl, Br, OH, CN, and $NR_aR_a$), —$(CR_dR_d)_r$—$C_{3-13}$ carbocyclyl substituted with 0-5 $R_{11}$, and —$(CR_dR_d)_r$-4- to 14-membered heterocyclyl comprising carbon atoms and 1 to 4 heteroatoms selected from N, $NR_9$, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN;

$R_5$ is selected from H, $C_{1-4}$alkyl substituted with 0-4 $R_e$, —$(CH_2)_r$—$C_{3-6}$ carbocyclyl substituted with 0-4 $R_e$, and —$(CH_2)_r$-4- to 14-membered heterocyclyl comprising carbon atoms and 1 to 3 heteroatoms selected from N, $NR_8$, O, S, and substituted with 0-4 $R_e$;

$R_6$ is selected from H, $C_{1-6}$alkyl substituted with 0-3 $R_e$, and $C_{3-6}$carbocyclyl substituted with 0-3 $R_e$; or $R_7$ is aryl substituted with 0-3 $R_e$;

$R_8$ is selected from H, $C_{1-4}$ alkyl substituted with 0-3 $R_e$, —$(CH_2)_r$CN, —$(CH_2)_r$$OR_b$, $(CH_2)_r$$S(O)_p$$R_c$, —$(CH_2)_r$$C(=O)R_b$, —$(CH_2)_r$$NR_aR_a$, —$(CH_2)_r$$C(=O)NR_aR_a$, —$(CH_2)_r$$C(=O)$—$C_{1-4}$ alkyl substituted with 0-3 $R_e$, —$(CH_2)_r$$NR_aC(=O)R_b$, —$(CH_2)_r$$NR_aC(=O)OR_b$, —$(CH_2)_r$$OC(=O)NR_aR_a$, —$(CH_2)_r$$NR_aC(=O)NR_aR_a$, —$(CH_2)_r$$C(=O)OR_b$, —$(CH_2)_r$$S(O)_2NR_aR_a$, —$(CH_2)_r$$NR_aS(O)_2NR_aR_a$, —$(CH_2)_r$$NR_aS(O)_2R_c$, $(CH_2)_r$—$C_{3-13}$ carbocyclyl substituted with 0-3 $R_e$, and —$(CH_2)_r$-4- to 14-membered heterocyclyl comprising carbon atoms and 1 to 4 heteroatoms selected from N, O, S and substituted with 0-3 $R_e$;

$R_9$ is selected from H, —$C(=O)R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-4- to 14-membered heterocyclyl comprising carbon atoms and 1 to 4 heteroatoms selected from N, O, S and substituted with 0-5 $R_e$;

$R_{11}$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —(CR$_d$R$_d$)$_r$-4- to 14-membered heterocyclyl comprising carbon atoms and 1 to 4 heteroatoms selected from N, O, S and substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-4- to 14-membered heterocyclyl comprising carbon atoms and 1 to 4 heteroatoms selected from N, O, S and substituted with 0-5 R$_e$; or R$_a$ and R$_a$ together with the nitrogen atom to which they are both attached form a 4- to 14-membered heterocyclic ring comprising carbon atoms and 1 to 4 heteroatoms selected from N, O, S and substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-4- to 14-membered heterocyclyl comprising carbon atoms and 1 to 4 heteroatoms selected from N, O, S and substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and 4- to 14-membered heterocyclyl comprising carbon atoms and 1 to 4 heteroatoms selected from N, O, S and;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

2. The compound according to claim 1 of Formula (II):

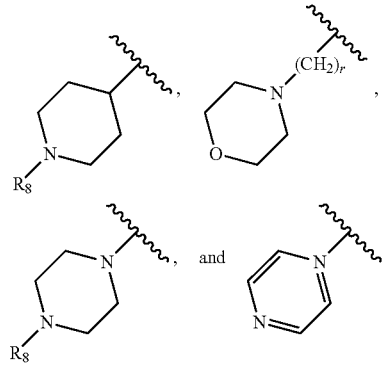

or a pharmaceutically acceptable salt thereof, wherein:
R$_e$' is selected from F, Cl, Br, and C$_{1-6}$ alkyl substituted with 0-5 R$_f$;
R$_5$ is selected from H, C$_{1-4}$alkyl substituted with 0-3 R$_e$, —(CH$_2$)$_r$—C$_{3-6}$ carbocyclyl substituted with 0-3 R$_e$, and —(CH$_2$)$_r$-4- to 14-membered heterocyclyl comprising carbon atoms and 1 to 3 heteroatoms selected from N, NR$_8$, O, S, and substituted with 0-3 R$_e$;

R$_6$ is selected from H, C$_{1-6}$alkyl substituted with 0-2 R$_e$, and C$_{3-6}$cycloalkyl substituted with 0-2 R$_e$; and R$_8$ is selected from H, C$_{1-4}$ alkyl substituted with 0-3 R$_e$—(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$ NR$_a$C(=O)R$_d$, —(CH$_2$)$_r$NR$_a$C(=O)OR$_b$, —(CH$_2$)$_r$ OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$ NR$_a$S(O)$_2$R$_c$, —(CH$_2$)$_r$—C$_{3-6}$ carbocyclyl substituted with 0-3 R$_e$, and —(CH$_2$)$_r$-4- to 14-membered heterocyclyl comprising carbon atoms and 1 to 4 heteroatoms selected from N, O, S and substituted with 0-3 R$_e$.

3. The compound according to claim 2, wherein:
R$_5$ is selected from H, C$_{1-4}$alkyl substituted with 0-1 R$_e$, C$_{3-6}$cycloalkyl, aryl, and —(CH$_2$)$_r$-heterocyclyl selected from pyridyl, pyrimidinyl, pyrazinyl, pyridazinyl, triazinyl, furyl, thienyl, imidazolyl, thiazolyl, indolyl, pyrrolyl, oxazolyl, isoxazolyl, pyrazolyl, triazolyl, tetrazolyl, indazolyl, 1,2,4-thiadiazolyl, isothiazolyl, azetidinyl, pyrrolidinyl, piperidinyl, piperazinyl, and morpholinyl.

4. The compound according to claim 3, wherein:
R$_5$ is selected from H,

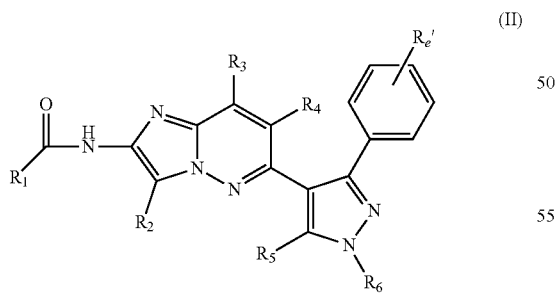

R$_8$ is selected from H, C$_{1-4}$ alkyl substituted with 0-3 R$_e$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$(C=O)CH$_2$NR$_a$R$_a$, —(CH$_2$)$_r$NR$_a$C(=O)R$_b$, —(CH$_2$)$_r$NR$_a$C(=O)OR$_b$, —(CH$_2$)$_r$C(=O)OR$_b$, and —(CH$_2$)$_r$-4- to 14-membered heterocyclyl comprising carbon atoms and 1 to 4 heteroatoms selected from N, O, S and substituted with 0-3 R$_e$;

R$_a$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-4- to 14-membered heterocyclyl comprising carbon atoms and 1 to 4 heteroatoms selected from N, O, S and substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-4- to 14-membered heterocyclyl comprising carbon atoms and 1 to 4 heteroatoms selected from N, O, S and substituted with 0-5 R$_e$;

R$_c$, at each occurrence, is independently selected from C$_{1-6}$ alkyl substituted with 0-5 R$_e$, C$_{3-6}$carbocyclyl, and 4- to 14-membered heterocyclyl comprising carbon atoms and 1 to 4 heteroatoms selected from N, O, S and;

$R_e$, at each occurrence, is independently selected from $C_{1-6}$ alkyl substituted with 0-5 $R_f$, —(CH$_2$)$_r$—C$_{3-6}$ cycloalkyl, F, Cl, Br, CN, NO$_2$, =O, CO$_2$H, (CH$_2$)$_r$OC$_{1-5}$alkyl, —(CH$_2$)$_r$OH, SH, and —(CH$_2$)$_r$NR$_f$R$_f$;

$R_f$, at each occurrence, is independently selected from H, $C_{1-5}$ alkyl, and phenyl, or $R_f$ and $R_f$ together with the nitrogen atom to which they are both attached form a heterocyclic ring.

5. The compound according to claim 1 of Formula (III):

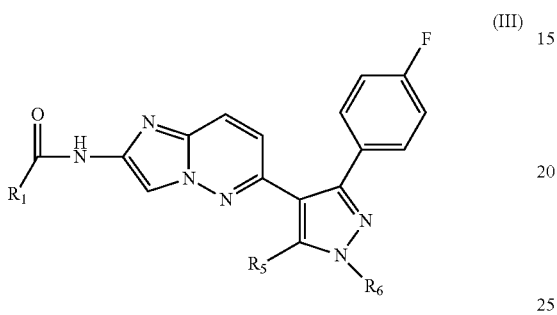

or a pharmaceutically acceptable salt thereof, wherein:

$R_1$ is selected from $C_{1-4}$alkyl (optionally substituted with F, Cl, Br, OH, CN, and NR$_a$R$_a$), —(CH$_2$)$_r$-carbocyclyl substituted with 0-4 $R_{11}$, and —(CH$_2$)$_r$-4- to 14-membered heterocyclyl comprising carbon atoms and 1 to 4 heteroatoms selected from N, NR$_9$, O, S and substituted with 0-4 $R_{11}$;

$R_{11}$, at each occurrence, is independently selected from H, F, Cl, Br, =O, CN, NO$_2$, —OR$_b$, —S(O)$_p$R$_c$, —C(=O)R$_b$, —(CH$_2$)$_r$NR$_a$R$_a$, —(CH$_2$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CH$_2$)$_r$C(=O)OR$_b$, $C_{1-6}$ alkyl substituted with 0-5 $R_e$, —(CH$_2$)$_r$—C$_{3-6}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$;

$R_a$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;

$R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$;

$R_e$, at each occurrence, is independently selected from $C_{1-6}$ alkyl substituted with 0-5 $R_f$, —(CH$_2$)$_r$—C$_{3-6}$ cycloalkyl, F, Cl, Br, CN, NO$_2$, =O, CO$_2$H, (CH$_2$)$_r$OC$_{1-5}$alkyl, —(CH$_2$)$_r$OH, SH, and —(CH$_2$)$_r$NR$_f$R$_f$; and $R_f$, at each occurrence, is independently selected from H, $C_{1-5}$ alkyl, and phenyl, or $R_f$ and $R_f$ together with the nitrogen atom to which they are both attached form a heterocyclic ring.

6. The compound according to claim 5, wherein:

$R_1$ is selected from aryl, cycloalkyl, and heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl.

7. The compound according to claim 6, wherein:

$R_1$ is selected from

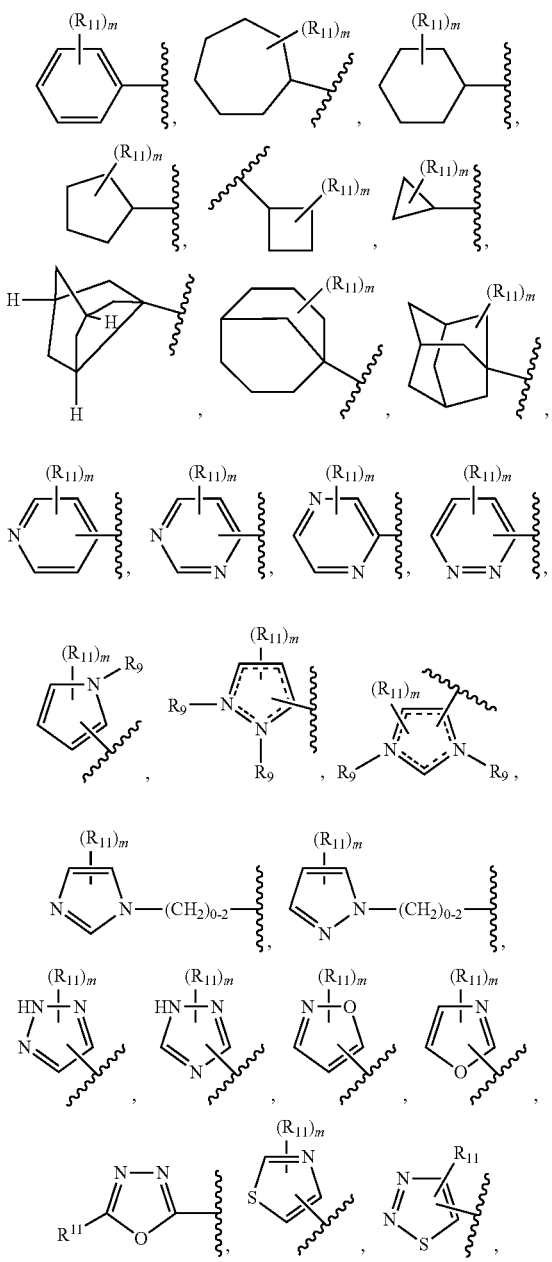

-continued

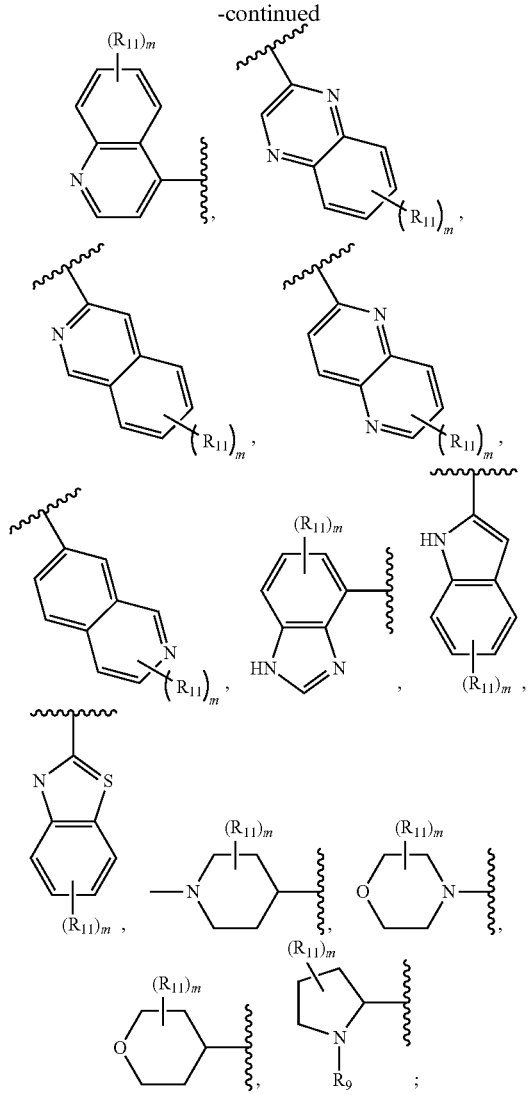

---- represents an optional bond;
$R_{11}$, at each occurrence, is independently selected from H, F, Cl, Br, =O, CN, —$OR_b$, —C(=O)$R_b$, —$(CH_2)_r$NR$_a$R$_a$, —$(CH_2)_r$C(=O)NR$_a$R$_a$, —NR$_a$C(=O)R$_b$, —$(CH_2)_r$C(=O)OR$_b$, $C_{1-6}$ alkyl substituted with 0-5 $R_e$, —$(CH_2)_r$—$C_{3-6}$carbocyclyl substituted with 0-5 $R_e$, and —$(CH_2)_r$-4- to 14-membered heterocyclyl comprising carbon atoms and 1 to 4 heteroatoms selected from N, O, S and substituted with 0-5 $R_e$;
$R_9$, at each occurrence, is independently selected from H, —C(=O)$R_b$, $C_{1-6}$ alkyl substituted with 0-5 $R_e$; and
m, at each occurrence, is independently selected from zero, 1, and 2.

8. The compound according to claim 2, wherein:
$R_1$ is selected from carbocyclyl substituted with 0-4 $R_{11}$, and —$(CH_2)_r$-5- to 10-membered heterocyclyl comprising carbon atoms and 1 to 4 heteroatoms selected from N, NR$_9$, O, S and substituted with 0-4 $R_{11}$;
$R_5$ is selected from H, $C_{1-4}$alkyl substituted with 0-3 Re and —$(CH_2)_r$-4- to 14-membered heterocyclyl comprising carbon atoms and 1 to 3 heteroatoms selected from N, NR$_8$, O, S, and substituted with 0-3 $R_e$;
$R_6$ is selected from H, $C_{1-6}$alkyl substituted with 0-2 $R_e$, and $C_{3-6}$cycloalkyl substituted with 0-3 $R_e$;

$R_8$ is selected from H, $C_{1-4}$ alkyl substituted with 0-3 $R_e$, —$(CH_2)_r$C(=O)$R_b$, and —$(CH_2)_r$-4- to 14-membered heterocyclyl comprising carbon atoms and 1 to 4 heteroatoms selected from N, O, S and substituted with 0-3 $R_e$;
$R_{11}$, at each occurrence, is independently selected from H, F, Cl, CN, —$OR_b$, —$(CH_2)_r$NR$_a$R$_a$, —NR$_a$C(=O)R$_b$, $C_{1-6}$ alkyl substituted with 0-5 $R_e$, —$(CH_2)_r$—$C_{3-6}$carbocyclyl substituted with 0-5 $R_e$, and —$(CH_2)_r$-5- to 10-membered heterocyclyl substituted with 0-5 $R_e$;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-4- to 14-membered heterocyclyl comprising carbon atoms and 1 to 4 heteroatoms selected from N, O, S and substituted with 0-5 $R_e$;
$R_e$, at each occurrence, is independently selected from $C_{1-6}$ alkyl substituted with 0-5 $R_f$, —$(CH_2)_r$—$C_{3-6}$cycloalkyl, F, Cl, Br, CN, NO$_2$, =O, CO$_2$H, —$(CH_2)_r$OC$_{1-5}$alkyl, —$(CH_2)_r$OH, S(O)$_2$C$_{1-4}$alkyl, and —$(CH_2)_r$NR$_f$R$_f$;
$R_f$, at each occurrence, is independently selected from H, $C_{1-5}$ alkyl, and phenyl, or $R_f$ and $R_f$ together with the nitrogen atom to which they are both attached form a heterocyclic ring; and
r, at each occurrence, is independently selected from zero, 1, 2, 3, and 4.

9. The compound according to claim 8, wherein:
$R_1$ is selected from

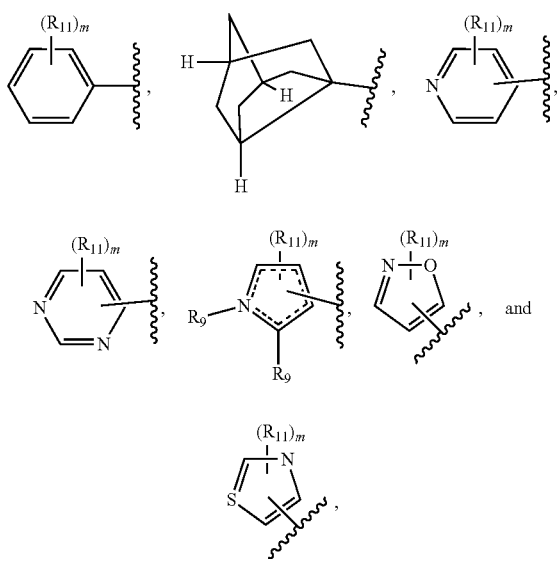

$R_5$ is selected from H, $C_{1-4}$alkyl substituted with 0-3 $R_e$,

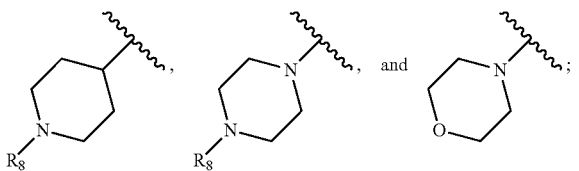

$R_6$ is selected from H, $C_{1-4}$alkyl, and $C_{3-6}$cycloalkyl;

$R_8$ is selected from H, $C_{1-4}$alkyl, —$(CH_2)_rCF_3$, —$(CH_2)_r$ $CH_2F$, —$(CH_2)_rCN$, —$(CH_2)_rOH$, —$CH_2CH(OH)$ $CF_3$, —$(CH_2)_rC(=O)NH_2$, —$C(=O)CH_2NH_2$, —$C(=O)CH_2CN$, —$C(=O)CH_2CF_3$, $C(=O)$ $CH_2OH$, —$(CH_2)_r$-heterocyclyl substituted with 0-3 $R_e$, —$C(=O)$-heterocyclyl substituted with 0-3 $R_e$, wherein said heterocyclyl is selected from

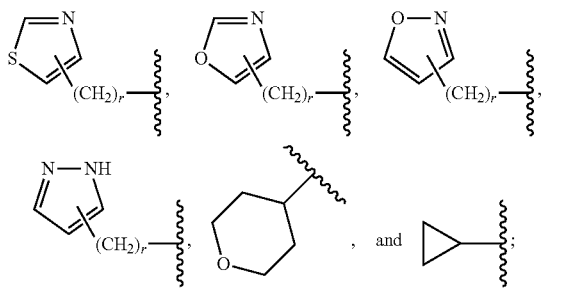

$R_{11}$, at each occurrence, is independently selected from F, Cl, CN, —$(CH_2)_rNR_aR_a$, OH, $OC_{1-4}$alkyl, $C_{1-4}$ alkyl substituted with 0-5 $R_e$,

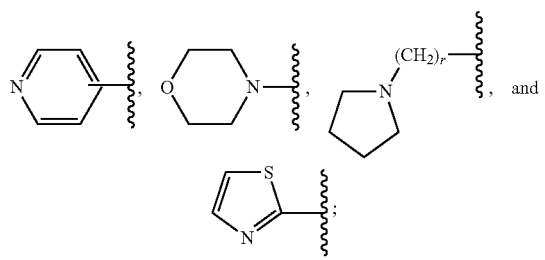

$R_9$, at each occurrence, is independently selected from H and $C_{1-4}$ alkyl;

$R_a$, at each occurrence, is independently selected from H and $C_{1-4}$ alkyl substituted with 0-5 $R_e$;

$R_e$, at each occurrence, is independently selected from $C_{1-6}$ alkyl F, Cl, Br, CN, and $NH_2$;

m, at each occurrence, is independently selected from zero, 1, and 2; and r, at each occurrence, is independently selected from zero, 1, and 2.

10. The compound according to claim 1, which is selected from:

N-(6-(3-(4-Fluorophenyl)-1-methyl-1H-pyrazol-4-yl) imidazo[1,2-b]pyridazin-2-yl)isonicotinamide;

2-chloro-N-(6-(3-(4-fluorophenyl)-1-methyl-1H-pyrazol-4-yl)imidazo[1,2-b]pyridazin-2-yl)quinoline-4-carboxamide;

2,6-difluoro-N-(6-(3-(4-fluorophenyl)-1-methyl-1H-pyrazol-4-yl)imidazo[1,2-b]pyridazin-2-yl)isonicotinamide;

N-(6-(3-(4-fluorophenyl)-1-methyl-1H-pyrazol-4-yl)imidazo[1,2-b]pyridazin-2-yl)-4-methyl-2-(pyridin-4-yl)thiazole-5-carboxamide;

N-(6-(3-(4-fluorophenyl)-1-methyl-1H-pyrazol-4-yl)imidazo[1,2-b]pyridazin-2-yl)-4-methyl-2-(pyridin-3-yl)thiazole-5-carboxamide;

N-(6-(3-(4-fluorophenyl)-1-methyl-1H-pyrazol-4-yl)imidazo[1,2-b]pyridazin-2-yl)-4-methyl-2-(pyridin-2-yl)thiazole-5-carboxamide;

N-(6-(3-(4-fluorophenyl)-1-methyl-1H-pyrazol-4-yl)imidazo[1,2-b]pyridazin-2-yl)-4-methyl-2-phenylthiazole-5-carboxamide;

N-(6-(3-(4-fluorophenyl)-1-methyl-1H-pyrazol-4-yl)imidazo[1,2-b]pyridazin-2-yl)-2-(pyridin-4-yl)thiazole-4-carboxamide;

N-(6-(3-(4-fluorophenyl)-1-methyl-1H-pyrazol-4-yl)imidazo[1,2-b]pyridazin-2-yl)-2-(pyridin-3-yl)thiazole-4-carboxamide;

N-(6-(3-(4-fluorophenyl)-1-methyl-1H-pyrazol-4-yl)imidazo[1,2-b]pyridazin-2-yl)-2-phenylthiazole-4-carboxamide;

2-(4-chlorophenyl)-N-(6-(3-(4-fluorophenyl)-1-methyl-1H-pyrazol-4-yl)imidazo[1,2-b]pyridazin-2-yl)thiazole-4-carboxamide;

N-(6-(3-(4-fluorophenyl)-1-methyl-1H-pyrazol-4-yl)imidazo[1,2-b]pyridazin-2-yl)-3-methylisoxazole-4-carboxamide;

2-bromo-N-(6-(3-(4-fluorophenyl)-1-methyl-1H-pyrazol-4-yl)imidazo[1,2-b]pyridazin-2-yl)thiazole-4-carboxamide;

N-(6-(3-(4-fluorophenyl)-1-methyl-1H-pyrazol-4-yl)imidazo[1,2-b]pyridazin-2-yl)thiazole-4-carboxamide;

N-(6-(3-(4-fluorophenyl)-1-methyl-1H-pyrazol-4-yl)imidazo[1,2-b]pyridazin-2-yl)-3-(pyridin-3-yl)benzamide;

N-(6-(3-(4-fluorophenyl)-1-methyl-1H-pyrazol-4-yl)imidazo[1,2-b]pyridazin-2-yl)-3-(pyridin-4-yl)benzamide;

N-(6-(3-(4-fluorophenyl)-1-methyl-1H-pyrazol-4-yl)imidazo[1,2-b]pyridazin-2-yl)-5-phenylnicotinamide;

5-(4-cyanophenyl)-N-(6-(3-(4-fluorophenyl)-1-methyl-1H-pyrazol-4-yl)imidazo[1,2-b]pyridazin-2-yl)nicotinamide;

N-(6-(3-(4-fluorophenyl)-1-methyl-1H-pyrazol-4-yl)imidazo[1,2-b]pyridazin-2-yl)-3-morpholinobenzamide;

2-fluoro-N-(6-(3-(4-fluorophenyl)-1-methyl-1H-pyrazol-4-yl)imidazo[1,2-b]pyridazin-2-yl)benzamide;

N-(6-(3-(4-fluorophenyl)-1-methyl-1H-pyrazol-4-yl)imidazo[1,2-b]pyridazin-2-yl)pyrimidine-2-carboxamide;

N-(6-(3-(4-fluorophenyl)-1-methyl-1H-pyrazol-4-yl)imidazo[1,2-b]pyridazin-2-yl)isoxazole-5-carboxamide;

3-fluoro-N-(6-(3-(4-fluorophenyl)-1-methyl-1H-pyrazol-4-yl)imidazo[1,2-b]pyridazin-2-yl)benzamide;

4-chloro-2-fluoro-N-(6-(3-(4-fluorophenyl)-1-methyl-1H-pyrazol-4-yl)imidazo[1,2-b]pyridazin-2-yl)benzamide;

N-(6-(3-(4-fluorophenyl)-1-methyl-1H-pyrazol-4-yl)imidazo[1,2-b]pyridazin-2-yl)pyridazine-4-carboxamide;

3-((dimethylamino)methyl)-N-(6-(3-(4-fluorophenyl)-1-methyl-1H-pyrazol-4-yl)imidazo[1,2-b]pyridazin-2-yl)benzamide;

2-((dimethylamino)methyl)-N-(6-(3-(4-fluorophenyl)-1-methyl-1H-pyrazol-4-yl)imidazo[1,2-b]pyridazin-2-yl)benzamide;

N-(6-(3-(4-fluorophenyl)-1-methyl-1H-pyrazol-4-yl)imidazo[1,2-b]pyridazin-2-yl)thiazole-5-carboxamide;

N-(6-(3-(4-fluorophenyl)-1-methyl-1H-pyrazol-4-yl)imidazo[1,2-b]pyridazin-2-yl)pyrimidine-2-carboxamide;

N-(6-(3-(4-fluorophenyl)-1-methyl-1H-pyrazol-4-yl)imidazo[1,2-b]pyridazin-2-yl)-4-(pyrrolidin-1-ylmethyl)benzamide;

4-((diethylamino)methyl)-N-(6-(3-(4-fluorophenyl)-1-methyl-1H-pyrazol-4-yl)imidazo[1,2-b]pyridazin-2-yl)benzamide;

6-(tert-butyl)-N-(6-(3-(4-fluorophenyl)-1-methyl-1H-pyrazol-4-yl)imidazo[1,2-b]pyridazin-2-yl)pyrimidine-4-carboxamide;

6-(4-fluorophenyl)-N-(6-(3-(4-fluorophenyl)-1-methyl-1H-pyrazol-4-yl)imidazo[1,2-b]pyridazin-2-yl)pyrimidine-4-carboxamide;

N-(6-(3-(4-fluorophenyl)-1-methyl-1H-pyrazol-4-yl)imidazo[1,2-b]pyridazin-2-yl)-4-methyl-1H-pyrazole-3-carboxamide;

3-fluoro-N-(6-(3-(4-fluorophenyl)-1-methyl-1H-pyrazol-4-yl)imidazo[1,2-b]pyridazin-2-yl)isonicotinamide;

3-chloro-N-(6-(3-(4-fluorophenyl)-1-methyl-1H-pyrazol-4-yl)imidazo[1,2-b]pyridazin-2-yl)picolinamide;

N-(6-(3-(4-fluorophenyl)-1-methyl-1H-pyrazol-4-yl)imidazo[1,2-b]pyridazin-2-yl)thiazole-2-carboxamide;

N-(6-(3-(4-fluorophenyl)-1-methyl-1H-pyrazol-4-yl)imidazo[1,2-b]pyridazin-2-yl)pyrimidine-4-carboxamide;

N-(6-(3-(4-fluorophenyl)-1-methyl-1H-pyrazol-4-yl)imidazo[1,2-b]pyridazin-2-yl)-2,6-dimethoxypyrimidine-4-carboxamide;

N-(6-(3-(4-fluorophenyl)-1-methyl-1H-pyrazol-4-yl)imidazo[1,2-b]pyridazin-2-yl)tetrahydro-2H-pyran-4-carboxamide;

2-fluoro-N-(6-(3-(4-fluorophenyl)-1-methyl-1H-pyrazol-4-yl)imidazo[1,2-b]pyridazin-2-yl)-4-(hydroxymethyl)benzamide;

4-bromo-2-fluoro-N-(6-(3-(4-fluorophenyl)-1-methyl-1H-pyrazol-4-yl)imidazo[1,2-b]pyridazin-2-yl)benzamide;

3,5-difluoro-N-(6-(3-(4-fluorophenyl)-1-methyl-1H-pyrazol-4-yl)imidazo[1,2-b]pyridazin-2-yl)benzamide;

2-fluoro-N-(6-(3-(4-fluorophenyl)-1-methyl-1H-pyrazol-4-yl)imidazo[1,2-b]pyridazin-2-yl)-5-methoxybenzamide;

3-fluoro-N-(6-(3-(4-fluorophenyl)-1-methyl-1H-pyrazol-4-yl)imidazo[1,2-b]pyridazin-2-yl)-5-methoxybenzamide;

5-chloro-N-(6-(3-(4-fluorophenyl)-1-methyl-1H-pyrazol-4-yl)imidazo[1,2-b]pyridazin-2-yl)nicotinamide;

5-chloro-2-fluoro-N-(6-(3-(4-fluorophenyl)-1-methyl-1H-pyrazol-4-yl)imidazo[1,2-b]pyridazin-2-yl)benzamide;

4-cyano-3-fluoro-N-(6-(3-(4-fluorophenyl)-1-methyl-1H-pyrazol-4-yl)imidazo[1,2-b]pyridazin-2-yl)benzamide;

N-(6-(3-(4-fluorophenyl)-1-methyl-1H-pyrazol-4-yl)imidazo[1,2-b]pyridazin-2-yl)-2-methoxyisonicotinamide;

2-(tert-butyl)-N-(6-(3-(4-fluorophenyl)-1-methyl-1H-pyrazol-4-yl)imidazo[1,2-b]pyridazin-2-yl)isonicotinamide;

2,5-difluoro-N-(6-(3-(4-fluorophenyl)-1-methyl-1H-pyrazol-4-yl)imidazo[1,2-b]pyridazin-2-yl)benzamide;

N-(6-(3-(4-fluorophenyl)-1-methyl-1H-pyrazol-4-yl)imidazo[1,2-b]pyridazin-2-yl)-2-methylisonicotinamide;

6-cyano-N-(6-(3-(4-fluorophenyl)-1-methyl-1H-pyrazol-4-yl)imidazo[1,2-b]pyridazin-2-yl)nicotinamide;

2-fluoro-N-(6-(3-(4-fluorophenyl)-1-methyl-1H-pyrazol-4-yl)imidazo[1,2-b]pyridazin-2-yl)isonicotinamide;

5-cyano-2-fluoro-N-(6-(3-(4-fluorophenyl)-1-methyl-1H-pyrazol-4-yl)imidazo[1,2-b]pyridazin-2-yl)benzamide; and 3-cyano-4-fluoro-N-(6-(3-(4-fluorophenyl)-1-methyl-1H-pyrazol-4-yl)imidazo, or a pharmaceutically acceptable salt thereof.

11. A pharmaceutical composition comprising one or more compounds of claim 1 and a pharmaceutically acceptable carrier.

12. A method of inhibiting casein kinase Iδ/ε activity in a patient, comprising administering to a patient in need thereof, a therapeutically effective amount of one or more compounds according to claim 1.

* * * * *